United States Patent
Amegadzie et al.

(10) Patent No.: US 7,179,804 B2
(45) Date of Patent: Feb. 20, 2007

(54) TACHYKININ RECEPTOR ANTAGONISTS

(75) Inventors: Albert Kudzovi Amegadzie, Indianapolis, IN (US); Kevin Matthew Gardinier, Indianapolis, IN (US); Erik James Hembre, Indianapolis, IN (US); Jian Eric Hong, Carmel, IN (US); Louis Nickolaus Jungheim, Indianapolis, IN (US); Michael Alan Robertson, Indianapolis, IN (US); Kenneth Allen Savin, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 49 days.

(21) Appl. No.: 10/512,248

(22) PCT Filed: Apr. 22, 2003

(86) PCT No.: PCT/US03/10682

§ 371 (c)(1),
(2), (4) Date: Oct. 20, 2004

(87) PCT Pub. No.: WO03/091227

PCT Pub. Date: Nov. 6, 2003

(65) Prior Publication Data

US 2005/0239776 A1 Oct. 27, 2005

Related U.S. Application Data

(60) Provisional application No. 60/440,865, filed on Jan. 16, 2003, provisional application No. 60/376,121, filed on Apr. 26, 2002.

(51) Int. Cl.
*A61K 31/4192* (2006.01)
*A61K 31/4406* (2006.01)
*A61K 31/4409* (2006.01)
*A61K 31/497* (2006.01)
*A61K 31/541* (2006.01)
*A61K 31/5377* (2006.01)
*C07D 261/08* (2006.01)
*C07D 413/06* (2006.01)
*C07D 417/14* (2006.01)
*C07F 7/10* (2006.01)

(52) U.S. Cl. ............... 514/227.8; 514/231.5; 514/255.05; 514/340; 514/359; 544/60; 544/140; 544/229; 546/14; 546/272.1; 548/248; 548/255

(58) Field of Classification Search ............ 514/359, 514/340, 255.05, 227.8, 231.5; 548/248, 548/255; 546/14, 272.1; 544/140, 229, 544/60

See application file for complete search history.

(56) References Cited

U.S. PATENT DOCUMENTS 5,998,444 A 12/1999 Russell
6,060,478 A 5/2000 Gilligan et al.
6,407,106 B1 6/2002 Jasserand et al.

FOREIGN PATENT DOCUMENTS

| EP | 0 699 665 A1 | 3/1996 |
|----|---|---|
| EP | 0 699 665 | 3/2003 |
| FR | 2 329 275 | 10/1976 |
| JP | P2002-123925 A | 4/2002 |
| WO | WO 95/11880 | 5/1995 |
| WO | WO 97/40025 | 10/1997 |
| WO | WO 99/07677 | 2/1999 |
| WO | WO 01/44200 | 6/2001 |
| WO | WO 02/08232 A1 | 1/2003 |

OTHER PUBLICATIONS

Theocharis, et al. Journal od Heterocyclic Chemistry, vol. 27, pp. 1685-1688 (1990).*
Biagi, et al., "N<6>-Cycloalkyl-2-Phenyl-3-Deaza-8-Azaad Nines: A New Class of A1 Adenosine Receptor Ligands. A Comparison With the Corresponding Adenines and 8-Azaadenines", *European J. of Medicinal Chemistry*, 38, pp. 983-990 (2003).
Ivanov, et al., "Synthesis of 1,2,3-Triazolo '5,4-e!-1,4-diazepine", *J. of Organic Chemistry of the USSR*, XP009037402, 25:9, pp. 1785-1789 (1989).
Katritzky, et al., "Synthesis of C-Carbomoyl-1,2,3-triazoles by Microwave-Induced 1,3-Dipolar Cycloaddition of Organic Azides to Acetylenic Amides", *J. Organ. Chem.*, XP002299474, 67, pp. 9077-9079 (2002).
Katritzky, et al., "1,3-Dipolar Cycloadditions of Organic Azides to Ester or Benzotriazolylcarbonyl Activated Acetylenic Amides", *ARKIVOC*, 15, XP002299475, 15, pp. 47-64 (2003).
L'Abbé, et al., "Synthesis and Thermolysis of 4-Substituted 5-Azido-1-Phenyl-1,2,3-Triazoles", *Tetrahedron*, 44:12, pp. 3617-3626 (1988).
Hajjaji, et al., "Synthesis and Evaluation of the Inhibitor Effect of a New Class of Triazole Compounds," *Progress in Organic Coatings*, 38, pp. 207-212 (2000).
Abu-Orabi, et al., "Dipolar Cycloaddition Reactions of Organic Azides," *J. Heterocyclic Chem.*, 26, pp. 1461-1468 (1989).
Theocharis, et al., "Synthesis and Spectral Data of 4,5-Bix[5-aryl-1,3,4-oxadiazol-2-yl]-l-benzyl-1,2,3-triazoles," *J. Heterocyclic Chem*, 27, pp. 1685-1688 (1990).
Cottrell, et al., "An Improved Procedure for the Preparation of 1-Benzyl-1*H*-1,2,3-triazoles from Benzyl Azides," *J. Heterocyclic Chem.*, 28, pp. 301-304 (1990).
ACS Chemcats 2001:1613994, Publication Date Jan. 7, 2001, Order No. AN-666/14744011, CAS Registry No. 354780-46-4.
Al-Talib, et al., "Synthesis of 4,5-Bis-[5-aryl-1,3,4-oxadiazol-2YL]-1-Substgituted Benzyl-1,2,3-Triazoles," Indian J. of Heterocyclic Chem., 8, pp. 183-188 (1999).

* cited by examiner

*Primary Examiner*—Joseph K. McKane
*Assistant Examiner*—Nyeemah Grazier
(74) *Attorney, Agent, or Firm*—Manisha A. Desai

(57) ABSTRACT

The present invention relates to selective NK-1 receptor antagonists of Formula (I); or a pharmaceutically acceptable salt thereof, for the treatment of disorders associated with an excess of tachykinins

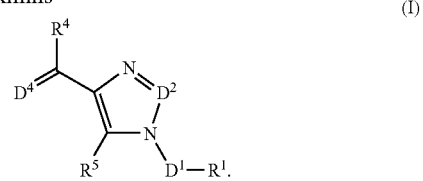

18 Claims, No Drawings

TACHYKININ RECEPTOR ANTAGONISTS

This application is a 371 of PCT/US03/10682 filed Apr. 22, 2003, which claims benefit of U.S. Provisional Application 60/376,121 filed Apr. 26, 2002 and claims benefit of U.S. Provisional Application 60/440,865, filed Jan. 16, 2003.

The present invention provides compounds of Formula (I), compositions thereof, and a method of antagonizing the NK-1 subtype of tachykinin receptor that comprises administering to a patient in need thereof an effective amount of a compound of Formula (I). In addition, the present invention relates to processes for preparing the compounds of Formula I and intermediates thereof.

BACKGROUND OF THE INVENTION

Tachykinins are a family of peptides that are widely distributed in both the central and peripheral nervous systems. These peptides exert a number of biological effects through actions at tachykinin receptors. To date, three such receptors have been characterized, including the NK-1, NK-2, and NK-3 subtypes of tachykinin receptor.

The role of the NK-1 receptor subtype in numerous disorders of the central nervous system and the periphery has been thoroughly demonstrated in the art. For instance, NK-1 receptors are believed to play a role in depression, anxiety, and central regulation of various autonomic, as well as cardiovascular and respiratory functions. NK-1 receptors in the spinal cord are believed to play a role in pain transmission, especially the pain associated with migraine and arthritis. In the periphery, NK-1 receptor activation has been implicated in numerous disorders, including various inflammatory disorders, asthma, and disorders of the gastrointestinal and genitourinary tract.

There is an increasingly wide recognition that selective NK-1 receptor antagonists would prove useful in the treatment of many diseases of the central nervous system and the periphery. While many of these disorders are being treated by new medicines, there are still many shortcomings associated with existing treatments. For example, the newest class of anti-depressants, selective serotonin reuptake inhibitors (SSRIs), are increasingly prescribed for the treatment of depression; however, SSRIs have numerous side effects, including nausea, insomnia, anxiety, and sexual dysfunction. This could significantly affect patient compliance rate. As another example, current treatments for chemotherapy-induced nausea and emesis, such as the 5-HT$_3$ receptor antagonists, are ineffective in managing delayed emesis. The development of NK-1 receptor antagonists will therefore greatly enhance the ability to treat such disorders more effectively. Thus, the present invention provides a class of potent, non-peptide NK-1 receptor antagonists, compositions comprising these compounds, and methods of using the compounds.

BRIEF SUMMARY OF THE INVENTION

The invention provides compounds of Formula (I):

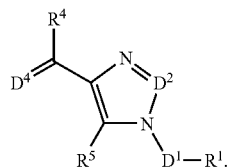

(I)

wherein:
$D^1$ is a $C_1$–$C_3$ alkane-diyl;
$D^2$ is CH or nitrogen;
$D^4$ is oxygen or sulfur;
$R^1$ is phenyl,
which is optionally substituted with one to three substitutents independently selected from the group consisting of halo, $C_1$–$C_4$ alkyl, $C_1$–$C_4$ alkoxy, cyano, difluoromethyl, trifluoromethyl, and trifluoromethoxy;
$R^4$ is a radical selected from the group consisting of:

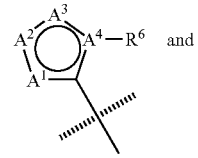

(IA)

and

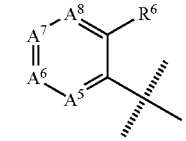

(IB)

wherein
$A^1$, $A^2$, $A^3$, and $A^4$, together with the atoms to which they are attached, form an unsaturated heterocyclic ring in which each of $A^1$, $A^2$, and $A^3$ is independently $CR^7$, nitrogen, which nitrogen is optionally substituted with $R^8$, oxygen, or sulfur, and $A^4$ is carbon or nitrogen, wherein only one of $A^1$, $A^2$, and $A^3$ can be oxygen or sulfur;
$A^5$, $A^6$, $A^7$, and $A^8$, together with the atoms to which they are attached, form an unsaturated carbocyclic or heterocyclic ring in which each of $A^5$, $A^6$, $A^7$, and $A^8$ is independently $CR^7$ or nitrogen, wherein at least one of $A^5$, $A^6$, $A^7$, and $A^8$ must be $CR^7$;
each $R^7$ is independently selected from the group consisting of hydrogen, halo, $C_1$–$C_4$ alkyl, substituted $C_1$–$C_4$ alkyl, $C_3$–$C_6$ cycloalkyl, $C_1$–$C_4$ alkoxycarbonyl, trifluoromethyl, trifluoromethoxy, and —$NR^9R^{10}$;
$R^9$ and $R^{10}$ are each independently hydrogen, $C_1$–$C_4$ alkyl, or —C(O)—CH$_3$, or $R^9$ and $R^{10}$, together with the nitrogen to which they are attached, form a 4–7 membered saturated heterocyclic ring;
each $R^8$ is independently selected from the group consisting of hydrogen, $C_1$–$C_4$ alkyl, substituted $C_1$–$C_4$ alkyl, and $C_1$–$C_3$ cycloalkyl;
$R^6$ is $C_1$–$C_4$ alkyl, $C_3$–$C_6$ cycloalkyl, phenyl, or pyridyl, which phenyl or pyridyl is optionally substituted with one to three substituents independently selected from the group consisting of halo, cyano, $C_1$–$C_4$ alkyl, $C_1$–$C_4$ alkoxy, trifluoromethyl, trifluoromethoxy, and —$NR^{11}R^{12}$;
$R^{11}$ and $R^{12}$ are each independently hydrogen or $C_1$–$C_4$ alkyl, or $R^{11}$ and $R^{12}$, together with the nitrogen to which they are attached, form a 4–7 membered saturated heterocyclic ring;
$R^5$ is hydrogen, halo, trifluoromethyl, $C_1$–$C_4$ alkyl, $C_3$–$C_6$ cycloalkyl, furyl, thienyl, pyrrolyl, imidazolyl, —$NR^{13}R^{14}$, pyridyloxy, phenyl, phenoxy, phenylthio, anilino,
which phenyl, phenoxy, phenylthio, or anilino group may be optionally substituted on the phenyl ring with one or two substituents independently selected from the group consisting of halo, $C_1$–$C_4$ alkyl, $C_1$–$C_4$ alkoxy, and —S(O)$_q$($C_1$–$C_4$ alkyl), or a radical selected from the group consisting of:

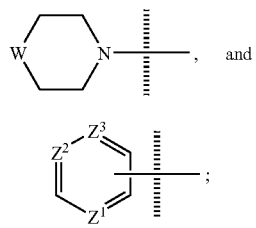

wherein
W is a bond, $CHR^{15}$, O, $NR^{15}$, or $S(O)_q$;
q is 0, 1, or 2;
$R^{15}$ is selected from the group consisting of hydrogen, $C_1$–$C_4$ alkyl, acetyl, carbamoyl, phenyl, benzyl, and —$S(O)_2CH_3$;
$Z^1$, $Z^2$, and $Z^3$ are each independently CH or nitrogen;
$R^{13}$ and $R^{14}$ are each independently hydrogen or $C_1$–$C_4$ alkyl;

or a pharmaceutically acceptable salt thereof.

The compounds of Formula I are antagonists of tachykinin receptors. Specifically, the compounds of Formula I are antagonists of the NK-1 subtype of tachykinin receptor. Because these compounds inhibit the physiological effects associated with an excess of tachykinins, the compounds are useful in the treatment of numerous disorders related to tachykinin receptor activation. These disorders include: anxiety, depression, psychosis, and schizophrenia and other psychotic disorders; neurodegenerative disorders such as dementia, including senile dementia of the Alzheimer's type, Alzheimer's disease, AIDS-associated dementia, and Down's syndrome; seizure disorders, such as epilepsy; demyelinating diseases such as multiple sclerosis and amyotrophic lateral sclerosis and other neuropathological disorders, such as peripheral neuropathy, diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease and irritable bowel syndrome; disorders of bladder function such as bladder detrusor hyper-reflexia and incontinence; atherosclerosis; fibrosin and collagen diseases such as scleroderma and eosinophilic fascioliasis; irritative symptoms of benign prostatic hypertrophy; disorders associated with blood pressure, such as hypertension; or disorders of blood flow caused by vasodilation and vasospastic diseases, such as angina, migraine, and Reynaud's disease; emesis, including chemotherapy-induced nausea and emesis; and pain or nociception, for example, that attributable to or associated with any of the foregoing conditions.

In one embodiment, this invention provides a pharmaceutical composition comprising, as an active ingredient, a compound of Formula I, or a pharmaceutically acceptable salt thereof, in combination with one or more pharmaceutically acceptable carriers, diluents, or excipients.

In a further embodiment, the present invention relates to a method of making a compound represented by Formula I, and intermediates thereof.

In another embodiment, the present invention provides a method of selectively antagonizing an NK-1 receptor by contacting the receptor with a compound of Formula I, or a pharmaceutically acceptable salt thereof.

In another embodiment, this invention provides methods of treating a condition associated with an excess of tachykinins, comprising: administering to a patient in need thereof an effective amount of a compound of Formula I, or a pharmaceutically acceptable salt thereof. That is, the present invention provides for the use of a compound of Formula I, or a pharmaceutical composition thereof, for the treatment of a disorder associated with an excess of tachykinins.

In another aspect, the present invention provides for the use of a compound of Formula I, or a pharmaceutically acceptable salt thereof, in the manufacture of a medicament for antagonizing the NK-1 receptor. Thus, the present invention provides for the use of a compound of Formula I, or a pharmaceutically acceptable salt thereof, in the manufacture of a medicament for the treatment of a disorder associated with an excess of tachykinins by means of the method described above.

Of the disorders listed above, depression, anxiety, schizophrenia and other psychotic disorders, emesis, pain, asthma, inflammatory bowel disease, irritable bowel syndrome, and dermatitis are of importance. Of these disorders, depression and anxiety are of particular importance.

Thus, in a preferred embodiment, the present invention provides a method for treating major depressive disorder, comprising: administering to a patient in need thereof an effective amount of a compound of Formula I, or a pharmaceutically acceptable salt thereof.

In another preferred embodiment, the present invention provides a method for treating generalized anxiety disorder, comprising: administering to a patient in need thereof an effective amount of a compound of Formula I, or a pharmaceutically acceptable salt thereof.

In another preferred embodiment, the present invention provides a method for treating panic disorder, comprising: administering to a patient in need thereof an effective amount of a compound of Formula I, or a pharmaceutically acceptable salt thereof.

In another preferred embodiment, the present invention provides a method for treating obsessive compulsive disorder, comprising: administering to a patient in need thereof an effective amount of a compound of Formula I, or a pharmaceutically acceptable salt thereof.

In another preferred embodiment, the present invention provides a method for treating social phobia, comprising: administering to a patient in need thereof an effective amount of a compound of Formula I, or a pharmaceutically acceptable salt thereof.

In another preferred embodiment, the present invention provides a method for treating irritable bowel syndrome, comprising: administering to a patient in need thereof an effective amount of a compound of Formula I, or a pharmaceutically acceptable salt thereof.

In another preferred embodiment, the present invention provides a method for treating inflammatory bowel disease, comprising: administering to a patient in need thereof an effective amount of a compound of Formula I, or a pharmaceutically acceptable salt thereof.

In another preferred embodiment, the present invention provides a method for treating emesis (chemotherapy-induced nausea and acute or delayed emesis), comprising: administering to a patient in need thereof an effective amount of a compound of Formula I, or a pharmaceutically acceptable salt thereof.

DETAILED DESCRIPTION OF THE INVENTION

The terms and abbreviations used in the preparations and examples have their normal meanings unless otherwise designated. For example "° C." refers to degrees Celsius; "N" refers to normal or normality; "mol" refers to mole or moles; "h" refers to hour(s); "eq" refers to equivalent; "g" refers to gram or grams; "L" refers to liter or liters; "M" refers to molar or molarity; "brine" refers to a saturated aqueous sodium chloride solution; "J" refers to hertz; "ES" refers to electrospray; "MS" refers to mass spectrometry; "NMR" refers to nuclear magnetic resonance spectroscopy; "TLC" refers to thin layer chromatography; "ACN" refers to acetonitrile; "DMF" refers to N,N-dimethylformamide; "DMSO" refers to dimethylsulfoxide; "Et$_2$O" refers to diethyl ether; "EtOAc" refers to ethyl acetate; "MeOH" refers to methanol; "EtOH" refers to ethanol; "iPrOH" refers to isopropanol; "TEA" refers to triethylamine; "TFA" refers to trifluoroacetic acid; "THF" refers to tetrahydrofuran.

As used herein, the term "$C_1$–$C_4$ alkyl" refers to straight or branched, monovalent, saturated aliphatic chains of 1 to 4 carbon atoms and includes, but is not limited to, methyl, ethyl, propyl, isopropyl, butyl, isobutyl, sec-butyl, and tert-butyl. The terms "$C_1$–$C_3$ alkyl" and "$C_1$–$C_2$ alkyl" are encompassed within the definition of "$C_1$–$C_4$ alkyl."

The term "substituted $C_1$–$C_4$ alkyl" refers to a straight or branched, monovalent, saturated aliphatic chain of 1 to 4 carbon atoms, as encompassed in the definition of $C_1$–$C_4$ alkyl above, that is further substituted on any of the carbon atoms with one to three substituents independently selected from the group consisting of hydroxy, oxo, halo, $C_1$–$C_4$ alkoxy, =N(OH), and —NR$^a$R$^b$, wherein R$^a$ is H or $C_1$–$C_4$ alkyl, R$^b$ is H, $C_1$–$C_4$ alkyl, or —C(O)—CH$_3$, or R$^a$ and R$^b$, together with the N to which they are attached, form a 4–7 membered saturated heterocyclic ring. Examples of such 4–7 membered saturated heterocyclic rings include, but are not limited to, pyrrolidinyl, piperidino, and morpholino.

"$C_1$–$C_4$ alkane-diyl" refers to a straight or branched, divalent, saturated aliphatic chain of 1 to 4 carbon atoms and includes, but is not limited to, methylene, ethylene, ethane-1,1-diyl, propane-1,1-diyl, propane-1,2-diyl, propane-1,3-diyl, propane-2,2-diyl, and butane-1,4-diyl. The terms "$C_1$–$C_2$ alkane-diyl" and "$C_1$–$C_3$ alkane-diyl" are encompassed within the definition of "$C_1$–$C_4$ alkane-diyl."

"$C_1$–$C_4$ alkoxy" represents a $C_1$–$C_4$ alkyl group, as defined above, linked to the parent molecule through an oxygen atom. Typical $C_1$–$C_4$ alkoxy groups include methoxy, ethoxy, propoxy, isopropoxy, butoxy, sec-butoxy, tert-butoxy, and the like. The term "$C_1$–$C_4$ alkoxy" includes within its definition the term "$C_1$–$C_3$ alkoxy" and "$C_1$–$C_2$ alkoxy."

"$C_3$–$C_6$ cycloalkyl" represents a saturated hydrocarbon ring structure containing from three to six carbon atoms. Typical $C_3$–$C_6$ cycloalkyl groups include cyclopropyl, cyclopentyl, cyclohexyl, and the like.

"Halo," "halogen," and "halide" represent a chloro, fluoro, bromo or iodo atom. Preferred halogens include chloro and fluoro.

"$C_1$–$C_4$ alkoxycarbonyl" represents a straight or branched $C_1$–$C_4$ alkoxy chain, as defined above, that is attached via the oxygen atom of the alkoxy to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

The term "Pg" refers to an alcohol, carboxyl, or amino protecting group. Typical protecting groups include tetrahydropyranyl (THP), silanes such as trimethylsilane (TMS), tert-butyldimethylsilane (TBDMS), and tert-butyldiphenylsilane (TBDPS), methoxymethyl (MOM), benzyl (Bn), p-methoxybenzyl, formyl, acetyl (Ac), and tert-butoxycarbonyl (t-BOC). Typical carboxyl protecting groups may include methyl, ethyl, and tert-butyl. The selection and use of protecting groups is well known and appreciated in the art. See for example, *Protecting Groups in Organic Synthesis*, Theodora Greene (Wiley-Interscience); *Protecting Groups*, Philip J. Kocienski, Thieme Medical Publishers, inc: New York 1994, chapters 2, 4, 6.

It is understood that when R$^5$ or R$^6$ is pyridyl, the radical may be a pyridin-2-yl, pyridin-3-yl, or pyridin-4-yl. When R$^5$ is furyl or thienyl, the radical may be attached at the 2-, or 3-position of the radical. When R$^5$ is pyrrolyl or imidazolyl, the radical may be attached at the 1-, 2-, or 3 position of the pyrrolyl, or the 1, 2, or 4 position of the imidazolyl.

The skilled artisan will recognize that when R$^4$ is a radical of Formula (IA), and A$^1$, A$^2$, or A$^3$ is nitrogen, the nitrogen may only be optionally substituted with R$^8$ when such substitution creates an uncharged heterocyclic ring.

The compounds of the present invention may exist as stereoisomers. The Cahn-Prelog-Ingold designations of (R)- and (S)- and the designations of L- and D- for stereochemistry relative to the isomers of glyceraldehyde are used herein to refer to specific isomers. The specific stereoisomers can be prepared by stereospecific synthesis or can be resolved and recovered by techniques known in the art, such as chromatography on chiral stationary phases, and fractional recrystallization of addition salts formed by reagents used for that purpose. Useful methods of resolving and recovering specific stereoisomers are known in the art and described in E. L. Eliel and S. H. Wilen, *Stereochemistry of Organic Compounds*, (Wiley-Interscience 1994), and J. Jacques, A. Collet, and S. H. Wilen, *Enantiomers, Racemates, and Resolutions*, Wiley-Interscience 1981). It is understood that the present invention contemplates all enantiomers and mixtures of enantiomers, including racemates.

The skilled artisan will recognize that compounds of the present invention may exist as tautomers. It is understood that tautomeric forms of the compounds of Formula (I) are also encompassed in the present invention.

This invention includes the pharmaceutically acceptable salts of the compounds of Formula I. A compound of this invention can possess a sufficiently basic functional group, which can react with any of a number of inorganic and organic acids, to form a pharmaceutically acceptable salt.

The term "pharmaceutically-acceptable salt" as used herein, refers to a salt of a compound of the above Formula I. It should be recognized that the particular counterion forming a part of any salt of this invention is usually not of a critical nature, so long as the salt as a whole is pharmacologically acceptable and as long as the counterion does not contribute undesired qualities to the salt as a whole.

The compounds of Formula I and the intermediates described herein form pharmaceutically-acceptable acid addition salts with a wide variety of organic and inorganic acids and include the physiologically-acceptable salts which are often used in pharmaceutical chemistry. Such salts are also part of this invention. A pharmaceutically-acceptable acid addition salt is formed from a pharmaceutically-acceptable acid, as is well known in the art. Such salts include the pharmaceutically acceptable salts listed in *Journal of Pharmaceutical Science*, 66, 2–19 (1977), which are known to the skilled artisan. See also, The Handbook of Pharmaceutical Salts; Properties, Selection, and Use. P. H. Stahl and C. G. Wermuth (ED.s), Verlag, Zurich (Switzerland) 2002.

Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartarate, and the like.

As used herein, the term "patient" refers to a mammal that is afflicted with one or more disorders associated with excess tachykinins. Guinea pigs, dogs, cats, rats, mice, horses, cattle, sheep, and humans are examples of mammals within the scope of the meaning of the term. It will be understood that the most preferred patient is a human. It is also understood that this invention relates specifically to the inhibition of mammalian NK-1 receptors.

It is also recognized that one skilled in the art may affect the disorders by treating a patient presently afflicted with the disorders or by prophylactically treating a patient afflicted with the disorders with an effective amount of the compound of Formula I. Thus, the terms "treatment" and "treating" are intended to refer to all processes wherein there may be a slowing, interrupting, arresting, controlling, or stopping of the progression of the disorders described herein, and is intended to include prophylactic treatment of such disorders, but does not necessarily indicate a total elimination of all disorder symptoms.

As used herein, the term "effective amount" of a compound of Formula I refers to an amount that is effective in treating the disorders described herein.

As with any group of pharmaceutically active compounds, some groups are preferred in their end use application. Preferred embodiments of the present invention are discussed below.

Thus, when $R^4$ is a radical of Formula (IA), preferred embodiments of the unsaturated heterocyclic rings of Formula (IA) include the following:

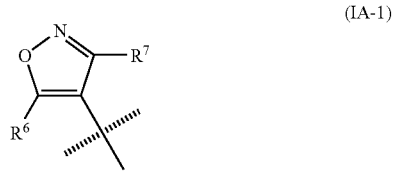

(IA-1)

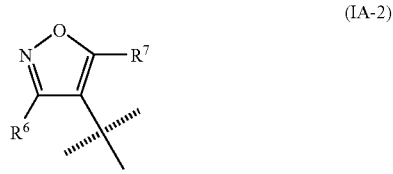

(IA-2)

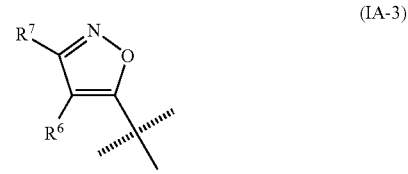

(IA-3)

(IA-4)

(IA-5)

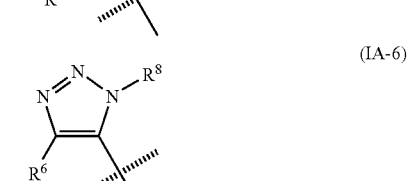

(IA-6)

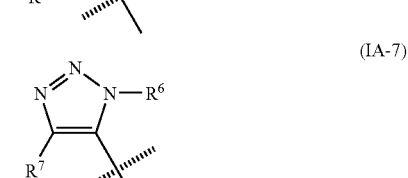

(IA-7)

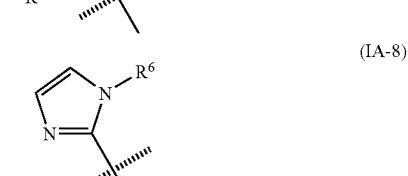

(IA-8)

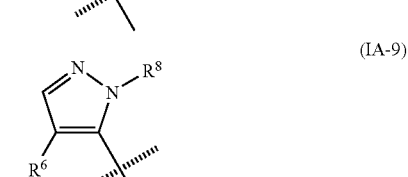

(IA-9)

-continued

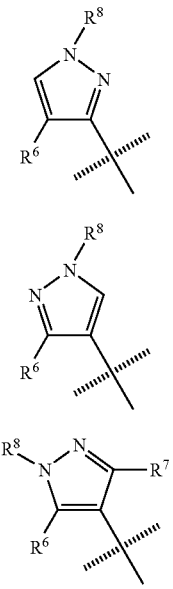

(IA-10)

(IA-11)

(IA-12)

When R⁴ is a radical of Formula (IB), preferred embodiments of the unsaturated carbocyclic or heterocyclic rings of Formula (IB) include the following:

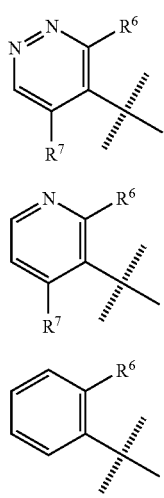

(IB-1)

(IB-2)

(IB-3)

Especially preferred embodiments of the compounds of Formula (I) are given below:
(a) D⁴ is oxygen.
(b) D² is nitrogen.
(c) D¹ is methylene.
(d) R¹ is phenyl, which is substituted with two substituents selected from the group consisting of halo and trifluoromethyl.
(e) R¹ is 3,5-bis-trifluoromethyl-phenyl.
(f) R⁵ is a radical of Formula (ID).
(g) R⁵ is phenyl.
(h) R⁵ is pyridin-4-yl.
(i) R⁵ is pyridin-3-yl.
(j) R⁵ is pyrimidin-5-yl.
(k) R⁵ is imidazolyl.

(l) R⁵ is a radical of Formula (IC) in which W is O.
(m) R⁴ is a radical of Formula (IA).
(n) A¹ is CR⁷, A² is nitrogen, A³ is oxygen, and A⁴ is carbon.
(O) A¹ is CR⁷, A² is oxygen, A³ is nitrogen, and A⁴ is carbon.
(p) A¹ is oxygen, A² is CR⁷, A³ is nitrogen, and A⁴ is carbon.
(q) A¹ is NR⁸; A² is nitrogen, A³ is CR⁷, and A⁴ is carbon.
(r) R⁴ is a radical of Formula (IA-1).
(s) R⁴ is a radical of Formula (IA-2).
(t) R⁴ is a radical of Formula (IA-4).
(u) R⁴ is a radical of Formula (IA-9).
(v) R⁷ is $C_1-C_4$ alkyl or substituted $C_1-C_4$ alkyl.
(w) R⁷ is substituted $C_1-C_4$ alkyl in which the $C_1-C_4$ alkyl is substituted with one hydroxy.
(x) R⁷ is $C_3-C_6$ cycloalkyl.
(y) R⁶ is phenyl, which is substituted with one substituent selected from the group consisting of halo, cyano, $C_1-C_4$ alkyl, $C_1-C_4$ alkoxy, trifluoromethyl, trifluoromethoxy, and —NR¹¹R¹².
(z) R⁶ is 2-chloro-phenyl.

Most preferred compounds of Formula I include: [1-(3,5-bis-trifluoromethylbenzyl)-5-imidazol-1-yl-1H-[1,2,3]triazol-4-yl]-[5-(2-chlorophenyl)-3hydroxymethyl-isoxazol-4-yl]-methanone (Example 269), [1-(3,5-bis-trifluoromethyl-benzyl)-5-imidazol-1-yl-1H-[1,2,3]triazol-4-yl]-[4-(2-chloro-phenyl)-2-cyclopropyl-oxazol-5-yl]-methanone (Example 131), [1-(3,5-bis-trifluoromethyl-benzyl)-5-phenyl-1H-[1,2,3]triazol-4-yl]-[5-(2-chloro-phenyl)-3-hydroxymethyl-isoxazol-4-yl]-methanone (Example 35), [1-(3,5-bis-trifluoromethyl-benzyl)-5-pyridin-4-yl-1H-[1,2,3]triazol-4-yl]-[5-(2-chloro-phenyl)-3-hydroxymethyl-isoxazol-4-yl]-methanone (Example 39), [1-(3,5-bis-trifluoromethyl-benzyl)-5-pyridin-3-yl-1H-[1,2,3]triazol-4-yl]-[5-(2-chloro-phenyl)-3-hydroxymethyl-isoxazol-4-yl]-methanone (Example 38), [1-(3,5-bis-trifluoromethyl-benzyl)-5-pyridin-3-yl-1H-[1,2,3]triazol-4-yl]-[5-(2-chloro-phenyl)-3-(1-hydroxy-1-methyl-ethyl)-isoxazol-4-yl]-methanone (Example 28), [1-(3,5)-bis-trifluoromethyl-benzyl)-5-pyrimidin-5-yl-1H-[1,2,3]triazol-4-yl]-[5-(2-chloro-phenyl)-3-(1-hydroxy-1-methyl-ethyl)-isoxazol-4-yl]-methanone (Example 29), [1-(3,5-bis-trifluoromethyl-benzyl)-5-imidazol-1-yl-1H-[1,2,3]triazol-4-yl]-[5-(2-chloro-phenyl)-3-methyl-isoxazol-4-yl]-methanone (Example 97), [1-(3,5-bis-trifluoromethyl-benzyl)-5-pyridin-4-yl-1H-[1,2,3]triazol-4-yl]-[4-(2-chloro-phenyl)-2-cyclopropyl-oxazol-5-yl]-methanone (Example 255), [1-(3,5-bis-trifluoromethyl-benzyl)-5-pyridin-4-yl-1H-[1,2,3]triazol-4-yl]-[4-(2-chloro-phenyl)-2-cyclopropyl-oxazol-5-yl]-methanone (Example 254), [1-(3,5-bis-trifluoromethyl-benzyl)-5-morpholin-4-yl-1H-[1,2,3]triazol-4-yl]-[4-(2-chloro-phenyl)-1-methyl-1H-pyrazol-5-yl]-methanone (Example 246), [1-(3,5-bis-trifluoromethyl-benzyl)-5-morpholin-4-yl-1H-[1,2,3]triazol-4-yl]-[3-(2-chloro-phenyl)-5-hydroxymethyl-isoxazol-4-yl]-methanone (Example 106), [1-(3,5-bis-trifluoromethyl-benzyl)-5-pyridin-3-yl-1H-[1,2,3]triazol-4-yl]-[3-(2-chloro-phenyl)-5-hydroxy, ethyl-isoxazol-4-yl]-methanone (Example 64).

SCHEMES

The compounds disclosed herein can be made according to the following schemes. The schemes, preparations, and examples should in no way be understood to be limiting in any way as to how the compounds may be made.

The skilled artisan will appreciate that the introduction of certain substituents will create asymmetry in the compounds of Formula (I). The present invention contemplates all stereoisomers, enantiomers, and mixtures of enantiomers, including racemates and diastereomers. It is preferred that the compounds of the invention containing chiral centers are single enantiomers.

As the following schemes, preparations, and examples demonstrate, many of the compounds of the present invention are not only selective NK-1 receptor antagonists, but are also useful intermediates for the preparation of additional compounds of Formula (I). It will be recognized by one of skill in the art that the individual steps in the following schemes may be varied to provide the compounds of Formula (I). The particular order of steps required to produce the compounds of Formula (I) is dependent upon the particular compound being synthesized, the starting compound, and the relative lability of the substituted moieties. Some substituents have been eliminated in the following schemes for the sake of clarity and are not intended to limit the teaching of the schemes in any way.

Scheme 1

Route 1

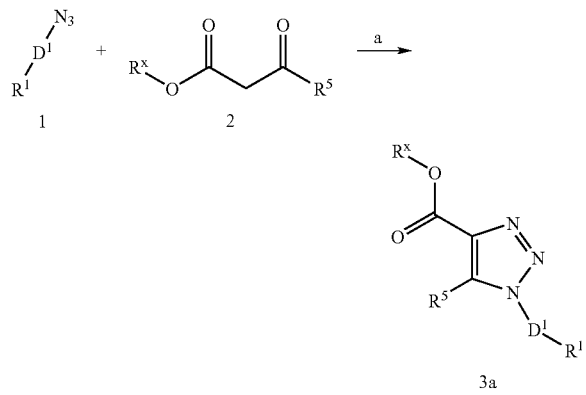

In Scheme 1, Route 1, the triazole compounds of Formula (3a) are formed by reacting a beta keto ester of Formula (2), in which $R^x$ is $C_1$–$C_4$ alkyl or benzyl, with an azide of Formula (1). Such ring formations are well known and appreciated in the art. See Savini et al., *Farmaco* (1994) 49(5): 363–370; Martini et al., *J. Pharm. Sci.* (1988) 77(11): 977–980; Sun et al., *Magn. Reson. Chem.* (1998) 36(6): 459–460; Settimo et al., *Farmaco Ed. Sci.* (1983) 38(10): 725–737; Olesen et al., *J. Heterocycl. Chem.* (1984) 21: 1603–1608; L'abbe et al., *Bull. Soc. Chim. Belg.* (1987) 96(10): 823–824; Julino et al., *J. Chem. Soc. Perkin Trans.* 1 (1998) 10: 1677–1684; Mamedov et al., *Chem. Heterocycl. Compd.* (*Engl. Transl.*) (1993) 29(5): 607–611; Wender et al., *Tetrahedron Lett.* (1987) 28(49): 6125–6128; Freitas et al., *J. Heterocycl. Chem.* (1995) 32(2): 457–462; Cottrell et al., *J. Heterocycl. Chem.* (1991) 28(2): 301–304. The product of Formula (3) can be isolated and purified by techniques well known in the art, such as precipitation, filtration, extraction, evaporation, trituration, chromatography, or recrystallization.

Azides of Formula (1) are commercially available or can be synthesized from the corresponding halide or sulfonate ester derivatives by reaction with an azide source, such as $NaN_3$, $LiN_3$, or tetrabutyl ammonium azide ($Bu4NN_3$), with $NaN_3$ being preferred, in a suitable solvent mixture such as DMSO and water. Alternatively, azides of Formula (1) may be prepared from the corresponding alcohol derivative by reaction with hydrazoic acid, diphenylphosphoryl azide, or zinc azide, in the presence of triphenylphosphine and diethyl- or diisopropyl-azodicarboxylate, in a solvent such as THF or toluene. See Scriven, E., Turbull, K., "Azides: Their Preparation and Synthetic Uses", Chem Rev. 1988, 88, 351–368.

The skilled artisan will also appreciate that a malonate derivative of Formula (2), in which $R^5$ is an oxygen-linked substituent such as a $C_1$–$C_4$ alkoxy, may be used in the reaction of step a, instead of a beta keto ester, to provide a triazole of Formula (3). The reaction of both malonates and beta keto esters with azides is well known and appreciated in the art. See Benetti, S.; Romagnoli, R.; De Risi, C.; Zanirato, Z "Mastering β-Keto Esters," Chem. Rev. 1995, 95, 1065–1114.

When dialkylmalonates are chosen as the starting reagent, $R^5$ in the resulting product of Formula (3a) is a hydroxyl group. The hydroxyl group may be readily converted to the corresponding halide. Examples of reagents for this reaction include $PCl_5$, $POCl_3$, $PBr_3$, $POBr_3$, and thionyl chloride, with $PCl_5$ as the preferred reagent. This type of transformation is well known and appreciated in the art. See Buckle, D. R.; Rockell, C. J. M. *J. Chem. Soc., Perkin I*, 1982, 627–630.

Route 2

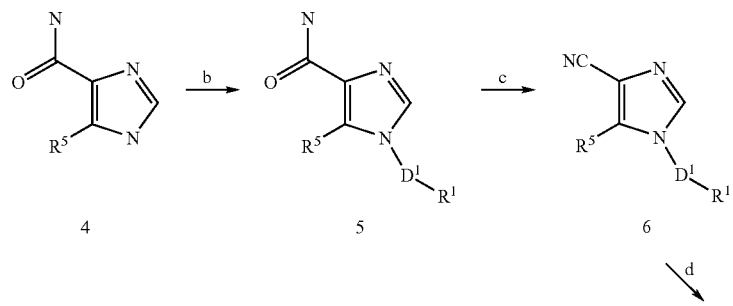

-continued

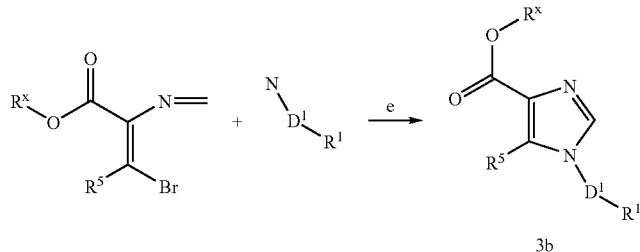

3b

In Route 2, compounds of Formula (5) may be prepared by exposing the free base or the hydrochloride salt of compounds of Formula (4), wherein $R^5$ is —$NH_2$, to a combination of a suitable base and an appropriate alkylating agent in a suitable solvent. Preferred bases include, but are not limited to, sodium or potassium hydride, sodium or potassium hexamethyldisilazide, or butyl lithium. Preferred alkylating agents include alkyl halides or alkyl sulfonate esters. Preferred solvents include DMF, DME, or THF. This transformation is well-known in the literature. (See for example: Kelly, J. L., *J. Heterocyclic Chem.*, 1995, 32, 1417.)

Compounds of Formula (5) may be dehydrated by treating the compound with tosyl chloride and pyridine to provide the nitrile containing compounds of Formula (6). This transformation is well known to one skilled in the art and may be performed using other dehydrating agents. For a list of alternate dehydrating conditions see: Larock, Comprehensive Organic Transformations $2^{nd}$ ed., Wiley-VCH, New York, pp 1983–1985.

Compounds of Formula (6) in which $R^5$ is —$NH_2$ may be readily converted to other $R^5$ substituents of Formula (I) by reactions well known in the art. For examples, see Larock, Comprehensive Organic Transformations $2^{nd}$ ed., Wiley-VCH, New York, pp 678–679; Gajewski and Beck, *J. Heterocyclic Chem.* (1987) 24: 243.

In step d, the nitrile functionality of compounds of Formula (6) is converted to an ester-containing compound of Formula (3b). This tranformation may be accomplished by treating the nitrile with an acid, such as hydrochloric acid or sulfuric acid, in a solution of an alcohol, such as methanol or ethanol, and water. Such transformations are well known in the art. For alternate conditions see: Larock, Comprehensive Organic Transformations $2^{nd}$ ed., Wiley-VCH, New York, pp 1986–1987.

Alternatively, compounds of Formula (3b) may be prepared by combining an amine of Formula (8) and a properly substituted bromo isocyanoacrylate of Formula (7), wherein $R^x$ is a $C_1$–$C_4$ alkyl or benzyl, in the presence of a base, preferably triethylamine, and an appropriate solvent, preferably DMF. Compounds of Formula (7) may be prepared according to the literature. See: K. Nunami et al, *J. Org. Chem.* 1994, 59, 7635–7642.

Route 3

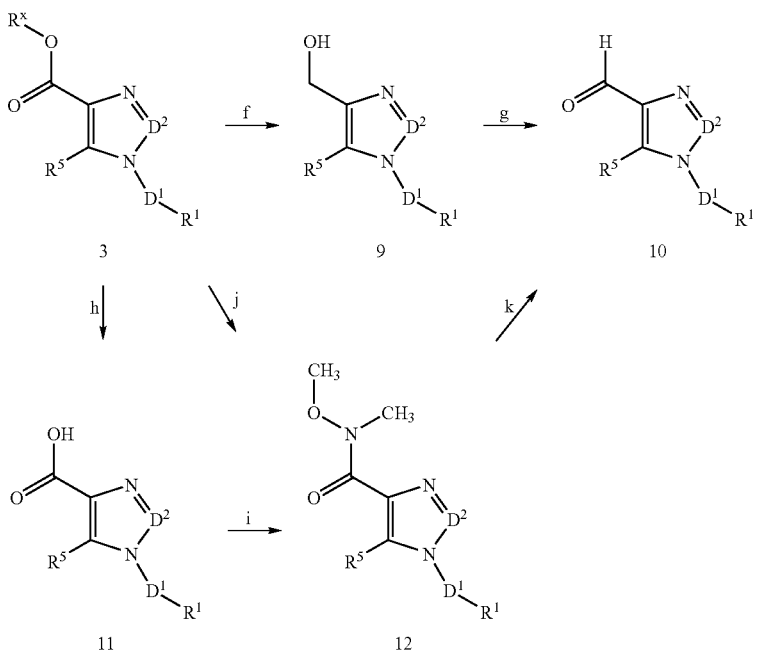

Step f depicts the reduction of the carboxylic acid ester of Formula (3), in which $R^x$ is $C_1$–$C_4$ alkyl or benzyl, to give a substituted methanol of Formula (9). Such reduction steps are well known and appreciated in the art. See Larock, R. C., Comprehensive Organic Transformations, $2^{nd}$ Ed., copyright 1999, John Wiley & Sons, pp 1117–1120.

In one variation of step f, the carboxylic acid ester of Formula (3) may be reduced by a suitable reducing agent, such as sodium borohydride, lithium aluminumhydride, lithium borohydride, or diisobutyl aluminumhydride, with sodium borohydride being the preferred reducing agent. Such reductions are generally carried out in a solvent, such as MeOH, EtOH, iPrOH, THF, toluene, methylene chloride, or mixtures thereof. The preferred solvent is absolute ethanol. The product can be isolated and purified by techniques described above.

Oxidation of an alkyl-hydroxy group of Formula (9) to the corresponding aldehyde of Formula (10) is well known in the art. A representative example is shown in step g, in which the methanol of Formula (9) can be oxidized by reacting it with an appropriate oxidizing agent, such as manganese oxide. Other oxidizing agents include pyridine sulfurtrioxide complex, 1,1,1-triacetoxy-1,1-dihydro-1,2-benziodoxol-3 (1H)-one (Dess-Martin reagent), pyridinium chlorochromate, pyridinium dichromate, and catalytic tetrapropylammonium perruthenate (TPAP) with N-methylmorpholine N-oxide (NMO) as a co-oxidant. The aldehydes of Formula (10) can be isolated by techniques described above.

Hydrolysis of the carboxyl esters of Formula (3) to give the corresponding carboxylic acids of Formula (11), as shown in step h, is a well-known reaction. See Larock, R. C., Comprehensive Organic Transformations, $2^{nd}$ Ed., copyright 1999, John Wiley & Sons, pp 1959–1968. For example, an appropriate ester of Formula (3) may be dissolved in a suitable solvent, such as methanol or dioxane and water, and treated with a suitable base, such as NaOH or LiOH, to give a compound of Formula (11).

The reaction of step i is well known to the skilled artisan. A carboxylic acid, such as that of Formula (11), is coupled with an appropriate amine, under peptide coupling conditions, to provide amines of Formula (12). Suitable peptide coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Suitable catalysts for the coupling reaction include N,N-[dimethyl]-4-aminopyridine (DMAP). Such coupling reactions are well known and appreciated in the art. See Larock, R. C., Comprehensive Organic Transformations, $2^{nd}$ Ed., copyright 1999, John Wiley & Sons, pp 1941–1949.

Alternatively, a compound of Formula (11) may be converted to an acid chloride derivative, preferably by reaction with oxalyl chloride and DMF, and used to acylate an amine to give a compound of Formula (12). Such acylation reactions are well known and appreciated in the art. See Larock, R. C., Comprehensive Organic Transformations, $2^{nd}$ Ed., copyright 1999, John Wiley & Sons, pp 1929–1930. The product can be isolated and purified by techniques described above.

One skilled in the art could also appreciate the formation of the amides of Formula (12) by a direct conversion of the carboxyl ester of Formula (3) by the use of a trialkylaluminum reagent with an appropriate amine or by use of a magnesium amide, as depicted in step j.

Compounds of Formula (12) can further undergo a reduction (shown in step k) by treatment with a suitable reducing agent, such as diisobutylaluminum hydride, lithium aluminum hydride or a borane-methyl sulfide complex to afford aldehydes of Formula (10). See Larock, R., Comprehensive Organic Transformations, $2^{nd}$ ed. Wiley-VCH: New York, 1999, pp 1269–1271.

Scheme 2

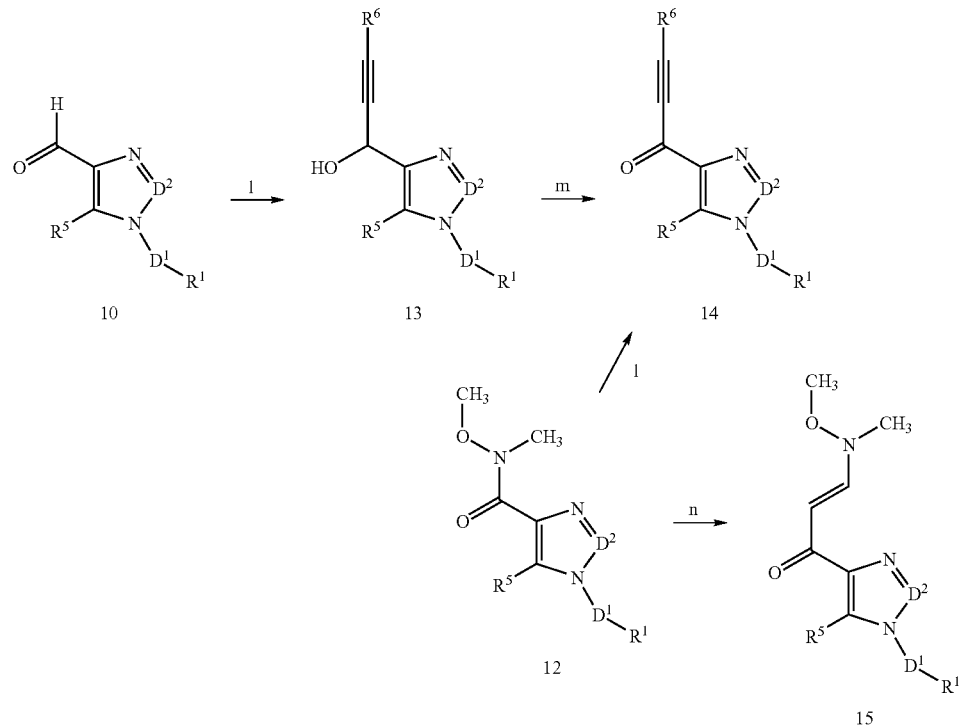

Alkynyl-ketones of Formula (14) can be synthesized from the aldehydes of Formula (10) or the N-methyl-N-methoxyamide derivatives of Formula (12).

Step 1 depicts the addition of an alkynyl anion to an aldehyde of Formula (10) or a N-methyl-N-methoxyamide of Formula (12). The alkynyl anion is generated by treating the appropriate alkyne with a suitable base, such as methyl lithium, n-butyl lithium, tert-butyl lithium, lithium diisopropylamine, or preferably methyl or ethyl magnesium bromide. When the aldehydes of Formula (10) are used, the hydroxy intermediate, Formula (13), can be oxidized to afford the ketone of Formula (14). Such reactions are well known in the art. See Larock, R. C., *Comprehensive Organic Transformations*, 2$^{nd}$ ed., Wiley-VCH: New York, 1999, pp 1234–1246. Alternatively, N-methyl-N-methoxyamide derivatives of Formula (12) are reacted with a suitable alkynyl anion to provide compounds of Formula (14) directly.

Step n depicts the addition of an ethynyl anion reagent, such as ethynyl magnesium bromide, to an N-methyl-N-methoxyamide of Formula (12) to give the vinylogous amide of Formula (15).

reaction is complete. The compound of Formula (19) is isolated and purified by techniques known in the art and described above.

The stannyl-acetylenes of Formula (17) are readily available from commercial sources or can be prepared from compounds of Formula (16) or alternatively, from compounds of Formula (18). A compound of Formula (16) may be dissolved in an appropriate solvent, such as THF, followed by addition of bis(tributyl)tin oxide and an appropriate desilylating agent, such as TBAF (tetrabutyl ammonium fluoride), or potassium trimethylsilanolate. Alternatively, the compound of Formula (17) is made by dissolving an alkyne in an appropriate solvent, such as ether or THF, at −15 to −10° C. To this mixture is added nBuLi, followed by tributyltin chloride. The compound of Formula (17) may be used directly or isolated and purified by techniques described above.

The formation of various stannyl acetylenes of Formula (17) is well known in the art. For example, see WO 00/51614; WO 00/01702; WO 98/46228; Lambert et al., *Journal of the Chemical Society, Perkin Transactions 2*

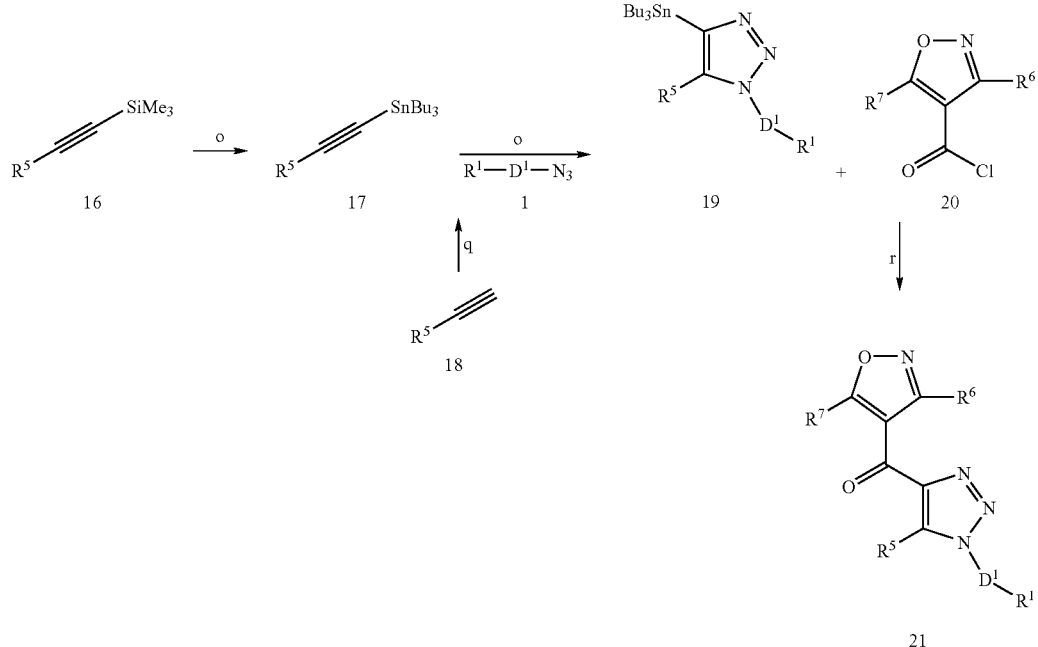

Scheme 3

In step r, the compounds of Formula (21) are readily prepared by cross-coupling of a stannyl-triazole of Formula (19) and an acid chloride of Formula (20). This is accomplished by heating a mixture of acyl chloride and stannane, in roughly molar equivalence, in the presence of PdCl$_2$(PPh$_3$)$_2$ in degassed 1,4-dioxane at temperatures ranging from RT to 100° C. Other suitable catalysts include Pd(OAc)$_2$, Pd(PPh$_3$)$_4$, and Pd$_2$(dba)$_3$.CHCl$_3$. Alternative solvents include DMF, toluene, and THF. The compound of Formula (21) is concentrated and purified by techniques known in the art and described herein.

Stannyl triazoles of Formula (19) can be made from the reaction of an appropriate azide of Formula (1) with an appropriate stannyl-acetylene of Formula (17). The reactants are combined in a suitable solvent, such as benzene, chloroform, THF, or preferably toluene, and heated until the (2001) 6: 964–974; Yamamoto et al., *J. Chem. Soc., Perkin Trans.* 1 (1991) 12: 3253–7; Zhou et al., *J. Chem. Soc., Perkin Trans.* 1 (1991) 11: 2827–30; Warner et al., *J. Org. Chem.* (1994), 59(19): 5822–23; and Jacobi et al., *Journal of the American Chemical Society* (2000), 122(18): 4295–4303.

The silyl-acetylenes of Formula (16) are readily available from commercial sources. Alternatively, the skilled artisan will recognize that compounds of Formula (16) may be prepared by reacting an appropriate aryl halide compound with trimethylsilyl acetylene to give the silyl-alkyne. The reaction proceeds in the presence of copper iodide and a palladium catalyst, such as dichlorobis(triphenyl-phosphine) palladium (II). Other suitable catalysts include Pd(Ph$_3$)$_4$, Pd$_2$dba$_3$.CHCl$_3$, or Pd(OAc)$_2$.

Scheme 4

Route 1

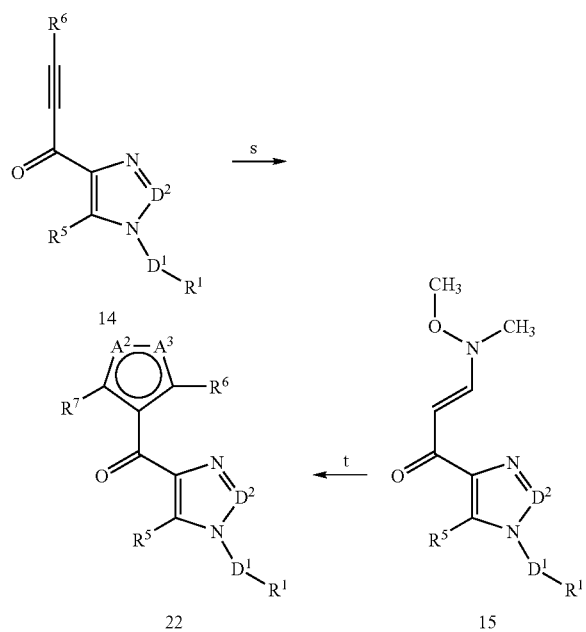

The skilled artisan will appreciate the cyclization of an alkyne of Formula (14) with a nitrile oxide to afford compounds of Formula (I), as represented here by Formula (22), in which one of $A^2$ and $A^3$ is nitrogen, and the other is oxygen. For examples of such cyclizations, see Joule, J. A.; Mills, K., *Heterocyclic Chemistry*, $4^{th}$ ed. Blackwell Science, Inc.:Malden, Mass., 2000, pp 442–448; Hussein, Ahmed Q.; El-Abadelah, Mustafa M.; Sabri, Wail S. Heterocycles from nitrile oxides I; *J. Heterocycl. Chem.* (1983), 20(2), 301–4.

For compounds of Formula (I) in which $R^5$ is a halide, such as chloride, a substitution can be performed with an appropriate nucleophile such as, but not limited to, primary amines, secondary amines, alcohols or thiols to further encompass compounds of the present invention. See March, J., *Advanced Organic Chemistry*,. 1985, John Wiley and Sons, Inc., pp 255–446.

Alternatively, [3+2] cyclization of a vinylogous amide of Formula (15) with a nitrile oxide under the above same cyclization conditions affords compounds of Formula (22), in which one of $A^2$ and $A^3$ is nitrogen, and the other is oxygen, and in which $R^7$ is hydrogen.

Route 2

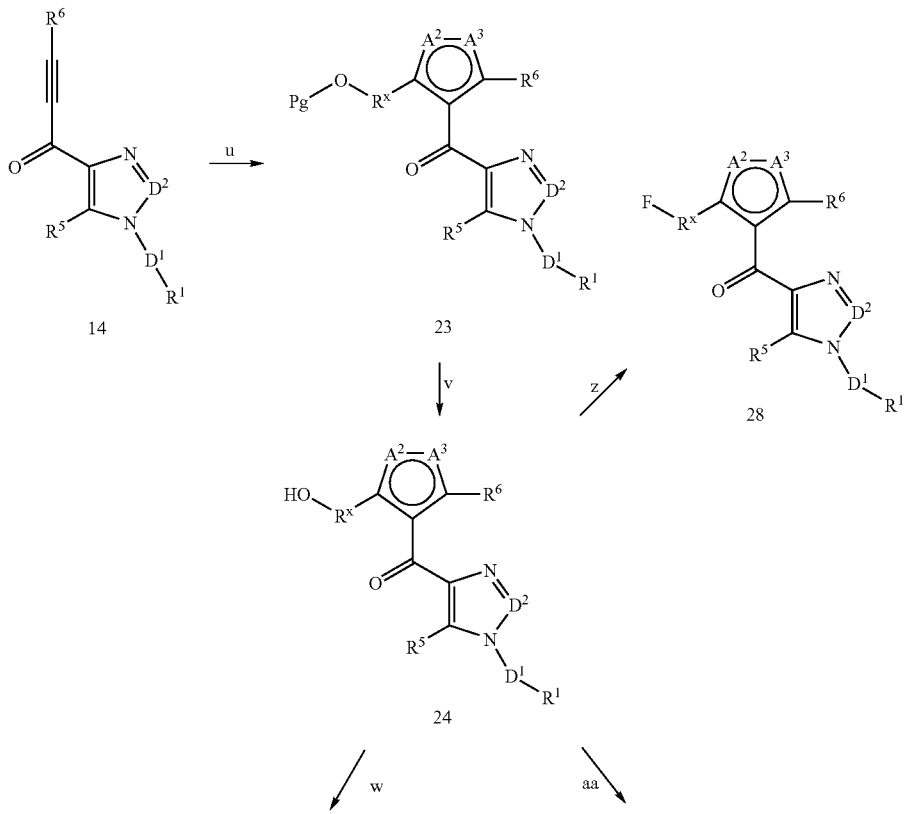

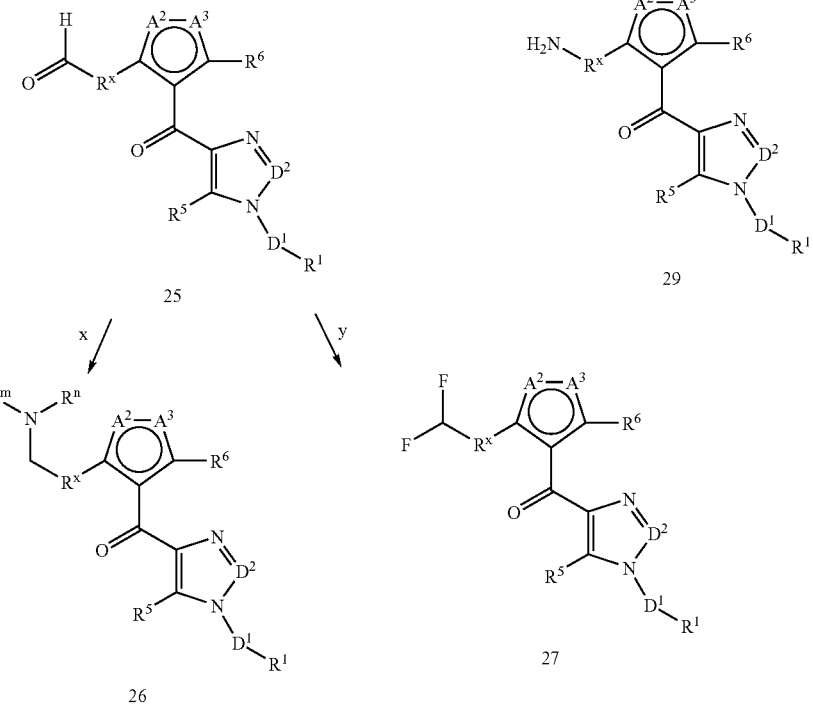

As shown in Scheme 4, Route 2, cyclization of compounds of Formula (14) can proceed to yield compounds of Formula (23). $R^x$ represents a $C_1$–$C_4$ alkane-diyl, unless otherwise specified. The skilled artisan will recognize that compounds of Formula (23), in which Pg is a hydroxyl protecting group such as THP or trimethylsilane, may be deprotected, as shown in step v, to give a compound of Formula (24), which is encompassed in the scope of Formula (I). For example, the compound of Formula (23) is dissolved in a suitable solvent, such as MeOH or EtOH, and treated with a suitable acid, such as p-TsOH.H$_2$O (para-toluene sulfonic acid) or CSA (camphor sulfonic acid). Alternatively, the alcohol may be liberated by treating with acetic acid in a mixture of THF and water. The product is isolated and purified as described previously, or can be used without purification.

Additional transformations known to the skilled artisan or described herein may be carried out to yield compounds of Formula (25–29), which are all encompassed in the invention of Formula (I).

As shown in step w, alcohol-containing compounds of Formula (24), in which $R^x$ is $C_1$–$C_4$ alkane-diyl, may be oxidized to give aldehydes of Formula (25), wherein $R^x$ is a bond or $C_1$–$C_3$ alkane-diyl. For example, the alcohol may be oxidized by reaction with a combination of DMSO, oxalyl chloride, and triethylamine in CH$_2$Cl$_2$. These and other oxidizing conditions are described in Larock, R. C., *Comprehensive Organic Transformations*, 2$^{nd}$ ed., Wiley-VCH: New York, 1999, pp 1234–1246. The skilled artisan will appreciate that aldehydes of Formula (25) may also be produced from the corresponding acetal by treatment with aqueous acidic conditions.

As shown in step x, aldehydes of Formula (25) may undergo further transformation to yield a compound of Formula (26), in which $R^x$ is a bond or $C_1$–$C_3$ alkane-diyl. The skilled artisan will appreciate that this transformation may yield morpholino-substituted alkyl groups in addition to the —NR$^m$R$^n$ groups depicted in step q. The amine is added to a solution of carbaldehyde in a solvent such as THF, or preferably 1,2-dichloroethane, followed by addition of a suitable reducing agent, such as NaHB(OAc)$_3$ or NaBH$_3$CN. The compound is isolated and purified using conditions well known to the skilled artisan and described above.

Alternatively, the compound of Formula (25) may undergo the reaction depicted in step y to provide di-fluoro substituted compounds of Formula (27), in which $R^x$ is a bond or $C_1$–$C_3$ alkane-diyl. In this reaction, (diethylamino) sulfur trifluoride or [bis(2-methoxyethyl)-amino]sulfur trifluoride may be used as fluorinating agents. The fluorinating agent is added to dichloromethane, THF, or ether, and the reaction proceeds at temperatures ranging from RT to 50° C., for 1 to 6 hours. The compound of Formula (27) is isolated and purified as described above.

As shown in step z, (diethylamino)sulfur trifluoride or [bis(2-methoxyethyl)-amino]sulfur trifluoride may be used as fluorinating agents to convert the alcohol of Formula (24) to the compound of Formula (28). As in step y, dichloromethane, THF, or ether may be used as solvents, and the reaction proceeds at temperatures ranging from –78° C. to 0° C. The reaction is stirred briefly and then warmed to RT. After 0.5 to 24 hours, the product may be isolated and purified as described above.

For synthesis of amines of Formula (29), the reaction is carried out as shown in step aa. When $R^x$ is —CH$_2$—, the methanol of Formula (24) is combined with diphenyl phosphoryl azide and 1,8-diazabicyclo[5.4.0]undec-7-ene in a suitable solvent, such as dichloromethane, ether, DMF, or preferably THF, and stirred overnight at temperatures ranging from RT to 80° C. When $R^x$ is $C_2$–$C_4$ alkyl, the alcohol of Formula (24) is converted to a suitable leaving group, such as chloro, bromo, or sulfonate ester, under standard conditions, which is displaced by an azide source, such as NaN$_3$ or LiN$_3$. The crude product is dissolved in a solvent, such as THF, and triphenylphosphine is added with several drops of water. The reaction proceeds after stirring for several hours to overnight. The resulting amine of Formula (29) is purified by techniques well known to the skilled artisan.

Scheme 5

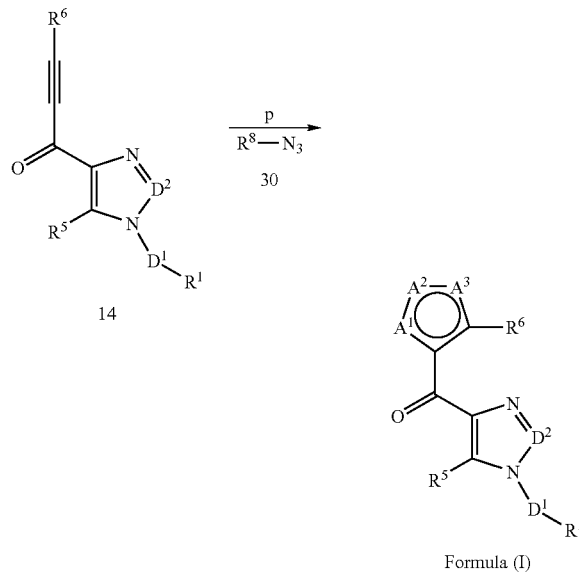

In Scheme 5, a compound of Formula (14) may be combined with the appropriate azide of Formula (30) to give keto-triazole compounds of Formula (1), in which —A¹—A²-A³— is —NR⁸—N=N— or —N=N—NR⁸—. The azide of Formula (30) is prepared in a similar manner as the azides of Formula (1). The reaction is carried out essentially as described in Scheme 3, step p, above. The skilled artisan will appreciate that the R⁸ substituent may undergo transformations similar to those described elsewhere to give alternatively-substituted compounds of Formula (I).

Scheme 6

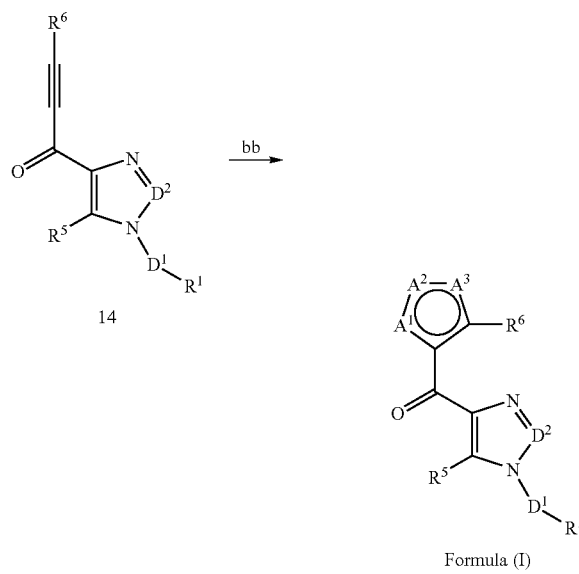

To synthesize the keto-pyrazole compounds of Formula (I), as shown in step bb, Compound (14) is dissolved in a solvent, such as toluene, benzene, or preferably THF/ether. A suitable diazoalkyl reagent, preferably trimethylsilyl diazomethane, is added. The reaction proceeds at temperatures ranging from RT to 80° C. for 24 to 72 hours to provide a regioisomeric mixture of pyrazoles of Formula (I), in which —A¹—A²—A³— is —NR⁸—N=CR⁷—, —N—NR⁸—CR⁷—, —CR⁷=N—NR⁸—, or CR⁷—NR⁸—N—, wherein R⁷ is hydrogen or $C_1$–$C_4$ alkyl, and R⁸ is hydrogen. The mixture can be separated by methods well known to the skilled artisan.

To synthesize the above compounds of Formula (I) in which R⁸ is $C_1$–$C_4$ alkyl, the desired pyrazole is dissolved in a solvent, such as ether, or preferably THF, and cooled under $N_2$. Temperatures may range from −20° C. to RT, with 0° C. preferred. To the mixture is added a base, such as t-BuLi, sec-BuLi, NaH, or preferably n-BuLi, with stirring for 1 hour, followed by addition of a suitable alkylating agent, such as an alkyl halide or alkyl sulfonate. Preferred alkylating agents include dimethylsulfate or iodomethane. The reaction is stirred overnight while warming to RT. The reaction is quenched with water and extracted with EtOAc. The desired product is isolated and purified by techniques well known to the skilled artisan.

Scheme 7

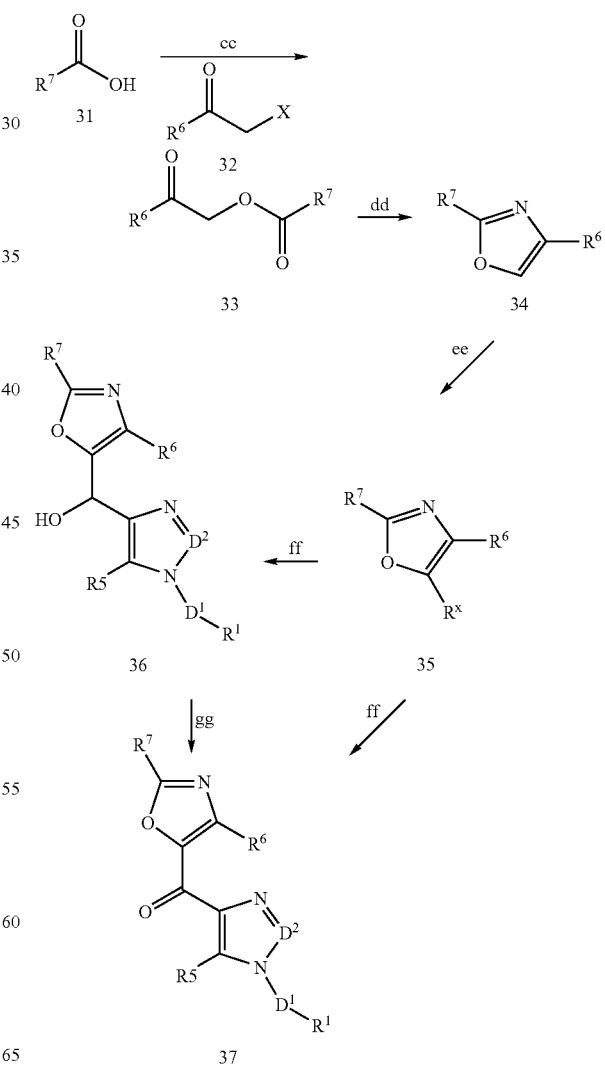

In Scheme 7, the formation of compounds of Formula (37), which are encompassed in the description of Formula (I), are shown. Step cc is carried out by addition of a sodium carboxylate salt of the compound of Formula (31) to a solution of an alpha-halo acetophenone of Formula (32), in which X is halo, such as chloro or bromo. The reaction is carried out in a suitable solvent, such as DMF. The reaction proceeds at temperatures ranging from RT to 50° C. to yield the compound of Formula (33). The desired compound is extracted, concentrated, and purified by methods well known to the skilled artisan.

Oxazoles of Formula (34) may be prepared by cyclization of compounds of Formula (33) with acetamide, as shown in step dd. The reaction is conveniently carried out in the presence of an acid such as $BF_3.OEt_2$. The mixture is warmed to 100–130° C. for several hours, then cooled to RT. Extraction, concentration, and purification of the compound of Formula (34) is carried out by methods well known to the skilled artisan. The reaction may be carried out neat, or in a suitable solvent, such as toluene, diphenyl ether, or chlorobenzene. Formation of oxazoles is well known in the art. For example, see Pei et al., *Synthesis* (1998) 1298–1304; Joule and Mills, "Heterocylic Chemistry" (4$^{th}$ ed., 2000) Blackwell Science, Ltd: Malden, Mass.; Chapter 21.

As shown in step ee, compounds of Formula (35), in which $R^x$ is a halo such as bromo or iodo, can be prepared from compounds of Formula (34). Where $R^x$ is bromo, freshly recrystallized N-Bromo-Succinimide (NBS) and $(PhCO)_2O_2$ are added to a solution of the compound of Formula (34) in $CCl_4$. The skilled artisan will recognize that AIBN may be used as a radical initiator. Alternatively, iodination of the oxazole may be carried out with N-Iodo-Succinimide (NIS) to make a compound of Formula (35) in which $R^x$ is iodo.

In step ff, t-BuLi is added to a solution of the 5-bromo-oxazole of Formula (35), at −78 to −40° C., in a suitable solvent, such as THF or ether. To this solution is added a solution of an aldehyde of Formula (10) in THF or ether. The reaction is stirred at this temperature, and then warmed to RT for 24 to 60 hours. The alcohol of Formula (36) is concentrated and purified by techniques well known in the art.

Alternatively, in step ff, if the Grignard reagent of Formula (35) is used, Mg turnings and a small crystal of iodine are added to a solution of the 5-bromo-oxazole of Formula (35) in a freshly distilled solvent, such as THF or ether. The mixture is stirred at reflux temperature, then cooled to RT. A solution of the aldehyde of Formula (10) in a suitable solvent, such as THF or ether, is added to the Grignard solution, and the solution is stirred for 1–4 hours. The alcohol of Formula (36) is extracted, concentrated, and purified by techniques well known in the art.

In step gg, the alcohol of Formula (36) may react in the presence of a suitable oxidizing agent, such as $MnO_2$, to give the keto-oxazole of Formula (37). The reaction is conveniently carried out in a solvent such as $CH_2Cl_2$. Other solvents, such as diethyl ether or toluene, may be used, and the reaction may be carried out at RT or heated. The oxidation reaction of step gg may also be carried out by other procedures well known to the skilled artisan, such as Dess-Martin periodinane, Swern, or PDC.

Ketones of Formula (37) may also be prepared directly from oxazoles of Formula (35) by treatment with an activated amide of Formula (12). In this variant, the oxazole is converted to the organo-lithium or organomagnesium bromide reagent as described above (step ff) and a solution of the amide of Formula (12) in a suitable solvent, such as THF or ether, is added. The resulting mixture is stirred for 4–60 hours at RT. The product of Formula (37) is isolated and purified as described above.

Scheme 8

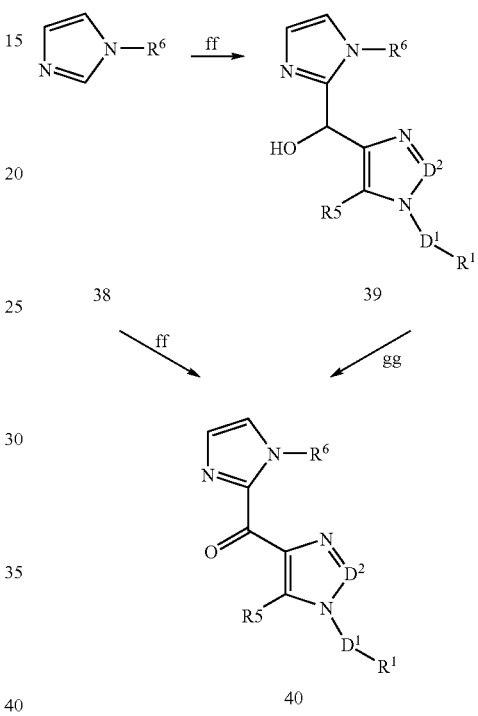

In Scheme 8, synthesis of compounds of Formula (40), which are encompassed in the description of Formula (I), is shown. The compound of Formula (38) undergoes a reaction similar to that shown in Scheme 7, to give the alcohol of Formula (39) or the keto-imidazole of Formula (40). The alcohol of Formula (39) may be oxidized to give the compound of Formula (40) by methods well known to the skilled artisan and described above.

Scheme 9

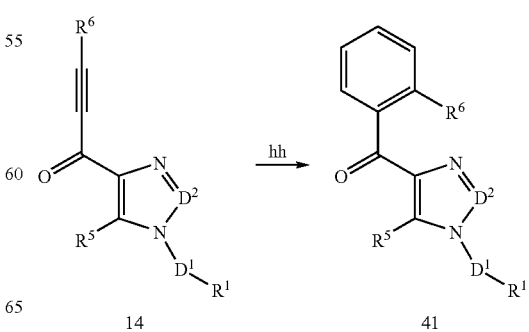

In Scheme 9, compounds of Formula (41), which are included in the invention of Formula (I), may be prepared by dissolving the propynone of Formula (14) in chlorobenzene, followed by addition of alpha-pyrone. Additional pyrone is added to drive the reaction to completion. The reaction is carried out at 110–160° C., preferably 130° C., for 24 to 72 hours. The reaction may also be carried out with other solvents, such as toluene, bromobenzene, diphenylether, or xylene.

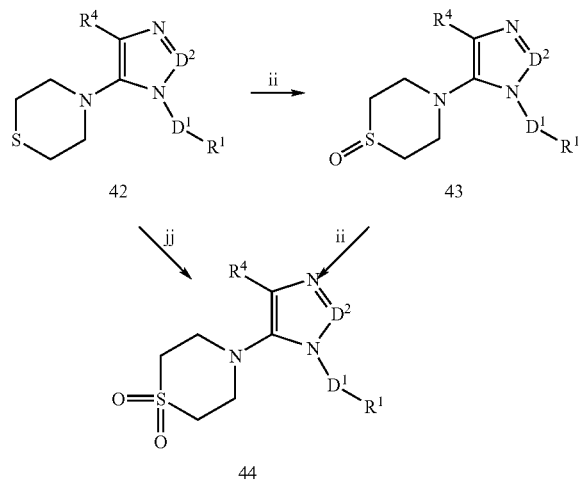

In Scheme 10, the compound of Formula (42) undergoes successive oxidation reactions to give the compounds of Formula (43) and (44), as shown in step ii. Thiomorpholino compounds of Formula (42) are synthesized by substitution of the corresponding halide, as recognized in the art and described elsewhere. The compound of Formula (44) may also be synthesized directly from compounds of Formula (42), as shown in step jj. Each of the compounds of Formula (42), (43), and (44) is encompassed in the scope of compounds of Formula (I).

In step ii, aqueous hydrogen peroxide is added to a solution of the thiomorpholinyl substrate of Formula (42) in a suitable solvent such as EtOH, $CH_2Cl_2$, or preferably, MeOH. The reaction proceeds, with stirring, at 0 to 40° C. for 8 to 48 hours. The products of Formula (43) or (44) may be purified by methods well known to the skilled artisan and described above.

Alternatively, the compound of Formula (44) may be synthesized directly, as shown in step jj, by reaction with 3-chloroperoxybenzoic acid in dichloromethane. The reaction may also be carried out with MeOH or EtOH as the solvent. The reaction proceeds, with stirring, at 0 to 40° C. for 1 to 3 hours. The product is purified by techniques well known in the art.

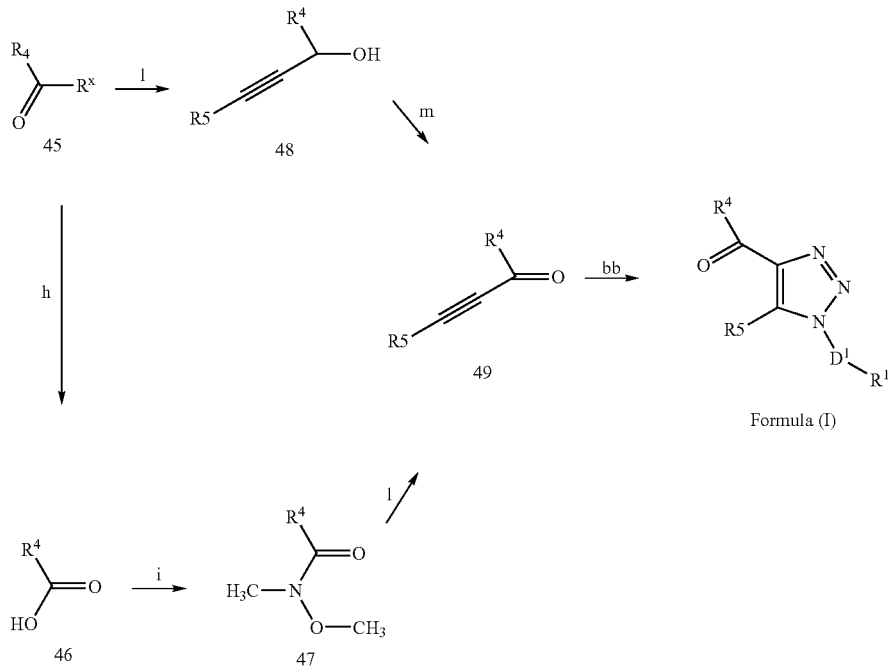

As shown in Scheme 11, compounds of Formula (I) in which $D^2$ is nitrogen can be synthesized by forming the triazole in the final step. The steps described here correspond to those for similar reactions described above. Compounds of Formula (45), in which $R^x$ is hydrogen or $C_1$–$C_4$ alkoxy, are synthesized from the corresponding alkyne, as described previously.

In the synthesis of the triazole compounds of Formula (I), a compound of Formula (49) is reacted with the appropriate azide, as described elsewhere.

The alkynyl-ketones of Formula (49) can be synthesized essentially as described in Scheme 2. Briefly, in step 1, an alkynyl anion is added to a compound of Formula (45) in which $R^x$ is hydrogen, or to an N-methyl-N-methoxyamide of Formula (47). The alkynyl anion is generated by treating the appropriate alkyne with a suitable base, such as methyl lithium, n-butyl lithium, tert-butyl lithium, lithium diisopropylamine, or preferably methyl or ethyl magnesium bromide. When aldehydes of Formula (45) are used, the hydroxy intermediate, Formula (48), can be oxidized to afford the ketone of Formula (49). Such reactions are well known in the art. See Larock, R. C., *Comprehensive Organic Transformations, 2nd ed.*, Wiley-VCH: New York, 1999, pp 1234–1246. Alternatively, N-methyl-N-methoxyamide derivatives of Formula (47) are reacted with a suitable alkynyl anion to provide compounds of Formula (49) directly.

The N-methyl-N-methoxyamide derivatives of Formula (47) are synthesized, as described herein, from compounds of Formula (45) in which $R^x$ is $C_1$–$C_4$ alkoxy. See also, Larock, R. C., *Comprehensive Organic Transformations, 2nd Ed.*, 1999, John Wiley & Sons, pp 1941–1949; 1959–1968.

Scheme 12 depicts the synthesis of compounds of Formula (54), which are used in the reaction of Scheme 13.

Alkynes of Formula (50) may be prepared from an aldehyde of Formula (10) through reaction with a diazo alkyl phosphonate, such as (1-diazo-2-oxo-propyl)-phosphonic acid dimethyl ester. The reaction is carried out in an appropriate solvent, such as MeOH or EtOH, and a base, such as $K_2CO_3$. As shown in step nn, the compound of Formula (51), in which X is —CH(OH)—, can be made from alkynes of Formula (50) by deprotonation with a suitable base, such as LDA, NaH, or BuLi, followed by treatment with an appropriate aldehyde. The alcohol of Formula (51) may be oxidized to give the corresponding methanone, in which X is —C(O)—, by techniques well known in the art and described above.

In step oo, the methanone compound of Formula (51) may be treated with a substituted nitroalkyl compound and an isocyanate, such as 1,4-phenyl-diisocyanate, in the presence of a suitable base such as triethylamine to give an isoxazole of Formula (52), in which $R^x$ is $C_1$–$C_2$ alkane-diyl.

The skilled artisan will recognize that the hydroxyl group of Formula (52) can be oxidized, as shown in step pp, to give compounds of Formula (53), wherein $R^x$ is a bond or methylene. The alcohol can be oxidized by a number of different oxidizing reagents, for example, under Dess-Martin periodinane oxidizing conditions or using combination of DMSO and triethylamine with oxalyl chloride. Such oxidations are readily accomplished by methods well known in the art. (Larock, R. C., Comprehensive Organic Transformations, $2^{nd}$ ed., Wiley-VCH: New York, 1999, pp 1234–1246). The product of the reaction can be isolated and purified using techniques well know in the art.

Alternatively, compounds of Formula (53) can be made by deprotection of the appropriate acetal. Such deprotections

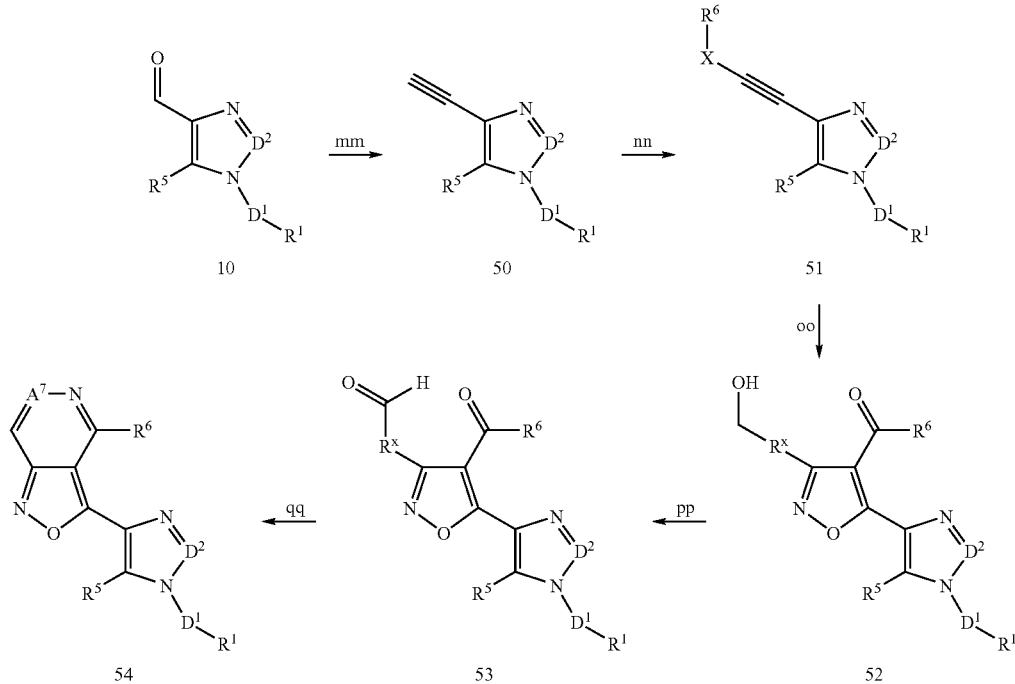

are readily accomplished by methods well known in the art. (Protecting Groups in Organic Synthesis, Theodora Greene (Wiley-Interscience)).

Compounds of Formula (54) can be synthesized by reacting the appropriate aldehyde-containing compound of Formula (53) with ammonium acetate or hydrazine under acidic conditions such acetic acid. For example, when $R^x$ is methylene in the compound of Formula (53), reaction with ammonium acetate provides compounds of Formula (54) in which $A^7$ is $CR^7$. When $R^x$ is a bond, reaction with hydrazine provides compounds of Formula (54) in which $A^7$ is nitrogen.

Scheme 13 shows the formation of compounds of Formula (I), in which $R^4$ is a radical of Formula (IB), through a reduction of compounds of Formula (54). Specifically, the bicyclic isoxazole is dissolved in a suitable solvent, such as acetonitrile. To the reaction, is added molybdenum hexacarbonyl and water. The skilled artisan will recognize that the solution may be heated for the reaction to proceed. The reduction reaction may optionally be carried out using $H_2$/Pt-C in a pressure sealed vessel. The product of Formula (I) is purified by techniques well known in the art, such as silica gel chromatography or recrystallization. Such reactions have been described in the art. See Nitta et al., *J. Chem. Soc., Chem. Commun.* (1982) 877.

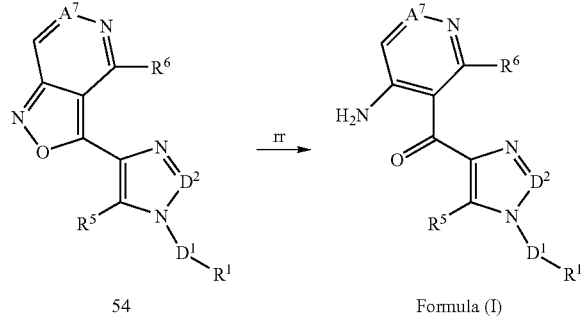

Scheme 13

54

Formula (I)

PREPARATIONS

General Preparation A

Combine the appropriate alkyl halide (1 eq) and sodium azide (3 eq) in DMSO/water (10:1, ca. 10 mL/g $NaN_3$) and stir for 2–12 h at RT. Non-benzylic alkyl halides may require heating to 50–80° C. to facilitate the reaction. When the reaction is complete, add water and extract with ether. Wash the organic layer with water (2×) and brine. Dry the organic layer ($Na_2SO_4$), filter, and concentrate under reduced pressure. Generally, the resulting azide may be used without further purification.

By the method of General Preparation A, the following compounds can be prepared and isolated.

| Prep. # | Product | Physical Data |
|---|---|---|
| 1 | 1-azidomethyl-3-trifluoromethoxybenzene | TLC $R_f$ = 0.70 (20% EtOAc/hexanes) |
| 2 | 2-azidomethyl-1,4-bis-trifluoromethylbenzene | TLC $R_f$ = 0.90 (20% EtOAc/hexanes) |
| 3 | 1-azidomethyl-3-fluoro-5-trifluoromethylbenzene | TLC $R_f$ = 0.78 (20% EtOAc/hexanes) |
| 4 | 1-azidomethyl-5-fluoro-2-trifluoromethylbenzene | TLC $R_f$ = 0.76 (20% EtOAc/hexanes) |
| 5 | 1-azidomethyl-2-fluoro-5-trifluoromethylbenzene | TLC $R_f$ = 0.78 (20% EtOAc/hexanes) |
| 6 | 1-azidomethyl-3-trifluoromethylbenzene | TLC $R_f$ = 0.70 (20% EtOAc/hexanes) |
| 7 | 4-azidomethyl-1-fluoro-2-trifluoromethylbenzene | TLC $R_f$ = 0.89 (20% EtOAc/hexanes) |
| 8 | 1-azidomethyl-3,5-dichlorobenzene | TLC $R_f$ = 0.57 (20:1 hex/EtOAc) $^1$H NMR ($CDCl_3$, 250 MHz) δ 7.36 (m, 1H), 7.25 (s, 2H), 4.36 (s, 2H). |
| 9 | 1-azidomethyl-3,5-dimethylbenzene | TLC $R_f$ = 0.68 (20:1 hex/EtOAc) $^1$H NMR ($CDCl_3$, 250 MHz) δ 7.03 (s, 1H), 6.96 (s, 2H), 4.30 (s, 2H), 2.37 (s, 6H). |
| 10 | 1-azidomethyl-3,5-bis-trifluoromethylbenzene | TLC $R_f$ = 0.42 (20:1 hex/EtOAc) $^1$H NMR ($CDCl_3$, 250 MHz) δ 7.95 (s, 1H), 7.82 (s, 2H), 4.58 (s, 2H) IR: 2105 $cm^{-1}$ |
| 11 | 2-Azidomethyl-[1,3]dioxolane | $^1$H NMR (300 MHz, $CDCl_3$): δ 5.12 (t, J = 3.5 Hz, 1H), 4.02 (m, 4H), 3.36 (d, J = 3.5 Hz, 2H). |
| 12 | 2-Azido-1,1-dimethoxy-ethane | $^1$H NMR (300 MHz, $CDCl_3$): δ 4.57 (t, J = 5.8 Hz, 1H), 3.42 (s, 6H), 3.39 (d, J = 5.5 Hz, 2H). |
| 13 | (2-Azido-ethoxy)-tert-butyl-dimethylsilane | $^1$H NMR (300 MHz, $CDCl_3$): δ 3.80 (t, J = 6.6 Hz, 2H), 3.31 (t, J = 6.6 Hz, 2H), 0.82 (s, 9H), 0.00 (s, 6H); TLC $R_f$ 0.67 (30% EtOAc/Hexane) |

Preparation 14

(2-methoxy-5-trifluoromethoxy-phenyl)-methanol

Dissolve 2-methoxy-5-trifluoromethoxy-benzaldehyde (9.0 g, 40.9 mmol) in MeOH (100 mL) and treat with sodium borohydride (1.45 g, 38.3 mmol). Stir at RT for 1 h., then carefully quench with 1N HCl to pH 3. Concentrate, then extract the aqueous mixture with $CH_2Cl_2$ (3×100 mL). Combine the organic phases and wash with saturated $NaHCO_3$ (100 mL) and brine (100 mL). Dry the organic layer, then filter, and concentrate. Purify the crude material by flash chromatography using a linear gradient of 100% hexanes to 40% EtOAc/hexanes to give (2-methoxy-5-trifluoromethoxy-phenyl)-methanol (6.86 g, 75%) as a colorless oil. $^1$H NMR (400 MHz, $CDCl_3$) δ 7.19 (m, 1H), 7.10 (dd, 1H, J=2.9, 8.8 Hz), 6.83 (d, 1H, J=8.8 Hz), 4.66 (d, 2H, J=6.4 Hz), 3.85 (s, 3H), 2.21 (t, 1H, J=6.4 Hz).

Preparation 15

2-Azidomethyl-1-methoxy-4-trifluoromethoxy-benzene

Dissolve (2-methoxy-5-trifluoromethoxy-phenyl)-methanol (4.49 g, 20.2 mmol) in DMF (40 mL) and treat with thionyl chloride (1.65 g, 22.6 mmol). Stir at RT for 2 h, then treat with potassium carbonate (5.57 g, 40.3 mmol), sodium azide (2.35 g, 36.1 mmol), and DMSO (40 mL). Stir the resulting mixture at RT overnight, then pour into water (100 mL) and extract with ether (3×100 mL). Combine the organic phases and wash with water (2×100 mL) and brine (100 mL). Dry the organic layer ($MgSO_4$), filter, and concentrate to give the title compound (4.77 g, 96%) as a colorless oil that may be used without further purification. $^1$H NMR (400 MHz, $CDCl_3$) δ 7.14 (m, 2H), 6.87 (m, 1H), 4.34 (s, 2H), 3.85 (s, 3H).

Preparation 16

3-Oxo-3-pyrimidin-5-yl-propionic acid methyl ester

Add a 25 wt % solution of sodium methoxide in methanol (4.5 mL, 19.8 mmol) to toluene (40 mL) and heat to 85° C. under $N_2$. Dissolve pyrimidine-5-carboxylic acid ethyl ester (2.0 g, 13.2 mmol) in EtOAc (2.1 mL) and add dropwise to the toluene solution. Heat the reaction mixture for 1 h, then add a suspension of sodium methoxide (715 mg, 13.2 mmol) in EtOAc (15 mL) dropwise. Heat the reaction mixture at 85° C. overnight, then cool to RT and pour into a solution of glacial acetic acid (12 mL) and water. (50 mL). After stirring for 1 h at RT, extract with EtOAc (3×100 mL). Wash the organic phase with brine (200 mL), dry over sodium sulfate, filter, and concentrate under reduced pressure to give the title compound as a mixture of tautomers: $^1$H NMR (300 MHz, $CDCl_3$) enol form δ 12.43 (s, 1H), 9.26 (s, 1H), 9.10 (s, 2H), 5.76 (s, 1H), 3.86 (s, 3H); keto form δ 9.42 (s, 1H), 9.30 (s, 2H), 4.06 (s, 3H), 3.74 (s, 2H).

Preparation 17

3-Oxo-3-pyrazin-2-yl-propionic acid methyl ester

Dissolve NaOMe (1.5 eq) in toluene and heat to 90° C. Add a solution of 2-pyrazine methylester (1.0 eq) and EtOAc (2.0 eq) in toluene dropwise and heat at 90° C. After 20 h, concentrate the mixture in vacuo. Slurry in excess EtOAc and reflux 20 h. Cool to RT, then add water and extract with EtOAc. Dry ($Na_2SO_4$), filter and concentrate in vacuo to give the title compound. TLC $R_f$=0.58 (1:1 EtOAc/hexanes).

Preparation 18

1-(3,5-bis-trifluoromethyl-benzyl)-5-pyridin-4-yl-1H-[1,2,3]triazole-4-carboxylic acid ethyl ester Treat a solution of ethyl isonicotinoylacetate (2.52 g, 13.0 mmol) and 3,5-bis-trifluourobenzyl azide (3.54 g, 13.1 mmol) in DMSO (20 mL) with milled $K_2CO_3$ (5.72 g, 41.4 mmol). Warm the mixture to 40° C. and stir for 18 h, then dilute with $H_2O$ and treat with 1N HCl until mixture reaches pH 7. Extract the mixture with EtOAc (2×50 mL). Combine the organic phases and wash with $H_2O$ (2×50 mL) and brine (50 mL), then dry, filter, and concentrate organic layer. Triturate crude material with hexanes, then recrystallize solid from 40% EtOAc/hexanes to give the title compound (2.80 g, 48%). MS (EI+) 445.2 (M+H); $^1$H NMR (400 MHz, $CDCl_3$): δ 8.74 (dd, 2H, J=1.5, 4.4 Hz), 7.80 (s, 1H), 7.45 (s, 2H), 7.13 (dd, 2H, J=2.0, 4.4 Hz), 5.56 (s, 2H), 4.27 (q, 2H, J=7.3 Hz), 1.28 (t, 3H, J=7.3 Hz). Analytical ($C_{19}H_{14}F_6N_4O_2$): Calculated C, 51.36; H, 3.18; N, 12.61. Found C, 51.35; H, 3.21; N, 12.52.

By a method analogous to Preparation 18, the following compounds may be prepared and isolated.

| Prep. # | Product | Physical Data |
| --- | --- | --- |
| 19 | 1-(3,5-bis-trifluoromethyl-benzyl)-5-methyl-1H-[1,2,3]triazole-4-carboxylic acid ethyl ester | MS (ES) 382.1 (M+1), MS (ES−) 380.0 (M−1). $^1$H NMR (400 MHz, $CDCl_3$) δ 7.86 (s, 1H), 7.64 (s, 2H), 5.62 (s, 2H), 4.42 (q, 2H, J = 7.4 Hz), 2.50 (s, 3H), 1.41 (t, 3H, J = 7.4 Hz). |
| 20 | 1-(3,5-bis-trifluoromethyl-benzyl)-5-pyridin-3-yl-1H-[1,2,3]triazole-4-carboxylic acid ethyl ester | MS (ES) 431.1 (M+H). $^1$H NMR (400 MHz, $CDCl_3$): δ 8.76 (s, 1H), 8.49 (s, 1H), 7.79 (s, 1H), 7.51 (m, 1H), 7.41 (s, 2H), 7.40 (m, 1H), 5.59 (s, 2H), 3.83 (s, 3H). |
| 21 | 1-(3,5-bis-trifluoromethyl-benzyl)-5-phenyl-1H-[1,2,3]triazole-4-carboxylic acid ethyl ester | $R_f$ = 0.42 (2:1 hexanes/EtOAc); MS (ES): 444.1 (M+1); $^1$H NMR ($CDCl_3$, 250 MHz) δ 7.82 (s, 1H), 7.4–7.6 (m, 5H), 7.20 (m, 2H), 5.58 (s, 2H), 4.35 (q, 2H), 1.27 (t, 3H). |
| 22 | 1-(3,5-bis-trifluoromethyl-benzyl)-5-pyrazin-2-yl-1H-[1,2,3]triazole-4-carboxylic acid methyl ester | MS (ES) 431.29 (M+1); TLC $R_f$ = 0.29 (1:1 EtOAc/hexanes) |

-continued

| Prep. # | Product | Physical Data |
|---|---|---|
| 23 | 1-(3,5-bis-trifluoromethyl-benzyl)-5-pyrimidin-5-yl-1H-[1,2,3]triazole-4-carboxylic acid methyl ester | $^1$H NMR (300 MHz, CDCl$_3$) δ 9.34 (s, 1H), 8.62 (s, 2H), 7.82 (s, 1H), 7.48 (s, 2H), 5.63 (s, 2H), 3.91 (s, 3H) |
| 24 | 1-(3,5-dichloro-benzyl)-5-pyridin-4-yl-1H-[1,2,3]triazole-4-carboxylic acid ethyl ester | MS (ES) 377.0, 379.0 (M+1); TLC R$_f$ = 0.50 (7% MeOH/CH$_2$Cl$_2$). |
| 25 | 1-(3,5-dichloro-benzyl)-5-pyridin-3-yl-1H-[1,2,3]triazole-4-carboxylic acid methyl ester | MS (ES) 363.0, 365.0 (M+1)$^+$; R$_f$ = 0.38 (6.7% MeOH/CH$_2$Cl$_2$). |
| 26 | 5-pyridin-3-yl-1-(3-trifluoromethyl-benzyl)-1H-[1,2,3]triazole-4-carboxylic acid methyl ester | MS (ES) 363.2, 364.2 (M+1)$^+$. |
| 27 | 5-pyridin-3-yl-1-(4-trifluoromethyl-benzyl)-1H-[1,2,3]triazole-4-carboxylic acid methyl ester | MS (ES) 363.2, 364.2 (M+1)$^+$; R$_f$ = 0.28 (6.7% MeOH/CH$_2$Cl$_2$). |
| 28 | 1-(2,5-bis-trifluoromethyl-benzyl)-5-pyridin-3-yl-1H-[1,2,3]triazole-4-carboxylic acid methyl ester | MS (ES) 431.2, 432.2 (M+1)$^+$. |
| 29 | 1-(3,5-bis-trifluoromethyl-benzyl)-5-pyridin-3-yl-1H-[1,2,3]triazole-4-carboxylic acid methyl ester | MS (ES+) 431.0 (M+1)$^+$, MS (ES−) 429.0 (M−1)$^-$; $^1$H NMR (400 MHz, CDCl$_3$) δ 8.70 (dd, 1H, J = 1.8, 4.9 Hz), 8.49 (d, 1H, J = 2.3 Hz), 7.91 (s, 1H), 7.51 (dt, 1H, J = 1.9, 7.8 Hz), 7.41 (s, 2H), 7.40 (m, 1H), 5.59 (s, 2H), 3.84 (s, 3H). |
| 30 | 1-(3,4-difluoro-benzyl)-5-pyridin-3-yl-1H-[1,2,3]triazol-4-carboxylic acid methyl ester | MS (ES) 331.1, 332.2 (M$^+$+1); R$_f$ = 0.19 (6.7% MeOH/CH$_2$Cl$_2$) |

Preparation 31

1-(3,5-bis-trifluoromethyl-benzyl)-5-hydroxy-1H-[1,2,3]triazole-4-carboxylic acid ethyl ester Combine a solution of sodium ethoxide (5.5 mL, 21 wt % in ethanol) and diethyl malonate (2.50 mL, 16.5 mmol) in ethanol (26 mL) with a solution of 1-azidomethyl-3,5-bis-trifluoromethyl-benzene (4.40 g, 16.3 mmol) in ethanol (6 mL) and heat to 80° C. After 7 h, cool to RT and concentrate the mixture in vacuo. Dissolve the viscous oil in H$_2$O (20 mL) and add aqueous 1N HCl until the solution reaches pH 2–3. Collect the white precipitate by filtration and dry under reduced pressure to give the title compound. MS (ES) 384.0 (M+H)$^+$, MS (ES−) 382.1 (M−H); $^1$H NMR (400 MHz, CDCl$_3$) δ 8.05 (s, 1H), 7.92 (s, 2H), 5.41 (s, 2H), 4.15 (q, 2H, J=7.3 Hz), 1.22 (t, 3H, J=7.3 Hz).

Preparation 32

1-(3,5-bis-trifluoromethyl-benzyl)-5-chloro-1H-[1,2,3]triazole-4-carboxylic acid ethyl ester Combine PCl$_5$ (5.73 g, 27.5 mmol) with a solution of 1-(3,5-bis-trifluoromethyl-benzyl)-5-hydroxy-1H-[1,2,3]triazole-4-carboxylic acid ethyl ester (5.30 g, 13.8 mmol) in toluene (150 mL) and heat to 50° C. After 2 h, cool to RT, concentrate solution and dissolve crude material in ether (100 mL). Wash the organic solution with saturated NaHCO$_3$ (2×100 mL) and brine (100 mL), dry, filter, and concentrate. Purify the crude material by passing through a short plug of silica gel using a linear gradient of 50% to 80% EtOAc/hexanes, then recrystallize from 1:1 diethyl ether: petroleum ether (150 mL). MS (ES) 402.0 (M+H)$^+$; $^1$H NMR (400 MHz, CDCl$_3$) δ 7.88 (s, 1H), 7.76 (s, 2H), 5.67 (s, 2H), 4.43 (q, 2H, J=7.0 Hz), 1.40 (t, 3H, J=7.0 Hz).

Preparation 33

1-(3,5-Dichloro-benzyl)-5-hydroxy-1H-[1,2,3]triazole-4-carboxylic acid ethyl ester Combine diethylmalonate (1.91 g, 11.9 mmol), 3,5-dichlorobenzylazide (2.40 mL, 11.9 mmol), and potassuim carbonate (4.94 g, 35.8 mmol) in DMSO (15 mL) and heat the mixture 8 h at 50° C. Dilute the cooled mixture with water, adjust pH to 5–6 with aqueous HCl, and extract with CH$_2$Cl$_2$. Wash the combined extracts with water, dry over Na$_2$SO$_4$, filter, and concentrate in vacuo. Chromatography of the resulting residue over silica gel using a CH$_2$Cl$_2$/MeOH gradient yields 3.28 g of the title compound as an oil. MS(ES) 316.0, 318.0 (M+1)$^+$.

Preparation 34

5-chloro-1-(3,5-dichloro-benzyl)-1H-[1,2,3]triazole-4-carboxylic acid ethyl ester Combine 1-(3,5-dichloro-benzyl)-5-hydroxy-1H-[1,2,3]triazole-4-carboxylic acid ethyl ester (1 eq) with PCl$_5$ (2 eq) in toluene and heat at 40–50° C. until reaction is complete. Concentrate the mixture, treat with aqueous NaHCO$_3$, and extract with Et$_2$O. Dry the combined extracts over Na$_2$SO$_4$, concentrate, and purify by chromatography on silica gel. MS (ES) 334.0, 336.0 (M+1)$^+$.

General Preparation B

Add a solution of LiOH.H$_2$O (10 eq) in water to a solution of the appropriate ester (1 eq) in dioxane and stir overnight. Acidify to a pH of 1–2 with 5N HCl solution and collect the precipitate by filtration. Dry the material in vacuo to afford the desired product.

By the method of General Preparation B, the following compounds may be prepared.

| Prep. # | Product | Physical Data |
|---|---|---|
| 35 | 1-(3,5-bis-trifluoromethyl-benzyl)-5-chloro-1H-[1,2,3]triazole-4-carboxylic acid | MS (ES) 372 (M$^+$–1); $^1$H NMR (400 MHz, DMSO): 5.89 (s, 2H); 8.03 (s, 2H); 8.15 (s, 1H) |
| 36 | 1-(3,5-bis-trifluoromethyl-benzyl)-5-pyridin-4-yl-1H-[1,2,3]triazole-4-carboxylic acid | MS (ES) 415 (M$^+$–1); $^1$H NMR (400 MHz, DMSO): 5.76 (s, 2H); 7.43 (d, 2H, J = 5.9 Hz); 7.70 (s, 2H); 8.04 (s, 1H); 8.66 (d, 2H, J = 5.9 Hz) |
| 37 | 1-(3,5-bis-trifluoromethyl-benzyl)-5-pyrazin-2-yl-1H-[1,2,3]triazole-4-carboxylic acid | MS (ES) 418.1 (M+1) |
| 38 | 1-(3,5-dichloro-benzyl)-5-pyridin-4-yl-1H-[1,2,3]triazole-4-carboxylic acid | MS (ES) 349.0, 351.0 (M+1) |
| 39 | 5-chloro-1-(3,5-dichloro-benzyl)-1H-[1,2,3]triazole-4-carboxylic acid | MS (FAB) 305.9 M$^+$; TLC R$_f$ = 0.05 (7% MeOH/CH$_2$Cl$_2$) |
| 40 | 1-(3,5-bis-trifluoromethyl-benzyl)-5-pyridin-3-yl-1H-[1,2,3]triazole-4-carboxylic acid | MS (ES–) 415.1 (M–H); $^1$H NMR (400 MHz, DMSO-d$_6$): δ 13.05 (br s, 1H), 8.66 (m, 1H), 8.56 (d, 1H, J = 1.5 Hz), 8.05 (s, 1H), 7.85 (dt, 1H, J = 2.0, 7.8 Hz), 7.71 (s, 2H), 7.48 (dd, 1H, J = 4.9, 7.8 Hz), 5.79 (s, 2H). |
| 41 | 1-(3,5-bis-trifluoromethyl-benzyl)-5-methyl-1H-[1,2,3]triazole-4-carboxylic acid | MS (ES–) 352.1 (M–H); $^1$H NMR (400 MHz, DMSO-d6) δ 7.31 (s, 1H), 7.14 (s, 2H), 5.00 (s, 2H), 2.50 (s, 3H). |
| 42 | 1-(3,5-bis-trifluoromethyl-benzyl)-5-phenyl-1H-[1,2,3]triazole-4-carboxylic acid | R$_f$ = 0.40 (2:1 CHCl$_3$/MeOH); MS (ES): 416.1 (M+1) |
| 43 | 1-(3,5-bis-trifluoromethyl-benzyl)-5-pyrimidin-5-yl-1H-[1,2,3]triazole-4-carboxylic acid | $^1$H NMR (300 MHz, CDCl$_3$) δ 9.27 (s, 1H), 8.64 (s, 2H), 7.84 (s, 1H), 7.50 (s, 2H), 5.69 (s, 2H) |
| 44 | 1-(3,5-dichloro-benzyl)-5-pyridin-3-yl-1H-[1,2,3]triazole-4-carboxylic acid | MS (ES) 349.0, 351.0 (M+1) |
| 45 | 5-pyridin-3-yl-1 (3-trifluoromethyl-benzyl)-1H-[1,2,3]triazole-4-carboxylic acid | MS (ES) 349.1, 350.2 (M+1) |
| 46 | 5-pyridin-3-yl-1 (4-trifluoromethyl-benzyl)-1H-[1,2,3]triazole-4-carboxylic acid | MS (ES) 349.2, 350.2 (M+1) |
| 47 | 1-(2,5-bis-trifluoromethyl-benzyl)-5-pyridin-3-yl-1H-[1,2,3]triazole-4-carboxylic acid | MS (ES) 417.2 (M+1) |
| 48 | 1-(2-methoxy-5-trifluoromethoxy-benzyl)-5-pyridin-3-yl-1H-[1,2,3]triazolic acid | MS (ES+) 395.2 (M+1)$^+$. $^1$H NMR (400 MHz, DMSO-δ$_6$) δ 12.99 (br s, 1H), 8.66 (d, 1H, J = 3.9 Hz), 8.58 (s, 1H), 7.88 (dt, 1H, J = 2.0, 7.8 Hz), 7.51 (dd, 1H, J = 4.9, 7.8 Hz), 7.29 (dd, 1H, J = 2.4, 8.8 Hz), 7.01 (m, 2H), 5.46 (s, 2H), 3.58 (s, 3H). |
| 49 | 1-(3,4-difluoro-benzyl)-5-pyridin-3-yl-1H-[1,2,3]triazol-4-carboxylic acid | MS (ES) 317.1, 318.2 (M$^+$+1) |

General Preparation C

Add N,O-dimethyl-hydroxylamine (1.3 eq), EDCI (1.3 eq), and DMAP (0.6–1.3 eq) to a solution of the appropriate carboxylic acid (1 eq) in CH$_2$Cl$_2$ (0.3 M). Stir the solution at RT for 5–24 h, then dilute with CH$_2$Cl$_2$ and wash with water, saturated NaHCO$_3$, and brine. Dry, filter, and concentrate the organic solution and purify the crude material by flash chromatography or by recrystallization.

By the method of General Preparation C, the following compounds may be prepared and isolated.

| Prep. # | Product | Physical Data |
|---|---|---|
| 50 | 1-(3,5-bis-trifluoromethyl-benzyl)-5-pyridin-3-yl-1H-[1,2,3]triazole-4-carboxylic acid methoxy-N-methyl-amide | MS (ES) 460.1 (M–H), MS (ES$^-$) 458.1 (M–H); $^1$H NMR (400 MHz, CDCl$_3$) δ 8.72 (s, 1H), 8.50 (s, 1H), 7.80 (s, 1H), 7.58 (d, 1H, J = 7.6 Hz), 7.43 (s, 2H), 7.36 (dd, 1H, J = 4.8, 7.7 Hz), 5.57 (s, 2H), 3.86 (s, 3H), 3.33 (br s, 3H). |
| 51 | 1-(3,5-bis-trifluoromethyl-benzyl)-5-methyl-1H-[1,2,3]triazole-4-carboxylic acid methoxy-N-methyl-amide | MS (ES) 397.1 (M+H), MS (ES–) 395.1 (M–H); $^1$H NMR (400 MHz, CDCl$_3$) δ 7.86 (s, 1H), 7.67 (s, 2H), 5.60 (s, 2H), 3.89 (s, 3H), 3.45 (br s, 3H), 2.46 (s, 3H) |

-continued

| Prep. # | Product | Physical Data |
|---|---|---|
| 52 | 1-(3,5-bis-trifluoromethyl-benzyl)-5-pyrazin-2-yl-1H-[1,2,3]triazole-4-carboxylic acid methoxy-N-methyl-amide | MS (ES) 461.2 (M+1); TLC $R_f$ = 0.47 (5% MeOH/CHCl$_3$) |
| 53 | 1-(3,5-bis-trifluoromethyl-benzyl)-5-chloro-1H-[1,2,3]triazole-4-carboxylic acid methoxy-N-methyl-amide | MS (ES) 417.0 (M+H); $^1$H NMR (400 MHz, CDCl$_3$) δ 7.88 (s, 1H), 7.78 (s, 2H), 5.64 (s, 2H), 3.86 (s, 3H), 3.40 (br s, 3H). |
| 54 | 1-(3,5-bis-trifluoromethyl-benzyl)-5-pyrimidin-5-yl-1H-[1,2,3]triazole-4-carboxylic acid methoxy-N-methyl-amide | $^1$H NMR (300 MHz, CDCl$_3$) δ 9.30 (s, 1H), 8.63 (s, 2H), 7.84 (s, 1H), 7.47 (s, 2H), 5.58 (s, 2H), 3.90 (s, 3H), 3.38 (br s, 3H). |
| 55 | 1-(3,5-bis-trifluoromethyl-benzyl)-5-pyridin-4-yl-1H-[1,2,3]triazole-4-carboxylic acid methoxy-N-methyl-amide | $^1$H NMR (500 MHz, CDCl$_3$) δ 8.75 (d, J = 5.7 Hz, 2H), 7.85 (s, 1H), 7.50 (s, 2H), 7.21 (d, J = 5.7 Hz, 2H), 5.57 (s, 2H), 3.87 (s, 3H), 3.32 (s, 3H); MS (m/e): 460.1 (M+H$^+$). |
| 56 | 1-(3,5-bis-trifluoromethyl-benzyl)-5-phenyl-1H-[1,2,3]triazole-4-carboxylic acid methoxy-N-methyl amide | $^1$H NMR (500 MHz, CDCl$_3$) δ 7.79 (s, 1H), 7.52–7.44 (m, 5H), 7.24–7.22 (m, 2H), 5.55 (s, 2H), 3.83 (s, 3H), 3.33 (s, 3H). MS (m/e): 459.1 (M+H$^+$). |
| 57 | 1-(3,5-dichloro-benzyl)-5-pyridin-4-yl-1H-[1,2,3]triazole-4-carboxylic acid methoxy-N-methyl-amide | MS (ES) 392.22 (M+1) |
| 58 | 1-(3,5-dichloro-benzyl)-5-pyridin-3-yl-1H-[1,2,3]triazole-4-carboxylic acid methoxy-N-methyl-amide | MS (ES) 392.1, 394.0 (M+1)$^+$. $R_f$ = 0.30 (6.7% MeOH/CH$_2$Cl$_2$). |
| 59 | 5-pyridin-3-yl-1 (3-trifluoromethyl-benzyl)-1H-[1,2,3]triazole-4-carboxylic acid methoxy-N-methyl-amide | MS (ES) 392.2, 393.2 (M+1)$^+$. $R_f$ = 0.31 (6.7% MeOH/CH$_2$Cl$_2$). |
| 60 | 5-pyridin-3-yl-1 (4-trifluoromethyl-benzyl)-1H-[1,2,3]triazole-4-carboxylic acid methoxy-N-methyl-amide | MS (ES) 392.2, 393.3 (M+1)$^+$. $R_f$ = 0.19 (6.7% MeOH/CH$_2$Cl$_2$). |
| 61 | 1-(2,5-bis-trifluoromethyl-benzyl)-5-pyridin-3-yl-1H-[1,2,3]triazole-4-carboxylic acid methoxy-N-methyl-amide | MS (ES) 460.2, 461.2 (M+1)$^+$. $R_f$ = 0.22 (6.7% MeOH/CH$_2$Cl$_2$). |
| 62 | 1-(2-methoxy-5-trifluoromethoxy-benzyl)-5-pyridin-3-yl-1H-[1,2,3]triazole-4-carboxylic acid methoxy-N-methyl-amide | MS (ES+) 438.2 (M+1)$^+$. $^1$H NMR (400 MHz, CDCl$_3$) δ 8.65 (dd, 1H, J = 2.0, 4.9 Hz), 8.48 (d, 1H, J = 1.5 Hz), 7.66 (dt, 1H, J = 2.0, 8.3 Hz), 7.34 (dd, 1H, J = 4.9, 8.3 Hz), 7.11 (dd, 1H, J = 2.0, 8.8 Hz), 6.82 (d, 1H, J = 2.4 Hz), 6.75 (d, 1H, J = 8.8 Hz), 5.45 (s, 2H), 3.84 (s, 3H), 3.63 (s, 3H), 3.34 (br s, 3H). |
| 63 | 1-(3,4-difluoro-benzyl)-5-pyridin-3-yl-1H-[1,2,3]triazol-4-carboxylic acid methoxy-N-methyl-amide | MS (ES) 360.2, 361.2 (M$^+$+1); $R_f$ = 0.07 (50% EtOAc/CH$_2$Cl$_2$) |

Preparation 64

[1-(3,5-bis-trifluoromethyl-benzyl)-5-pyridin-3-yl-1H-[1,2,3]triazol-4-yl]-methanol Dissolve 1-(3,5-bis-trifluoromethyl-benzyl)-5-pyridin-3-yl-1H-[1,2,3]triazole-4-carboxylic acid methyl ester (10.0 g) in MeOH (110 mL). Add NaBH$_4$ (2.64 g, 3 eq) and warm to reflux overnight (70° C.). Cool to RT and slowly pour into a separatory funnel containing an equal volume of water; extract with CH$_2$Cl$_2$. Dry the organic layer, concentrate, and recrystallize from EtOAc/Hexanes to give 7.0 g (75%) of the title compound. MS (ES) 403.2 (M+1); $^1$H NMR: (400 MHz, CD$_3$OD) δ: 8.65 (dd, J=5.2, 1.6 Hz, 1H) 8.53–8.52 (m, 1H), 7.89 (s, 1H), 7.86–7.83 (m, 1H), 7.60 (s, 2H), 7.56–7.53 (m, 1H), 5.83 (s, 2H), 4.59 (s, 2H).

Preparation 65

1-(3,5-bis-trifluoromethyl-benzyl)-5-chloro-1H-[1,2,3]triazole-4-carbaldehyde

Add a solution of LiBH$_4$ (65 mL, 2M in THF) to a solution of 1-(3,5-bis-trifluoromethyl-benzyl)-5-chloro-1H-[1,2,3]triazole-4-carboxylic acid ethyl ester (15.0 g, 37.3 mmol) in THF (150 mL) at 0° C. After addition is complete, stir solution at RT for 6 h, then cool again to 0° C. Carefully quench with slow addition of 5N HCl (50 mL). Stir at RT for 30 min., then neutralize with 5N NaOH. Dilute mixture with water (100 mL) and extract with EtOAc (2×50 mL). Combine the organic phases and wash with water (100 mL), and brine (100 mL) then dry, filter, and concentrate to give the alcohol, which can be used in the next reaction without further purification.

Add Dess-Martin periodinane (19.0 g, 44.8 mmol) to a 0° C. solution of the above alcohol in CH$_2$Cl$_2$ (100 mL). Stir solution at 0° C. for 15 min., then at RT for 2 h. Add additional Dess-Martin periodinane (1.7 g, 4.0 mmol) and stir at RT for 1 h. Pour solution into cold 5N NaOH (70 mL) and extract with ether (3×150 mL). Combine the organic phases and wash with 1N NaOH (100 mL), water (100 mL), and brine (100 mL), then dry, filter, and concentrate. Purify the crude material by flash chromatography to give the title compound. MS (ES) 358.1(M+H). $^1$H NMR (400 MHz, CDCl$_3$) δ 10.13 (s, 1H), 7.90 (s, 1H), 7.76 (s, 2H), 5.67 (s, 2H).

By a method similar to Preparation 65, the following compound may be prepared.

| Prep. # | Product | Physical Data |
|---|---|---|
| 66 | 1-(3,5-bis-trifluoro-methyl-benzyl)-5-pyridin-4-yl-1H-[1,2,3]triazole-4-carbaldehyde | MS (ES) 401.1 (M+1). $^1$H NMR (300 MHz, CDCl$_3$): δ 10.14 (s, 1H), 8.75 (d, J = 5.7 Hz, 2H), 7.80 (s, 1H), 7.47 (s, 2H), 7.13 (dd, J = 4.0, 1.7 Hz, 2H), 5.55 (s, 2H). |

Preparation 67

1-(3,5-bis-trifluoromethyl-benzyl)-5-phenyl-1H-[1,2,3]triazole-4-carbaldehyde

Add sodium borohydride (1.70 g, 0.045 mol) to a solution of 1-(3,5-bis-trifluoromethylbenzyl)-5-phenyl-1H-[1,2,3]triazole-4-carboxylic acid ethyl ester (5.0 g, 0.011 mol) in EtOH (70 mL) and heat the mixture to reflux. After 2 h, cool to RT and add the reaction mixture to 0.5 N HCl (200 mL) and methylene chloride (200 mL). Separate the layers and extract the aqueous layer with methylene chloride (50 mL). Dry the combined organic layers over MgSO$_4$, filter, and concentrate to give [1-(3,5-bis-trifluoromethyl-benzyl)-5-phenyl-1H-[1,2,3]triazol-4-yl]-methanol.

Dissolve the crude [1-(3,5-bis-trifluoromethyl-benzyl)-5-phenyl-1H-[1,2,3]triazol-4-yl]-methanol (3.90 g, 0.0097 mol) in DMSO (30 mL) and add N,N-diisopropylethylamine (6.77 mL, 0.039 mol). To this solution add sulfur trioxide pyridine complex (3.09 g, 0.019 mol) in DMSO (30 mL) and stir at RT. After 2 h., add the reaction mixture to EtOAc (150 mL) and 0.5 N HCl (200 mL), and separate the layers. Extract the aqueous layer with EtOAc (50 mL). Combine the organic layers and wash with saturated, aqueous sodium bicarbonate (100 mL) and 1.0 N HCl (100 mL). Dry the organic layer over MgSO$_4$, filter, and concentrate to give the title compound. $^1$H NMR (500 MHz, DMSO) δ 9.91 (s, 1H), 8.02 (s, 1H), 7.69 (s, 2H), 7.55–7.49 (m, 5H), 5.86 (s, 2H); MS (m/e): 400 (M$^+$+1).

Preparation 68

1-[1-(3,5-bis-trifluoromethyl-benzyl)-5-chloro-1H-[1,2,3]triazol-4-yl]-3-(2-chloro-2-yn-1-ol Dissolve 1-chloro-2-ethynyl-benzene (22.1 g, 162 mmol) in THF (300 mL) and slowly add methyl magnesium bromide (50 mL, 3.0 M in ether). Stir the solution at RT for 40 min., then add a solution of 1-(3,5-bis-trifluoromethyl-benzyl)-5-chloro-1H-[1,2,3]triazole-4-carbaldehyde (29.6 g, 82.8 mmol) in THF (160 ml). Stir the resulting solution at RT for 2 h, then pour into cold water (500 mL) and 1N HCl (150 mL) and extract with EtOAc (3×200 mL). Combine the organic phases and wash with saturated NaHCO$_3$ (200 mL) and brine (200 mL) then dry (MgSO$_4$), filter, and concentrate. Purify the crude material by triturating with 30% ether/hexanes to give the title compound. MS (ES) 494.0 (M+1), MS (ES–) 492.0 (M–1); $^1$H NMR (400 MHz, CDCl$_3$) δ 7.87 (s, 1H), 7.79 (s, 2H), 7.47 (dd, 1H, J=1.9, 7.3 Hz), 7.37 (dd, 1H, J=1.4, 7.9 Hz), 7.25 (dt, 1H, J=2.0, 7.3 Hz), 7.19 (dt, 1H, J=1.5, 7.3 Hz), 5.92 (d, 1H, J=6.7 Hz), 5.62 (s, 2H), 2.79 (d, 1H, J=6.4 Hz).

By a method similar to Preparation 68, using the appropriate aldehyde and alkyne, the following compounds may be prepared and isolated.

| Prep. # | Product | Physical Data |
|---|---|---|
| 69 | 1-[1-(3,5-bis-trifluoromethyl-benzyl)-5-phenyl-1H-[1,2,3]triazol-4-yl]-3-(2-chloro-phenyl)-prop-2-yn-1-ol | MS (ES) 536.0 (M+1); $^1$H NMR (300 MHz, CDCl$_3$): δ 7.82 (s, 1H), 7.56–7.12 (m, 11 H), 5.85 (s, 1H), 5.59 (s, 2H). |
| 70 | 1-[1-(3,5-bis-trifluoromethyl-benzyl)-5-phenyl-1H-[1,2,3]triazol-4-yl]-3-phenyl-prop-2-yn-1-ol | MS (ES) 502.2 (M+1), TLC R$_f$ 0.29 (50% EtOAc/Hexane) |
| 71 | 1-[1-(3,5-bis-trifluoromethyl-benzyl)-5-phenyl-1H-[1,2,3]triazol-4-yl]-3-(4-fluoro-phenyl)-prop-2-yn-1-ol | MS (ES) 520.2 (M+1), TLC R$_f$ 0.39 (50% EtOAc/Hexane) |
| 72 | 1-[1-(3,5-bis-trifluoromethyl-benzyl)-5-phenyl-1H-[1,2,3]triazol-4-yl]-3-(3-trifluoromethyl-phenyl)-prop-2-yn-1-ol | MS (ES) 570.1 (M+1), TLC R$_f$ 0.36 (50% EtOAc/Hexane) |
| 73 | 1-[1-(3,5-bis-trifluoromethyl-benzyl)-5-phenyl-1H-[1,2,3]triazol-4-yl]-3-(2-fluoro-phenyl)-prop-2-yn-1-ol | MS (ES) 520.1 (M+1), TLC R$_f$ 0.34 (50% EtOAc/Hexane) |
| 74 | 1-[1-(3,5-bis-trifluoromethyl-benzyl)-5-chloro-1H-[1,2,3]triazol-4-yl]-4-(tert-butyl-dimethyl-silanyloxy)-but-2-yn-1-ol | MS (ES) 528.1 (M+1); TLC (50% Et$_2$O in hexanes): R$_f$ = 0.2. |
| 75 | 1-[1-(3,5-bis-trifluoromethyl-benzyl)-5-phenyl-1H-[1,2,3]triazol-4-yl]-4-(tert-butyl-dimethyl-silanyloxy)-but-2-yn-1-ol | MS (ES) 570.1 (M+1); TLC (50% Et$_2$O in hexanes): R$_f$ = 0.1. |
| 76 | 1-[1-(3,5-bis-trifluoromethyl-benzyl)-5-chloro-1H-[1,2,3]triazol-4-yl]-5-(tert-butyl-dimethyl-silanyloxy)-pent-2-yn-1-ol | MS (ES) 542.0 (M$^+$+1); TLC (50% Et$_2$O in hexanes): R$_f$ = 0.2. |
| 77 | 1-[1-(3,5-bis-trifluoromethyl-benzyl)-5-pyridin-4-yl-1H-[1,2,3]triazol-4-yl]-4-(tert-butyl-dimethyl-silanyloxy)-but-2-yn-1-ol | MS (ES) 571.6 (M$^+$+1); TLC (50% ether in hexanes): R$_f$ = 0.3. |

General Preparation D

Combine the appropriate alcohol (1.0 eq) in dichloromethane, add 4 Å molecular sieves (powder) and stir the mixture. After 10 min, add N-methyl morpholine N-oxide (2.0 eq) into the above mixture and stir. After 10 min, add TPAP (0.1 eq) to the mixture and stir at RT. After 20 min, filter the mixture through a pad of silica gel and concentrate the filtrate in vacuo. Purify the residue by flash chromatography on silica gel to give the title compound.

By the method of General Preparation D, using the appropriate starting materials, the following compounds are prepared and isolated.

$MnO_2$ (50.0 g, 556 mmol). Stir mixture at RT overnight then filter through a pad of Celite® and concentrate the filtrate. Purify the crude material by triturating with 30% ether/hexanes. MS (ES) 492.1 (M+1). $^1$H NMR (400 MHz, $CDCl_3$) δ 7.89 (s, 1H), 7.81 (s, 2H), 7.47 (dd, 1H, J=1.5, 7.8 Hz), 7.46 (dd, 1H, J=1.4, 7.8 Hz), 7.40 (dt, 1H, J=1.5, 7.4 Hz), 7.29 (dt, 1H, J=1.5, 7.4 Hz), 5.68 (s, 2H).

General Preparation E

Under $N_2$, charge an oven-dried flask with oxalyl chloride (2 M in $CH_2Cl_2$, 1.2 eq) and chill in a dry ice/acetone slush. Add DMSO (3 eq) slowly by syringe and stir 45 min. Add the alcohol of interest (1 eq) in anhydrous $CH_2Cl_2$ (0.4 M) slowly by syringe and stir 1 h. Then add TEA (5 eq) slowly by syringe and stir for 90 min. while the bath is allowed to warm to RT. Quench the reaction with saturated aqueous $NH_4C_1$ and $H_2O$, extract with ether, wash combined organics with brine, dry over $MgSO_4$, filter, and concentrate under vacuum. Purify by chromatography on silica gel.

| Prep. # | Product | Physical Data |
|---|---|---|
| 78 | 1-[1-(3,5-bis-trifluoromethyl-benzyl)-5-chloro-1H-[1,2,3]triazol-4-yl]-4-(tert-butyl-dimethyl-silanyloxy)-but-2-yn-1-one | MS (ES) 526.1 (M+1); TLC (30% $Et_2O$ in hexanes): $R_f$ = 0.2. |
| 79 | 1-[1-(3,5-bis-trifluoromethyl-benzyl)-5-phenyl-1H-[1,2,3]triazol-4-yl]-4-(tert-butyl-dimethyl-silanyloxy)-but-2-yn-1-one | MS (ES) 568.1 (M+1); TLC (50% $Et_2O$ in hexanes): $R_f$ = 0.3. |
| 80 | 1-[1-(3,5-bis-trifluoromethyl-benzyl)-5-chloro-1H-[1,2,3]triazol-4-yl]-5-(tert-butyl-dimethyl-silanyloxy)-pent-2-yn-1-one | MS (ES) 539.9 ($M^+$+1); TLC (50% ether in hexanes): $R_f$ = 0.2. |
| 81 | 1-[1-(3,5-bis-trifluoromethyl-benzyl)-5-pyridin-4-yl-1H-[1,2,3]triazol-4-yl]-5-(tert-butyl-dimethyl-silanyloxy)-pent-2-yn-1-one | MS (ES) 582.9 ($M^+$+1); TLC (50% EtOAc in hexanes): $R_f$ = 0.4. |
| 82 | 1-[1-(3,5-bis-trifluoromethyl-benzyl)-5-pyridin-4-yl-1H-[1,2,3]triazol-4-yl]-4-(tert-butyl-dimethyl-silanyloxy)-but-2-yn-1-one | MS (ES) 569.0 ($M^+$+1); TLC (50% EtOAc in hexanes): $R_f$ = 0.1. |

Preparation 83

1-[1-(3,5-bis-trifluoromethyl-benzyl)-5-chloro-]H-[1,2,3)triazol-4-yl]-3-(2-chloro-phenyl)-propynone Dissolve 1-[1-(3,5-bis-trifluoromethyl-benzyl)-5-chloro-1H-[1,2,3]triazol-4-yl]-3-(2-chloro-phenyl)-prop-2-yn-1-ol (33.5 g, 67.8 mmol) in $CH_2Cl_2$ (300 mL) and treat with By the method of General Preparation E, using the appropriate starting materials, the following compounds may be prepared and isolated.

| Prep. # | Product | Physical Data |
|---|---|---|
| 84 | 1-[1-(3,5-bis-trifluoromethyl-benzyl)-5-phenyl-1H-[1,2,3]triazol-4-yl]-3-phenyl-propynone | MS (ES) 500.1 (M+1), TLC $R_f$ = 0.55 (50% EtOAc/Hexane) |
| 85 | 1-[1-(3,5-bis-trifluoromethyl-benzyl)-5-phenyl-1H-[1,2,3]triazol-4-yl]-3-(4-fluoro-phenyl)-propynone | MS (ES) 518.2 (M+1), TLC $R_f$ = 0.55 (50% EtOAc/Hexane) |
| 86 | 1-[1-(3,5-bis-trifluoromethyl-benzyl)-5-phenyl-1H-[1,2,3]triazol-4-yl]-3-(3-trifluoromethyl-phenyl)-propynone | MS (ES) 568.0 (M+1), TLC $R_f$ = 0.57 (50% EtOAc/Hexane) |
| 87 | 1-[1-(3,5-bis-trifluoromethyl-benzyl)-5-phenyl-1H-[1,2,3]triazol-4-yl]-3-(2-fluoro-phenyl)-propynone | MS (ES) 518.0 (M+1), TLC $R_f$ = 0.48 (50% EtOAc/Hexane) |

Preparation 88

1-[1-(3,5-bis-trifluoromethyl-benzyl)-5-pyridin-4-yl-1H-[1,2,3]triazol-4-yl]4-trimethylsilanyloxy-pent-2-yn-1-one Dissolve 3-methyl-3-trimethylsilyloxy-1-butyne (1.17 g, 7.5 mmol, 3 eq) in THF (7 mL) and cool to 0° C. Add ethylmagnesium bromide (2.3 mL of a 3.0 M solution in ether, 7.5 mmol, 3 eq) dropwise and stir at 0° C. for 30 min. Add 1-(3,5-bis-trifluoromethyl-benzyl)-5-pyridin-4-yl-1H-[1,2,3]triazole-4-carbaldehyde (1.0 g, 2.5 mmol) as a solution in THF (7 mL). Stir at 0° C. for 1 h, then warm to RT. After 3 h, quench by adding saturated NH$_4$Cl (25 mL). Extract with EtOAc (2×25 mL), wash the combined organic layers with brine (25 mL), dry (MgSO$_4$), filter, and concentrate.

Redissolve the crude alcohol in CH$_2$Cl$_2$ (12.5 mL) and add activated manganese oxide (1.09 g, 12.5 mmol, 5 eq.). Sonicate the mixture for 2 min, then stir at RT for 24 h. Filter the mixture through a plug of Celite® and concentrate the filtrate. Purify the residue by chromatography (silica gel, hexanes/EtOAc 3:1 to 1:1 gradient) to provide 605 mg (44%) of the desired alkynyl ketone. TLC: R$_f$=0.51 (1:2 hexanes/EtOAc); MS(ES): 555.1 (M+1), 465.1 (M−OSiMe$_3$).

Using a method similar to Preparation 88, with the appropriate starting materials, the following compounds may be prepared and isolated.

Preparation 94

1-[1-(3,5-bis-trifluoromethyl-benzyl)-5-phenyl-1H-[1,2,3]triazol-4-yl]-3-(2-chloro-phenyl)-propynone Chill a solution of 1-chloro-2-ethynylbenzene (4.0 mL, 32.8 mmol) in anhydrous THF (25 mL) under nitrogen to 0° C. Add by syringe ethylmagnesium bromide, 3.0 M in ether (9.7 mL, 29.3 mmol), while stirring. After 30 min, remove from ice-bath and add by syringe a solution of 1-(3,5-bis-trifluoromethyl-benzyl)-5-phenyl-1H-[1,2,3]triazole-4-carboxylic acid methoxy-N-methyl-amide (10.73 g, 23.4 mmol) in THF (35 mL). After 2 h, quench with saturated aqueous NH$_4$Cl and extract with EtOAc, dry over MgSO$_4$, filter and concentrate under vacuum. Purify by chromatography (silica gel, hexanes/EtOAc gradient) to give the title compound: MS (ES) 534.0 (M+1), $^1$H NMR (300 MHz, CDCl$_3$): δ 7.82 (s, 1H), 7.56–7.12 (m, 11H), 5.59 (s, 2H).

By a method similar to Preparation 94, using the appropriate starting materials, the following compounds may be prepared.

| Prep. # | Product | Physical Data |
|---|---|---|
| 89 | 1-[1-(3,5-bis-trifluoromethyl-benzyl)-5-pyridin-4-yl-1H-[1,2,3]triazol-4-yl]-4-methoxy-but-2-yn-1-one | TLC: R$_f$ = 0.33 (1:2 hexanes/EtOAc) MS (ES) 469.1 (M+1) |
| 90 | 1-[1-(3,5-bis-trifluoromethyl-benzyl)-5-pyridin-3-yl-1H-[1,2,3]triazol-4-yl]-4-methyl-4-trimethylsilanyloxy-pent-2-yn-1-one | m.p. = 105° C. TLC: R$_f$ = 0.86 (1:2 hexanes/EtOAc) MS (ES) 555.2 (M+1), 465.2 [(M-OSiMe$_3$)$^+$] |
| 91 | 1-[1-(3,5-bis-trifluoromethyl-benzyl)-5-chloro-1H-[1,2,3]triazol-4-yl]-4-tert-butoxy-pent-2-yn-1-one | m.p. 87–90° C. TLC: R$_f$ = 0.55 (2:1 hexanes/EtOAc) MS (ES) 482.0 (M+1), 426.0 [(M-C (CH$_3$)$_3$)$^+$] |
| 92 | 1-[1-(3,5-bis-trifluoromethyl-benzyl)-5-chloro-1H-[1,2,3]triazol-4-yl]-4-methoxy-but-2-yn-1-one | m.p. 94–96° C. TLC: R$_f$ = 0.35 (2:1 hexanes/EtOAc) MS (ES) 426.0 (M+1) |
| 93 | 1-[1-(3,5-bis-trifluoromethyl-benzyl)-5-chloro-1H-[1,2,3]triazol-4-yl]-4-methyl-4-trimethylsilanyloxy-pent-2-yn-1-one | TLC: R$_f$ = 0.58 (2:1 hexanes/EtOAc) MS (ES) 511.9 (M+1), 422.0 [(M-OSiMe$_3$)$^+$] |

| Prep. # | Product | Physical Data |
|---|---|---|
| 95 | 1-[1-(3,5-bis-trifluoromethyl-benzyl)-5-methyl-1H-[1,2,3]triazol-4-yl]-3-(2-chloro-phenyl)-propynone | MS (ES) 472.1 (M+H), 470.1 (M−H); $^1$H NMR (400 MHz, CDCl$_3$) δ 7.90 (s, 1H), 7.75 (dd, 1H, J = 7.9, 1.6 Hz), 7.71 (s, 2H), 7.47 (dd, 1H, J = 8.2, 1.3 Hz), 7.41 (dt, 1H, J = 7.9, 1.6 Hz), 7.31 (dt, 1H, J = 8.2, 1.3 Hz), 5.66 (s, 2H), 2.61 (s, 3H). |
| 96 | 1-[1-(3,5-bis-trifluoromethyl-benzyl)-5-pyridin-4-yl-1H-[1,2,3]triazole-4-yl]-3-(2-chloro-phenyl)-propynone | m.p. 50–54° C.; MS (m/e): 535 (M+H$^+$); TLC: R$_f$ = 0.34 (2:1 EtOAc:Hexanes) |
| 97 | 1-[1-(3,5-bis-trifluoromethyl-benzyl)-5-pyridin-3-yl-1H-[1,2,3]triazol-4-yl]-3-(2-chloro-phenyl)-propynone | m.p. 100–101° C.; MS (m/e): 535 (M+H$^+$); TLC: R$_f$ = 0.12 (1:1 EtOAc:Hexanes). |
| 98 | 1-[1-(3,5-bis-trifluoromethyl-benzyl)-5-pyrimidin-5-yl-1H-[1,2,3]triazol-4-yl]-3-(2-chloro-phenyl)-propynone | m.p. 168–169° C.; MS (m/e): 536 (M+H+); TLC: R$_f$ = 0.27 (Silica, 1:1 EtOAc:Hexanes). |
| 99 | 1-[1-(3,5-bis-trifluoromethyl-benzyl)-5-pyrazin-2-yl-1H-[1,2,3]triazol-4-yl]-4-(tert-butyl-dimethyl-silanyloxy)-but-2-yn-1-one | MS (ES) 570.2 (M+). TLC R$_f$ = 0.40 (40% EtOAc/hexanes) |
| 100 | 1-[1-(3,5-bis-trifluoromethyl-benzyl)-5-pyrazin-2-yl-1H-[1,2,3]triazol-4-yl]-4-methyl-4-trimethylsilanyloxy-pent-2-yn-1-one | MS (ES) 556.1 (M+). TLC R$_f$ = 0.31 (30% EtOAc/hexanes) |
| 101 | 1-[1-(3,5-Bis-trifluoromethyl-benzyl)-5-pyrazin-2-yl-1H-[1,2,3]triazol-4-yl]-3-(2-chlorophenyl)-propynone | MS (ES) 536.0 (M+) TLC R$_f$ = 0.62 (1:1 EtOAc/hexanes) |
| 102 | 3-(2-chloro-phenyl)-1-[1-(3,5-dichloro-benzyl)-5-pyridin-4-yl-1H-[1,2,3]triazol-4-yl]-propynone | MS (ES)467.1, 469.1 (M+1)$^+$. R$_f$ = 0.52 (6.7% MeOH/CH$_2$Cl$_2$). |
| 103 | 3-(2-chloro-phenyl)-1-[1-(3,5-dichloro-benzyl)-5-pyridin-3-yl-1H-[1,2,3]triazol-4-yl]-propynone | MS (ES)466.9, 468.9 (M+1)$^+$. R$_f$ = 0.51 (6.7% MeOH/CH$_2$Cl$_2$). |
| 104 | 3-(2-chloro-phenyl)-1-[5-pyridin-3-yl-1-(3-trifluoromethyl-benzyl)-1H-[1,2,3]triazol-4-yl]-propynone | MS (ES) 467.2, 469.2 (M+1)$^+$. R$_f$ = 0.41 (6.7% MeOH/CH$_2$Cl$_2$). |
| 105 | 3-(2-chloro-phenyl)-1-[5-pyridin-3-yl-1-(4-trifluoromethyl-benzyl)-1H-[1,2,3]triazol-4-yl]-propynone | MS (ES) 467.2, 469.2 (M+1)$^+$. R$_f$ = 0.40 (6.7% MeOH/CH$_2$Cl$_2$) |
| 106 | 1[1-(2,5-bis-trifluoromethyl-benzyl)-5-pyridin-3-yl-1H-[1,2,3]triazol-4-yl]-3-(2-chloro-phenyl)-propynone | MS (ES) 535.1, 537.1 (M+1)$^+$. R$_f$ = 0.67 (6.7% MeOH/CH$_2$Cl$_2$) |
| 107 | 3-(2-chloro-phenyl)-1-[1-(2-methoxy-5-trifluoromethoxy-benzyl)-5-pyridin-3-yl-1H-[1,2,3]triazol-4-yl]-propynone | MS (ES+) 513.1 (M+ 1)$^+$. $^1$H NMR (400 MHz, CDCl$_3$) δ 8.69 (dd, 1H, J = 1.5, 4.9 Hz), 8.52 (d, 1H, J = 1.5 Hz), 7.65 (dt, 1H, J = 2.0, 7.8 Hz), 7.61 (dd, 1H, J = 2.0, 7.8 Hz), 7.42 (m, 1H), 7.36 (m, 2H), 7.25 (dt, 1H, J = 1.5, 7.8 Hz), 7.12 (dd, 1H, J = 2.0, 8.8 Hz), 6.88 (d, 1H, J = 2.9 Hz), 6.75 (d, 1H, J = 9.3 Hz), 5.47 (s, 2H), 3.62 (s, 3H). |
| 108 | 3-(2-Chloro-phenyl)-1-[1-(3,4-difluoro-benzyl)-5-pyridin-3-yl-1H-[1,2,3]triazol-4-yl]-propynone | MS (ES) 435.2, 437.2 (M$^+$+1); R$_f$ = 0.48 (50% EtOAc/CH$_2$Cl$_2$) |

General Preparation F

Treat a solution of the appropriate N-methoxy-N-methyl-amide (1.0 eq.) in THF with ethynylmagnesium bromide (2.0 eq) at 0° C. Stir the mixture for 2 h, then warm to RT. Add aqueous saturated NH$_4$Cl solution slowly. Extract with ether. Dry the combined organic layers with anhydrous MgSO$_4$, filter and concentrate in vacuo. Purify by chromatography on silica gel.

By the method of General Preparation F, the following compounds may be prepared.

| Prep. # | Product | Physical Data |
|---|---|---|
| 109 | 1-[1-(3,5-bis-trifluoromethyl-benzyl)-5-pyridin-4-yl-1H-[1,2,3]triazol-4-yl]-3-(methoxy-methyl-amino)-2-propenone | MS (ES) 486.2 (M$^+$+1);TLC (33% acetone in hexanes): R$_f$ = 0.1. |
| 110 | 1-[1-(3,5-bis-trifluoromethyl-benzyl)-5-pyridin-3-yl-1H-[1,2,3]triazol-4-yl]-3-(methoxy-methyl-amino)-2-propenone | MS (ES) 486.2 (M$^+$+1); TLC (33% acetone in hexanes): R$_f$ = 0.1. |
| 111 | 1-[1-(3,5-bis-trifluoromethyl-benzyl)-5-chloro-1H-[1,2,3]triazol-4-yl]-3-(methoxy-methyl-amino)-2-propenone | MS (ES) 443.1 (M$^+$+1); TLC (33% acetone in hexanes): R$_f$ = 0.1. |

Preparation 112

(1,1-dimethyl-2-nitro-ethoxy)-trimethyl-silane

To a solution of nitromethane (100 g, 1.64 mmol) and acetone (5 mL), add a catalytic amount of tetramethylguanidine. Using a syringe pump, add acetone (115 mL, 1.64 mmol) over a period of 72 h. to the stirred solution at RT. In a separate flask, combine chlorotrimethylsilane (206 mL, 1.64 mmol) and imidazole (123 g, 1.8 mmol) at 0° C. Transfer the nitromethane/acetone solution into the trimethylsilyl-imidazole mixture and allow the resulting mixture to stir 18 h at RT. Then cool the reaction to 0° C., dilute with cold ether (450 mL) and wash with cold 1N HCl (200 mL×2). Wash the organic layer with brine (300 mL). Carefully concentrate the crude material in vacuo without heating. Purify by distillation to provide the title compound. $^1$H NMR (300 MHz, CDCl$_3$) δ 4.20 (s, 2H), 1.28 (s, 6H), 0.01 (s, 9H).

Preparation 113

1-Iodo-2-methoxy-ethane

Add sodium iodide (70.5 g, 0.47 mol) to a solution of 1-bromo-2-methoxy-ethane (47.0 g, 0.34 mol) in acetone and warm to reflux. After 50 h, pour the reaction mixture into ice water and extract with ether. Wash the organic layer with saturated sodium thiosulfate solution (3×), then water and brine. Dry over Na$_2$SO$_4$, filter, and concentrate under reduced pressure to give the title compound (54.0 g, 87%). $^1$H NMR (400 MHz, CDCl$_3$) δ 3.65 (t, 2H, J=6.9 Hz), 3.40 (s, 3H), 3.26 (t, 2H, J=6.9 Hz).

General Preparation G

Combine the alkyl halide of interest (1 eq) and AgNO$_2$ (1.1 eq) in ether, cover flask with aluminum foil and heat to reflux. Add additional AgNO$_2$ (0.3 eq) if necessary until complete by TLC. Then cool to RT and filter the mixture through Celite®. Dry the filtrate over MgSO$_4$, filter, and concentrate. Purify by vacuum distillation or by flash chromatography on silica gel.

By the method of General Preparation G, the following compounds may be prepared and isolated.

| Prep. # | Product | Physical Data |
|---|---|---|
| 114 | 2-(2-nitro-ethyl)-[1,3]dioxolane | $^1$H NMR (CDCl$_3$, 400 MHz): δ 5.02 (t, J = 3.7 Hz, 1H), 4.50 (t, J = 6.7 Hz, 2H), 4.02–3.94 (m, 4H), 2.43 (m, 2H). |
| 115 | 1-methoxy-2-nitro-ethane | GC/MS [EI$^+$] 105.0 (M)$^+$; $^1$H NMR (400 MHz, CDCl$_3$) δ 4.51 (t, 2H, J = 4.8 Hz), 3.90 (t, 2H, J = 4.8 Hz), 3.37 (s, 3H). |
| 116 | nitromethyl-cyclopropane | GC/MS [EI$^+$] 101.0 (M)$^+$; $^1$H NMR (400 MHz, CDCl$_3$) δ 4.20 (d, 2H, J = 7.3 Hz), 1.48 (m, 1H), 0.76 (m, 2H), 0.45 (m, 2H). |

Preparation 117

[1-(3,5-bis-trifluoromethylbenzyl)-5-chloro-1H-[1,2,3]triazol-4-yl]-[5-(2chlorophenyl)-3-(tetrahydropyran-2-yloxymethyl)-isoxazol-4-yl]-methanone Add triethylamine (17.9 mL, 0.128 mol) to a slurry of 1-[1-(3,5-bistrifluoromethylbenzyl)-5-chloro-1H-[1,2,3]triazol-4-yl]-3-(2-chlorophenyl)-propynone (60.0 g, 0.122 mol) and 1,4-diphenylene diisocyanate (58.6 g, 0.366 mol) in toluene (450 mL). Heat reaction to 80° C. and add a solution of 2-(2-nitroethoxy)tetrahydropyran (34.0 mL, 0.241 mol) in toluene (200 mL) over 3 h, then heat for an additional 5.5 h. Add more triethylamine (2.7 mL, 0.019 mol), 1,4-diphenylene diisocyanate (8.8 g, 0.055 mol), and 2-(2-nitroethoxy)tetrahydropyran (5.1 mL, 0.036 mol) and heat an additional 4 h. Stir overnight at RT, then filter through Celite® and concentrate filtrate under vacuum to an oil. With vigorous stirring, add heptane (1 L) over 30 min, stir for an additional 30 min, filter and dry to obtain crude title compound. Add the crude product to diethyl ether (700 mL), treat with acid-washed carbon (4 g), and filter through Celite®. Concentrate the solution to give 108 g of material. Add heptane (500 mL) over 30 min, stir 1 h, filter, and dry to obtain the title compound: MS (m/e): 649 (M$^+$). Analysis for C$_{14}$H$_{11}$ClF$_6$N$_4$O$_2$: calculated: C, 40.35; H, 2.66; N, 13.44. Found: C, 40.03; H, 2.70; N, 13.33.

By a method similar to Preparation 117, using the appropriate conditions and starting materials, the following compounds may be prepared and isolated.

| Prep. # | Product | Physical Data |
|---|---|---|
| 118 | [1-(3,5-bis-trifluoromethyl-benzyl)-5-phenyl-1H-[1,2,3]triazol-4-yl]-[5-(2-chloro-phenyl)-3-(2,2-dimethoxy-ethyl)-isoxazol-4-yl]-methanone | MS (aspci): m/z = 633.9 (M-(OMe)$^+$); $^1$H NMR (250 MHz, CDCl$_3$) δ 7.72 (s, 1H), 7.59 (dd, J = 6.2, 2.7 Hz, 1H), 7.48–7.10 (m, 10 H), 5.37 (s, 2H), 4.70 (t, J = 6.2 Hz, 1H), 3.41 (s, 6H), 3.70 (q, J = 6.25 Hz, 2H), 3.21 (s, 6H), 3.1–3.2 (m, 2H). |
| 119 | [1-(3,5-bis-trifluoromethyl-benzyl)-5-pyridin-3-yl-1H [1,2,3]triazol-4-yl]-{5-(2-chloro-phenyl)-3-[2-(tetrahydro-pyran-2-yloxy)-ethyl]-isoxazol-4-yl}-methanone | $^1$H NMR (300 MHz, CDCl$_3$) δ 1.34–1.70 (m, 6H), 3.23 (dt, 2H, J = 6.84, 1.70 Hz), 3.41–3.51 (m, 1H), 3.72–3.79 (m, 2H), 4.07 (dt, J = 9.83, 6.68 Hz, 1H), 4.59 (t, J = 3.30 Hz, 1H), 5.47 (s, 2H), 7.21 (dd, J = 7.06, 1.17 Hz, 1H), 7.32–7.36 (m, 3H), 7.39–7.44 (m, 2H), 7.61 (dt, J = 7.82, 2.12, 1H), 7.71 (dd, 1H, J = 7.64, 1.76 Hz), 7.83 (s, 1H), 8.50 (d, 1H, J = 2.05 Hz), 8.78 (dd, 1H, J = 4.87, 1.47 Hz). |
| 120 | [1-(3,5-bis-trifluoromethyl-benzyl)-5-pyridin-4-yl-1H-[1,2,3]triazol-4-yl]-[5-(2-chloro-phenyl)-3-(tetrahydro-pyran-2-yloxymethyl)-isoxazol-4-yl]-methanone | Exact Mass 691.14; MS (ESI) 714.1 m/z (M+Na); $^1$H NMR (300 MHz, CDCl$_3$) δ1.38–1.80 (m, 6H), 3.48 (m, 1H) 3.78 (m, 1H), 4.69 (m, 1H), 4.93 (ABq, 2H, J = 13.31 Hz, Δv = 64.63 Hz) 5.47 (s, 2H), 7.16 (m, 2H), 7.24 (m, 1H), 7.33–7.43 (m, 4H), 7.70 (dd, 1H, J = 7.51, 2.04 Hz), 7.86 (s, 1H), 8.78 (m, 2H). |

| Prep. # | Product | Physical Data |
|---|---|---|
| 121 | [1-(3,5-bis-trifluoromethyl-benzyl)-5-pyridin-3-yl-1H-[1,2,3]triazol-4-yl]-[5-(2-chloro-phenyl)-3-(tetrahydro-pyran-2-yloxymethyl)-isoxazol-4-yl]-methanone | $^1$H NMR (300 MHz, CDCl$_3$) δ 1.40–1.72 (m, 6H), 3.45–3.50 (m, 1H), 3.75–3.81 (m, 1H), 4.69 (t, 1H, J = 3.23 Hz), 4.94 (ABq, 2H, J = 13.19, Δν = 66.43 Hz), 5.51 (s, 2H), 7.25–7.30 (m, 1H), 7.35–7.44 (m, 5H), 7.57–7.60 (m, 1H), 7.69–7.71 (m, 1H), 7.84 (s, 1H), 8.48 (d, 1H, J = 2.1 Hz), 8.76 (dd, 1H, J = 4.86, 1.67 Hz); TLC R$_f$ = 0.3 (10% ether/dichloromethane). |
| 122 | [1-(3,5-bis-trifluoromethyl-benzyl)-5-pyridin-4-yl-1H-[1,2,3]triazol-4-yl]-{5-(2-chloro-phenyl)-3-[2-(tetrahydro-pyran-2-yloxy)-ethyl]-isoxazol-4-yl}-methanone | $^1$H NMR (300 MHz, CDCl$_3$) δ 1.32–1.72 (m, 6H), 3.23 (td, 2H, J = 6.75, 1.39 Hz) 3.44 (m, 1H), 3.76 (m, 2H), 4.07 (dt, 1H, J = 9.76, 6.83 Hz), 4.60 (bt, 1H, J = 3.32 Hz) 5.43 (s, 2H), 7.17–7.20 (m, 3H), 7.32–7.43 (m, 4H), 7.72 (dd, 1H, J = 7.71, 1.66 Hz), 7.86 (s, 1H), 8.80 (m, 2H). |
| 123 | [1-(3,5-bis-trifluoromethyl-benzyl)-5-phenyl-1H-[1,2,3]triazol-4-yl]-[5-(2-chloro-phenyl)-3-(tetrahydro-pyran-2-yloxymethyl)-isoxazol-4-yl]-methanone | MS (ES) 691.2 (M+1), $^1$H NMR (300 MHz, CDCl$_3$): δ 7.84 (s, 1H), 7.72–7.18 (m, 11H), 5.48 (s, 2 H), 4.96 (m, 2H), 4.73 (m, 1H), 3.81 (m, 1H), 3.50 (m, 1H), 1.80–1.37 (m, 6H). |
| 124 | [1-(3,5-bis-trifluoromethyl-benzyl)-5-phenyl-1H-[1,2,3]triazol-4-yl]-[5-(2-chloro-phenyl)-3-[1,3]dioxolan-2-ylmethyl-isoxazol-4-yl]-methanone | MS (ES) 663.1 (M+1), $^1$H NMR (300 MHz, CDCl$_3$): δ 7.80 (s, 1H), 7.67 (dd, J = 7.8 Hz, 1.7 Hz, 1H), 7.56–7.16 (m, 10H), 5.44 (s, 2H), 5.29 (t, J = 4.2 Hz, 1H), 3.84–3.74 (m, 4H), 3.33 (d, J = 4.4 Hz, 2H). |
| 125 | [1-(3,5-bis-trifluoromethyl-benzyl)-5-pyrazin-2-yl-1H-[1,2,3]triazol-4-yl]-[5-(2-chlorophenyl)-3-[1,3]dioxolan-2-yl-methyl-isoxazol-4-yl]-methanone | $^1$H NMR (300 MHz, CDCl$_3$): δ 9.18 (d, J = 1.3 Hz, 1H), 8.68 (m, 2H), 7.80 (s, 1H), 7.68 (m, 1H), 7.59 (s, 2H), 7.38–7.24 (m, 2H), 7.19 (m, 1H), 5.84 (s, 2H), 5.27 (t, J = 4.1 Hz, 1H), 3.78 (m, 4H), 3.38 (d, J = 4.1 Hz, 2H); TLC R$_f$ = 0.13 (50% EtOAc/Hexane). |
| 126 | [1-(3,5-bis-trifluoromethyl-benzyl)-5-phenyl-1H-[1,2,3]triazol-4-yl]-{5-(2-chloro-phenyl)-3-[2-(tetrahydro-pyran-2-yloxy)-ethyl]-isoxazol-4-yl}-methanone | MS (ES) 705.5 (M+1); TLC R$_f$ = 0.15 (30% EtOAc/Hexane). |
| 127 | [1-(3,5-bis-trifluoromethyl-benzyl)-5-pyrazin-2-yl-1H-[1,2,3]triazol-4-yl]-[5-(2-chloro-phenyl)-3-(tetrahydro-pyran-2-yloxymethyl)-isoxazol-4-yl]-methanone | MS (ES) 693.2 (M+1) TLC R$_f$ = 0.50 (10% CH$_3$CN/CH$_2$Cl$_2$) |
| 128 | [5-(2-chloro-phenyl)-3-(tetrahydro-pyran-2-yloxymethyl)-isoxazol-4-yl]-[1-(3,5-dichloro-benzyl)-5-pyridin-4-yl-1H-[1,2,3]triazol-4-yl]-methanone | MS (ES) 624.2, 626.2 (M+1)$^+$ |
| 129 | [5-(2-chloro-phenyl)-3-(tetrahydro-pyran-2-yloxymethyl)-isoxazol-4-yl]-[1-(3,5-dichloro-benzyl)-5-pyridin-3-yl-1H-[1,2,3]triazol-4-yl]-methanone | MS (ES) 624.1, 626.1 (M+1)$^+$ |
| 130 | [5-(2-chloro-phenyl)-3-(tetrahydro-pyran-2-yloxymethyl)-isoxazol-4-yl]-[5-pyridin-3-yl-1-(3-trifluoromethyl-benzyl)-1H-[1,2,3]triazol-4-yl]-methanone | MS (ES) 624.2, (M+1)$^+$; R$_f$ = 0.22 (6.7% MeOH/CH$_2$Cl$_2$). |
| 131 | [5-(2-chloro-phenyl)-3-(tetrahydro-pyran-2-yloxymethyl)-isoxazol-4-yl]-[5-pyridin-3-yl-1-(4-trifluoromethyl-benzyl)-1H-[1,2,3]triazol-4-yl]-methanone | MS (ES) 624.2, (M+1)$^+$; R$_f$ = 0.20 (6.7% MeOH/CH$_2$Cl$_2$) |
| 132 | [1-(2,5-bis-trifluoromethyl-benzyl)-5-pyridin-3-yl-1H-[1,2,3]triazol-4-yl]-[5-(2-chloro-phenyl)-3-(tetrahydro-pyran-2-yloxymethyl)-isoxazol-4-yl]-methanone | MS (ES) 692.2, 694.2, (M+1)$^+$. R$_f$ = 0.43 (6.7% MeOH/CH$_2$Cl$_2$) |
| 133 | [1-(3,5-bis-trifluoromethyl-benzyl)-5-pyrazin-2-yl-1H-[1,2,3]triazol-4-yl]-[5-(2-chloro-phenyl)-3-(1-methyl-1-trimethylsilanyloxy-ethyl)-isoxazol-4-yl]-methanone | R$_f$ = 0.49 (2:1 Hex/EtOAc); MS (ES) 709.2 (M+1) |

-continued

| Prep. # | Product | Physical Data |
|---|---|---|
| 134 | [1-(3,5-bis-trifluoromethyl-benzyl)-5-chloro-1H-[1,2,3]triazol-4-yl]-[5-(2-chloro-phenyl)-3-(1-methyl-1-trimethylsilanyloxy-ethyl)-isoxazol-4-yl]-methanone | $R_f$ = 0.85 (1:1 Hex/EtOAc); MS (ES) 665.1 (M+1) |
| 135 | [1-(3,5-bis-trifluoromethyl-benzyl)-5-phenyl-1H-[1,2,3]triazol-4-yl]-[5-(2-chloro-phenyl)-3-(1-methyl-1-trimethylsilanyloxy-ethyl)-isoxazol-4-yl]-methanone | $R_f$ = 0.31 (3:1 Hex/EtOAc); MS/ES (M+1): 707.2 |
| 136 | [1-(3,5-bis-trifluoromethyl-benzyl)-5-chloro-1H-[1,2,3]triazol-4-yl]-[5-(2-chloro-phenyl)-3-methoxymethyl-isoxazol-4-yl]-methanone | MS (ES) 579.2 (M+H). $^1$H NMR (400 MHz, CHCl$_3$) δ 7.91 (s, 1H), 7.66–7.68 (m, 3H), 7.31–7.39 (m, 2H), 7.22 (dd, 1H, J = 7.7, 1.5 Hz), 5.59 (s, 2H), 4.80 (s, 2H), 3.36 (s, 3H). |
| 137 | [1-(3,5-bis-trifluoromethyl-benzyl)-5-chloro-1H-[1,2,3]triazol-4-yl]-[5-(2-chloro-phenyl)-3-cyclopropyl-isoxazol-4-yl]-methanone | MS (ES) 575.0 (M+H). $^1$H NMR (400 MHz, CDCl$_3$) δ 7.92 (s, 1H), 7.67 (s, 2H), 7.62 (dd, 1H, J = 7.8, 1.4 Hz), 7.32 (dt, 1H, J = 7.8, 1.0 Hz), 7.26 (dt, 1H, J = 7.8, 1.4 Hz), 7.13 (dd, 1H, J = 7.8, 1.0 Hz), 5.55 (s, 2H), 2.31 (m, 1H), 1.16 (m, 2H), 1.06 (m, 2H). |
| 138 | [1-(3,5-bis-trifluoromethyl-benzyl)-5-chloro-1H-[1,2,3]triazol-4-yl]-[5-(2-chloro-phenyl)-3-methyl-isoxazol-4-yl]-methanone | MS (ES+) 549.0 (M+1). $^1$H NMR (400 MHz, CDCl$_3$) δ 7.89 (s, 1H), 7.65 (s, 2H), 7.62 (dd, 1H, J = 1.5, 7.8 Hz), 7.32 (dt, 1H, J = 1.4, 7.4 Hz), 7.26 (dt, 1H, J = 1.4, 7.8 Hz), 7.11 (dd, 1H, J = 1.0, 7.8 Hz), 5.53 (s, 2H), 2.52 (s, 3H). |
| 139 | [1-(3,5-Bis-trifluoromethyl-benzyl)-5-phenyl-1H-imidazol-4-yl]-[5-(2-chloro-phenyl)-3-(tetrahydro-pyran-2-yloxymethyl)-isoxazol-4-yl]-methanone | Exact Mass 689.1; MS (aspci): 690.0 (M+1), 687.9 (M−1); $^1$H NMR (300 MHz, CDCl$_3$) δ 7.72 (s, 1H), 7.45 (m, 1H), 7.32 (s, 1H), 7.32–7.18 (m, 6H), 7.10 (s, 2H), 7.02–7.08 (m, 2H), 5.02 (s, 2H), 4.81 (abq, J = 13.5, 22.5 Hz, 2H), 4.58 (m, 1H), 3.69 (m, 1H), 3.37 (m, 1H), 1.30–1.70 (m, 6H). |
| 140 | [5-(2-Chloro-phenyl)-3-(tetrahydro-pyran-2-yloxymethyl)-isoxazol-4-yl]-[1-(3,4-difluoro-benzyl)-5-pyridin-3-yl-1H-[1,2,3]triazol-4-yl]-methanone | MS (ES) 592.2 (M$^+$+1), Rf = 0.42 (50% EtOAc/CH$_2$Cl$_2$) |

Preparation 141

[1-(3,5-bis-trifluoromethyl-benzyl)-5-phenyl-1H-[1,2,3]triazol-4-yl]-[5-(2-chloro-phenyl)-3-[1,3]dioxolan-2-ylmethyl-3H-[1,2,3]triazol-4-yl]-methanone In a pressure vessel, combine 1-[1-(3,5-bis-trifluoromethyl-benzyl)-5-phenyl-1H-[1,2,3]triazol-4-yl]-3-(2-chlorophenyl)-propynone (0.506 g, 1 eq) in toluene (0.1 M), and 2-azido-methyl-[1,3]dioxolane (0.241 g, 2 eq). Heat in a 120° C. bath for 48 h. Then concentrate and purify by chromatography on silica gel to give the title compound. MS (ES) 663.6 (M+1), $^1$H NMR (300 MHz, CDCl$_3$): & 7.85 (br s, 1H), 7.78 (dd, J=7.7, 1.6 Hz, 1H), 7.61–7.49 (m, 3H), 7.41–7.10 (m, 7H), 5.46 (s, 2H), 5.32 (t, J=3.0 Hz, 1H), 4.97 (d, J=3.0 Hz, 2H), 3.70 (m, 4H).

Using a method similar to Preparation 141, the following compound may be prepared.

| Prep. # | Product | Physical Data |
|---|---|---|
| 142 | [1-(3,5-bis-trifluoromethyl-benzyl)-5-phenyl-1H-[1,2,3]triazol-4-yl]-[3-[2-(tert-butyl-dimethyl-silanyloxy)-ethyl-5-(2-chloro-phenyl)-3H-[1,2,3]triazol-4-yl]-methanone | MS (ES) 735.2 (M+1); TLC R$_f$ 0.35 (2% MeOH/CH$_2$Cl$_2$) |

Preparation 143

[1-(3,5-bis-trifluoromethyl-benzyl)-5-chloro-1H-[1,2,3]triazol-4-yl]-[5-(2-chloro-phenyl)-1H-[1,2,3]triazol-4-yl]-methanone Add trimethylsilylazide (4.0 mL, 30.1 mmol) to a solution of 1-[1-(3,5-bis-trifluoromethyl-benzyl)-5-chloro-1H-[1,2,3]triazol-4-yl]-3-(2-chloro-phenyl)-propynone (1.50 g, 3.04 mmol) in toluene (12 mL) in a sealed tube. Heat the solution to 110° C. for 8 h, then cool to RT and add additional trimethylsilyl azide (2.0 mL, 15 mmol). Heat to 110° C. for 16 h. Cool solution to RT, concentrate in vacuo, then add ether. Isolate the white precipitate by filtration to give 475 mg of the title compound. Concentrate the filtrate and purify the residue by flash chromatography using a linear gradient of 20% to 80% EtOAc/hexanes to give another 550 mg of the desired product. The solids are combined and dried under vacuum. (1.0 g, 63%). MS (ES+) 535.0 (M+1), MS (ES−) 533.0 (M−1); $^1$H NMR (400 MHz, CDCl$_3$) δ 14.56 (br s, 1H), 7.89 (s, 1H), 7.81 (s, 2H), 7.48 (m, 2H), 7.36 (m, 2H), 5.74 (s, 2H).

Preparation 144

[1-(3,5-bis-trifluoromethyl-benzyl)-5-chloro-1H-[1,2,3]triazol-4-yl]-[4-(2-chloro-phenyl)-2H-pyrazol-3-yl]-methanone and [1-(3,5-bis-trifluoromethyl-benzyl)-5-chloro-1H-[1,2,3]triazol-4-yl]-[5-(2-chloro-phenyl)-1H-pyrazol-4-yl]-methanone Add trimethylsilyldiazomethane (0.40 mL, 2 M in hexane) to a solution of 1-[1-(3,5-bis-trifluoromethyl-benzyl)-5-chloro-1H-[1,2,3]triazol-4-yl]-3-(2-chloro-phenyl)-propynone (0.15 g, 0.32 mmol) in 1:1 mixture THF and ether (2.0 mL). Stir at RT for 1 to 3 days, then concentrate under vacuum and purify the residue by flash chromatography (silica gel, hexanes/EtOAc gradient). Isomer 1: MS [ES] 534.1 (M+H)$^+$; $^1$H NMR (400 MHz, CHCl$_3$) δ 7.92 (s, 1H), 7.83 (s, 2H), 7.73 (s, 1H), 7.47 (m, 1H), 7.37 (m, 1H), 7.26–7.33 (m, 2H), 5.72 (s, 2H). Isomer 2: MS [ES] 534.1 (M+H)$^+$; $^1$H NMR (400 MHz, CHCl$_3$) δ 9.01 (s, 1H), 7.92 (s, 1H), 7.81 (s, 2H), 7.43–7.48 (m, 2H), 7.32–7.40 (m, 2H), 5.68 (s, 2H).

Using the method of General Preparation H, the following compounds may be prepared and isolated.

| Prep. # | Product | Physical Data |
|---|---|---|
| 145 | 3-chloropyridine-4-carboxaldehyde | MS (ES) 142.1 (M+1) |
| 146 | 4-chloropyridine-3-carboxaldehyde | MS (ES) 142.0, 144.0 (M+1) |
| 147 | 2-chloropyridine-3-carboxaldehyde | MS (electron impact) 141.2, 143.3 (M+) |

General Preparation I

Combine the appropriate aldehyde (1 eq) with hydroxylamine hydrochloride (1.1 eq) in a mixture of EtOH, water, and ice. Slowly add 1N NaOH (2.5 eq) and stir the mixture 2–4 h at RT. Adjust to pH 7 and extract with Et$_2$O or EtOAc. Dry the combined extracts over Na$_2$SO$_4$, concentrate, and dry the resulting solid. Use without further purification.

Using the above method, the following compounds may be prepared.

| Prep. # | Product | Physical Data |
|---|---|---|
| 148 | 3-chloropyridine-4-carboxaldehyde oxime | MS (ES) 157.1, 159.1 (M+1)$^+$. R$_f$ = 0.21 (6.25% MeOH/CH$_2$Cl$_2$). |
| 149 | 4-chloropyridine-3-carboxaldehyde oxime | MS (ES) 157.1, 159.1 (M+1) |
| 150 | 2-chloropyridine-3-carboxaldehyde oxime | MS (EI) 156.3, 158.3 (M+) |
| 151 | 2,6-dichlorobenzaldehyde oxime | R$_f$ = 0.51 (20:1 CHCl$_3$/MeOH); m.p. = 146.7–148.0° C. |
| 152 | 2,6-difluorobenzaldehyde oxime | R$_f$ = 0.35 (50:1 CHCl$_3$/MeOH); m.p. = 109.7–111.1° C. |

General Preparation H

Slowly add the appropriate halo-pyridine substrate (1 eq) to a cooled (−60 to −70° C.) solution of LDA (1.2 eq) in THF and stir for 1–3 h. Then add DMF (1.7 eq) dropwise the cold mixture for 1–2 h. Allow the mixture to warm to RT, quench with water, act with EtOAc. Dry the combined extracts over Na$_2$SO$_4$ and concentrate. Purify by chromatography on silica gel.

General Preparation J

Combine the appropriate oxime (1 eq) with N-chlorosuccinimide (1–1.2 eq) in DMF and stir at RT until reaction is complete. Then pour the reaction mixture into ice water and extract with Et$_2$O or EtOAc. Wash the combined extracts with water and dry over Na$_2$SO$_4$. Concentrate and dry the resulting solid under reduced pressure. Use without further purification.

Using the method of General Preparation J, the following compounds may be prepared and isolated.

| Prep. # | Product | Physical Data |
|---|---|---|
| 153 | 3-chloropyridine-4-carboxaldehyde chloro-oxime | R$_f$ = 0.71 (6.25% MeOH/CH$_2$Cl$_2$). $^1$H NMR (400 MHz, CDCl$_3$) δ 7.67 (d, 1H, J = 5.1 Hz), 8.67 (d, 1H, J = 5.1 Hz), 8.81 (s, 1H), 12.97 (s, 1H). |
| 154 | 4-chloropyridine-3-carboxaldehyde chloro-oxime | $^1$H NMR (400 MHz, CDCl$_3$) δ 7.74 (d, 1H, J = 5.5 Hz), 8.66 (d, 1H, J = 5.5 Hz), 8.74 (s, 1H), 12.85 (s, 1H). |
| 155 | 2-chloropyridine-3-carboxaldehyde chloro-oxime | MS (FD) 190.0, 192.0 (M+) |
| 156 | 2,6-dichlorobenzaldehyde chloro-oxime | R$_f$ = 0.36 (6:1 Hex/EtOAc); m.p. = 78.5–79.8° C. |
| 157 | 2,6-difluorobenzaldehyde chloro-oxime | m.p. = 109.8–110.8° C. |

General Preparation K

Combine the appropriate chloro-oxime (1.0 eq) and the alkyne of interest (1.0 eq) in EtOAc or Et$_2$O (0.5 M). Add triethylamine (2.5 eq) and stir the mixture at RT for 4–18 h. (The mixture may be heated to 50° C. to facilitate the reaction if desired.) When the reaction is complete, treat the mixture with saturated sodium bicarbonate solution, and extract with ether (2 times). Dry the combined organic layers over MgSO$_4$, then filter and concentrate in vacuo. Purify the residue by flash chromatography on silica gel to give the title compound.

By the above method, the following compounds may be prepared and isolated.

| Prep. # | Product | Physical Data |
|---|---|---|
| 158 | [1-(3,5-bis-trifluoromethyl-benzyl)-5-chloro-1H-[1,2,3]triazol-4-yl]-[5-(tert-butyl-dimethyl-silanyloxymethyl)-3-(2-chloro-phenyl)-isoxazol-4-yl]-methanone | MS (ES) 679.1 (M+1); TLC R$_f$ = 0.3 (50% Et$_2$O in hexanes). |
| 159 | [1-(3,5-bis-trifluoromethyl-benzyl)-5-phenyl-1H-[1,2,3]triazol-4-yl]-[5-(tert-butyl-dimethyl-silanyloxymethyl)-3-(2-chloro-phenyl)-isoxazol-4-yl]-methanone | MS (ES) 721.2 (M+1); TLC R$_f$ = 0.2 (50% Et$_2$O in hexanes). |
| 160 | [1-(3,5-bis-trifluoromethyl-benzyl)-5-chloro-1H-[1,2,3]triazol-4-yl]-[5-[2-(tert-butyl-dimethyl-silanyloxy)-ethyl]-3-(2-chloro-phenyl)-isoxazol-4-yl]-methanone | MS (ES) 692.9 (M$^+$+1); TLC R$_f$ = 0.5 (50% Et2O in hexanes). |
| 161 | [1-(3,5-bis-trifluoromethyl-benzyl)-5-pyridin-4-yl-1H-[1,2,3]triazol-4-yl]-[5-[2-(tert-butyl-dimethyl-silanyloxy)-ethyl]-3-(2-chloro-phenyl)-isoxazol-4-yl]-methanone | MS (ES) 736.0 (M$^+$+1); TLC R$_f$ = 0.3 (50% EtOAc in hexanes). |
| 162 | [1-(3,5-bis-trifluoromethyl-benzyl)-5-pyridin-4-yl-1H-[1,2,3]triazol-4-yl]-[5-(tert-butyl-dimethyl-silanyloxymethyl)-3-(2-chloro-phenyl)-isoxazol-4-yl]-methanone | MS (ES) 723 (M$^+$+1); TLC R$_f$ = 0.3 (50% EtOAc in hexanes). |
| 163 | [1-(3,5-bis-trifluoromethyl-benzyl)-5-pyridin-3-yl-1H-[1,2,3]triazol-4-yl]-[5-(tert-butyl-dimethyl-silanyloxymethyl)-3-(2-chloro-phenyl)-isoxazol-4-yl]-methanone | MS (ES) 722.0 (M$^+$+1); TLC R$_f$ = 0.4 (50% EtOAc in hexanes). |
| 164 | [1-(3,5-bis-trifluoromethyl-benzyl)-5-pyrazin-2-yl-1H-[1,2,3]triazol-4-yl]-[5-(tert-butyl-dimethyl-silanyloxymethyl)-3-(2-chloro-phenyl)-isoxazol-4-yl]-methanone | MS (ES) 723.3 (M+); TLC R$_f$ = 0.43 (40% EtOAc/hexanes) |
| 165 | [1-(3,5-bis-trifluoromethyl-benzyl)-5-pyrazin-2-yl-1H-[1,2,3]triazol-4-yl]-[3-(2-chloro-phenyl)-5-(1-methyl-1-trimethylsilanyloxy-ethyl)-isoxazol-4-yl]-methanone | MS (ES) 709.2 (M+); TLC R$_f$ = 0.25 (30% EtOAc/hexanes) |
| 166 | [1-(3,5-bis-trifluoromethyl-benzyl)-5-pyridin-4-yl-1H-[1,2,3]triazol-4-yl]-[3-(3-chloro-pyridin-4-yl)-5-(1-methyl-1-trimethylsilanyloxy-ethyl)-isoxazol-4-yl]-methanone | MS (ES) 709.1, 711.1 (M+1)$^+$. |
| 167 | [1-(3,5-bis-trifluoromethyl-benzyl)-5-chloro-1H-[1,2,3]triazol-4-yl]-[5-(tert-butyl-dimethyl-silanyloxymethyl)-3-(3-chloro-pyridin-4-yl)-isoxazol-4-yl]-methanone | MS (ES) 680.1, 683.1 (M+1)$^+$; R$_f$ = 0.21 (6.25% MeOH/CH$_2$Cl$_2$). |
| 168 | [1-(3,5-bis-trifluoromethyl-benzyl)-5-chloro-1H-[1,2,3]triazol-4-yl]-[5-(tert-butyl-dimethyl-silanyloxymethyl)-3-(4-chloro-pyridin-3-yl)-isoxazol-4-yl]-methanone | MS (ES) 680.1, 682.1 (M+1) |
| 169 | [1-(3,5-bis-trifluoromethyl-benzyl)-5-chloro-1H-[1,2,3]triazol-4-yl]-[5-(tert-butyl-dimethyl-silanyloxymethyl)-3-(2-chloro-pyridin-3-yl)-isoxazol-4-yl]-methanone | MS (ES) 680.3, 682.3 (M+1)$^+$; R$_f$ = 0.90 (6.25% MeOH/CH$_2$Cl$_2$). |
| 170 | [1-(3,5-bis-trifluoromethyl-benzyl)-5-chloro-1H-[1,2,3]triazol-4-yl]-[5-(tert-butyl-dimethyl-silanyloxymethyl)-3-(2,6-difluoro-phenyl)-isoxazol-4-yl]-methanone | R$_f$ = 0.41 (3:1 Hex/EtOAc); MS/ES (M+1) = 680.9 |
| 171 | [1-(3,5-bis-trifluoromethyl-benzyl)-5-chloro-1H-[1,2,3]triazol-4-yl]-[5-(tert-butyl-dimethyl-silanyloxymethyl)-3-(2,6-dichloro-phenyl)-isoxazol-4-yl]-methanone | R$_f$ = 0.44 (3:1 Hex/EtOAc); MS/ES (M+1) = 712.9 |

| Prep. # | Product | Physical Data |
|---|---|---|
| 172 | [1-(3,5-bis-trifluoromethyl-benzyl)-5-chloro-1H-[1,2,3]triazol-4-yl]-[5-(1-tert-butoxy-ethyl)-3-(2-chloro-phenyl)-isoxazol-4-yl]-methanone | TLC: $R_f$ = 0.57 (2:1 hexanes/EtOAc); MS (ES) 634.9 (M+1), 578.8 [(M−C(CH$_3$)$_3$)$^+$] |
| 173 | [1-(3,5-bis-trifluoromethyl-benzyl)-5-chloro-1H-[1,2,3]triazol-4-yl]-[3-(2-chloro-phenyl)-5-(1-methyl-1-trimethylsilanyloxy-ethyl)-isoxazol-4-yl]-methanone | TLC: $R_f$ = 0.63 (2:1 hexanes/EtOAc); MS (ES) 664.9 (M+1), 574.9 [(M−OSiMe$_3$)$^+$] |

General Preparation L

Dissolve the appropriate chlorotriazole (1 eq.) in the appropriate amine (20–120 eq.) and stir at 50–110° C. for 2–20 h. Dilute the solution with EtOAc and wash with 1N HCl, water, and saturated NaHCO$_3$. Dry the organic layer over MgSO$_4$, then filter and concentrate. Purify the crude material by flash chromatography on silica gel.

By the method of General Preparation L, using the appropriate starting materials, the following compounds may be prepared and isolated.

| Prep. # | Product | Physical Data |
|---|---|---|
| 174 | [1-(3,5-bis-trifluoromethyl-benzyl)-5-(4-methyl-piperazin-1-yl)-1H-[1,2,3]triazol-4-yl]-[5-[2-(tert-butyl-dimethyl-silanyloxy)-ethyl]-3-(2-chloro-phenyl)-isoxazol-4-yl]-methanone | MS (ES) 757.0 (M$^+$+1); TLC (1% MeOH in dichloromethane): $R_f$ = 0.1. |
| 175 | [1-(3,5-bis-trifluoromethyl-benzyl)-5-(thiomorpholin-4-yl)-1H-[1,2,3]triazol-4-yl]-[5-[2-(tert-butyl-dimethyl-silanyloxy)-ethyl]-3-(2-chloro-phenyl)-isoxazol-4-yl]-methanone | MS (ES) 760.0 (M$^+$+1); TLC (33% EtOAc in hexane): $R_f$ = 0.1. |
| 176 | [1-(3,5-bis-trifluoromethyl-benzyl)-5-dimethylamino-1H-[1,2,3]triazol-4-yl]-[5-[2-(tert-butyl-dimethyl-silanyloxy)-ethyl]-3-(2-chloro-phenyl)-isoxazol-4-yl]-methanone | MS (ES) 702.1 (M$^+$+1); TLC (33% EtOAc in hexane): $R_f$ = 0.1. |
| 177 | [1-(3,5-bis-trifluoromethyl-benzyl)-5-morpholin-4-yl-1H-[1,2,3]triazol-4-yl]-[5-[2-(tert-butyl-dimethyl-silanyloxy)-ethyl]-3-(2-chloro-phenyl)-isoxazol-4-yl]-methanone | MS (ES) 744.0 (M+1); 741.9 (M−1); TLC (50% Et$_2$O in hexane): $R_f$ = 0.1. |
| 178 | [1-(3,5-bis-trifluoromethyl-benzyl)-5-morpholin-4-yl-1H-[1,2,3]triazol-4-yl]-[5-(tert-butyl-dimethyl-silanyloxymethyl)-3-(3-chloro-pyridin-4-yl)-isoxazol-4-yl]-methanone | MS (ES) 731.0 (M+1)$^+$ |
| 179 | [1-(3,5-bis-trifluoromethyl-benzyl)-5-morpholin-4-yl-1H-[1,2,3]triazol-4-yl]-[5-(tert-butyl-dimethyl-silanyloxymethyl)-3-(4-chloro-pyridin-3-yl)-isoxazol-4-yl]-methanone | MS (ES) 731.1, 733.3 (M+1). |
| 180 | [1-(3,5-bis-trifluoromethyl-benzyl)-5-morpholin-4-yl-1H-[1,2,3]triazol-4-yl]-[5-(tert-butyl-dimethyl-silanyloxymethyl)-3-(2-chloro-pyridin-3-yl)-isoxazol-4-yl]-methanone | MS (ES) 731.4, 733.4 (M+1)$^+$; $R_f$ = 0.73 (6.25% MeOH/CH$_2$Cl$_2$). |
| 181 | [1-(3,5-bis-trifluoromethyl-benzyl)-5-morpholin-4-yl-1H-[1,2,3]triazol-4-yl]-[5-(tert-butyl-dimethyl-silanyloxymethyl)-3-(2,6-difluoro-phenyl)-isoxazol-4-yl]-methanone | $R_f$ = 0.23 (3:1 Hex/EtOAc); MS/ES (M+1) = 732.0 |
| 182 | [1-(3,5-bis-trifluoromethyl-benzyl)-5-morpholin-4-yl-1H-[1,2,3]triazol-4-yl]-[5-tert-butyl-dimethylsilanyloxymethyl)-3-(2,6-dichloro-phenyl)-isoxazol-4-yl]-methanone | $R_f$ = 0.24 (3:1 Hex/EtOAc); MS/ES (M+1) = 764.0 |
| 183 | [1-(3,5-bis-trifluoromethyl-benzyl)-5-morpholin-4-yl-1H-[1,2,3]triazol-4-yl]-[5-(2-chloro-phenyl)-3-(1-methyl-1-trimethylsilanyloxy-ethyl)-isoxazol-4-yl]-methanone | $R_f$ = 0.53 (2:1 Hex/EtOAc); MS/ES (M+1): 716.3 |

-continued

| Prep. # | Product | Physical Data |
|---|---|---|
| 184 | [1-(3,5-bis-trifluoromethyl-benzyl)-5-morpholin-4-yl-1H-[1,2,3]triazol-4-yl]-[5-(1-tert-butoxy-ethyl)-3-(2-chloro-phenyl)-isoxazol-4-yl]-methanone | TLC: $R_f$ = 0.35 (1:2 hexanes/EtOAc) MS (ES) 686.0 (M+1), 629.8 [(M—C(CH$_3$)$_3$)$^+$] |
| 185 | [1-(3,5-bis-trifluoromethyl-benzyl)-5-morpholin-4-yl-1H-[1,2,3]triazol-4-yl]-[3-(2-chloro-phenyl)-5-(1-methyl-1-trimethylsilanyloxy-ethyl)-isoxazol-4-yl]-methanone | m.p. 142–143° C.; TLC: $R_f$ = 0.47 (2:1 hexanes/EtOAc); MS (ES) 715.9 (M+1), 625.9 [(M—OSiMe$_3$)$^+$] |

Preparation 186

1-(3,5-bis-trifluoromethyl-benzyl)-4-(tri-n-butylstannanyl)-5-phenyl-1H-[1,2,3]triazole Heat a mixture of tri-n-butyl-phenylethynyl-stannane (11.0 g, 30.0 mmol) and 3,5-bis-trifluoromethyl-benzyl azide (9.68 g, 36.0 mmol) in toluene (40 mL) at reflux until reaction is complete. Concentrate to remove the solvent in vacuo and purify the residue by flash chromatography on silica gel (elution with 17% ether in hexanes) to give the title compound (17.5 g, 26.4 mmol, 88%). MS (ES) 660.1, 662.1 (M+1); LC Rf=0.1 (17% ether in hexanes).

Preparation 187 tert-Butoxycarbonylamino-acetic acid 4-[1-(3,5-bis-trifluoromethyl-benzyl)-5-morpholin-4-yl-1H-[1,2,3]triazole-4-carbonyl]-3-(2-chloro-phenyl)-isoxazol-5-yl methyl ester Add TEA (124 mg, 1.22 mmol), EDCI (75 mg, 0.39 mmol) and DMAP (30 mg, 0.24 mmol) to a solution of N-Boc glycine (68 mg, 0.39 mmol) and [1-(3,5-bis-trifluoromethyl-benzyl)-5-morpholin-4-yl-1H-[1,2,3]triazol-4-yl]-[3-(2-chloro-phenyl)-5-hydroxymethyl-isoxazol-4-yl]-methanone (150 mg, 0.244 mmol) in CH$_2$Cl$_2$. Stir the mixture at RT until the reaction is complete. Dilute the reaction mixture with CH$_2$Cl$_2$ (100 mL) and wash with water (3×50 mL). Dry the combined organic layers over MgSO$_4$, filter and concentrate in vacuo. Purify by chromatography on silica gel. MS (ES) 773.1 (M$^+$+1); TLC $R_f$=0.2 (50% EtOAc in hexanes).

General Preparation M

Heat a mixture of the appropriate heteroaryl bromide (1.0 eq), ethynyl-trimethyl-silane (2.0 eq), PdCl$_2$(PPh$_3$)$_2$ (0.1 eq), CuI (0.2 eq) and diisopropyl ethyl amine (10 eq) in DMF at 70° C. After 18 h., dilute with methylene chloride, and wash with water. Dry over MgSO$_4$, filter and concentrate in vacuo. Purify the residue by flash chromatography on silica gel to give the desired compound.

By the method of General Preparation M, using the appropriate starting materials, the following compound may be prepared and isolated.

| Prep. # | Product | Physical Data |
|---|---|---|
| 188 | 4-trimethylsilanylethynyl-pyridine | MS (ES) 176.0 (M+1); TLC $R_f$ = 0.1 (20% ether in hexanes). |

-continued

| Prep. # | Product | Physical Data |
|---|---|---|
| 189 | 2-trimethylsilanylethynyl-pyrazine | $^1$H NMR (300 MHz, CDCl$_3$) δ 8.65–8.71 (m, 1H), 8.52–8.55 (m, 1H), 8.45–8.48 (m, 1H), 0.30 (s, 9H). |

Preparation 190

5-trimethylsilanylethynyl-pyrimidine

Dissolve 5-bromopyrimidine (50.0 g, 314.4 mmol) in triethylamine (400 mL), add copper (1) iodide (1.20 g, 6.2 mmol) and stir mixture under nitrogen. After 15 min., add trimethylsilyl acetylene (53.3 mL, 377.3 mmol), followed by dichlorobis(triphenyl-phosphine) palladium (11) (8.82 g, 12.5 mmol) and stir at RT. After 3 h, filter the solution through Celite®, rinsing with ether. Concentrate the filtrate under reduced pressure. Purification by flash chromatography on silica gel eluting first with hexanes (100%), then with hexanes:EtOAc (3:1) gives the title compound: $^1$H NMR (300 MHz, CDCl$_3$) δ 9.10 (s, 1H), 8.77 (s, 2H), 0.27 (s, 9H).

Preparation 191

4-ethynyl-pyridine

Add K$_2$CO$_3$ (3.32 g, 24.0 mmol) to a solution of 4-trimethylsilanylethynyl-pyridine (3.51 g, 20.0 mmol) in MeOH (40 mL). After 10 min., add sat. aq. NH$_4$Cl solution (approx. 10 mL) and stir. After 10 min., add MgSO$_4$, filter and concentrate at RT. Purify by Kugelrohr distillation (50–55° C.) to afford the title compound (1.31 g, 64%). MS(ES) 104 (M+1). $^1$H NMR (400 MHz, CDCl$_3$) δ 3.29 (s, 1H); 7.34 (d, 2H, J=5.9 Hz); 8.59 (d, 2H, J=5.9 Hz).

Preparation 192

4-methyl-4-trimethylsilanyloxy-pent-2-ynal

Dissolve 3-methyl-3-trimethylsilyloxy-1-butyne (8.35 g, 53.4 mmol) in THF (200 mL) and cool to 40° C. Add n-butyllithium (26.7 mL of a 2.0 M solution in cyclohexane, 53.4 mmol, 1 eq.) dropwise over a 5 minute period. Stir for 10 min., then add dry DMF (8.27 mL, 7.81 g, 107 mmol, 2 eq.) in one portion. After 30 min., pour into a cooled (0° C.), vigorously stirred mixture of 10% $KH_2PO_4$ (290 mL, 213 mmol) and ether (300 mL). Separate the layers and wash the organic layer with water (2×200 mL). Dry (MgSO4), filter, and concentrate to give 9.4 g (94% crude) of a light oil. Use without further purification. TLC: $R_f$=0.40 (20:1 hexanes/EtOAc); $^1$H NMR (CDCl$_3$, 300 MHz) δ 9.03 (s, 1H), 1.35 (s, 6H), 0.02 (s, 9H).

General Preparation N

Dissolve the alkyne (1.0 eq) in ether (0.25 M) and add triethylamine (2.4 eq.). Add 2-chloro-N-hydroxybenzenecarboximidoyl chloride (1.2 eq.) as a solution in ether (1 M) dropwise via an addition funnel over a period of 2 h. After 24 h, dilute with ether and wash with water (2×) and brine. Dry (MgSO$_4$), filter, and concentrate to give a yellow oil. Purify by crystallization from hexanes, or by chromatography (silica gel, hexanes/EtOAc gradient).

By the method of General Preparation N, the following compounds may be prepared and isolated.

| Prep. # | Product | Physical Data |
|---|---|---|
| 193 | 3-(2-chloro-phenyl)-5-(tetrahydro-pyran-2-yloxymethyl)-isoxazole-4-carbaldehyde | $R_f$ = 0.63 (1:1 Hex/EtOAc); MS (ES) 322.1 (M+1). |
| 194 | 3-(2-chloro-phenyl)-5-(1-methyl-1-trimethylsilanyloxy-ethyl)-isoxazole-4-carbaldehyde | m.p. 88–90° C.; TLC: $R_f$ = 0.29 (10:1 hexanes/EtOAc); MS (ES) 338.2 (M+1), 248.0[(M—OSiMe$_3$)$^+$]. |

Preparation 195

5-(2-chloro-phenyl)-3-(tetrahydro-pyran-2-yloxymethyl)-isoxazole-4-carboxylic acid ethyl ester Add 2-(2-nitroethoxy)tetrahydropyran (41 mL, 270 mmol) dropwise in toluene (100 mL) to a solution of (2-chloro-phenyl)-propynoic acid ethyl ester (28.3 g, 135 mmol), 1,4-phenylene diisocyanate (67 g, 420 mmol) and triethylamine (15 mL) in toluene (900 mL). Stir at reflux for 10 h. While still warm (~70° C.), filter the reaction mixture through Celite®, washing the solids with EtOAc. Wash the filtrate with 1N HCl (500 mL) and brine (500 mL). Dry the organics over Na$_2$SO$_4$, filter and concentrate under reduced pressure. Purification by flash chromatography (silica gel, 85:15 Hexanes/EtOAc) gives the title compound (46.5 g, 94%). MS (m/e): 282 (M−C$_5$H$_8$O+H$^+$); $^1$H NMR (300 MHz, CDCl$_3$) δ 7.35–7.55 (m, 4H), 5.09 (d, J=13 Hz, 1), 4.85–4.91 (m, 2H), 4.15–4.22 (m, 2H), 3.91–4.01 (m, 1H), 3.52–3.61 (m, 1H), 1.49–1.92 (m, 6H), 1.12 (t, J=7 Hz, 3H); TLC $R_f$=0.53 (7:3 Hexanes/EtOAc).

Preparation 196

5-(2-chloro-phenyl)-3-(tetrahydro-pyran-2-yloxymethyl)-isoxazole-4-carboxylic acid methoxy-N-methyl-amide Add 2M iso-propylmagnesium chloride (717 mL, 1.4 mol) to a −10° C. solution of 5-(2-chloro-phenyl)-3-(tetrahydro-pyran-2-yloxymethyl)-isoxazole-4-carboxylic acid ethyl ester (175 g, 478 mmol) and N,O-dimethylhydroxylamine hydrochloride (56 g, 574 mmol) in THF (2 L). Stir the reaction for 45 min. and then slowly quench with a 1:1 mixture of sat. NH$_4$Cl and water (750 mL). Extract the mixture with EtOAc (3×500 mL). Wash the organic phase with brine (1000 mL), dry over Na$_2$SO$_4$, filter, and concentrate under reduced pressure. Purification by flash chromatography (silica gel, 7:3 hexanes/EtOAc) gives the title compound (27 g, 52%). MS (m/e): 381 (M+H)$^+$; m.p.=51–56° C.; $^1$H NMR (300 MHz, CDCl$_3$) δ7.32–7.60 (m, 4H), 5.00 (d, J=14 Hz, 1H), 4.78–4.81 (m, 1H), 4.73 (d, J=14 Hz, 1H), 3.85–3.98 (m, 1H), 3.52–3.61 (m, 1H), 3.40 (s, 3H), 3.10–3.29 (m, 3H), 1.50–1.82 (m, 6H); HPLC >99%; TLC $R_f$=0.41 (1:1 Hexanes/EtOAc).

Preparation 197

1-[5-(2-chloro-phenyl)-3-(tetrahydro-pyran-2-yloxymethyl)-isoxazol-4-yl]-3-pyridin-4-yl-propynone Add 2.5 M butyllithium (18.8 mL, 47 mmol) to a −10° C. solution of 4-ethynyl pyridine (4.2 g, 40.7 mmol) in THF (100 mL). Stir this solution for 15 min. and then add 5-(2-chloro-phenyl)-3-(tetrahydro-pyran-2-yloxymethyl)-isoxazole-4-carboxylic acid methoxy-methyl-amide (5.0 g, 13.1 mmol) in THF (100 mL). Stir the reaction at RT 15 h and then quench with water (100 mL) and extract with EtOAc (2×150 mL). Wash the organics with brine (150 mL), dry (Na$_2$SO$_4$), filter and concentrate under reduced pressure. Purification by flash chromatography (silica gel, 7:3 to 1:1 hexanes/EtOAc) gives the title compound (4.5 g, 81%). MS (m/e): 423 (M+H$^+$); $^1$H NMR (300 MHz, CDCl$_3$)δ 8.56 (d, J=5.8 Hz, 2H), 7.41–7.59 (m, 4H), 6.91 (d, J=5.8 Hz, 2H), 5.15 (d, J=14 Hz, 1H), 4.90–4.96 (m, 2H), 3.94–4.01 (m, 1H), 3.51–3.62 (m, 1H), 1.52–1.92 (m, 6H); TLC $R_f$=0.42 (9:1 EtOAc/Hexanes).

By a method analogous to Preparation 197, using the appropriate starting materials, the following compounds may be prepared and isolated.

| Prep. # | Product | Physical Data |
|---|---|---|
| 198 | 1-[5-(2-chloro-phenyl)-3-(tetrahydro-pyran-2-yloxymethyl)-isoxazol-4-yl]-3-pyridin-3-yl-propynone | MS (m/e): 423 (M+H$^+$); $^1$H NMR (300 MHz, CDCl$_3$) δ 8.57–8.59 (m, 1H), 8.12 (s, 1H), 7.41–7.62 (m, 5H), 7.21–7.25 (m, 1H), 5.15 (d, J = 14 Hz, 1H), 4.91–4.96 (m, 2H), 3.94–4.01 (m, 1H), 3.58–3.62 (m, 1H), 1.54–1.86 (m, 6H); TLC R$_f$ = 0.38 (7:3 EtOAc/Hexanes). |
| 199 | 1-[5-(2-chloro-phenyl)-3-(tetrahydro-pyran-2-yloxymethyl)-isoxazol-4-yl]-4-methyl-pent-2-yn-1-one | MS (m/e): 304 (M–C$_5$H$_8$O+H$^+$); $^1$H NMR (300 MHz, CDCl$_3$) δ 7.40–7.57 (m, 4H), 5.10 (d, J = 14 Hz, 1H), 4.87–4.93 (m, 2H), 3.93–4.00 (m, 1H), 3.57–3.61 (m, 1H), 2.24–2.31 (m, 1H), 1.52–1.92 (m, 6H), 0.87 (s, 3H), 0.85 (s, 3H); TLC R$_f$ = 0.34 (4:1 Hexanes/EtOAc). |
| 200 | 1-[5-(2-chloro-phenyl)-3-(tetrahydro-pyran-2-yloxymethyl)-isoxazol-4-yl]-but-2-yn-1-one | MS (m/e): 360 (M+H$^+$); $^1$H NMR (300 MHz, CDCl$_3$) δ 7.41–7.58 (m, 4H), 5.10 (d, J = 14 Hz, 1H), 4.88–4.93 (m, 2H), 3.93–3.99 (m, 1H), 3.57–3.60 (m, 1H), 1.53–1.88 (m, 9H); HPLC>99%; TLC R$_f$ = 0.53 (3:7 EtOAc/Hexanes). |
| 201 | 1-[5-(2-chloro-phenyl)-3-(tetrahydro-pyran-2-yloxymethyl)-isoxazol-4-yl]-3-pyridin-2-yl-propynone | MS [ES] 422.1 (M+H)+. 1H NMR (400 MHz, CHCl$_3$) δ 8.55 (m, 1H), 7.58 (m, 2H), 7.44 (m, 1H), 7.37 (m, 2H), 7.28 (m, 1H), 7.04 (dt, 1H, J = 7.8, 1.0 Hz), 5.16 (d, 1H, J = 13.8 Hz), 4.96 (d, 1H, J = 13.8 Hz), 4.94 (m, 1H), 3.94–4.00 (m, 1H), 3.57–3.62 (m, 1H), 1.53–1.91 (m, 6H). |

Preparation 202

1-[5-(2-chloro-phenyl)-3-(tetrahydro-pyran-2-yloxymethyl)-isoxazol-4-yl]-3-cyclopropyl-propynone Cool THF (200 mL) to –10° C. under nitrogen and add a 2.5 M solution of n-butyllithium in hexanes (56 mL, 140 mmol) dropwise, keeping the temperature below 5° C. Add 5-chloropentyne (6.89 g, 67.2 mmol) at 5° C. and stir for 6 h. Add a solution of 5-(2-chloro-phenyl)-3-(tetrahydro-pyran-2-yloxymethyl)-isoxazole-4-carboxylic acid methoxy-methyl-amide (8.5 g, 22.4 mmol) in THF (100 mL) dropwise to the reaction mixture and stir for 30 min., not allowing the temperature to rise above 10° C. Quench the reaction mixture with water (100 mL), extract with EtOAc (2×200 mL), wash with brine (200 mL), dry over sodium sulfate, filter and concentrate under reduced pressure. Purification by flash chromatography, eluting with 4:1 hexanes:EtOAc to 7:3 hexanes:EtOAc followed by reverse phase prep HPLC eluting with acetonitrile:water gives the title compound as a colorless oil (3.24 g, 38%): MS (m/e): 386 (M+H$^+$); $^1$H NMR (300 MHz, CDCl$_3$) δ 7.38–7.54 (m, 4H), 4.90–5.13 (m, 3H), 3.91–4.00 (m, 1H), 3.55–3.62 (m, 1H), 1.55–1.95 (m, 6H), 0.92–1.02 (m, 1H), 0.71–0.77 (m, 2H), 0.37–0.46 (m, 2H); TLC R$_f$=0.43 (7:3 Hexanes:EtOAc).

Preparation 203

5-(2-chloro-phenyl)-3-tetrahydro-pyran-2-yloxymethyl)-isoxazole-4-carbaldehyde Add 1 M diisobutylaluminum hydride (316 mL, 316 mmol) dropwise to a –78° C. solution of 5-(2-chloro-phenyl)-3-(tetrahydro-pyran-2-yloxymethyl)-isoxazole-4-carboxylic acid methoxy-methyl-amide (80 g, 211 mmol) in THF (1 L). Warm the reaction to RT and stir for 2 h. Quench the reaction with 1N HCl and add potassium sodium tartrate tetrahydrate (30 g). Stir for 30 min. and extract with methylene chloride (2×600 mL). Wash the organic phase with brine, dry over Na$_2$SO$_4$, filter and concentrate under reduced pressure to give the title compound (61.5 g, 90%): $^1$H NMR (300 MHz, CDCl$_3$) δ 9.90 (s, 1H), 7.41–7.62 (m, 4H), 5.12 (d, J=14 Hz, 1H), 4.88–4.96 (m, 2H), 3.90–4.01 (m, 1H), 3.55–3.62 (m, 1H), 1.54–1.86 (m, 6H); TLC R$_f$=0.59 (7:3 Hexanes:EtOAc).

Preparation 204

1-[5-(2-chloro-phenyl)-3-(tetrahydro-pyran-2-yloxymethyl)-isoxazol-4-yl]-3-pyrimidin-5-yl-prop-2-yn-1-ol Add 3M ethylmagnesium bromide (36 mL, 109 mmol) in diethyl ether to a 0° C. solution of 5-ethynyl-pyrimidine (8.1 g, 77 mmol) in THF (75 mL). Add 5-(2-chloro-phenyl)-3-(tetrahydro-pyran-2-yloxymethyl)-isoxazole-4-carbaldehyde (10 g, 31 mmol) in THF (75 mL) and stir 15 h at RT. Quench the reaction with 1N HCl and extract with diethyl ether (2×150 mL). Wash the organic phase with brine (150 mL), dry over sodium sulfate, filter and concentrate under reduced pressure. Purification by flash chromatography (silica gel, 1:1 to 3:7 hexanes/EtOAc) gives the title compound (5.3 g, 40%): $^1$H NMR (300 MHz, CDCl$_3$) δ 9.18 (s, 1H), 8.35 (s, 2H), 7.44–7.62 (m, 4H), 5.65 (t, J=14 Hz, 1H), 5.08–5.28 (m, 1H), 4.80–4.95 (m, 2H), 4.42–4.60 (m, 1H), 3.80–4.01 (m, 1H), 3.51–3.68 (m, 1H), 1.54–1.90 (m, 6H); TLC R$_f$=0.20 (3:7 Hexanes:EtOAc).

Preparation 205

1-[3-(2-chloro-phenyl)-5-(1-methyl-1-trimethylsilanyloxy-ethyl)-isoxazol-4-yl]-3-pyridin-3-yl-prop-2-yn-1-ol Dissolve 3-ethynylpyridine (206 mg, 2.0 mmol, 2 eq.) in THF (3 mL). Cool to 0° C. and add LDA (1.47 mL of a 1.5 M soln. in THF, 2.2 mmol, 2.2 eq.) dropwise. After 30 min., add 3-(2-chloro-phenyl)-5-(1-methyl-1-trimethylsilanyloxy-ethyl)-isoxazole-4-carbaldehyde (340 mg, 1.0 mmol) as a solution in THF (2 mL). Warm the mixture to RT. After 45 min., quench with 10% KH$_2$PO$_4$ (10 mL). Extract with EtOAc (2×15 mL), and wash the combined organic layers with brine (15 mL). Dry (MgSO$_4$), filter, and concentrate. Purify by chromatography (silica gel, hexanes/EtOAc 2:1 to 1:1 gradient) to provide 370 mg (84%) alcohol as an oil. TLC: R$_f$=0.33 (2:1 hexanes/EtOAc); MS(ES) 441.2 (M+1)$^+$.

Using a method similar to Preparation 205, with the appropriate starting materials, the following compound may be prepared.

| Prep. # | Product | Physical Data |
|---|---|---|
| 206 | 1-[3-(2-chloro-phenyl)-5-(tetrahydro-pyran-2-yloxymethyl)-isoxazol-4-yl]-3-pyridin-3-yl-prop-2-yn-1-ol | R$_f$ = 0.09 2:1 Hex/EtOAc MS (ES) 425.1 (M+1) |

General Preparation O

To the alcohol of interest (1 eq) in toluene, add MnO$_2$ (10 eq). Heat the reaction at 110° C. for 18 h. Cool the mixture to RT, add Celite®, and filter. Concentrate the filtrate and purify the residue by chromatography on silica gel (hexanes/EtOAc gradient) to afford the title compound.

Using the method of General Preparation O, the following compounds may be prepared and isolated.

| Prep. # | Product | Physical Data |
|---|---|---|
| 207 | 1-[3-(2-chloro-phenyl)-5-(tetrahydro-pyran-2-yloxymethyl)-isoxazol-4-yl]-3-pyridin-3-yl-propynone | R$_f$ = 0.19 (1:1 Hex/EtOAc); MS (ES) 423.1 (M+1)$^+$ |
| 208 | 1-[3-(2-chloro-phenyl)-5-(1-methyl-1-trimethylsilanyloxy-ethyl)-isoxazol-4-yl]-3-pyridin-3-yl-propynone | TLC: R$_f$ = 0.44 (2:1 hexanes/EtOAc); MS (ES) 439.1 (M+1)$^+$ |
| 209 | 1-[5-(2-chloro-phenyl)-3-(tetrahydro-pyran-2-yloxymethyl)-isoxazol-4-yl]-3-pyrimidin-5-yl-propynone | MS (m/e): 340 (M−C$_5$H$_8$O+H$^+$); $^1$H NMR (300 MHz, CDCl$_3$) δ 9.18 (s, 1H), 8.35 (s, 2H), 7.44–7.62 (m, 4H), 5.15 (d, J = 14 Hz, 1H), 4.90–495 (m, 2H), 3.94–4.00 (m, 1H), 3.58–3.62 (m, 1H), 1.54–1.85 (m, 6H); TLC R$_f$ = 0.53 (7:3 EtOAc/Hexanes). |

General Preparation P

To a solution of the THP-protected alcohol (1 eq) in THF/H$_2$O (1:1, 0.20 M) add an equal volume of glacial acetic acid. Heat solution at 60° C. for 18 h. Cool reaction to 0° C. and dilute with H$_2$O. Add 5N NaOH until reaction is basic, and extract with CH$_2$Cl$_2$, wash the organic layer with brine, dry over MgSO$_4$, and concentrate. Recrystallize the product from Hex/EtOAc (two crops). Dry crystals to afford the title compound.

Using the above method and the appropriate starting materials, the following compounds may be prepared.

| Prep. # | Product | Physical Data |
|---|---|---|
| 210 | 1-[5-(2-chloro-phenyl)-3-hydroxymethyl-isoxazol-4-yl]-4-methyl-pent-2-yn-1-one | R$_f$ = 0.25 (3:1 Hex/EtOAc); MS (ES) 304.1 (M+1) |
| 211 | 1-[5-(2-chloro-phenyl)-3-hydroxymethyl-isoxazol-4-yl]-but-2-yn-1-one | R$_f$ = 0.24 (2:1 Hex/EtOAc); MS (ES) 276.0 (M+1) |

General Preparation Q

To a solution of the appropriate alkyne (1 eq) in toluene (0.25 M) add the azide of interest (2 eq). Heat the mixture at 120° C. for 18 h in a sealed tube, then cool to r.t. and concentrate. Purify the residue by chromatography on silica gel to yield title compound.

Using the procedure above and the appropriate alkynes and azides, the following compounds may be prepared.

| Prep. # | Product | Physical Data |
|---|---|---|
| 212 | [3-(2-chloro-phenyl)-5-(tetrahydro-pyran-2-yloxymethyl)-isoxazol-4-yl]-[1-(3,5-dichloro-benzyl)-5-pyridin-3-yl-1H-[1,2,3]triazol-4-yl]-methanone | R$_f$ = 0.38 (1:1 Hex/EtOAc); MS (ES) 624.0, 626.0 (M+1). |
| 213 | [3-(2-chloro-phenyl)-5-(tetrahydro-pyran-2-yloxymethyl)-isoxazol-4-yl]-[5-pyridin-3-yl-1-(3-trifluoromethoxy-benzyl)-1H-[1,2,3]triazol-4-yl]-methanone | R$_f$ = 0.55 (1:2 Hex/EtOAc); MS (ES) 640.1 (M+1). |
| 214 | [3-(2-chloro-phenyl)-5-(tetrahydro-pyran-2-yloxymethyl)-isoxazol-4-yl]-[1-(3,5-dimethyl-benzyl)-5-pyridin-3-yl-1H-[1,2,3]triazol-4-yl]-methanone | R$_f$ = 0.54 (1:2 Hex/EtOAc); MS (ES) 584.2 (M+1). |
| 215 | [3-(2-Chloro-phenyl)-5-(tetrahydro-pyran-2-yloxymethyl)-isoxazol-4-yl]-[1-(2-fluoro-5-trifluoromethyl-benzyl)-5-pyridin-3-yl-1H-[1,2,3]triazol-4-yl]-methanone | Rf = 0.31 (1:2 Hex/EtOAc) MS (ES) 642.1 (M+1) |

-continued

| Prep. # | Product | Physical Data |
|---|---|---|
| 216 | [3-(2-Chloro-phenyl)-5-(tetrahydro-pyran-2-yloxymethyl)-isoxazol-4-yl]-[1-(2-methoxy-5-trifluoromethoxy-benzyl)-5-pyridin-3-yl-1H-[1,2,3]triazol-4-yl]-methanone | Rf = 0.62 (1:2 Hex/EtOAc)<br>MS (ES) 670.1 (M+1) |

General Preparation R

Add the appropriate sodium carboxylate (2 eq.) to a solution of 2-bromo-1-(2-chloro-phenyl)-ethanone (1 eq.) in DMF (0.8M). Stir mixture at RT overnight, then dilute with water and brine and extract with ether. Combine the organic layers and wash with 20% $Na_2SO_3$ (50 mL) and brine (50 mL), then dry, filter, and concentrate to give the product.

Alternatively, add sodium hydride (1.6 eq.) to a solution of the appropriate carboxylic acid (1.7 eq.) in DMF (0.5M). Stir mixture at RT for 1 h., then add 2-bromo-1-(2-chloro-phenyl)-ethanone (1 eq.). Stir solution at RT overnight. Add water and brine, then extract with ether. Combine the organic layers and wash with water, and brine, then dry, filter and concentrate. Purify the crude material by flash chromatography.

Using one of the above methods and the appropriate starting materials, the following compounds may be prepared and isolated.

| Prep. # | Product | Physical Data |
|---|---|---|
| 217 | acetic acid 2-(2-chloro-phenyl)-2-oxo-ethyl ester | MS (ES+) 213.0 (M+1);<br>$^1$H NMR (400 MHz, CDCl$_3$) δ 7.60 (m, 1H), 7.43 (m, 2H), 7.34 (m, 1H), 5.18 (s, 2H), 2.16 (s, 3H). |
| 218 | isobutyric acid 2-(2-chloro-phenyl)-2-oxo-ethyl ester | MS (ES+) 241.0 (M+1);<br>$^1$H NMR (400 MHz, CDCl$_3$) δ 7.57 (m, 1H), 7.41 (m, 2H), 7.33 (m, 1H), 5.14 (s, 2H), 2.64 (m, 1H), 1.16 (d, 6H, J = 7.3 Hz). |
| 219 | cyclopropane-carboxylic acid 2-(2-chloro-phenyl)-2-oxo-ethyl ester | MS (ES+) 239.1 (M+H)$^+$;<br>$^1$H NMR (400 MHz, CDCl$_3$) δ 7.60 (m, 1H), 7.43 (m, 2H), 7.34 (m, 1H), 5.18 (s, 2H), 1.73 (m, 1H), 1.05 (m, 2H), 0.93 (m, 2H). |

General Preparation S

Add $BF_3.OEt_2$ (0.5 eq.) to a mixture of acetamide (5.2 eq.) and the appropriate ester (1 eq.). Warm mixture to 130° C. for 4 h., then cool to RT. Add saturated $NaHCO_3$ or 20% $Na_2CO_3$ solution, and extract with ether. Combine the organic layers and wash with brine, then dry, filter, and concentrate to give the crude material. Purify by flash chromatography. The above method may be used to prepare the following compounds.

| Prep. # | Product | Physical Data |
|---|---|---|
| 220 | 4-(2-chloro-phenyl)-2-methyl-oxazole | MS (ES+) 194.0 (M+1);<br>$^1$H NMR (400 MHz, CDCl$_3$) δ 8.22 (s, 1H), 8.07 (dd, 1H, J = 1.5, 7.8 Hz), 7.41 (dd, 1H, J = 1.0, 7.8 Hz), 7.32 (dt, 1H, J = 1.0, 7.8 Hz), 7.21 (dt, 1H, J = 1.5, 7.8 Hz), 2.51 (s, 3H). |
| 221 | 4-(2-chloro-phenyl)-2-isopropyl-oxazole | MS (ES+) 222.0 (M+1);<br>$^1$H NMR (400 MHz, CDCl$_3$) δ 8.22 (s, 1H), 8.11 (dd, 1H, J = 2.0, 7.8 Hz), 7.41 (dd, 1H, J = 1.5, 7.8 Hz), 7.32 (dt, 1H, J = 1.5, 7.8 Hz), 7.20 (dt, 1H, J = 2.0, 7.8 Hz), 3.14 (septet, 1H, J = 7.3 Hz), 1.38 (d, 6H, J = 7.3 Hz). |
| 222 | 4-(2-chloro-phenyl)-2-cyclopropyl-oxazole | MS (ES+) 220.1 (M+H);<br>$^1$H NMR (400 MHz, CDCl$_3$) δ 8.16 (s, 1H), 8.09 (dd, 1H, J = 7.8, 1.4), 7.42 (dd, 1H, J = 7.8, 1.4), 7.33 (dt, 1H, J = 7.8, 1.4), 7.21 (dt, 1H, J = 7.8, 1.4), 2.13 (m, 1H), 1.12–1.15 (m, 2H), 1.03–1.10 (m, 2H). |

General Preparation T

To a solution of the appropriate oxazole (1 eq.) in $CCl_4$ (1 M), add freshly recrystallized NBS (1.1 eq.) and $(PhCO)_2O_2$ (5 mg). Stir mixture at RT for 18–24 h, then filter through a pad of Celite® and concentrate the filtrate. Purify the crude material by flash chromatography. The following compounds may be prepared and isolated using the method of General Preparation T.

| Prep. # | Product | Physical Data |
|---|---|---|
| 223 | 5-bromo-4-(2-chloro-phenyl)-2-methyl-oxazole | MS (ES+) 271.9, 273.9 (M+1);<br>$^1$H NMR (400 MHz, CDCl$_3$) δ 7.44 (m, 2H), 7.31 (m, 2H), 2.51 (s, 3H). |
| 224 | 5-bromo-4-(2-chloro-phenyl)-2-isopropyl-oxazole | MS (ES+) 300.0, 302.0 (M+1);<br>$^1$H NMR (400 MHz, CDCl$_3$) δ 7.44 (m, 2H), 7.30 (m, 2H), 3.12 (septet, 1H, J = 6.8 Hz), 1.38 (d, 6H, J = 6.8 Hz). |
| 225 | 5-bromo-4-(2-chloro-phenyl)-2-cyclopropyl-oxazole | MS (ES+) 298.0, 300.0 (M+2);<br>$^1$H NMR (400 MHz, CDCl$_3$) δ 7.44 (m, 2H), 7.32 (m, 2H), 2.11 (m, 1H), 1.05–1.17 (m, 4H). |

General Preparation U

Add Mg turnings (1.2 eq.) and a small crystal of iodine to a solution of the appropriate 5-bromo-oxazole (1 eq.) in freshly distilled THF (0.2 M). Stir the mixture at reflux for 14 h., then cool to RT. Add via cannula a solution of desired carbaldehyde (0.8 eq.) in THF (0.3 M). Stir the solution at RT for 2–18 h. Dilute solution with water and add saturated $NaHCO_3$ or 1N HCl, then extract with EtOAc. Combine the organic layers and wash with aqueous saturated $NaHCO_3$ and brine, then dry, filter, and concentrate. Purify the crude material by flash chromatography.

Alternatively, add t-BuLi (2 eq.) to a −78° C. solution of the appropriate 5-bromo-oxazole (1 eq.) in THF (0.9 M). Stir solution at −78° C. for 15 min., then add via cannula a solution of desired carbaldehyde (0.9 eq.) in THF (0.2 M). Stir the solution at −78° C. for 30 min., then at RT for 60 h. Dilute the solution with EtOAc and wash with NaHCO₃ and brine, then dry, filter, and concentrate the organic phase. Purify the crude material by flash chromatography.

Using one of the methods described above, the following compounds may be prepared and isolated.

zole-4-carbaldehyde (1.44 g, 3.60 mmol) as a solution in 5 mL of methanol. To this mix, add (995 mg, 7.20 mmol) of potassium carbonate and mix the solution for 18 h. Dilute with ether and saturated NaHCO₃, and extract with ether 3 times, wash the organics again with saturated NaHCO₃, and dry the combined organics with MgSO₄. Filter and concentrate. Purify by chromatography (silica gel, hexanes/EtOAc

| Prep. # | Product | Physical Data |
| --- | --- | --- |
| 226 | [1-(3,5-bis-trifluoromethyl-benzyl)-5-pyridin-4-yl-1H-[1,2,3]triazol-4-yl]-[4-(2-chloro-phenyl)-2-methyl-oxazol-5-yl]-methanol | MS (ES+) 593.9 (M+1), MS (ES−) 591.9 (M−1). |
| 227 | [1-(3,5-bis-trifluoromethyl-benzyl)-5-chloro-1H-[1,2,3]triazol-4-yl]-[4-(2-chloro-phenyl)-2-methyl-oxazol-5-yl]-methanol | MS (ES+) 551.1 (M+1), MS (ES−) 549.1 (M−1). |
| 228 | [1-(3,5-bis-trifluoromethyl-benzyl)-5-chloro-1H-[1,2,3]triazol-4-yl]-[4-(2-chloro-phenyl)-2-isopropyl-oxazol-5-yl]-methanol | MS (ES+) 579.0 (M+1)⁺, MS (ES−) 577.0 (M−1)⁻. ¹H NMR (400 MHz, CDCl₃) δ 7.86 (s, 1H), 7.73 (s, 2H), 7.34 (m, 2H), 7.20 (m, 2H), 5.96 (d, 1H, J = 5.9 Hz), 5.52 (s, 2H), 3.52 (d, 1H, J = 5.9 Hz), 3.07 (sept., 1H, J = 7.3 Hz), 1.31 (d, 3H, J = 6.8 Hz), 1.30 (d, 3H, J = 7.3 Hz). |
| 229 | [1-(3,5-bis-trifluoromethyl-benzyl)-5-chloro-1H-[1,2,3]triazol-4-yl]-[4-(2-chloro-phenyl)-2-cyclopropyl-oxazol-5-yl]-methanol | MS (ES+) 577.1 (M+H)+. ¹H NMR (400 MHz, CDCl₃) δ 7.89 (s, 1H), 7.77 (s, 2H), 7.37 (m, 2H), 7.25 (m, 2H), 5.95 (d, 1H, J = 6.6 Hz), 5.55 (s, 2H), 3.13 (d, 1H, J = 6.6 Hz), 2.08 (m, 1H), 1.15 (m, 2H), 1.06 (m, 2H). |

Preparation 230

1-(3,5-bis-trifluoromethyl-benzyl)₄-ethynyl-5-phenyl-1H-[1,2,3]triazole

To sodium hydride (188 mg of a 60% solution in mineral oil, 113 mg clean, 4.70 mmol) in 14 mL of benzene and 2.5 mL of tetrahydrofuran, add (2-oxo-propyl)-phosphonic acid dimethyl ester (743 mg, 618 μL, 4.48 mmol) as a solution in 5 mL of benzene at 0° C. dropwise. The mix remains white and produces some gas. After 1 h at 0° C., add tosyl azide (940 mg, 4.70 mmol) as a solution in 2.5 mL of benzene and warm the mixture to RT. After 2.3 hours, pour the mix through a plug of Celite® rinsing with tetrahydrofuran, benzene, and ether. Concentrate the filtrate and purify the residue by chromatography (Hexanes/EtOAc gradient) to provide 794 mg of (1-Diazo-2-oxo-propyl)-phosphonic acid dimethyl ester as a yellow solid. This material may be used directly. Exact Mass 192.03: mass spectrum (aspci): m/z=165.0 (M+1 (—N₂).

To the (1-Diazo-2-oxo-propyl)-phosphonic acid dimethyl ester (794 mg, 4.20 mmol) in 70 mL of methanol, add 1-(3,5-bis-trifluoromethyl-benzyl)-5-phenyl-1H-[1,2,3]triagradient) to provide 764 mg of the title compound. Exact Mass 395.09 spectrum (aspci): m/z=396.1 (M+1), 394.0 (M−1); ¹H NMR (250 MHz, CDCl₃) δ 7.73 (s, 1H), 7.55–7.40 (m, 4H), 7.42–7.30 (m, 3H), 5.52 (s, 2H), 3.21 (s, H).

By a method analogous to Preparation 230, the following compounds may be prepared and isolated.

| Prep. # | Product | Physical Data |
| --- | --- | --- |
| 231 | 4-[3-(3,5-bis-trifluoromethyl-benzyl)-5-ethynyl-3H-[1,2,3]triazol-4-yl]-pyridine | Exact Mass 396.08 spectrum (aspci): m/z = 397.1 (M+1), 395.1 (M−1); ¹H NMR (250 MHz, CDCl₃) δ 8.72 (d, J = 6.0 Hz, 2H), 7.77 (s, 1H), 7.48 (s, 2H), 7.22 (d, J = 6.0 Hz, 2H), 5.64 (s, 2H), 3.22 (s, 1H). |

General Preparation V

Dissolve the appropriate alkyne (9.76 mmol) in THF (50 mL) and cool to −78° C. Add a solution of MeMgBr (3eq, 3.0M in ether) and stir at −78° C. for 1.5 hours, then add 2-chlorobenzaldehyde (3eq). Stir solution at −78° C. for 1 hour, then at RT for 2 hours. Dilute the solution with ether (100 mL) and wash with 1N HCl (30 mL), saturated NaHCO₃ (50 mL), and brine (50 mL). Dry, filter, and concentrate the organic phase then purify the crude material by flash chromatography (silica gel, hexanes/EtOAc gradient) to give the title compound.

By a method similar to General Preparation V, the following compounds may be prepared and isolated.

| Prep # | Product | Physical Data |
|---|---|---|
| 232 | 3-[1-(3,5-bis-trifluoromethyl-benzyl)-5-phenyl-1H-[1,2,3]triazol-4-yl]-1-(2-chloro-phenyl)-prop-2-yn-1-ol | MS (ES) 536.0 (M+1); $^1$H NMR (250 MHz, CDCl$_3$) δ 7.71 (s, 1H), 7.56 (m, 1H), 7.43 (s, 2H), 7.35–7.48 (m, 3H), 7.09–7.34 (m, 5H), 5.90 (s, 1H), 5.57 (s, 2H). |
| 233 | 3-[1-(3,5-bis-trifluoromethyl-benzyl)-5-pyridin-4-yl-1H-[1,2,3]triazol-4-yl]-1-(2-chloro-phenyl)-prop-2-yn-1-ol | MS (ES) 537.0 (M+1) 535.0 (M−1); $^1$H NMR (250 MHz, CDCl$_3$) δ 8.65 (d, J = 6.25 Hz, 2H), 7.77 (s, 1H), 7.60 (m, 1H), 7.48 (s, 2H), 7.10–7.35 (m, 5H), 5.92 (s, 1H), 5.63 (s, 2H). |

General Preparation W

Under N$_2$, charge an oven-dried flask with oxalyl chloride (2M in CH$_2$Cl$_2$, 1.2 eq) and chill in a dry ice/acetone slush. Add DMSO (3 eq) slowly by syringe and stir 45 minutes. Add the alcohol of interest (1 eq) in anhydrous CH$_2$Cl$_2$ (0.4 M) slowly by syringe and stir 1 hour. Add TEA (5 eq) slowly by syringe and stir 90 minutes while warming to room temp. Quench with saturated aqueous NH$_4$Cl and H$_2$O, extract with ether, wash combined organics with brine, dry over MgSO$_4$, filter and concentrate under vacuum. Purify by flash chromatography (silica gel, EtOAc/Hexane gradient) to give the title compound.

By a method similar to General Preparation W, the following compounds may be prepared and isolated.

General Preparation X

Combine the alkyne of interest (1 eq) in benzene or toluene (0.1 M), with the appropriate nitro compound (1.5 eq), 1,4-phenylene diisocyanate (3 eq) and TEA (10 drops/mmol A). Attach a reflux condensor and heat to reflux. After 20 hours, add additional nitro compound (0.5 eq), 1,4-phenylene diisocyanate (1 eq) and TEA, stir 6 hours. Remove from heat, add H$_2$O and stir 20 min. Filter through Celite®, remove H$_2$O, dry over MgSO$_4$, filter and concentrate under vacuum. Purify by chromatography on silica gel to give the title compound.

By a method similar to General Preparation X, the following compounds may be prepared and isolated.

| Prep. # | Product | Physical Data |
|---|---|---|
| 234 | 3-[1-(3,5-bis-trifluoromethyl-benzyl)-5-phenyl-1H-[1,2,3]triazol-4-yl]-1-(2-chloro-phenyl)-propynone | MS (ES) 534.0 (M+1), $^1$H NMR (CDCl3): δ 8.03 (m, 1H), 7.86 (s, 1H), 7.63–7.30 (m, 10H), 5.70 (s, 2H) |
| 235 | 3-[1-(3,5-bis-trifluoromethyl-benzyl)-5-pyridin-4-yl-1H-[1,2,3]triazol-4-yl]-1-(2-chloro-phenyl)-propynone | MS (ES) 534.9 (M+1), $^1$H NMR (300 MHz, CDCl3): δ 8.86 (d, J = 6.0 Hz, 2H), 8.02 (ap d, 1H), 7.90 (s, 1H), 7.60 (s, 2H), 7.56–7.31 (m, 5H), 5.74 (s, 2H). |

| Prep. # | Product | Physical Data |
|---|---|---|
| 236 | [5-[1-(3,5-bis-trifluoromethyl-benzyl)-5-pyridin-4-yl-1H-[1,2,3]triazol-4-yl]-3-(tetrahydro-pyran-2-yloxymethyl)-isoxazol-4-yl]-(2-chloro-phenyl)-methanone | MS (ES) 691.9 (M+1), 607.8 (M − C$_5$H$_8$O) + H$^+$); TLC (3% MeOH/CH$_2$Cl$_2$), Rf = 0.53. |
| 237 | [5-[1-(3,5-bis-trifluoromethyl-benzyl)-5-phenyl-1H-[1,2,3]triazol-4-yl]-3-(tetrahydro-pyran-2-yloxymethyl)-isoxazol-4-yl]-(2-chloro-phenyl)-methanone | MS (ES) 689.0 (M−1); TLC (30% EtOAc/Hexane × 2), Rf = 0.30. |
| 238 | [5-[1-(3,5-bis-trifluoromethyl-benzyl)-5-pyridin-4-yl-1H-[1,2,3]triazol-4-yl]-3-(2,2-dimethoxy-ethyl)-isoxazol-4-yl]-(2-chloro-phenyl)-methanone | MS (ES) 665.9 (M+1); TLC (30% EtOAc/Hexane), Rf = 0.16. |
| 239 | [5-[1-(3,5-bis-trifluoromethyl-benzyl)-5-phenyl-1H-[1,2,3]triazol-4-yl]-3-(2,2-dimethoxy-ethyl)-isoxazol-4-yl]-(2-chloro-phenyl)-methanone | MS (ES) 665.9 (M+1); TLC (30% EtOAc/Hexane), Rf = 0.42. |

General Preparation Y

Dilute the THP-protected alcohol of interest (1 eq) in a solution of acetic acid/H$_2$O/THF (2/1/1). Attach a reflux condensor, place in 60° C. bath, and stir 24 hours. Purify chromatography on silica gel to give the title compound.

Using a method similar to General Preparation Y, with the appropriate starting material, the title compounds are prepared and isolated.

| Prep. # | Product | Physical Data |
|---|---|---|
| 240 | {5-[1-(3,5-bis-trifluoromethyl-benzyl)-5-phenyl-1H-[1,2,3]triazol-4-yl]-3-hydroxymethyl-isoxazol-4-yl}-(2-chloro-phenyl)-methanone | MS (ES) 607.0 (M+1), $^1$H NMR (CDCl$_3$): δ 7.88 (s, 1H), 7.63–7.46 (m, 4H), 7.41 (s, 2H), 7.29–7.08 (m, 5H), 5.46 (s, 2H), 4.87 (d, J = 7.3 Hz, 2H), 3.86 (t, J = 7.3 Hz, 1H) |
| 241 | {5-[1-(3,5-bis-trifluoromethyl-benzyl)-5-pyridin-4-yl-1H-[1,2,3]triazol-4-yl]-3-hydroxymethyl-isoxazol-4-yl}-(2-chloro-phenyl)-methanone | MS (ES) 607.9 (M+1), $^1$H NMR (CDCl$_3$): δ 8.78 (dd, J = 4.3, 1.8 Hz, 2H), 7.89 (s, 1H), 7.53 (dd, J = 7.6, 2.2 Hz, 1H), 7.43 (s, 2H), 7.33–7.27 (m, 2H), 7.12 (dd, J = 4.5, 1.8 Hz, 2H), 7.07 (dd, J = 7.6, 1.9 Hz, 1H), 5.46 (s, 2H), 4.85 (s, 2H). |

General Preparation Z

Under N$_2$, charge an oven-dried flask with oxalyl chloride (2M in CH$_2$Cl$_2$, 1.2 eq) and chill in a dry ice/acetone slush. Add DMSO (3 eq) slowly by syringe and stir 15 minutes. Add the hydroxymethyl isoxazole of interest (1 eq) in anhydrous CH$_2$Cl$_2$ (0.4 M) slowly by syringe and stir 1 hour. Add TEA (5 eq) slowly by syringe and stir 2 hours and allow to warm to RT. Quench with H$_2$O, extract with ether, dry over MgSO$_4$, filter and concentrate under vacuum.

By using a method similar to General Preparation Z, the following compounds are prepared and isolated.

Preparation 244

[5-[1-(3,5-bis-trifluoromethyl-benzyl)-5-phenyl-1H-[1,2,3]triazol-4-yl]4-(2-chloro-benzoyl)-isoxazol-3-yl]-acetaldehyde Combine [5-[1-(3,5-bis-trifluoromethyl-benzyl)-5-phenyl-1H-[1,2,3]triazol-4-yl]-3-(2,2-dimethoxy-ethyl)-isoxazol-4-yl]-(2-chloro-phenyl)-methanone (1 eq) in acetone/H$_2$O (4:1) and p-toluenesulfonic acid (1 eq) with stirring. Attach a reflux condensor and stir overnight in a 60° C. oil bath. Neutralize with saturated aqueous NaHCO$_3$, extract with ethyl acetate, dry over MgSO$_4$, filter, and concentrate under vacuum. $^1$H NMR (CDCl$_3$): δ 9.84 (s, 1H), 7.83 (s, 1H), 7.56–7.09 (m, 11H), 5.43 (s, 2H), 4.09 (s, 2H).

By a method similar to Preparation 244, using the appropriate starting materials, the following compound may be prepared and isolated.

| Prep. # | Product | Physical Data |
|---|---|---|
| 242 | 5-[1-(3,5-bis-trifluoromethyl-benzyl)-5-pyridin-4-yl-1H-[1,2,3]triazol-4-yl]-4-(2-chloro-benzoyl)-isoxazole-3-carbaldehyde | $^1$H NMR (CDCl$_3$): δ 10.11 (s, 1H), 8.78 (ap d, 2H). 7.86 (s, 1H), 7.75 (dd, J = 7.5, 1.8 Hz, 1H), 7.45–6.88 (m, 7H), 5.54 (s, 2H). |
| 243 | 5-[1-(3,5-bis-trifluoromethyl-benzyl)-5-phenyl-1H-[1,2,3]triazol-4-yl]-4-(2-chloro-benzoyl)-isoxazole-3-carbaldehyde | MS (ES) 605.1 (M+1), $^1$H NMR (CDCl$_3$): δ 10.06 (s, 1H), 7.75 (s, 1H), 7.63 (dd, J = 7.5, 1.8 Hz, 1H), 7.48–6.97 (m, 10H), 5.43 (s, 2H). |

| Prep. # | Product | Physical Data |
|---|---|---|
| 245 | [5-[1-(3,5-bis-trifluoromethyl-benzyl)-5-pyridin-4-yl-1H-[1,2,3]triazol-4-yl]-4-(2-chloro-benzoyl)-isoxazol-3-yl]-acetaldehyde | $^1$H NMR (CDCl$_3$): δ 9.84 (s, 1H), 8.78 (app t, 2H), 7.87 (br s, 2H), 7.59–7.06 (m, 7H), 5.46 (s, 2H), 4.10 (s, 2H) |

General Preparation AA

Combine the appropriate keto-aldehyde (1 eq) in AcOH, then add hydrazine (1–3 eq) and stir at 25–80° C. After 1–4 hours, concentrate the solution and dissolve the crude material in EtOAc and wash with saturated NaHCO$_3$ and brine. Dry, filter, and concentrate the organic phase and purify the crude material by flash chromatography (silica gel) to give the title compound.

Using the method of General Preparation AA, with the appropriate starting materials, the title compounds are prepared and isolated.

| Prep # | Product | Physical Data |
|---|---|---|
| 246 | 3-[1-(3,5-bis-trifluoromethyl-benzyl)-5-phenyl-1H-[1,2,3]triazol-4-yl]-4-(2-chloro-phenyl)-isoxazolo[3,4-d]pyridazine | MS (ES) 601.1 (M+1), $^1$H NMR (CDCl$_3$): δ 9.59 (s, 1H), 7.87 (s, 1H), 7.75–7.15 (m, 11H), 5.56 (s, 2H). |
| 247 | 3-[1-(3,5-bis-trifluoromethyl-benzyl)-5-pyridin-4-yl-1H-[1,2,3]triazol-4-yl]-4-(2-chloro-phenyl)-isoxazolo[3,4-d]pyridazine | MS (ES) 601.9 (M+1), TLC Rf 0.15 (50% EtOAc/Hexane × 2). |

General Preparation BB

Dissolve the appropriate keto-aldehyde (1 eq.) in acetic acid (0.15 M), add ammonium acetate (5 eq.), and stir at 65° C. for 90 min. Remove the acetic acid under reduced pressure, and neutralize the residue with saturated aqeous NaHCO$_3$. Extract with ether, dry over MgSO$_4$, filter, and concentrate under vacuum. Purify by chromatography on silica gel (Hexanes/EtOAc gradient) to give the desired compounds.

By using the method of General Preparation BB, using the appropriate starting materials, the title compounds can be prepared and isolated.

| Prep# | Product | Physical Data |
|---|---|---|
| 248 | 3-[1-(3,5-bis-trifluoromethyl-benzyl)-5-phenyl-1H-[1,2,3]triazol-4-yl]-4-(2-chloro-phenyl)-isoxazolo[4,3-c]pyridine | MS (ES) 599.9 (M+1), $^1$H NMR (CDCl$_3$): δ 8.35 (d, J = 6.5 Hz, 1H), 7.84 (s, 1H), 7.58–7.13 (m, 12H), 5.52 (s, 2H). |
| 249 | 3-[1-(3,5-bis-trifluoromethyl-benzyl)-5-pyridin-4-yl-1H-[1,2,3]triazol-4-yl]-4-(2-chloro-phenyl)-isoxazolo[4,3-c]pyridine | MS (ES) 600.9 (M+1), $^1$H NMR (CDCl$_3$): δ 8.76 (br s, 2H), 8.38 (d, J = 6.7 Hz, 1H), 7.89 (s, 1H), 7.60–7.36 (m, 6H), 7.12 (m, 3H), 5.56 (ap d, 2H). |

Preparation 250

5-Amino-1-(3,5-bis-trifluoromethyl-benzyl)-1H-imidazole-4-carboxylic acid amide Wash sodium hydride (2.71 g of a 60% solution in mineral oil, 67.66 mmol) three times with hexanes, then dilute with 85 mL of DMF. To this mixture add the HCl salt of 5-amino-1H-imidazole-4-carboxylic acid amide (5.0 g, 30.75 mmol) neat in four portions. The mixture generates gas and remains cloudy and turns a slightly green color. After mixing for 40 min., add 1-chloromethyl-3,5-bis-trifluoromethyl-benzene (8.88 g, 33.83 mmol). (The mixture again generates gas and darkens). Stir at RT for 2 days, then pour through a plug of Celite and wash with DMF (50 mL) and xylenes (50 mL). Remove the DMF via azeotropic distillation with xylenes under reduced pressure (5×50 mL), and then concentrate the residue under a steady stream of nitrogen for 18 h to provide the title compound as a dark purple solid. MS (ES) 351.1, 353.1 (M+1); $^1$H NMR (300 MHz, CDCl$_3$) δ 7.70 (s, 1H), 7.58 (s, 2H), 7.31 (s, 2H), 6.96 (s, 1H), 5.46 (s, 2H), 5.10 (s, 2H).

Preparation 251

5-Amino-1-(3,5-bis-trifluoromethyl-benzyl)-1H-imidazole-4-carbonitrile

Combine 5-Amino-1-(3,5-bis-trifluoromethyl-benzyl)-1H-imidazole-4-carboxylic acid amide (0.106 g, 0.30 mmol) and p-toluenesulfonyl chloride (0.069 g, 0.36 mmol) in pyridine (0.1 M), and stir at RT. After 2 h, quench the reaction with MeOH and concentrate. Redissolve in EtOAc, wash with H$_2$O and brine, then dry (MgSO$_4$), filter, and concentrate. Purify by radial chromatography on silica gel to give the title compound. MS (ES) 335.1 (M+1); $^1$H NMR (300 MHz, CD$_3$OD): δ 7.96 (s, 1H), 7.77 (s, 2H), 7.37 (s, 1H), 5.31 (s, 2H).

Preparation 252

1-(3,5-Bis-trifluoromethyl-benzyl)-5-iodo-1H-imidazole-4-carbonitrile

Combine 5-Amino-1-(3,5-bis-trifluoromethyl-benzyl)-1H-imidazole-4-carbonitrile (0.066 g, 0.20 mmol), CH$_2$I$_2$ (3 mL), and isoamyl nitrite (250 μL, 2 mmol) in a round bottom flask and stir the mixture at 100° C. After 30 min., remove from heat and concentrate. Purify by flash chromatography on silica gel to give the title compound. MS (ES) 443.9 (M−1); $^1$H NMR (300 MHz, CDCl$_3$) δ 7.93 (s, 1H), 7.78 (s, 1H), 7.58 (s, 2H), 5.31 (s, 2H).

Preparation 253

1-(3,5-Bis-trifluoromethyl-benzyl)-5-pyridin-3-yl-1H-imidazole-4-carbonitrile

In a pressure vessel dissolve 1-(3,5-Bis-trifluoromethyl-benzyl)-5-iodo-1H-imidazole-4-carbonitrile (0.52 g, 1.2 mmol) in acetonitrile. Add 3-tributylstannanyl-pyridine (0.64 g, 1.7 mmol) and bis(benzonitrile)dichloropalladium (II) (22 mg, 0.06 mmol), and stir at 100° C. After 72 h, quench with sat. aq. NaHCO$_3$, and extract with ether. Wash the organic layer with brine, dry over MgSO$_4$, filter, and concentrate. Purify by radial chromatography on silica gel to give the title compound: MS (ES) 397.2 (M+1); $^1$H NMR (300 MHz, CDCl$_3$) δ 8.75 (d, J=4.6 Hz, 1H), 8.60 (ap d, 1H), 7.84 (s, 1H), 7.75 (s, 1H), 7.66 (m, 1H), 7.44 (m, 1H), 7.36 (s, 2H), 5.30 (s, 2H).

Preparation 254

1-(3,5-Bis-trifluoromethyl-benzyl)-5-pyridin-3-yl-1H-imidazole-4-carboxylic acid methyl ester In a pressure vessel dissolve 1-(3,5-Bis-trifluoromethyl-benzyl)-5-pyridin-3-yl-1H-imidazole-4-carbonitrile (0.043 g, 0.11 mmol) in MeOH (1 mL), add H$_2$O (0.1 mL), and concentrated sulfuric acid (0.3 mL), and stir at 100° C. After 24 h., neutralize with sat. aq. NaHCO$_3$, and extract with EtOAc (3×). Dry over MgSO$_4$, filter, and concentrate. Purify by radial chromatography on silica gel to give the title compound: MS (ES) 430.2 (M+1); $^1$H NMR (300 MHz, CDCl$_3$): δ 8.68 (ap d, 1H), 8.52 (ap d, 1H), 7.80 (s, 1H), 7.78 (s, 1H), 7.56 (d, J=7.8 Hz, 1H), 7.37 (m, 1H), 7.29 (s, 2H), 5.30 (s, 2H), 3.81 (s, 3H).

Preparation 255

1-(3,5-Bis-trifluoromethyl-benzyl)-5-pyridin-3-yl-1H-imidazole-4-carboxylic acid methoxy-N-methyl-amide Combine 1-(3,5-Bis-trifluoromethyl-benzyl)-5-pyridin-3-yl-1H-imidazole-4-carboxylic acid methyl ester (0.46 g, 1.1 mmol) and N,O-dimethyl-hydroxylamine-HCl (0.16 g, 1.6 mmol) in THF (5.5 mL). Chill to 0° C., then slowly add isopropyl magnesium chloride (2M/THF, 1.6 mL, 3.2 mmol). After 45 min., warm to RT. Add 70% sat. aq. NH$_4$Cl, and extract with EtOAc. Dry over MgSO$_4$, filter, and concentrate. Purify by flash chromatography on silica gel to give the title compound: MS (ES) 459.2 (M+1); $^1$H NMR (300 MHz, CDCl$_3$) δ 8.63 (d, J=4.8 Hz, 1H), 8.52 (app d, 1H), 7.79 (s, 1H), 7.73 (s, 1H), 7.63 (app d, J=8.1 Hz, 1H), 7.35–7.31 (m, 1H), 7.30 (s, 2H), 5.21 (s, 2H), 3.79 (s, 3H), 3.37 (br s, 3H).

Preparation 256

1-[1-(3,5-Bis-trifluoromethyl-benzyl)-5-pyridin-3-yl-1H-imidazol-4-yl]-3-(2-chloro-phenyl)-propynone To a solution of 1-chloro-2-ethynylbenzene (0.11 mL, 0.92 mmol) in anhydrous THF (2.5 mL) add by syringe ethylmagnesium bromide, (0.26 mL of a 3.0 M soln. in ether, 0.78 mmol). After 30 min., add by syringe a solution of 1-(3,5-Bis-trifluoromethyl-benzyl)-5-pyridin-3-yl-1H-imidazole-4-carboxylic acid methoxy-methyl-amide (0.30 g, 0.65 mmol) in THF (2.5 mL). After 1 h., quench with sat. aq. NH$_4$Cl, and extract with EtOAc. Dry over MgSO$_4$, filter and concentrate under vacuum to give the title compound. MS (ES) 534.1 (M+1); $^1$H NMR (300 MHz, CDCl$_3$) δ 8.65 (s, 1H), 8.56 (s, 1H), 7.86–7.21 (m, 10H), 5.23 (s, 2H).

Preparation 257

[1-(3,5-Bis-trifluoromethyl-benzyl)-5-pyridin-3-yl-1H-imidazol-4-yl]-[5-(2-chloro-phenyl)-3-(tetrahydro-pyran-2-yloxymethyl)-isoxazol-4-yl]-methanone To a solution of 1-[1-(3,5-Bis-trifluoromethyl-benzyl)-5-pyridin-3-yl-1H-imidazol-4-yl]-3-(2-chloro-phenyl)-propynone (0.257 g, 0.48 mmol) in benzene (6 mL) add 2-(2-nitroethoxy)tetrahydropyran (0.15 mL, 0.72 mmol), 1,4-phenylene diisocyanate (0.23 g, 1.44 mmol), and TEA (9 drops) with stirring. Attach a reflux condenser and set in a 100° C. oil bath. After 30 h., remove from heat, add H$_2$O (5 mL), and stir 20 min. Filter the mixture through celite, wash with sat. aq. NaHCO$_3$, dry over MgSO$_4$, filter and concentrate under vacuum. Purify the residue by flash chromatography, (EtOAc/Hexane 10%–85% then 7.5% MeOH/EtOA) to give the title compound. MS (ES) 691.2 (M+1); TLC R$_f$ 0.25 (85% EtOAC/Hexane).

Preparation 258

[1-(3,5-Bis-trifluoromethyl-benzyl)-5-pyridin-3-yl-1H-imidazol-4-yl]-[5-(2-chloro-phenyl)-3-[1,3]dioxolan-2-ylmethyl-isoxazol-4-yl]-methanone Using a method similar to Preparation 257, the title compound may be prepared and isolated. MS (ES) 663.3 (M+1), TLC R$_f$=0.08 (85% EtOAC/Hexane).

Preparation 259

[4-[1-(3,5-Bis-trifluoromethyl-benzyl)-5-pyridin-3-yl-1H-imidazole-4-carbonyl]-5-(2-chloro-phenyl)-isoxazol-3-yl]-acetaldehyde Dissolve [1-(3,5-Bis-trifluoromethyl-benzyl)-5-pyridin-3-yl-1H-imidazol-4-yl]-[5-(2-chloro-phenyl)-3-[1,3]dioxolan-2-ylmethyl-isoxazol-4-yl]-methanone (0.23 g, 0.35 mmol) in acetic acid (4 mL) and add H$_2$O (2 mL). Attach a reflux condenser and warm to 100° C. After 18 h., concentrate the solution under reduced pressure, neutralize with sat. aq. NaHCO$_3$, and extract with CH$_2$Cl$_2$ and EtOAc (2×). Dry the combined organic layers over MgSO$_4$, filter, and concentrate to give the title compound: MS (ES) 619.2 (M+1); TLC R$_f$=0.35 (5% MeOH/EtOAc).

Preparation 260

1-(3,5-Bis-trifluoromethyl-benzyl)-S-phenyl-1H-imidazole-4-carboxylic acid methyl ester Add 3,5-bis triflouromethyl benzyl amine (5.66 g, 23.30 mmol) to a solution (E/Z)-3-bromo-2-methyleneamino-3-phenyl-acrylic acid methyl ester (K. Nunami et al, *J. Org. Chem.* 1994, 59, 7635.) (5.20 g, 19.4 mmol) and triethylamine (2.7 mL, 19.4 mmol) in DMF (60 mL). Stir the reaction mixture at RT for 16 h, then pour the mixture into saturated aqueous NaHCO$_3$ and extract with CH$_2$Cl$_2$ (once) and EtOAc (three times). Dry the combined organic layers over MgSO$_4$, filter, and concentrate. Remove the excess DMF via azeoptropic distillation at reduced pressure with xylenes. Purify the residue by flash chromatography (hexanes/EtOAc gradient) to yield 3.0 g (36%) of the title compound as a brown-orange solid. $^1$H NMR (300 MHz, CDCl$_3$) 7.83 (s, 2H) 7.79 (s, 1H), 7.75 (s 1H), 7.35–7.5 (m, 3H), 7.25–7.49 (m, 2H), 5.15 (s, 2H), 3.77 (s, 3H); MS/ES 429.1 (M+1).

Preparation 261

1-(3,5-Bis-trifluoromethyl-benzyl)-5-phenyl-1H-imidazole-4-carboxylic acid

Add 5N NaOH (200 mL) to a solution of 1-(3,5-bis-trifluoromethyl-benzyl)-5-phenyl-1H-imidazole-4-carboxylic acid methyl ester (3.0 g, 7.0 mmol) in EtOH (200 mL). Warm the mixture to 70° C. and stir for 16 h. Then cool to RT and concentrate to 220 mL under reduced pressure. Cool this solution to 0° C. and add conc. HCl to pH 1. Filter the resulting precipitate and dry under vacuum to provide 3.0 g (1100%) of the title compound as a light brown solid. $^1$H NMR (300 MHz, DMSO-d$_6$) δ 7.95 (s, 1H), 7.85 (s, 1R), 7.19–7.34 (m, SR), 7.15–7.02 (m, 2R), 5.20 (s, 2R), 3.20 (br s, 11H); MS/ES 415.2 (M+1).

Preparation 262

1-(3,5-Bis-trifluoromethyl-benzyl)-5-phenyl-1H-imidazole-4-carboxylic acid methoxy-N-methyl-amide To a solution of 1-(3,5-Bis-trifluoromethyl-benzyl)-S-phenyl-1H-imidazole-4-carboxylic acid (1.20 g, 2.90 mmol) in DMF (30 mL), add N-methoxy-N-methyl amine hydrochloride (424.1 mg, 4.35 mmol), EDCI (609.6 mg, 3.19 mmol), TEA (325.1 mg, 0.448 mL, 3.19 mmol), DMAP (11 mg, 0.087 mmol), and HOAT (433.6, 3.19 mmol). Stir the mixture at RT for 20 h., then pour into a solution of CH$_2$Cl$_2$ (100 ml) and brine (60 mL). Separate the layers and extract the aqueous layer with CH$_2$Cl$_2$ (5×) and EtOAc (2×). Dry the combined organic layers over MgSO$_4$, filter and concentrate to provide the title compound that may be used without further purification. MS/ES 458.0 (M+1), 456.0 (M−1).

Preparation 263

1-[1-(3,5-Bis-trifluoromethyl-benzyl)-5-phenyl-1H-imidazol-4-yl]-3-(2-chloro-phenyl)-propynone Add ethyl magnesium bromide (1.26 ml of a 3 molar solution in THF, 3.77 mmol) to a cooled (0° C.) soln. of 2-chlorophenyl acetylene (562 mg, 4.12 mmol) in THF (35 mL). Stir for 1 h., then add 1-(3,5-bis-trifluoromethyl-benzyl)-5-phenyl-1H-imidazole-4-carboxylic acid methoxy-methyl-amide (627 g, 1.371 mmol) as a solution in THF (10 mL).

After 1 h., warm to RT and stir for another 8 h. Pour the mix into sat. NH$_4$Cl and extract with CH$_2$Cl$_2$ (2×), and EtOAc (2×). Dry over MgSO$_4$, filter, and concentrate. Purify by radial chromatography (hexanes/EtOAc gradient) to provide 560 mg of the title compound. $^1$H NMR (300 MHz, CDCl$_3$) δ 7.85 (s, 1H), 7.82 (s, 1H), 7.45–7.15 (m, 11H), 5.21 (s, 2H).

Preparation 264

1-[1-(3,5-Bis-trifluoromethyl-benzyl)-5-phenyl-1H-[1,2,3]triazol-4-yl]-3-trimethylsilanyl-2-yn-1-ol Add n-butyl lithium (2.19 mL of a 1.6 molar solution in hex, 3.51 mmol) to a solution of trimethylsilylacetylene (444 mg, 639 uL, 4.52 mmol) in THF (40 mL) at −78° C. After 25 min., add a solution of 1-(3,5-Bis-trifluoromethyl-benzyl)-5-phenyl-1H-[1,2,3]triazole-4-carbaldehyde (1.0 g, 2.51 mmol) in THF (6 mL) dropwise via cannula. After 1 h., warm the mixture to RT. After 2 h, pour the mixture into sat. aq. NH$_4$Cl (15 mL) and CH$_2$Cl$_2$ (15 mL). Separate the layers and extract the aqueous layer with CH$_2$Cl$_2$ (3×15 mL) and with EtOAc (15 mL). Dry the combined organic layers over MgSO$_4$, filter, and concentrate. Purify the residue by chromatography on silica gel (hexanes/EtOAc gradient) to provide 245 mg of the title compound as a yellow liquid. MS 497.14, ES/MS (M+1) 498.3, ES/MS (M−1) 496.8. $^1$H NMR (300 MHz, CDCl$_3$) δ 7.80–70 (m, 3H), 7.60–7.18 (m, 5H), 5.51 (s, 2H), 5.35 (m, 1H), 0.02 (s, 9H).

Preparation 265

1-[1-(3,5-Bis-trifluoromethyl-benzyl)-5-phenyl-1H-[1,2,3]triazol-4-yl]-3-trimethylsilanyl-propynone To a solution of 1-[1-(3,5-Bis-trifluoromethyl-benzyl)-5-phenyl-1H-[1,2,3]triazol-4-yl]-3-trimethylsilanyl-prop-2-yn-1-ol (20 mg, 0.040 mmol) in CH$_2$Cl$_2$ (2 mL) add oven dried 4 Å mol sieves (40 mg), NaOAc (6.6 mg, 0.080 mmol), and pyridinium chlorochromate (13 mg, 0.060 mmol). The mixture turns from orange to dark brown. After 2.5 h., dilute the mixture with Et$_2$O (6 mL) and stir for 5 min, then pour the mixture through a plug of Celite (1 cm) and silica gel (2 cm). Concentrate the filtrate and purify the residue by chromatography on silica gel (hexanes/EtOAc gradient) to provide 6 mg of the title compound as a faintly yellow liquid. R$_f$=0.6 (50:50 EtOAc/hexanes).

Preparation 266

[1-(3,5-Bis-trifluoromethyl-benzyl)-5-phenyl-1H-[1,2,3]triazol-4-yl]-(3-phenyl-5-trimethylsilanyl-3H-[1,2,3]triazol-4-yl)-methanone In a pressure vessel add phenyl azide (0.029 g, 0.23 mmol) with stirring to a solution of 1-[1-(3,5-Bis-trifluoromethyl-benzyl)-5-phenyl-1H-[1,2,3]triazol-4-yl]-3-trimethylsilanyl-propynone (0.058 g, 0.12 mmol) in toluene (1 mL). Seal the vessel and set in a 120° C. oil bath. After 24 h., remove from heat, concentrate, and purify by flash chromatography, (EtOAc/Hexane 0%–50%) to give the title compound. MS(ES) 615.2 (M+1), TLC R$_f$=0.24 (30% EtOAc/Hexane).

EXAMPLES

General Example A

Dissolve the alkyne of interest (1 eq.) in benzene (0.1 M). Add the appropriate nitro compound (1.5 eq.), 1,4-phenylene diisocyanate (3 eq.), and TEA (10 drops/mmol alkyne). Attach a reflux condenser and place in 110° C. bath, and stir. After 20 h., add additional nitro compound (0.5 eq.), 1,4-phenylene diisocyanate (1 eq.) and TEA. After an additional 6 h., remove from heat, add H$_2$O, and stir 20 min. Filter through Celite®, remove H$_2$O, and dry over MgSO$_4$. Filter and concentrate under vacuum. Purify by chromatography on silica gel.

By the method of General Example A, the following compounds may be prepared.

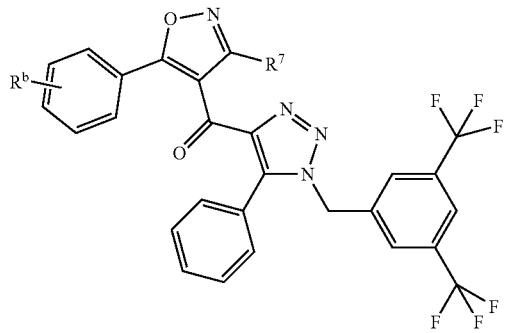

| Ex. # | R⁷ | R^b | Physical Data |
|---|---|---|---|
| 1 | methyl | 2-chloro | MS (ES) 591.1 (M+1), $^1$H NMR (300 MHz, CDCl$_3$): δ 7.84 (s, 1H), 7.74 (d, J = 2.5 Hz, 1H), 7.70 (d, J = 2.2 Hz, 1H), 7.56–7.19 (m, 9H), 5.44 (s, 2H), 2.51 (s, 3H). |
| 2 | ethyl | 2-chloro | MS (ES) 605.1 (M+1), $^1$H NMR (300 MHz, CDCl$_3$): δ 7.66 (s, 1H), 7.54 (dd, J = 7.8, 3.0 Hz, 1H), 7.45–7.00 (m, 10H), 5.26 (s, 2H), 2.77 (q, J = 6.5 Hz, 2H), 1.16 (t, J = 6.5 Hz, 3H). |
| 3 | propyl | 2-chloro | MS (ES) 619.1 (M+1), $^1$H NMR (300 MHz, CDCl$_3$): δ 7.73 (s, 1H), 7.60 (dd, J = 6.5, 1.0 Hz, 1H), 7.48–7.05 (m, 10H), 5.32 (s, 2H), 2.80 (appt, J = 7.0 Hz, 2H), 1.68 (app t. J = 7.0 Hz, 2H), 0.90 (t, J = 6.5 Hz, 3H). |
| 4 | methyl | hydrogen | MS (ES) 557.3 (M+1), TLC (30% EtOAc/Hexane), R$_f$ = 0.26 |
| 5 | methyl | 4-fluoro | MS (ES) 575.3 (M+1), TLC (30% EtOAc/Hexane), R$_f$ = 0.28 |
| 6 | methyl | 3-trifluoro-methyl | MS (ES) 625.0 (M+1), TLC (50% EtOAc/Hexane ×2), R$_f$ = 0.38 |
| 7 | methyl | 2-fluoro | MS (ES) 575.0 (M+1), $^1$H NMR (300 MHz, CDCl$_3$): δ 7.77–7.11 (m, 12H), 5.40 (s, 2H), 2.37 (s, 3H). |
| 8 | methoxy-carbonyl | 2-chloro | Exact Mass 634.1: MS (aspci): m/z = 635.1 (M+1), 633.1 (M−1); $^1$H NMR (250 MHz, CDCl$_3$) δ 7.74 (s, 1H), 7.56-7.08 (m, 11H), 5.50 (5, 2H), 3.85 (s, 3H). |
| 9 | methoxy-methyl | 2-chloro | Exact Mass 620.1: MS (aspci): m/z = 622.9 (M+1); $^1$H NMR (300 MHz, CDCl$_3$) δ 7.74 (s, 2H), 7.60 (m, 1H), 7.49–7.35 (m, 3H), 7.34 (m, 1H), 7.27 (s, 2H), 7.23–7.10 (m, 3H), 5.39 (s, 2H), 4.67 (s, 2H), 3.26 (s, 3H). |

By the method of General Example A, the following compounds may be prepared.

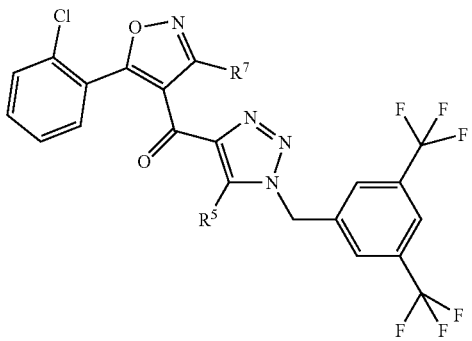

| Ex. # | R⁵ | R⁷ | Physical Data |
|---|---|---|---|
| 10 | pyridin-4-yl | methyl | Exact Mass 591.09: MS (ESI) m/z 592.2 (M+1). $^1$H NMR (300 MHz, CDCl$_3$) δ2.49 (s, 3H), 5.43 (s, 2H), 7.18 (m, 3H), 7.24–7.48 (m, 4H), 7.72 (dd, 1H, J = 7.61, 1.56 Hz), 7.86 (s, 1H), 8.80 (m, 2H). |

-continued

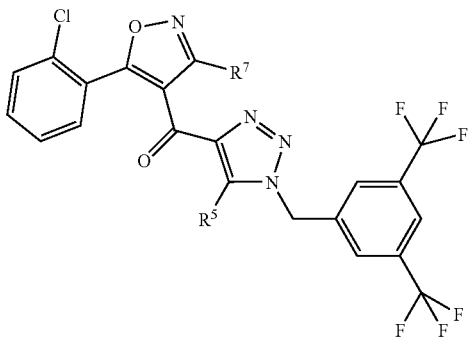

| Ex. # | R⁵ | R⁷ | Physical Data |
|---|---|---|---|
| 11 | pyridin-3-yl | methyl | Exact Mass;/591.09; MS (ESI) m/z 592.2 (M+1). ¹H NMR (300 MHz, CDCl₃) δ 2.49 (s, 3H), 5.47 (s, 2H), 7.20–7.45 (m, 6H), 7.61 (m, 1H), 7.72 (dd, 1H, J = 7.52, 1.77 Hz), 7.84 (s, 1H), 8.51 (s, 1H), 8.78 (m, 1H). |
| 12 | pyrimidin-5-yl | methyl | ¹H NMR (400 MHz, CDCl₃) δ2.50 (s, 3H), 5.49 (s, 2H), 7.22 (d, J = 8.4 Hz, 1H), 7.35–7.39 (m, 3H), 7.44 (t, J = 7.6 Hz, 1H), 7.75 (d, J = 7.6 Hz, 1H), 7.88 (s, 1H), 8.66 (s, 2H), 9.36 (s, 1H); MS (apci) m/z 593.1 (M+1) |
| 13 | methyl | methyl | MS (ES) 529.1 (M+H), 527.1 (M—H). ¹H NMR (400 MHz, CHCl₃) δ 7.89 (s, 1H), 7.67 (dd, 1H, J = 7.9, 2.0 Hz), 7.54 (s, 2H), 7.37 (dt, 1H, J = 7.6, 1.5 Hz), 7.31 (dt, 1H, J = 7.6, 2.0 Hz), 7.20 (dd, 1H, J = 7.9, 1.5 Hz), 5.52 (s, 2H), 2.53 (s, 3H), 2.52 (s, 3H). |
| 14 | chloro | methyl | MS (ES+) 549.0 (M+1). ¹H NMR (400 MHz, CDCl₃) δ 7.89 (s, 1H), 7.65 (s, 2H), 7.62 (dd, 1H, J = 1.5, 7.8 Hz), 7.32 (dt, 1H, J = 1.4, 7.4 Hz), 7.26 (dt, 1H, J = 1.4, 7.8 Hz), 7.11 (dd, 1H, J = 1.0, 7.8 Hz), 5.53 (s, 2H), 2.52 (s, 3H). |
| 15 | pyridin-3-yl | cyclo-propyl | MS (ES+) 618.2 (M+H). ¹H NMR (400 MHz, CDCl₃) δ 8.78 (br s, 1H), 8.52 (br s, 1H), 7.82 (s, 1H), 7.70 (dd, 1H, J = 7.8, 1.8), 7.62 (m, 1H), 7.41 (m, 2H), 7.33 (m, 3H), 7.20 (dd, 1H, J = 7.8, 10), 5.47 (s, 2H), 2.25 (m, 1H), 1.14(m, 2H), 1.03(m, 2H). |

By the method of General Example A, the following compounds may be prepared.

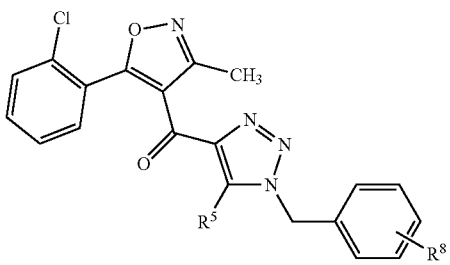

| Ex. # | Rᵃ | R⁵ | Physical Data |
|---|---|---|---|
| 16 | 3,5-dichloro | pyridin-4-yl | MS (ES) 524.3, 526.3 (M⁺+1). |
| 17 | 2-methoxy-5-trifluoromethoxy | pyridin-3-yl | MS (ES+) 570.1 (M+1)⁺. ¹H NMR (400 MHz, CDCl₃) δ 8.71 (m, 1H), 8.46 (m, 1H), 7.68 (m, 2H), 7.36 (m, 3H), 7.24 (m, 1H), 7.12 (m, 1H), 6.75 (m, 1H), 6.50 (s, 1H), 5.34 (s, 2H), 3.61(s, 3H), 2.47(s, 3H). |

Example 18

[1-(3,5-Bis-trifluoromethyl-benzyl)-5-phenyl-1H-imidazol-4-yl]-[5-(2-chloro-phenyl)-3-methyl-isoxazol-4-yl]-methanone

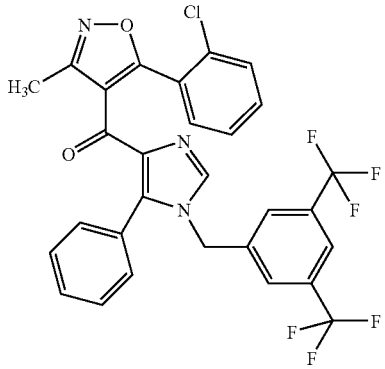

Using the method of General Example A, and the appropriate starting materials, the title compound may be prepared and isolated. Exact Mass 589.1; MS (aspci) m/z=589.9 (M+1), m/z=588.0 (M−1); $^1$H NMR (300 MHz, CDCl$_3$) δ 7.79 (s, 1H), 7.60 (m, 1H), 7.50–7.35 (m, 3H), 7.35–7.18 (m, 6), 7.18 (s, 2H), 5.05 (s, 2H), 2.45 (s, 3H).

General Example B

Dissolve the appropriate alkyne (1 eq.) in toluene (0.1 M) and treat the solution with the appropriate nitroalkoxy-tetrahydropyran (5 eq.), 1,4-diisocyanato-benzene (5 eq.), and triethylamine (5 eq.). Heat the solution at 110° C. overnight, then add water and filter through a pad of Celite®. Wash the solid with EtOAc and wash the filtrate with brine. Dry over MgSO$_4$, filter, and concentrate to give the crude isoxazole.

Dissolve the residue in MeOH (0.1M) and treat with AcOH or p-TsOH.H$_2$O (2eq.). Stir the solution at RT for 18 h. Concentrate the solution and re-dissolve the crude material in EtOAc. Wash the organic solution with saturated NaHCO$_3$, then dry, filter, and concentrate. Purify the crude material by flash chromatography to give the title compound.

By the method of General Example B, the following compounds may be prepared and isolated.

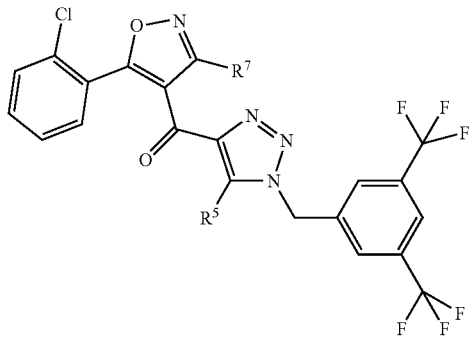

| Ex. # | R$^5$ | R$^7$ | Physical Data |
|---|---|---|---|
| 19 | chloro | hydroxy-methyl | MS (ES) 565.0 (M+1). $^1$H NMR (400 MHz, CDCl$_3$) δ 7.91 (s, 1H), 7.65 (s, 2H), 7.63 (dd, 1H, J = 1.8, 8.0 Hz), 7.36 (dt, 1H, J = 1.5, 7.3 Hz), 7.31 (dt, 1H, J = 1.9, 7.8 Hz), 7.11 (dd, 1H, J = 1.5, 7.8 Hz), 5.55 (s, 2H), 4.84 (d, 2H, J = 7.4 Hz), 3.74 (t, 1H, J = 7.4 Hz). |
| 20 | chloro | 2-hydroxy-ethyl | MS (ES) 579.0 (M+1); $^1$H NMR (400 MHz, CDCl$_3$) δ 7.90 (s, 1H), 7.64 (s, 2H), 7.63 (m, 1H), 7.33 (dt, 1H, J = 1.0, 7.3 Hz), 7.27 (dt, 1H, J = 1.5, 7.8 Hz), 7.12 (dd, 1H, J = 1.0, 7.8 Hz), 5.53 (s, 2H), 4.05 (t, 2H, J = 5.9 Hz), 3.19 (t, 2H, J = 5.9 Hz), 2.35 (br s, 1H). |
| 21 | methyl | hydroxy-methyl | MS (ES) 545.1 (M+H), 543.1 (M—H). $^1$H NMR (400 MHz, CDCl$_3$) δ 7.90 (s, 1H), 7.69 (dd, 1H, J = 7.6, 2.2 Hz), 7.55 (s, 2H), 7.35–7.40 (m, 2H), 7.22 (dd, 1H, J = 8.0, 1.6 Hz), 5.53 (s, 2H), 4.85 (d, 2H, J = 7.6 Hz), 4.08 (t, 1H, J = 7.6 Hz , 2.55 (s, 3H). |
| 22 | methyl | 2-hydroxy-ethyl | MS (ES) 558.9 (M$^+$), MS (ES-) 556.9 (M-1)$^-$. $^1$H NMR (400 MHz, CDCl$_3$) δ 7.87 (s, 1H), 7.67 (dd, 1H, J = 2.0, 7.3 Hz), 7.51 (s, 2H), 7.36 (dt, 1H, J = 1.5, 7.3 Hz), 7.30 (dt, 1H, J = 2.0, 7.8 Hz), 7.18 (dd, 1H, J = 1.5, 7.8 Hz), 5.49 (s, 2H), 4.05 (t, 2H, J = 5.4 Hz), 3.17 (t, 2H, J = 5.4 Hz), 2.51 (s, 3H), 1.70 (br s, 1H). |
| 23 | pyrimidin-5-yl | hydroxy-methyl | $^1$H NMR (400 MHz, CDCl$_3$) δ 3.59 (t, J = 7.2 Hz, 1H), 4.82 (d, J = 6 Hz, 2H), 5.52 (s, 2H), 7.26 (d, J = 0.8 Hz, 1H), 7.35–7.40 (m, 3H), 7.42 (t, J = 6 Hz, 1H), 7.76 (d, J = 4 Hz, 1H), 7.89 (s, 1H), 8.66 (s, 2H), 9.38 (s, 1H); MS (apci) m/z 609.0 (M+1) |

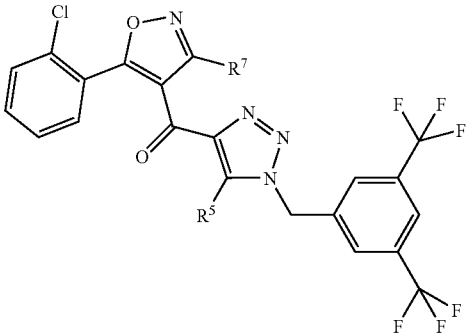

| Ex. # | R⁵ | R⁷ | Physical Data |
|---|---|---|---|
| 24 | pyridin-3-yl | 2-hydroxy-ethyl | $^1$H NMR (300 MHz, CDCl$_3$) δ 3.15 (t, J = 5.93 Hz, 2H), 4.02 (t, J = 5.86 Hz, 2H), 5.47 (s, 2H), 7.21–7.45 (m, 6H), 7.61 (m, 1H), 7.72 (dd, J = 7.59, 1.87 Hz, 1H), 7.84 (s, 1H), 8.51 (d, J = 1.63 Hz, 1H), 8.78 (m, 1H); MS(ESI) m/z 604.1 (M—OH). |
| 25 | pyrimidin-5-yl | 2-hydroxy-ethyl | $^1$H NMR (400 MHz, CDCl$_3$) δ 2.34 (t, J = 6.4 Hz, 1H), 3.16 (t, J = 5.6 Hz, 2H), 4.03 (q, J = 5.6 Hz, 2H), 5.49 (s, 2H), 7.23 (d, J = 8 Hz, 1H), 7.36–7.40 (m, 3H), 7.45 (t, J = 7.6 Hz, 1H), 7.76 (d, J = 8 Hz, 1H), 7.88 (s, 1H), 8.66 (s, 2H), 9.36 (s, 1H); MS (apci) m/z 623.0 (M+1). |

Example 26

[5-(2-chloro-phenyl)-3-hydroxymethyl-isoxazol-4-yl]-[1-(2-methoxy-5-trifluoromethoxy-benzyl-5-pyridin-3-yl-1H-[1,2,3]triazol-4-yl]-methanone

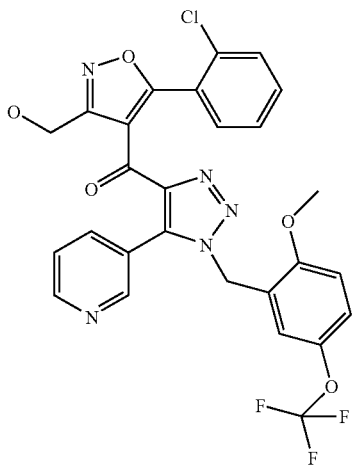

Using the method of General Example B, the title compound may be prepared. MS (ES+) 586.1 (M+1)⁺. $^1$H NMR (400 MHz, CDCl$_3$) δ 8.72 (m, 1H), 8.48 (m, 1H), 7.68 (m, 2H), 7.40 (m, 3H), 7.26 (m, 1H), 7.15 (m, 1H), 6.76 (d, 1H, J=8.8 Hz), 6.55 (m, 1H), 5.35 (s, 2H), 4.80 (d, 2H, J=6.8 Hz), 3.90 (t, 1H, J=6.8 Hz), 3.63 (s, 3H).

Example 27

[1-(3,5-bis-trifluoromethyl-benzyl)-5-pyridin-4-yl-1H-[1,2,3]triazol-4-yl]-[5-(2chloro-phenyl)-3-(1-hydroxy-1-methyl-ethyl)-isoxazol-4-yl]-methanone

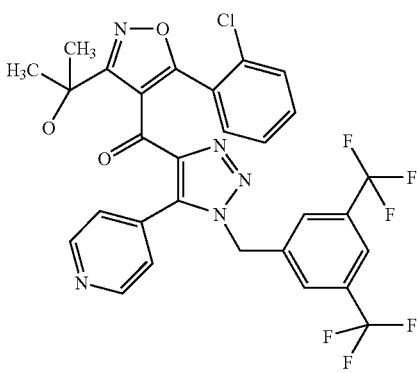

Combine 1-[1-(3,5-bis-trifluoromethyl-benzyl)-5-pyridin-4-yl-1H-[1,2,3]triazol-4-yl]-3-(2-chloro-phenyl)-propynone (0.31 g, 0.58 mmol), 1,4-phenylene diisocyanate (0.48 g, 3.0 mmol), (1,1-dimethyl-2-nitro-ethoxy)-trimethyl-silane (3.0 g, 1.5 mmol), triethylamine (8 drops) and benzene (10 mL), stir, and heat at reflux. After 18 h., cool to ambient temperature, filter the brown precipitate, wash with ethyl acetate, and concentrate. Purify the resulting mixture by silica gel chromatography eluting with 1:1 EtOAc/hexanes to give [1-(3,5-bis-trifluoromethyl-benzyl)-5-pyridin-4-yl-1H-[1,2,3]triazol-4-yl]-{5-(2-chloro-phenyl)-(1-methyl-1-trimethylsilanyloxy-ethyl)-isoxazol-4-yl}-methanone (0.20 g, 0.28 mmole).

Dissolve the residue in THF (5 mL) and add TBAF (0.31 mL of a 1M soln., 0.31 mmole). Stir for 30 min., then evaporate the solvent and purify the product by flash chromatography, eluting with 2:1 EtOAc/hexane to give the title compound (35 mg, 23%). $^1$H NMR (300 MHz, CDCl$_3$) δ 1.55 (s, 6H), 5.40 (s, 2H), 7.15 (d, J=7.81 Hz, 1H), 7.19 (m, 2H), 7.31 (t, J=7.81 Hz, 1H), 7.36 (s, 2H), 7.41 (t, J=7.66, Hz, 1H), 7.70 (m, 1H), 7.87 (s, 1H), 8.82 (m, 2H); MS (ESI) m/z 636.0(M+1).

By a method similar to Example 27, with the appropriate starting materials, the following compounds are prepared and isolated.

ate alkyne (1.0 eq.) in EtOAc. Stir the mixture at RT to 50° C. until the reaction is complete. Treat the reaction mixture with saturated sodium bicarbonate solution, extract with ether (3×50 mL). Dry the combined organic layers with MgSO$_4$, filter, and concentrate in vacuo. Purify by chromatography on silica gel.

By the method of General Example C, the following compounds may be prepared and isolated.

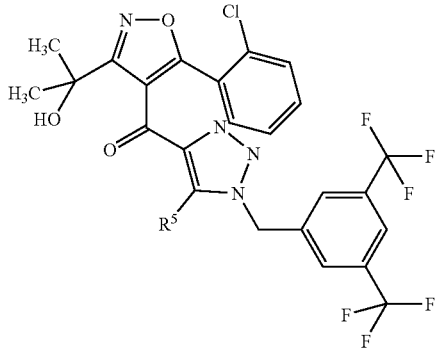

| Ex. # | R$^5$ | Physical Data |
|---|---|---|
| 28 | pyridin-3-yl | Exact Mass 635: MS (aspci): m/z = 618.17 (M—H$_2$O); $^1$H NMR (300 MHz, CDCl$_3$) δ 8.68 (d, J = 3.3 Hz, 1H), 8.51 (d, J = 0.9 Hz, 1H), 8.05 (s, 1H), 7.82 (d, J = 2.7 Hz, 1H), 7.38–7.59 (m, 7H), 5.82 (s, 2H), 1.54 s, 6H. |
| 29 | pyrimidin-5-yl | $^1$H NMR (400 MHz, CDCl$_3$) δ 1.66 (s, 6H), 4.78 (s, 1H), 5.46 (s, 2H), 7.19 (d, J = 8 Hz, 1H), 7.37–7.42 (m, 3H), 7.44 (t, J = 7.6 Hz, 1H), 7.74 (d, J = 7.6 Hz, 1H), 7.89 (s, 1H), 8.67 (s, 2H), 9.39 (s, 1H); MS (apci) m/z 619.1 (M+1-H$_2$O). |

General Example C

Add triethylamine (2.5 eq.) to a solution of 2-chlorophenylhydroximimoyl acid chloride (2.0 eq.) and the appropri-

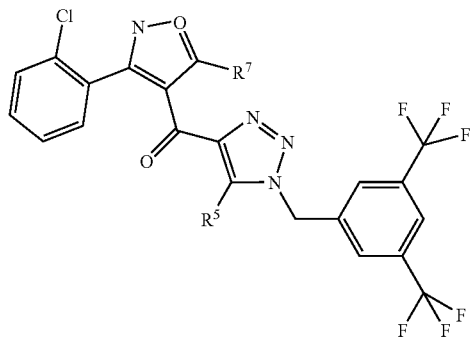

| Ex. # | R$^5$ | R$^7$ | Physical Data |
|---|---|---|---|
| 30 | pyridin-4-yl | Hydrogen | MS (ES) 578.1 (M$^+$+1); TLC (50% EtOAc in hexanes): R$_f$ = 0.3. |
| 31 | pyridin-3-yl | Hydrogen | MS (ES) 578.1 (M$^+$+1); TLC (50% acetone in hexanes): R$_f$ = 0.3. |
| 32 | pyridin-4-yl | methoxymethyl | m.p. 128° C. (decomp.) TLC: R$_f$ = 0.16 (1:1 hexanes/EtOAc) MS(ES) 621.9 (M$^+$) |
| 33 | chloro | methoxymethyl | TLC: R$_f$ = 0.38 (2:1 hexanes/EtOAc) MS(ES) 578.9 (M$^+$) |

General Example D

Dissolve the appropriate tetrahydropyranyl-protected alcohol (1 eq.) in THF, water and HOAc and heat at 60° C. Stir 5–24 h., concentrate in vacuo, extract with EtOAc, wash with water, saturated aqueous NaHCO₃, brine, dry (Na₂SO₄), filter and concentrate in vacuo. Purify by chromatography to give the title compound.

Using the method of General Example D, the following compounds may be prepared and isolated.

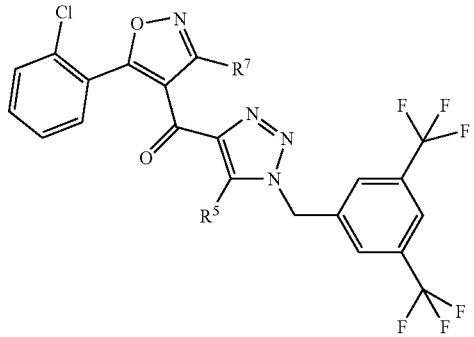

| Ex. # | R⁵ | R⁷ | Physical Data |
|---|---|---|---|
| 34 | pyrazin-2-yl | hydroxy-methyl | MS(ES) 609.1 (M+1); TLC R$_f$ = 0.50(20% CH₃CN/CH₂Cl₂) |
| 35 | phenyl | hydroxy-methyl | MS (ES) 607.0 (M+1); ¹H NMR (300 MHz, CDCl₃): δ 7.85 (s, 1H), 7.74 (d, J = 7.4 Hz, 1H), 7.62–7.37 (m, 5H), 7.35 (s, 2H), 7.27–7.20 (m, 3H), 5.45 (s, 2H), 4.83 (d, J = 7.2 Hz, 2H), 3.85 (t, J = 7.2 Hz, 1H). |
| 36 | phenyl | 2-hydroxy-ethyl | MS (ES) 620.1 (M⁺); ¹H NMR (300 MHz, CDCl₃): δ 7.74 (s, 1H), 7.63 (dd, J = 7.5, 1.9 Hz, 1H), 7.50–7.09 (m, 10H), 5.34 (s, 2H), 3.94 (t, J = 6.0 Hz, 2H), 3.08 (t, J = 6.0 Hz, 2H. |
| 37 | pyrimidin-5-yl | hydroxy-methyl | Exact Mass 608.08; MS (apci): m/z = 609.0 (M+1); ¹H NMR (400 MHz, CDCl₃): δ 9.38 (s, 1H), 8.67 (s, 2H), 7.89 (s, 1H), 7.76 (d, J = 7.6 Hz, 1H), 7.47 (t, J = 7.6 Hz, 1H), 7.44 (d, J = 7.6 Hz, 1H), 7.42 (s, 2H), 7.24 (d, J = 8 Hz, 1H), 5.51 (s, 2H), 4.82 (d, J = 7.2 Hz, 2H), 3.58 (t, J = 7.2 Hz, 1H). |
| 38 | pyridin-3-yl | hydroxy-methyl | MS(APCI) m/z 608(M+1); ¹H NMR (300 MHz, CDCl₃) δ 4.81 (d, J = 7.26 Hz, 2H), 5.48 (s, 2H), 7.23 (d, J = 7.82 Hz, 1H), 7.34–7.46 (m, 5H), 7.58–7.61 (m, 1H), 7.73 (dd, J = 7.65, 1.72 Hz, 1H), 7.85 (s, 1H), 8.52 (d, J = 1.84 Hz, 1H), 8.80(m, 1H). |
| 39 | pyridin-4-yl | hydroxy-methyl | MS(ESI) m/z 608.1(M+1); ¹H NMR (300 MHz, CDCl₃) δ 3.64 (br s, 1H), 4.81(s, 2H), 5.45 (s, 2H), 7.14–7.22 (m, H), 7.38–7.47 (m, 4H), 7.74 (dd, J = 7.61, 1.76 Hz, 1H), 7.87 (s, 1H), 8.82 (br s, 2H). |
| 40 | hydrogen | hydroxy-methyl | ¹H NMR (300 MHz, CDCl₃) δ 4.84 (s, 2H), 5.61 (s, 2H), 7.22–7.25 (m, 1H), 7.33–7.39 (m, 2H), 7.63 (s, 2H), 7.93 (s, 1H), 8.11 (s, 1H); MS (APCI) m/z 530.9 (M+1). |
| 41 | pyridin-4-yl | 2-hydroxy-ethyl | ¹H NMR (300 MHz, CDCl₃) δ 2.50 (br s, 1H), 3.15 (t, J = 5.87 Hz, 2H), 4.02 (t, J = 6.05 Hz, 2H), 5.45 (s, 2H), 7.16–7.22 (m, 3H), 7.32–7.38 (m, 3H), 7.42 (td, J = 7.61, 1.17 Hz, 1H), 7.73 (dd, J = 7.71, 1.66 Hz, 1H), 7.86 (s, 1H), 8.79 (m, 2H); MS (ESI) m/z 622.3 (M+1). |
| 42 | hydrogen | 2-hydroxy-ethyl | ¹H NMR (300 MHz, CDCl₃) δ 1.62 (bs, 1H), 3.19–3.23 (m, 2H), 4.05–4.09 (m, 2H), 5.59 (s, 2H), 7.21–7.37 (m, 3H), 7.63–7.65 (m, 3H), 7.93 (s, 1H), 8.07 (m, 1H); MS (APCI) m/z 527.1 (M−17). |

Example 43

[1-(3,5-Bis-trifluoromethyl-benzyl)-5-pyridin-3-yl-1H-[1,2,3]triazol-4-yl]-[4-(2-chloro-phenyl)-3-hydroxymethyl-isoxazol-5-yl]-methanone

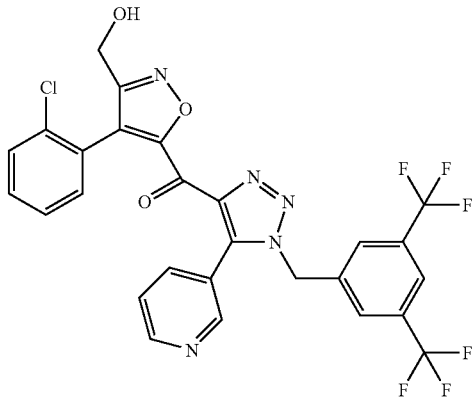

By the method of General Example D, the title compound is prepared and isolated. $^1$H NMR (500 MHz, DMSO-d$_6$): δ 8.67 (dd, 1H, J=1.5, 5.0), 8.59 (d, 1H, J=2.0), 8.07 (s, 1H), 7.88 (dt, 1H, J=1.9, 8.0), 7.72 (s, 2H), 7.50 (m, 2H), 7.44 (m, 1H), 7.36 (m, 2H), 5.84 (m, 2H), 5.50 (br t, 1H, J=5.8), 4.49 (br s, 2H).

By the method of General Example D, the following compounds may be prepared and isolated.

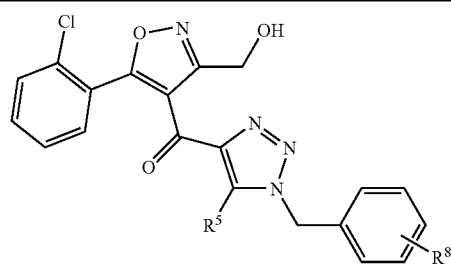

| Ex. # | R$^a$ | R$^5$ | Physical Data |
|---|---|---|---|
| 44 | 3,5-dichloro | pyridin-4-yl | MS (ES) 540.2 (M$^+$+1) |
| 45 | 3,5-dichloro | pyridin-3-yl | MS (ES) 539.9, 541.9 (M$^+$+1), R$_f$ = 0.355 (6.7% MeOH/CH$_2$Cl$_2$) |
| 46 | 3-trifluoromethyl | pyridin-3-yl | MS (ES) 540.1, 542.1 (M$^+$+1), R$_f$ = 0.15 (6.7% MeOH/CH$_2$Cl$_2$) |
| 47 | 4-trifluoromethyl | pyridin-3-yl | MS (ES) 540.1, 542.2 (M$^+$+1), R$_f$ = 0.11(6.7% MeOH/CH$_2$Cl$_2$) |
| 48 | 2,5-bis-trifluoromethyl | pyridin-3-yl | MS (ES) 608.1, 610.2 (M$^+$+1), R$_f$ = 0.37 (50% EtOAc/CH$_2$Cl$_2$) |

By the method of General Example D, the following compounds may be prepared and isolated.

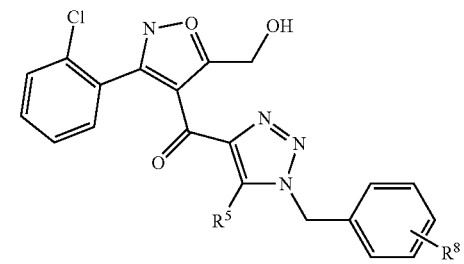

| Ex. # | R$^a$ | R$^5$ | Physical Data |
|---|---|---|---|
| 49 | 3,5-dichloro | pyridin-3-yl | R$_f$ = 0.15 (2:1 Hex/EtOAc); MS (ES) 540.0 (M+1) |

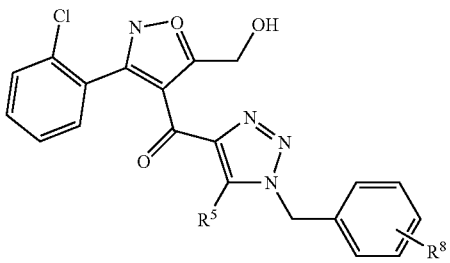

| Ex. # | $R^a$ | $R^5$ | Physical Data |
|---|---|---|---|
| 50 | 3-trifluoro-methoxy | pyridin-3-yl | $R_f$ = 0.14 (1:2 Hex/EtOAc); MS (ES) 556.0 (M+1) |
| 51 | 3,5-dimethyl | pyridin-3-yl | MS (ES) 500.1 (M+1) |
| 52 | 2-fluoro-5-trifluro-methyl | pyridin-3-yl | $R_f$ = 0.22 1:2 Hex/EtOAc; MS (ES) 558.0 (M+1) |
| 53 | 2-methoxy-5-trifluoro-methoxy | pyridin-3-yl | $R_f$ = 0.13 1:2 Hex/EtOAc; MS (ES) 586.0 (M+1) |

Example 54

[1-(3,5-Bis-trifluoromethyl-benzyl)-5-phenyl-1H-imidazol-4-yl]-[5-(2-chloro-phenyl)-3-hydroxymethyl-isoxazol-4-yl]-methanone

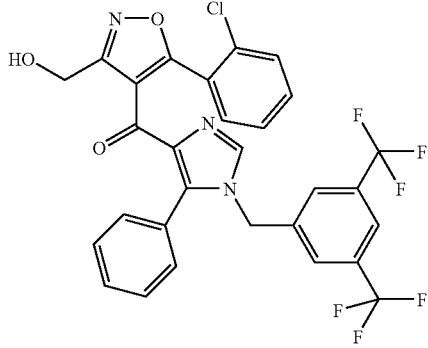

Using the method of General Example D, the title compound may be prepared and isolated. Exact Mass 605.09; mass spectrum (aspci): m/z=605.9(M+1), m/z=603.9(M−1); $^1$H NMR (300 MHz, CDCl$_3$) δ 7.73 (s, 2H), 7.52 (m, 1H), 7.45–7.05 (m, 10H), 4.98 (s, 2H), 4.67 (s, 2H).

Example 55

[1-(3,5-Bis-trifluoromethyl-benzyl)-5-pyridin-3-yl-1H-imidazol-4-yl]-[5-(2-chloro-phenyl)-3-hydroxymethyl-isoxazol-4-yl]-methanone

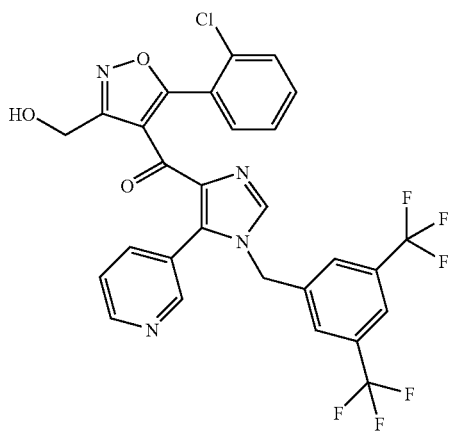

Dissolve [1-(3,5-Bis-trifluoromethyl-benzyl)-5-pyridin-3-yl-1H-imidazol-4-yl]-[5-(2-chloro-phenyl)-3-(tetrahydropyran-2-yloxymethyl)-isoxazol-4-yl]-methanone (0.136 g, 0.20 mmol) in THF (1.5 mL), add acetic acid (1.5 mL) and H$_2$O (0.5 mL). Attach a reflux condenser and stir 20 hours in a 60° C. oil bath. Concentrate under vacuum, neutralize with saturated aqueous NaHCO$_3$, and extract with EtOAc. Dry over MgSO$_4$, filter through paper, and concentrate under vacuum. Recrystallize in ether/hexane (1:10) to give the title compound: MS (ES) 607.1 (M+1), $^1$H NMR (CDCl$_3$) δ 8.69 (br s, 1H), 8.58 (br s, 1H), 7.82 (s, 1H), 7.64 (m, 2H), 7.44–7.28 (m, 5H), 7.23 (s, 2H), 5.14 (s, 2H), 4.76 (s, 2H).

General Example E

Combine the appropriate protected alcohol (1.0 eq.) in MeOH, add p-toluenesulfonic acid (1.3 eq.) and allow the mixture to stir at RT. After 18 h., concentrate the solution in vacuo, dilute the residue in ether, and wash the solution with aqueous saturated sodium bicarbonate solution. Dry over MgSO$_4$, filter, and concentrate in vacuo. Purify the residue by flash chromatography on silica gel to give the title compound.

By the method of General Example E, the following compounds are prepared and isolated.

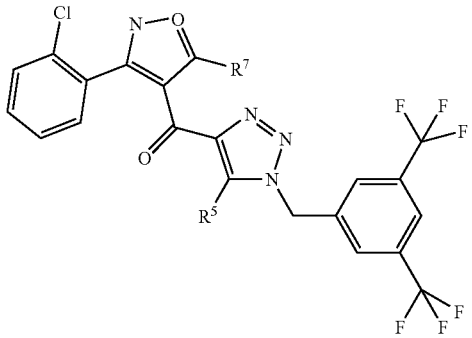

| Ex. # | R$^5$ | R$^7$ | Physical Data |
|---|---|---|---|
| 56 | chloro | hydroxy-methyl | MS (ES) 564.9 (M+1); TLC R$_f$ = 0.1 (30% hexanes in Et$_2$O). |
| 57 | phenyl | hydroxy-methyl | MS (ES) 607.0 (M+1); TLC R$_f$ = 0.1(20% ether in hexanes). |
| 58 | 4-methyl-piperazin-1-yl | 2-hydroxy-ethyl | MS (ES) 643.0 (M$^+$+1); TLC R$_f$ = 0.1 (2.5% MeOH in dichloromethane). |
| 59 | thio-morphlino | 2-hydroxy-ethyl | MS (ES) 645.9 (M$^+$+1); TLC R$_f$ = 0.1, (50% EtOAc in hexanes). |
| 60 | dimethyl-amino | 2-hydroxy-ethyl | MS (ES) 587.9 (M$^+$+1); TLC R$_f$ = 0.1 (50% EtOAc in hexanes). |
| 61 | morpholino | 2-hydroxy-ethyl | MS (ES) 629.9 (M$^+$+1); TLC R$_f$ = 0.1 (50% EtOAc in hexanes). |
| 62 | pyridin-4-yl | 2-hydroxy-ethyl | MS (ES) 621.9 (M$^+$+1); TLC R$_f$ = 0.5 (50% EtOAc in hexanes). |
| 63 | pyridin-4-yl | hydroxy-methyl | MS (ES) 608.0 (M$^+$+1); TLC R$_f$ = 0.1 (50% EtOAc in hexanes). |
| 64 | pyridin-3-yl | hydroxy-methyl | MS (ES) 607.9 (M$^+$+1); TLC R$_f$ = 0.1(50% EtOAc in hexanes). |
| 65 | chloro | 1-hydroxy-1-methyl-ethyl | m.p. 116° C. TLC: R$_f$ = 0.35 (2:1 hexanes/EtOAc) MS(ES) 592.8 (M+1), 574.8 [(M—OH)$^+$] |

By the method of General Example E, the following compounds are prepared and isolated.

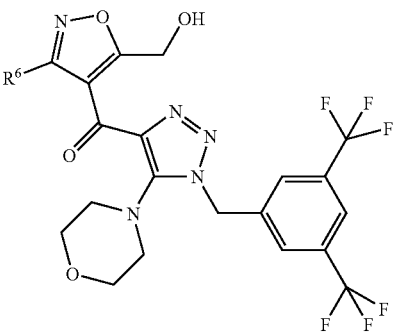

| Ex. # | R$^6$ | Physical Data |
|---|---|---|
| 66 | 3-chloro-pyridin-4-yl | MS (ES) 617.0, 619.0 (M$^+$+1). R$_f$ = 0.27 (6.25% MeOH/CH$_2$Cl$_2$) |
| 67 | 4-chloro-pyridin-3-yl | R$_f$ = 0.30 (6.67% MeOH/CH$_2$Cl$_2$) |

-continued

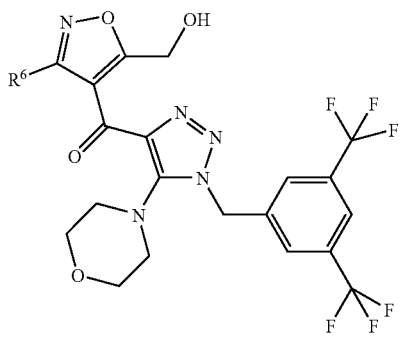

| Ex. # | R⁶ | Physical Data |
|---|---|---|
| 68 | 2-chloro-pyridin-3-yl | MS (ES) 617.0, 619.0 (M⁺+1). R$_f$ = 0.29 (6.25% MeOH/CH$_2$Cl$_2$) |
| 69 | 2,6-difluoro-phenyl | MS (ES) 617.9 (M⁺+1); R$_f$ = 0.40 (10:1 CHCl$_3$/MeOH) |
| 70 | 2,6-dichloro-phenyl | MS (ES) 649.9 (M⁺+1); R$_f$ = 0.43 (10:1 CHCl$_3$/MeOH) |

Example 71
[1-(3,5-bis-trifluoromethyl-benzyl)-5-pyrazin-2-yl-1H-[1,2,3]triazol-4-yl]-[3-(2-chloro-5-hydroxymethyl-isoxazol-4-yl]-methanone

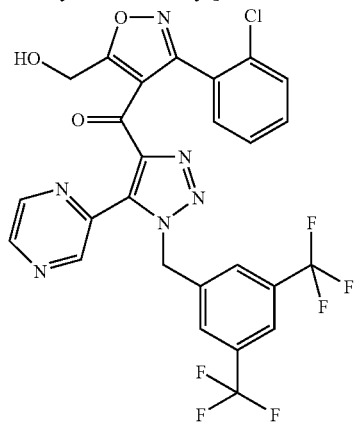

Dissolve [1-(3,5-Bis-trifluoromethyl-benzyl)-5-pyrazin-2-yl-1H-[1,2,3]triazol-4-yl]-[5-(tert-butyl-dimethyl-silanyloxymethyl)-3-(2-chloro-phenyl)-isoxazol-4-yl]-methanone (0.45 g, 1 eq.) in THF and add tetrabutylammonium flouride solution (0.74 mL 1.2 eq., 1N in THF). Stir 1.5 h. at RT, then dilute with EtOAc and wash with saturated aqueous NaHCO$_3$ and brine. Dry over Na$_2$SO$_4$, filter and concentrate in vacuo. Purify the residue by chromatography on silica gel. MS (ES) 609.1 (M+1)⁺; TLC R$_f$=0.43 (10% MeOH/CHCl$_3$).

By the method of Example 71, using the appropriate silylether, the following compounds may be prepared.

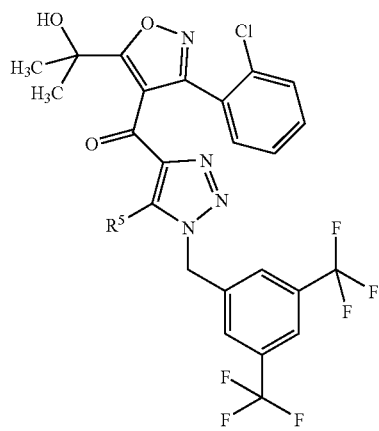

| Ex. # | R⁵ | Physical Data |
|---|---|---|
| 72 | pyrazin-2-yl | MS (ES) 637.2 (M+1)⁺; TLC R$_f$ = 0.50 10% MeOH/CHCl$_3$) |
| 73 | morpholino | m.p. 188° C.; TLC: R$_f$ = 0.38 (1:1 hexanes/EtOAc); MS(ES) 643.9 (M+1), 625.9 (M−OH) |

Example 74

[1-(3,5-bis-trifluoromethyl-benzyl)-5-pyridin-4-yl-1H-[1,2,3]triazol-4-yl]-[3-(3-chloro-pyridin-4-yl)-5-(1-hydroxy-1-methyl-ethyl)-isoxazol-4-yl]-methanone

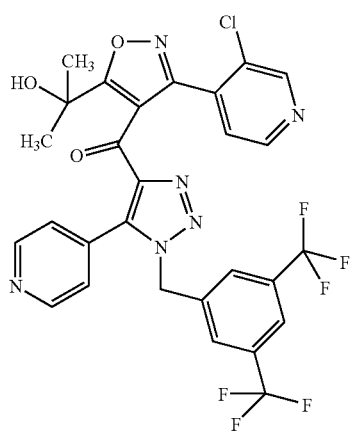

Using the method of Example 71, with the appropriate silylether, the title compound may be prepared and isolated. MS (ES) 637.0 (M$^+$+1); R$_f$=0.29 (6.67% MeOH/CH$_2$Cl$_2$).

By a method similar to Example 71, the following compounds may be prepared and isolated.

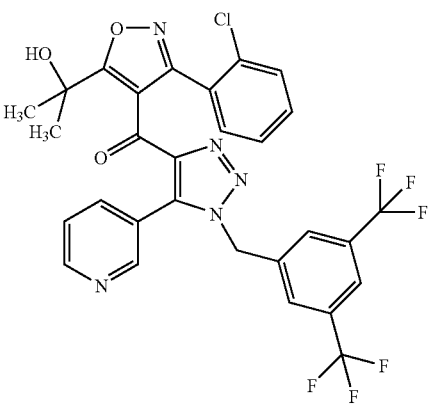

| Ex. # | R$^5$ | Physical Data |
|---|---|---|
| 75 | pyrazin-2-yl | R$_f$ = 0.53 (1:2 Hex/EtOAc); MS (ES) 637.3 (M+1) |
| 76 | morpholino | R$_f$ = 0.12 (2:1 Hex/EtOAc); MS (ES) 644.1 (M+1). |
| 77 | phenyl | MS (ES) 635.1 (M+1); R$_f$ = 0.32 (2:1 Hex/EtOAc) |

Example 78

[1-(3,5-bis-trifluoromethyl-benzyl)-5-pyridin-4-yl-1H-[1,2,3]triazol-4-yl]-[3-(2-chloro-phenyl)-5-(1-hydroxy-1-methyl-ethyl)-isoxazol-4-yl]-methanone

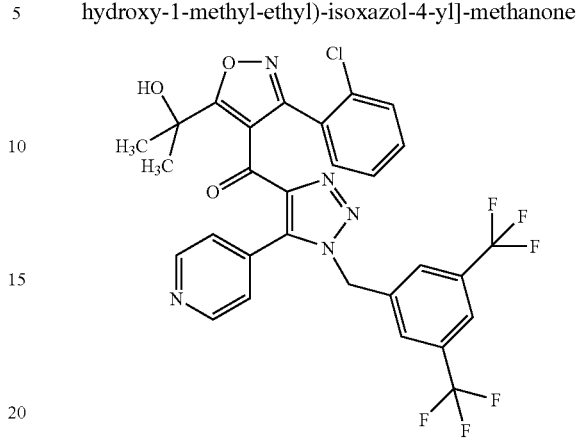

Dissolve 2-chloro-N-hydroxybenzenecarboximidoyl chloride (380 mg, 2.0 mmol, 2 eq.) and 1-[1-(3,5-bis-trifluoromethyl-benzyl)-5-pyridin-4-yl-1H-[1,2,3]triazol-4-yl]-4-methyl-4-trimethylsilanyloxy-pent-2-yn-1-one (555 mg, 1.0 mmol) in EtOAc (2.5 mL). Add TEA (348 µL, 252 mg, 2.5 eq.) dropwise and stir at RT. After 18 h., dilute with EtOAc (10 mL). Wash with saturated NaHCO$_3$ (10 mL), and brine (5 mL), then dry (MgSO$_4$), filter, and concentrate.

Dissolve the crude residue in THF (5 mL) and cool to 0° C. Add TBAF (Aldrich, 1.2 mL of a 1M soln in THF, 1.2 mmol, 1.2 eq.). After 2 h., dilute with EtOAc (20 mL). Wash with water (10 mL) and brine (10 mL). Dry (MgSO$_4$), filter, and concentrate. Purify by chromatography (silica gel, hexanes/EtOAc 1:1 to 1:2 gradient) to give the title compound as a yellow solid. Recrystallize from hexanes/EtOAc to give 173 mg (26%) of the title compound as a white solid. TLC: R$_f$=0.2 (1:2 hexanes/EtOAc); MS(ES): 636.0 (M+1).

Example 79

[1-(3,5-bis-trifluoromethyl-benzyl)-5-pyridin-3-yl-1H-[1,2,3]triazol-4-yl]-[3-(2-chloro-phenyl)-5-(1-hydroxy-1-methyl-ethyl)-isoxazol-4-yl]-methanone Using the method of Example 78, the title compound may be prepared and isolated. m.p.=105° C.; TLC: R$_f$=0.86 (1:2 hexanes/EtOAc); MS(ES) 618.2 [M–OH]$^+$.

Example 80

[1-(3,5-bis-trifluoromethyl-benzyl)-5-imidazol-1-yl-1H-[1,2,3]triazol-4-yl]-[5-(2-chloro-phenyl-3-(1-hydroxy-1-methyl-ethyl)-isoxazol-4-yl]-methanone

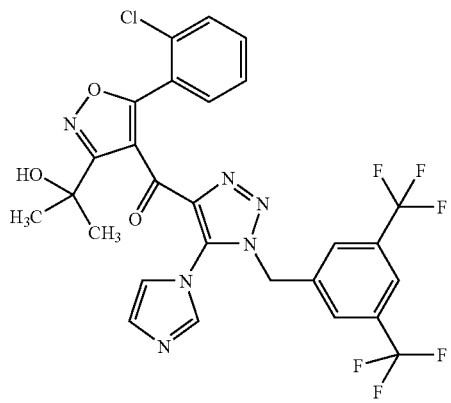

To a solution of [1-(3,5-Bis-trifluoromethyl-benzyl)-5-chloro-1H-[1,2,3]triazol-4-yl]-[5-(2-chloro-phenyl)-3-(1-methyl-1-trimethylsilanyloxy-ethyl)-isoxazol-4-yl]-methanone (40 mg, 0.06 mmol) in DMSO (0.5 mL), add imidazole (41 mg, 0.60 mmol) and heat to 80° C. for 12 h. Cool to RT and dilute with EtOAc (3 mL). Wash the solution with 1N HCl (3 ml) and H$_2$O (3 mL). Pass organic layer through Varian ChemElute® drying cartridge and concentrate. Chromatograph crude material using a gradient (10:1 to 1:5 Hex/EtOAc) to afford the title compound (18.2 mg, 49%). R$_f$=0.53 (1:5 Hex/EtOAc); MS/ES 625.1 (M+1).

Example 81

[1-(3,5-bis-trifluoromethyl-benzyl)-5-morpholin-4-yl-1H-[1,2,3]triazol-4-yl]-[3-(2-chloro-phenyl)-5-(1-hydroxy-ethyl)-isoxazol-4-yl]-methanone

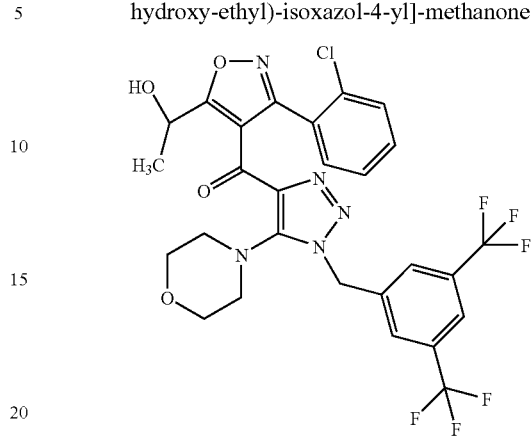

Dissolve 1-(3,5-bis-trifluoromethyl-benzyl)-5-morpholin-4-yl-1H-[1,2,3]triazo-4-yl]-[5-(1-tert-butoxy-ethyl)-3-(2-chloro-phenyl)-isoxazol-4-yl]-methanone (160 mg, 0.23 mmol) in TFA (1 mL) and stir at RT overnight. Dilute with EtOAc (10 mL) and wash with 1N NaOH (3×5 mL), saturated NaHCO$_3$ (5 mL), and brine (5 mL). Dry (MgSO$_4$), filter, and concentrate. Purify the residue by chromatography (silica gel, hexanes/EtOAc 2:1 to 1:1 gradient) to give 126 mg of a white solid. Recrystallize from hexanes/EtOAc to provide 92 mg (63%) of the title compound. m.p. 145–146° C.; TLC: R$_f$=0.28 (1:1 hexanes/EtOAc); MS(ES) 629.9 (M+1).

General Example F

Dissolve the appropriate 5-chlorotriazole (1 eq.) in the appropriate amine (20–120 eq.) and stir at 80–110° C. The amine may be in solution in a suitable solvent, such as MeOH, DMSO, or THF. After 2–20 h., dilute the solution with EtOAc (25 mL) and wash with 1N HCl (20 mL), water (20 mL), and saturated NaHCO$_3$ (20 mL). Dry, filter, and concentrate the organic phase then purify the residue by flash chromatography on silica gel.

Using the above method, with the appropriate starting materials, the following compounds may be prepared and isolated.

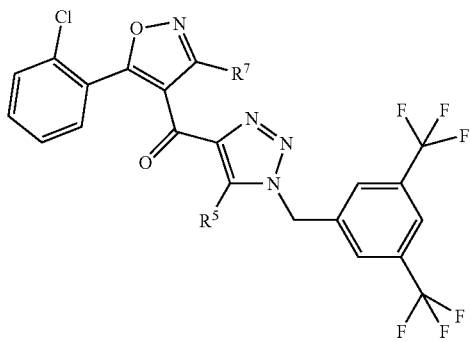

| Ex. # | R$^5$ | R$^7$ | Physical Data |
|---|---|---|---|
| 82 | morpholino | hydroxy-methyl | MS (ES) 616.1 (M+1), MS (ES−) 614.1 (M−1); $^1$H NMR (400 MHz, CDCl$_3$) δ 7.87 (s, 1H), 7.67 (dd, 1H, |

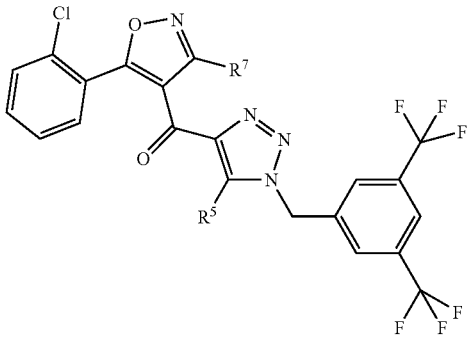

| Ex. # | R⁵ | R⁷ | Physical Data |
|---|---|---|---|
| | | | J = 1.5, 7.8 Hz), 7.62 (s, 2H), 7.37 (dt, 1H, J = 1.4, 7.4 Hz), 7.29 (dt, 1H, J = 1.4, 7.8 Hz), 7.12 (dd, 1H, J = 1.0, 7.8 Hz), 5.43 (s, 2H), 4.82 (d, 2H, J = 6.8 Hz), 4.03 (t, 1H, J = 7.6 Hz), 3.74 (m, 4H), 3.00 (m, 4H). |
| 83 | morpholino | 2-hydroxy-ethyl | MS (ES) 630.1 (M+1), MS (ES−) 628.0 (M−1); ¹H NMR (400 MHz, CDCl₃) δ 7.86 (s, 1H), 7.66 (dd, 1H, J = 1.4, 7.8 Hz), 7.62 (s, 2H), 7.34 (dt, 1H, J = 1.0, 7.4 Hz), 7.26 (dt, 1H, J = 2.0, 7.9 Hz), 7.12 (dd, 1H, J = 1.0, 7.9 Hz), 5.42 (s, 2H), 4.07 (t, 2H, J = 6.0 Hz), 3.73 (m, 4H), 3.18 (t, 2H, J = 6.0 Hz), 3.00 (m, 4H), 2.24 (br s, 1H). |
| 84 | dimethyl-amino | hydroxy-methyl | MS (ES) 574.3 (M+H). ¹H NMR (400 MHz, CDCl₃) δ 7.88 (s, 1H), 7.67 (dd, 1H, J = 7.7, 1.9 Hz), 7.60 (s, 2H), 7.35 (dt, 1H, J = 8.0, 1.7 Hz), 7.29 (dt, 1H, J = 7.7, 2.0 Hz), 7.15 (dd, 1H, J = 8.0, 1.3 Hz), 5.42 (s, 2H), 4.83 (br s, 2H), 4.22 (br s, 1H), 2.78 (s, 6H). |
| 85 | dimethyl-amino | 2-hydroxy-ethyl | MS (ES) 588.1 (M+H), 586.1 (M−H). ¹H NMR (400 MHz, CDCl₃) δ 7.87 (s, 1H), 7.67 (dd, 1H, J = 7.8, 1.8 Hz), 7.60 (s, 2H), 7.33 (dt, 1H, J = 7.9, 1.5 Hz), 7.27 (dt, 1H, J = 8.3, 1.8 Hz), 7.16 (dd, 1H, J = 8.3, 1.1 Hz), 5.41 (s, 2H), 4.07 (dt, 2H, J = 6.7, 6.1 Hz), 3.20 (t, 2H, J = 6.1 Hz), 2.78 (t, 1H, J = 6.7 Hz), 2.76 (s, 6H). |
| 86 | thio-morpholino | 2-hydroxy-ethyl | MS (ES) 646.1 (M+H); ¹H NMR (400 MHz, CDCl₃) δ 7.88 (s, 1H), 7.68 (dd, 1H, J = 7.7, 1.8 Hz), 7.62 (s, 2H), 7.36 dt, 1H, J = 8.0, 1.5 Hz), 7.28 (dt, 1H, J = 7.7, 1.1 Hz), 7.15 (dd, 1H, J = 8.0, 1.1 Hz), 5.40 (s, 2H), 4.09 (m, 2H), 3.25 (m, 4H), 3.19 (t, 2H, J = 6.3 Hz), 2.69 (m, 4H). |
| 87 | morpholino | methyl | MS (ES+) 600.1 (M+1), MS (ES−) 598.0 (M−1); ¹H NMR (400 MHz, CDCl₃) δ 7.89 (s, 1H), 7.65 (dd, 1H, J = 1.9, 7.8 Hz), 7.63 (s, 2H), 7.33 (dt, 1H, J = 1.5, 8.0 Hz), 7.25 (dt, 1H, J = 1.8, 7.4 Hz), 7.10 (dd, 1H, J = 1.1, 8.0 Hz), 5.42 (s, 2H), 3.73 (m, 4H), 3.00 (m, 4H), 2.51 (s, 3H). |
| 88 | morpholino | cyclo-propyl | MS (ES) 626.0 (M+H). ¹H NMR (400 MHz, CHCl₃) δ 7.88 (s, 1H), 7.65 (m, 3H), 7.33 (dt, 1H, J = 7.8, 1.5 Hz), 7.25 (dt, 1H, J = 7.8, 1.5 Hz), 7.12 (dd, 1H, J = 7.8, 1.0 Hz), 5.44 (s, 2H), 3.75 (m, 4H), 3.04 (m, 4H), 2.32 (m, 1H), 1.67 (m, 2H), 1.06 (m, 2H). |
| 89 | morpholino | methoxy-methyl | MS (ES) 630.1 (M+H). ¹H NMR (400 MHz, CHCl₃) δ 7.81 (s, 1H), 7.70 (dd, 1H, J = 7.3, 1.9 Hz), 7.68 (s, 2H), 7.31–7.40 (m, 2H), 7.22 (dd, 1H, J = 7.8, 1.5 Hz), 5.49 (s, 2H), 4.77 (s, 2H), 3.74 (m, 4H), 3.33 (s, 3H), 3.01 (m, 4H). |
| 90 | morpholino | 2,2-dimethoxy-ethyl | MS (ES) 674.2 (M+H). ¹H NMR (400 MHz, CHCl₃) δ 7.88 (s, 1H), 7.70 (dd, 1H, J = 7.8, 1.5 Hz), 7.66 (s, 2H), 7.36 (dt, 1H, J = 7.8, 1.5 Hz), 7.29 (dt, 1H, J = 7.8, 1.5 Hz), 7.16 (dd, 1H, J = 7.8, 1.5 Hz), 5.46 (s, 2H), 4.81 (t, 1H, J = 5.7 Hz), 3.75 (m, 4H), 3.31 (s, 6H), 3.30 (d, 2H, J = 5.7 Hz), 3.01 (m, 4H). |
| 91 | dimethyl-amino | methyl | MS (ES) 558.1 (M+H), 556.1 (M−H). ¹H NMR (400 MHz, CHCl₃) δ 7.86 (s, 1H), 7.64 (dd, 1H, J = 7.8, 1.9 Hz), 7.61 (s, 2H), 7.32 (dt, 1H, J = 7.2, 1.6 Hz), 7.24 (dt, 1H, J = 7.2, 1.9 Hz), 7.14 (dd, 1H, J = 7.8, 1.6Hz), 5.41 (s, 2H), 2.76 (s, 6H), 2.52 (s, 3H). |
| 92 | dimethyl-amino | methoxy-methyl | MS (ES) 588.2 (M+H). ¹H NMR (400 MHz, CHCl₃) δ 7.85 (s, 1H), 7.66 (dd, 1H, J = 7.4, 1.5 Hz), 7.64 (s, 2H), 7.28–7.37 (m, 2H), 7.24 (m, 1H), 5.46 (s, 2H), 4.76 (s, 2H), 3.31 (s, 3H), 2.74 (s, 6H). |

-continued

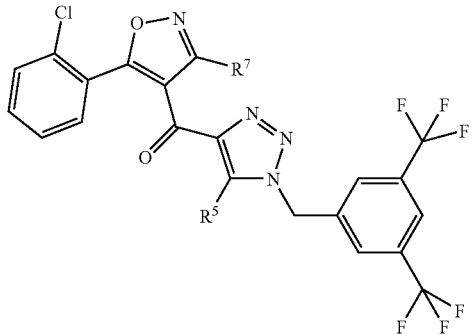

| Ex. # | R⁵ | R⁷ | Physical Data |
|---|---|---|---|
| 93 | dimethyl-amino | 2,2-dimethoxy-ethyl | MS (ES) 632.1 (M+H). ¹H NMR (400 MHz, CHCl₃) δ 7.87 (s, 1H), 7.70 (dd, 1H, J = 7.8, 1.5 Hz), 7.66 (s, 2H), 7.36 (dt, 1H, J = 7.8, 1.5 Hz), 7.29 (dt, 1H, J = 7.8, 1.5Hz), 7.16 (dd, 1H, J = 7.8, 1.5Hz), 5.46 (s, 2H), 4.81 (t, 1H, J = 5.7 Hz), 3.31 (s, 6H), 3.30 (d, 2H, J = 5.7 Hz), 2.76 (s, 6H). |
| 94 | thio-morpholino | hydroxy-methyl | MS (ES) 632.3 (M+H). ¹H NMR (400 MHz, CHCl₃) δ 7.89 (s, 1H), 7.67 (dd, 1H, J = 7.8, 1.7 Hz), 7.63 (s, 2H), 7.37 (dt, 1H, J = 7.8, 1.7 Hz), 7.29 (dt, 1H, J = 7.8, 1.7 Hz), 7.15 (dd, 1H, J = 7.8, 1.0Hz), 5.42 (s, 2H), 4.83 (br s, 2H), 4.10 (br s, 1H), 3.26 (m, 4H), 2.69 (m, 4H). |
| 95 | thio-morpholino | methyl | MS (ES) 616.1 (M+H), 614.1 (M−H). ¹H NMR (400 MHz, CHCl₃) δ 7.87 (s, 1H), 7.67 (dd, 1H, J = 7.8, 1.9) 7.63 (s, 2H), 7.36 (dt, 1H, J = 7.2, 1.6), 7.27 (dt, 1H, J = 7.2, 1.9), 7.13 (dd, 1H, J = 7.8, 1.6), 5.41 (s, 2H), 3.26 (m, 4H), 2.69 (m, 4H), 2.53 (s, 3H). |
| 96 | imidazol-1-yl | hydroxy-methyl | MS [ES] 597.1 (M+H)⁺, 595.1 (M−H)⁻. ¹H NMR (400 MHz, CHCl₃) δ 7.91 (s, 1H), 7.74 (dd, 1H, 1 7.6, 1.6 Hz) 7.70 (br s, 1H), 7.45–7.49 (m, 3H), 7.41 (dt, 1H, J = 7.6, 2.0 Hz), 7.34 (br s, 1H), 7.21 (dd, 1H, J = 8.0, 1.2 Hz), 6.92 (br s, 1H), 5.42 (s, 2H), 4.83 (m, 2H), 3.00 (br s, 1H). |
| 97 | imidazol-1-yl | methyl | MS [ES] 581.1 (M+H)⁺, 579.1 (M−H)⁻. ¹H NMR (400 MHz, CHCl₃) δ 7.91 (s, 1H), 7.73 (dd, 1H, J = 7.7, 1.9 Hz) 7.60 (m, 1H), 7.41–7.45 (m, 3H), 7.35 (dt, 1H, J = 8.3, 1.8 Hz), 7.32 (m, 1H), 7.17 (dd, 1H, J = 8.3, 1.4 Hz), 6.92 (m, 1H), 5.38 (s, 2H), 2.50 (s, 3H). |
| 98 | imidazol-1-yl | cyclo-propyl | MS (ES) 607.1 (M+H). ¹H NMR (400 MHz, CHCl₃) δ 7.91 (s, 1H), 7.71 (dd, 1H, J = 7.8, 1.0 Hz) 7.62 (s, 1H), 7.43 (s, 2H), 7.42 (t, 1H, J = 7.8, 1.0 Hz), 7.34 (m, 2H), 7.17 (dd, 1H, J = 7.8, 1.0 Hz), 6.94 (s, 1H), 5.38 (s, 2H), 2.29 (m, 1H), 1.14 (m, 2H), 1.05 (m, 2H). |
| 99 | imidazol-1-yl | methoxy-methyl | MS (ES) 611.2 (M+H). ¹H NMR (400 MHz, CHCl₃) δ 7.89 (s, 1H), 7.72 (dd, 1H, J = 7.5, 2.1 Hz) 7.63 (s, 1H), 7.46 (s, 2H), 7.37–7.45 (m, 2H), 7.29 (s, 1H), 7.25 (dd, 1H, J = 7.5, 1.4 Hz), 6.91 (s, 1H), 5.45 (s, 2H), 4.75 (s, 2H), 3.33 (s, 3H). |
| 100 | 4-methyl-piperazin-1-yl | hydroxy-methyl | MS (ES) 629.3 (M+H). ¹H NMR (400 MHz, CHCl₃) δ 7.89 (s, 1H), 7.67 (dd, 1H, J = 7.7, 1.9 Hz), 7.65 (s, 2H), 7.37 (dt, 1H, J = 7.7, 1.3Hz), 7.29 (dt, 1H, J = 7.7, 1.8 Hz), 7.13 (dd, 1H, J = 7.7, 1.3 Hz), 5.42 (s, 2H), 4.82 (d, 2H, J = 7.4 Hz), 4.18 (t, 1H, J = 7.4 Hz), 3.06 (br s, 4H), 2.48 (br s, 4H), 2.35 (s, 3H). |
| 101 | 4-methyl-piperazin-1-yl | methyl | MS (ES) 613.2 (M+H), 611.2 (M−H). ¹H NMR (400 MHz, CHCl₃) δ 7.87 (s, 1H), 7.63–7.65 (m, 3H) 7.33 (dt, 1H, J = 7.2, 1.6 Hz), 7.25 (dt, 1H, J = 7.2, 1.9 Hz), 7.13 (dd, 1H, J = 7.8, 1.6 Hz), 5.40 (s, 2H), 3.04 (m, 4H), 2.51 (s, 3H), 2.45 (m, 4H), 2.32 (s, 3H). |

-continued

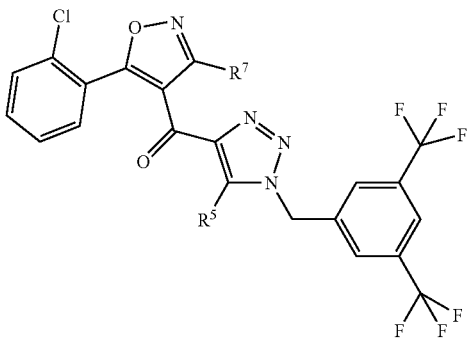

| Ex. # | R⁵ | R⁷ | Physical Data |
|---|---|---|---|
| 102 | 4-isopropyl-piperazin-1-yl | hydroxymethyl | MS (ES) 657.2 (M+H). ¹H NMR (400 MHz, CHCl₃) δ 7.89 (s, 1H), 7.64–7.68 (m, 3H), 7.37 (m, 1H), 7.31 (dt, 1H, J = 7.4, 1.6Hz), 7.14(dd, 1H, J = 7.7, 1.6Hz), 5.42 (s, 2H), 4.82 (m, 2H), 4.20 (br s, 1H), 3.04 (m, 4H), 2.74 (s, 1H, J = 6.7 Hz), 2.55 (m, 4H), 1.05 (d, 6H, J = 6.7 Hz). |
| 103 | 4-isopropyl-piperazin-l-yl | 2-hydroxyethyl | MS (ES) 671.2 (M+H). ¹H NMR (400 MHz, CHCl₃) δ 7.87 (s, 1H), 7.65 (m, 1H), 7.63 (s, 2H), 7.33 (dt, 1H, J = 8.1, 1.6 Hz), 7.27 (m, 1H), 7.14 (dd, 1H, J = 7.8, 1.6 Hz), 5.40 (s, 2H), 4.06 (m, 2H), 3.19 (t, 2H, J = 5.8 Hz), 3.04 (br s, 4H), 2.75 (m, 1H), 2.55 (br s, 4H), 1.04 (d, 6H, J = 7.0 Hz). |
| 104 | 4-carbamoyl-piperidin-1-yl | methyl | MS [ES] 641.2 (M+H)⁺. ¹H NMR (400 MHz, CHCl₃) δ 7.86 (s, 1H), 7.66 (m, 3H) 7.34 (dt, 1H, J = 7.3, 1.5 Hz), 7.25 (m, 1H), 7.12 (dd, 1H, J = 8.0, 1.0 Hz), 5.37–5.47 (m, 4H), 3.33 (dt, 2H, J = 11.7, 2.3 Hz), 2.81 (m, 2H), 2.53 (s, 3H), 2.37–2.44 (m, 1H), 1.79–1.97 (m, 4H). |

Example 105
[1-(3,5-Bis-trifluoromethyl-benzyl)-5-dimethylamino-1H-[1,2,3]triazol-4-yl]-[4-(2-chloro-phenyl)-3-(2-hydroxy-ethyl)-isoxazol-5-yl]-methanone

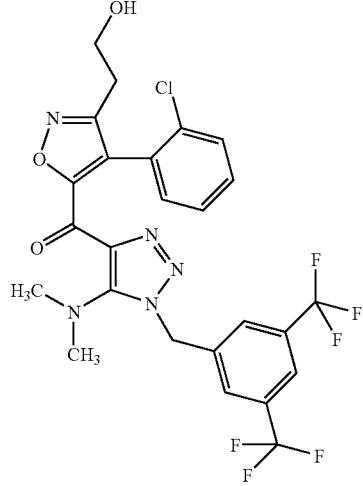

Following a method similar to General Example F, the title compound may be prepared and isolated. MS [ES] 588.1 (M+H)⁺, 586.1 (M−H)⁻; ¹H NMR (400 MHz, CHCl₃) δ 7.87 (s, 1H), 7.71 (s, 2H), 7.37 (m, 1H), 7.26–7.32 (m, 3H), 5.50 (s, 2H), 3.93 (m, 2H), 2.87 (m, 2H), 2.74 (s, 6H).

By the method of General Example F, the following compounds may be prepared and isolated.

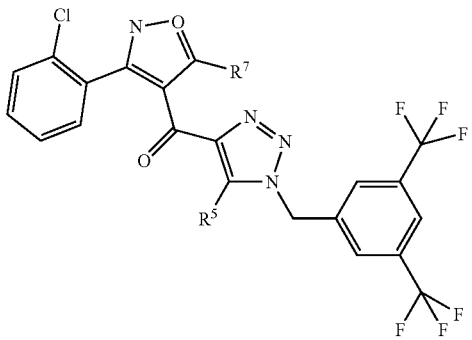

| Ex. # | R⁵ | R⁷ | Physical Data |
|---|---|---|---|
| 106 | morpholino | hydroxy-methyl | MS (ES) 616.0 (M+1); TLC $R_f = 0.1$ (50% EtOAc in hexanes). |
| 107 | 4-methyl-piperazin-1-yl | hydroxy-methyl | MS (ES) 629.1 (M⁺+1); TLC $R_f = 0.3$ (5% MeOH in dichloromethane). |
| 108 | dimethyl-amino | hydroxy-methyl | MS (ES) 574.0 (M⁺+1); TLC): $R_f = 0.4$ (50% EtOAc in hexanes |
| 109 | (2-dimethyl-amino-ethyl)-methyl-amino | hydroxy-methyl | MS (ES) 631.1(M⁺+l); TLC $R_f = 0.2$ (5% MeOH in dichloromethane). |
| 110 | thio-morpholino | hydroxy-methyl | MS (ES) 632.0 (M⁺+1); TLC $R_f = 0.2$ (50% EtOAc in hexanes). |
| 111 | morpholino | 2-(morpholino)-ethyl | MS (ES) 698.9 (M⁺+1); TLC $R_f = 0.1$ (5% MeOH in dichloromethane). |
| 112 | imidazol-1-yl | hydroxy-methyl | MS (ES) 597.1 (M⁺+1); TLC $R_f = 0.1$ (elute with 20% then 25% acetone in hexanes). |
| 113 | morpholino | hydrogen | MS (ES) 586.2 (M⁺+1); TLC $R_f = 0.1$ (50% ether in hexanes). |
| 114 | imidazol-1-yl | hydrogen | MS (ES) 586.2 (M⁺+1); TLC $R_f = 0.1$ (50% ether in hexanes). |
| 115 | morpholino | methoxy-methyl | m.p. 119° C.; TLC: $R_f = 0.15$ (2:1 hexanes/EtOAc) MS(ES) 629.9 (M+1) |

By the method of General Example F, the following compounds may be prepared and isolated.

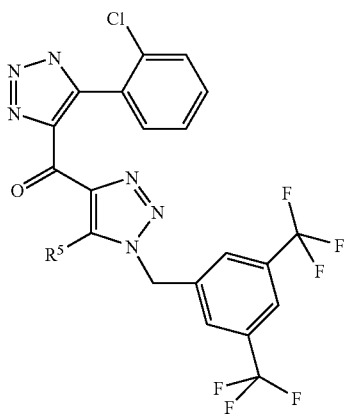

| Ex. # | R⁵ | Physical Data |
|---|---|---|
| 116 | morpholino | MS (ES+) 586.0 (M+1)⁺, MS (ES−) 584.0 (M−1). ¹H NMR (400 MHz, CDCl₃) δ 14.68 (br s, 1H), 7.87 (s, 1H), 7.84 (s, 2H), 7.54 (m, 1H), 7.46 (m, 1H), 7.38 (m, 2H), 5.64 (s, 2H), 3.74 (m, 4H), 2.99 (m, 4H). |
| 117 | dimethyl-amino | MS (ES) 544.0 (M+H), 542.0 (M−H). ¹H NMR (400 MHz, CHCl₃) δ 7.88 (s, 1H), 7.82 (s, 2H) 7.56 (m, 1H), 7.46 (m, 1H), 7.38 (m, 2H), 5.62 s, 2H, 2.75 s, 6H. |

-continued

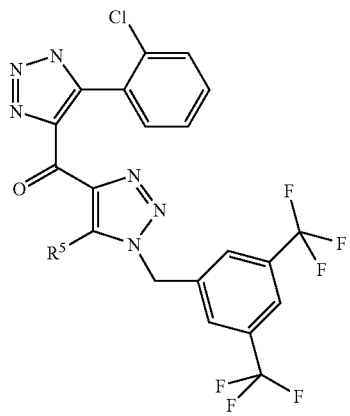

| Ex. # | R⁵ | Physical Data |
|---|---|---|
| 118 | 4-methyl-piperazin-1-yl | MS [ES] 599.1 (M+H). ¹H NMR (400 MHz, CHCl₃) δ 7.89 (s, 1H), 7.85 (s, 2H), 7.54 (m, 1H), 7.44 (m, 1H), 7.33–7.40 (m, 2H), 5.61 (s, 2H), 3.04(brs, 4H), 2.48(brs, 4H), 2.33(s, 3H). |

By the method of General Example F, the following compounds may be prepared and isolated.

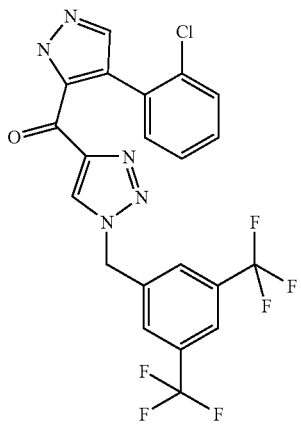

| Ex. # | R⁵ | Physical Data |
|---|---|---|
| 119 | morpholino | MS (ES) 585.1 (M+H). ¹H NMR (400 MHz, CHCl₃) δ 13.25 (br s, 1H), 7.89 (s, 1H), 7.86 (s, 2H), 7.60 (s, 1H), 7.46 (m, 1H), 7.38 (m, 1H), 7.30–7.32 (m, 2H), 5.65 (s, 2H), 3.75 (m, 4H), 2.99 (m, 4H). |
| 120 | dimethyl-amino | MS [ES] 543.1 (M+H)⁺. ¹H NMR (400 MHz, CHCl₃) δ 13.25 (br s, 1H), 7.89 (s, 1H), 7.83 (s, 2H), 7.67 (s, 1H), 7.46 (m, 1H), 7.38 (m, 1H), 7.30–7.32 (m, 2H), 5.59 (s, 2H), 2.72 (s, 6H). |
| 121 | 4-methyl-piperazin-1-yl | MS [ES] 598.2 (M+H)⁺, 596.1 (M−H)⁻. ¹H NMR (400 MHz, CHCl₃) δ 13.25 (br s, 1H), 7.89 (s, 1H), 7.86 (s, 2H), 7.66 (s, 1H), 7.43 (m, 1H), 7.36 (m, 1H), 7.27–7.30 (m, 2H), 5.59 (s, 2H), 3.00 (br s, 4H), 2.45 (br s, 4H), 2.31 (s, 3H). |
| 122 | thio-morpholino | MS [ES] 601.0 (M+H)⁺. ¹H NMR (400 MHz, CHCl₃) δ 7.89 (s, 1H), 7.83 (s, 2H), 7.68 (s, 1H), 7.47 (m, 1H), 7.38 (m, 1H), 7.31–7.33 (m, 2H), 5.59 (s, 2H), 3.23 (m, 4H), 2.69 (m, 4H). |

By the method of General Example F, the following compounds may be prepared and isolated.

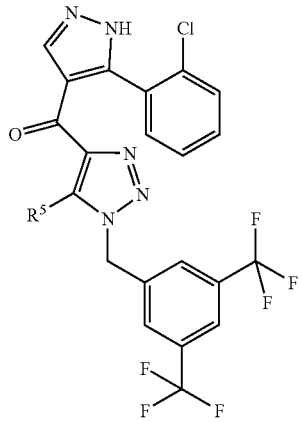

| Ex. # | R⁵ | Physical Data |
|---|---|---|
| 123 | morpholino | MS [ES] 585.1 (M+H)⁺. ¹H NMR (400 MHz, CHCl₃) δ 8.84 (s, 1H), 7.88 (s, 1H), 7.83 (s, 2H), 7.48 (m, 1H), 7.43 (m, 1H), 7.33–7.40 (m, 2H), 5.58 (s, 2H), 3.73 (m, 4H), 2.97 (m, 4H). |
| 124 | dimethyl-amino | MS [ES] 542.9 (M)⁺. ¹H NMR (400 MHz, CHCl₃) δ 11.67 (br s, 1H), 8.77 (s, 1H), 7.86 (s, 1H), 7.81 (s, 2H), 7.47 (m, 1H), 7.42 (m, 1H), 7.32–7.36 (m, 2H), 5.54 (s, 2H), 2.68 (s, 6H). |
| 125 | thio-morpholino | MS [ES] 601.1 (M+H)⁺. ¹H NMR (400 MHz, CHCl₃) δ 8.70 (s, 1H), 7.88 (s, 1H), 7.80 (s, 2H), 7.48 (m, 1H), 7.43 (m, 1H), 7.33–7.37 (m, 2H), 5.53 (s, 2H), 3.20 (m, 4H), 2.65 (m, 4H). |

By the method of General Example F, the following compounds may be prepared and isolated.

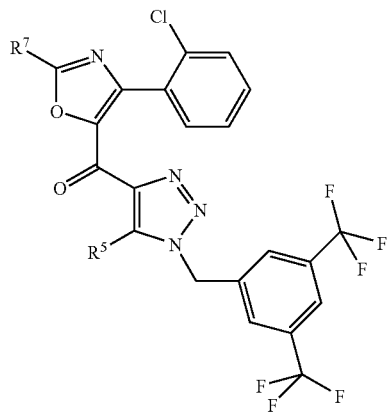

| Ex. # | R⁵ | R⁷ | Physical Data |
|---|---|---|---|
| 126 | morpholino | methyl | MS (ES) 600.2 (M+1), (ES) 598.2 (M−1). ¹H NMR (400 MHz, CDCl₃) δ 7.86 (s, 1H), 7.72 (s, 2H), 7.55 (dd, 1H, J = 1.5, 7.4Hz), 7.30 (dt, 1H, J = 1.3, 7.3 Hz), 7.23 (dt, 1H, J = 1.9, 7.4 Hz), 7.17 (dd, 1H, J = 1.1, 7.8 Hz), 5.47 (s, 2H), 3.71 (m, 4H), 2.98 (m, 4H), 2.64 (s, 3H). |

-continued

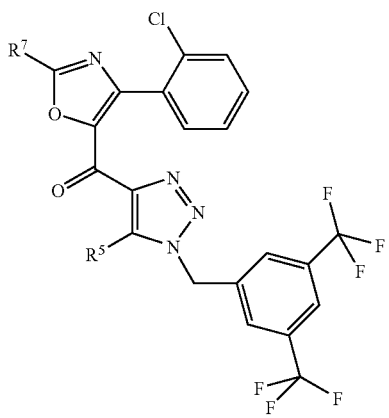

| Ex. # | R⁵ | R⁷ | Physical Data |
|---|---|---|---|
| 127 | morpholino | isopropyl | MS (ES) 628.2 (M+H). ¹H NMR (400 MHz, CHCl₃) δ 7.88 (s, 1H), 7.72 (s, 2H), 7.60 (dd, 1H, J = 7.8, 1.4 Hz), 7.31 (dt, 1H, J = 7.8, 1.4 Hz), 7.22 (dt, 1H, J = 7.8, 1.4 Hz), 7.14 (dd, 1H, J = 7.8, 1.4Hz), 5.48 (s, 2H), 3.73 (m, 4H), 3.26 (s, 1H, J = 6.7 Hz), 3.01 (m, 4H), 1.46 (d, 6H, J = 6.7 Hz). |
| 128 | morpholino | cyclo-propyl | MS [ES] 626.1 (M+H)⁺. ¹H NMR (400 MHz, CHCl₃) δ 7.88 (s, 1H), 7.72 (s, 2H), 7.55 (dd, 1H, J = 7.3, 1.4 Hz), 7.31 (dt, 1H, J = 7.3, 1.4 Hz), 7.22 (dt, 1H, J = 7.3, 1.4 Hz), 7.16 (dd, 1H, J = 7.8, 1.4 Hz), 5.48 (s, 2H), 3.73 (m, 4H), 3.00 (m, 4H), 2.24 (m, 1H), 1.17–1.34 (m, 4H). |
| 129 | imidazol-1-yl | methyl | MS (ES) 581.1 (M+H), ¹H NMR (400 MHz, CDCl₃) δ 7.90 (s, 1H), 7.72 (s, 1H) 7.56 (m, 3H), 7.28–7.37 (m, 4H), 6.94 (s, 1H), 5.50 (s, 2H), 2.65 (s, 3H). |
| 130 | imidazol-1-yl | isopropyl | MS (ES) 609.1 (M+H). ¹H NMR (400 MHz, CHCl₃) δ 7.89(s, 1H), 7.68(s, 1H) 7.58 (dd, 1H, J = 7.5, 1.7 Hz), 7.52 (s, 2H), 7.22–7.36 (m, 4H), 6.94 (s, 1H), 5.46 (s, 2H), 3.25 (s, 1H, J = 6.9 Hz), 1.45 (d, 6H, J = 6.9 Hz). |

Example 131

[1-(3,5-Bis-trifluoromethyl-benzyl)-5-imidazol-1-yl-1H-[1,2,3]triazol-4-yl]-[4-(2-chloro-phenyl)-2-cyclopropyl-oxazol-5-yl]-methanone

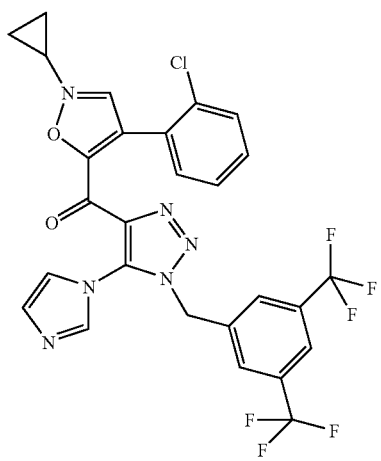

Add imidazole (0.37 g, 5.44 mmol) to a solution of [1-(3,5-bis-trifluoromethyl-benzyl)-5-chloro-1H-[1,2,3]triazol-4-yl]-[4-(2-chloro-phenyl)-2-cyclopropyl-oxazol-5-yl]-methanone (0.16 g, 0.28 mmol) in DMSO (1.0 mL) and heat to 80° C. for 18 h. Dilute reaction mixture with EtOAc and wash with water and brine, then dry, filter, and concentrate. Purify by flash chromatography using a linear gradient of 30% to 70% EtOAc in hexane to give the title compound (0.15 g, 76%). MS (ES) 607.1 (M+H). ¹H NMR (400 MHz, CHCl₃) δ 7.88 (s, 1H), 7.61 (s, 1H) 7.51 (m, 3H), 7.21–7.33 (m, 4H), 6.92 (s, 1H), 5.43 (s, 2H), 2.20 (m, 1H), 1.17–1.31 (m, 4H).

Example 132

[1-(3,5-bis-trifluoromethyl-benzyl)-5-(1,1-dioxo-1λ-thiomorpholin-4-yl)-1H-[1,2,3]triazol-4-yl]-[5-(2-chloro-phenyl)-3-(2-hydroxy-ethyl)-isoxazol-4-yl]-methanone

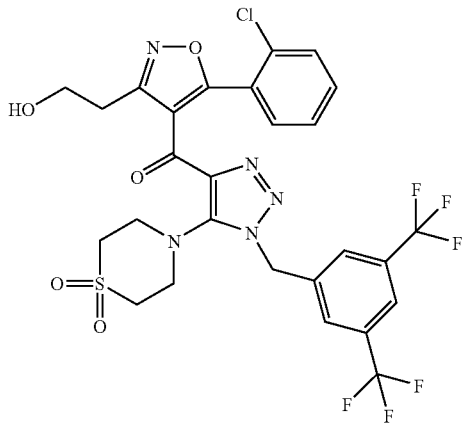

Combine [1-(3,5-bis-trifluoromethyl-benzyl)-5-(thiomorpholin-4-yl)-1H-[1,2,3]triazol-4-yl]-[5-(2-chloro-phenyl)-3-hydroxymethyl-isoxazol-4-yl]-methanone (0.17 g, 0.26 mmol) in dichloromethane (3.0 mL), add 3-chloroperoxybenzoic acid (0.12 g, 0.50 mmol) and stir at RT. After 2 h., dilute with EtOAc, wash with 1N NaOH, water and brine, dry, filter, and concentrate. Purify by flash chromatography using a linear gradient of 50% to 80% EtOAc in hexane to give the title compound. MS (ES) 678.0 (M+H). $^1$H NMR (400 MHz, CD$_3$COCD$_3$) δ 8.09(s, 1H), 7.99 (s, 2H), 7.65 (m, 1H), 7.42 (m, 2H), 7.35 (m, 1H), 5.86 (s, 2H), 3.89 (m, 3H), 3.62 (m, 4H), 3.26 (m, 4H), 3.14 (m, 2H).

By a method similar to Example 132, the following compounds may be prepared and isolated.

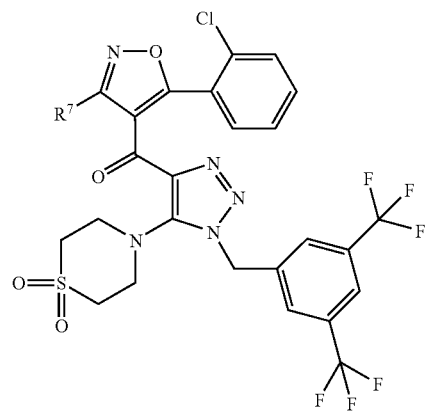

| Ex. # | R$^7$ | Physical Data |
|---|---|---|
| 133 | hydroxymethyl | MS (ES) 664.0 (M+H). $^1$H NMR (400 MHz, CHCl$_3$) δ 7.92 (s, 1H), 7.74 (dd, 1H, J = 7.8, 1.6 Hz) 7.61 (s, 2H), 7.44 (dt, 1H, J = 7.8, 1.6 Hz), 7.36 (dt, 1H, J = 7.8, 1.6 Hz), 7.18 (dd, 1H, J = 8.1, 0.9 Hz), 5.48 (s, 2H), 4.85 (d, 2H, J = 6.6 Hz), 3.75 (t, 1H), 3.55 (m, 4H), 3.15 (m, 4H). |
| 134 | methyl | MS [ES] 648.1 (M+H)$^+$, 646.0 (M−H). $^1$H NMR (400 MHz, CHCl$_3$) δ 7.91 (s, 1H), 7.73 (dd, 1H, J = 7.7, 1.9 Hz) 7.62 (s, 2H), 7.41 (m, 1H), 7.31 (dt, 1H, J = 7.9, 2.2 Hz), 7.15 (m, 1H), 5.47 (s, 2H), 3.56 (m, 4H), 3.15 (m, 4H), 2.53 (s, 3H). |

By a method analogous to Example 132, the following compounds may be prepared and isolated.

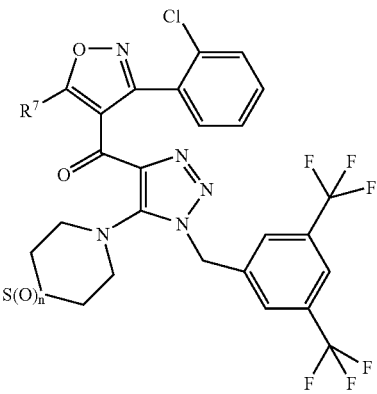

| Ex. # | n | R⁷ | Physical Data |
|---|---|---|---|
| 135 | 1 | hydroxy-methyl | MS (ES) 648.0 (M⁺+1); TLC $R_f$ = 0.2 (acetone). |
| 136 | 2 | hydroxy-methyl | MS (ES) 664.0 (M⁺+1); TLC $R_f$ = 0.1 (60% EtOAc in hexanes). |
| 137 | 2 | 2-hydroxy-ethyl | MS (ES) 645.9 (M⁺+1); TLC $R_f$ = 0.1 (50% EtOAc in hexanes). |

Example 138

[1-(3,5-bis-trifluoromethyl-benzyl)-5-(1,1-dioxo-1λ-thiomorpholin-4-yl)-1H-[1,2,3]triazol-4-yl]-[4-(2-chloro-cyclohexa-2,4-dienyl)-2H-pyrazol-3-yl]-methanone

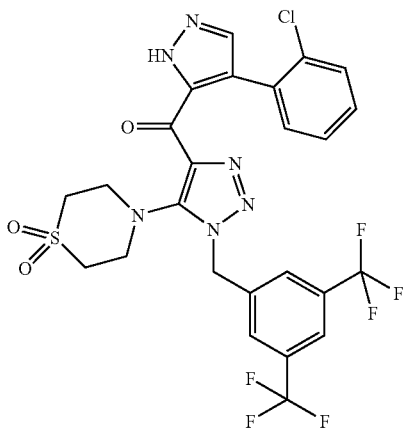

Using the method of Example 132, with the appropriate starting materials, the title compound can be prepared and isolated. MS [ES] 633.0 (M+H)⁺. ¹H NMR (400 MHz, CD₃COCD₃) δ 13.4 (br s, 1H), 8.10 (s, 2H), 8.04 (s, 1H), 7.64 (br s, 1H), 7.38 (m, 2H), 7.28 (m, 2H), 5.93 (s, 2H), 3.55 (m, 4H), 3.20 (m, 4H).

Example 139

[1-(3,5-bis-trifluoromethyl-benzyl)-5-(1-oxo-1λ-thiomorpholin-4-yl)-1H-[1,2,3]triazol-4-yl]-[5-(2-chloro-phenyl)-3-methyl-isoxazol-4-yl]-methanone

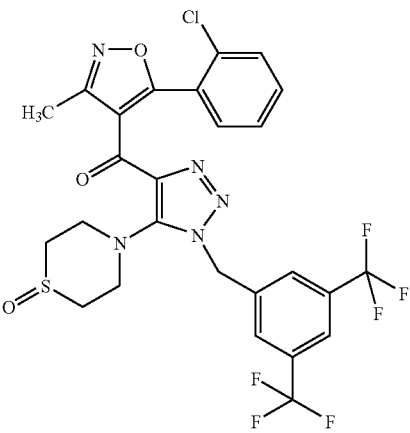

Add 30% aqueous hydrogen peroxide (2.0 mL, excess) to a solution of [1-(3,5-bis-trifluoromethyl-benzyl)-5-thiomorpholin-4-yl-1H-[1,2,3]triazol-4-yl]-[5-(2-chloro-phenyl)-3-methyl-isoxazol-4-yl]-methanone (0.9 g, 0.15 mmol) in MeOH (4.0 mL) and stir at RT for 24 h. Dilute reaction mixture with water, extract with EtOAc, then dry, filter, and concentrate. Purify by flash chromatography using a linear gradient of 2% to 4% MeOH in dichloromethane to give the title compound (15 mg, 16%). MS [ES] 632.1 (M+H)⁺, 630.1 (M−H)⁻. ¹H NMR (400 MHz, CHCl₃) δ 7.90 (s, 1H), 7.71 (dd, 1H, J=7.8, 1.9 Hz) 7.62 (s, 2H), 7.38 (dt, 1H, J=7.9, 1.6 Hz), 7.31 (dt, 1H, J=7.9, 1.9 Hz), 7.15 (dd, 1H, J=7.8, 1.6 Hz), 5.45 (s, 2H), 3.83 (m, 2H), 3.10 (m, 2H), 2.87–2.96 (m, 4H), 2.52 (s, 3H).

General Example G

In a pressure vessel, dissolve the alkyne of interest (1 eq.) in toluene (0.1 M), add the azide of interest (2 eq.), and place in a 120 IC bath. After 48 h., concentrate and purify by chromatography on silica gel. Trimethylsilyl azide may be used to prepare unsubstituted triazoles.

By the method of General Example G, the following compounds may be prepared and isolated.

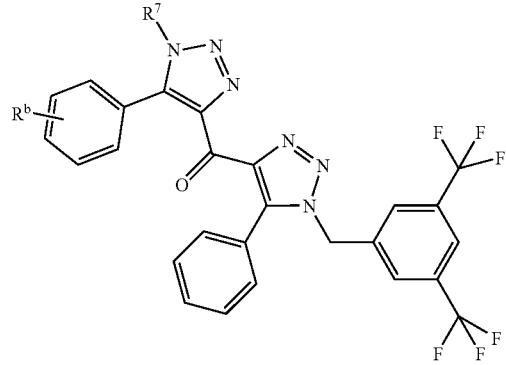

| Ex. # | $R^7$ | $R^b$ | Physical Data |
| --- | --- | --- | --- |
| 140 | hydrogen | 2-chloro | MS (ES) 577.2 (M+1), $^1$H NMR (300 MHz, CDCl$_3$): δ 7.89 (s, 1H), 7.62–7.25 (m, 12H), 5.68 (s, 2H). |
| 141 | hydrogen | hydrogen | MS (ES) 543.3 (M+1), $^1$H NMR (300 MHz, CDCl$_3$): δ 7.99 (ap q, 1H), 7.89 (s, 1H), 7.66–7.23 (m, 11H), 5.67 (s, 2H). |
| 142 | hydrogen | 4-fluoro | MS (ES) 561.3 (M+1), $^1$H NMR (300 MHz, CDCl$_3$): δ 8.04 (m, 1H), 7.88 (s, 1H), 7.68–7.09 (m, 11H), 5.67 (s, 2H). |
| 143 | hydrogen | 3-trifluoromethyl | MS (ES) 611.3 (M+1), δ 8.19 (m, 1H), 8.11 (d, J = 7.8 Hz, 1H), 7.76 (s, 1H), 7.60–7.13 (m, 9H), 5.56 (s, 2H). |
| 144 | hydrogen | 2-fluoro | MS (ES 561.3 (M+1), δ 7.75 (s, 1H), 7.61–6.96 (m, 11H), 5.54 (s, 2H). |
| 145 | 2-pyrrolidin-1-yl-ethyl | 2-chloro | MS (ES) 674.2 (M+1), TLC (50% EtOAc/Hexane), $R_f$ = 0.59 |
| 146 | ([1,3]-dioxalan-2-yl)-methyl | 2-chloro | MS (ES) 663.6 (M+1), $^1$H NMR (300 MHz, CDCl$_3$): δ 7.82 (s, 1H), 7.51–7.37 (m, 9H), 7.22 (m, 2H), 5.58 (s, 2H), 5.28 (ab q, 1H), 4.54 (dd, J = 14.5, 3.2 Hz, 1H), 4.18 (dd, J = 14.5, 5.0 Hz, 1H), 3.83–3.63 (m, 4H). |

By the method of General Example G, the following compounds may be prepared and isolated.

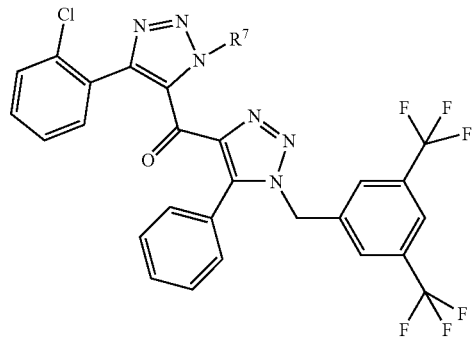

| Ex. # | $R^7$ | Physical Data |
| --- | --- | --- |
| 147 | 2-pyrrolidin-1-yl-ethyl | MS (ES) 674.2 (M+1); TLC $R_f$ = 0.59 (50% EtOAc/Hexane). |

-continued

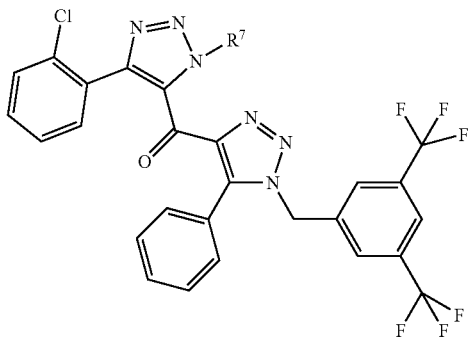

| Ex. # | R[7] | Physical Data |
|---|---|---|
| 148 | ([1,3]-dioxalan-2-yl)-methyl | MS (ES) 663.6 (M+1), $^1$H NMR (300 MHz, CDCl$_3$): δ 7.85 (br s, 1H), 7.78 (dd, J = 7.7, 1.6 Hz, 1H), 7.61–7.49 (m, 3H), 7.41–7.10 (m, 7H), 5.46 (s, 2H), 5.32 (t, J = 3.0 Hz, 1H), 4.97 (d, J = 3.0 Hz, 2H), 3.70 (m, 4H). |

By the method of General Example G, the following compounds may be prepared and isolated.

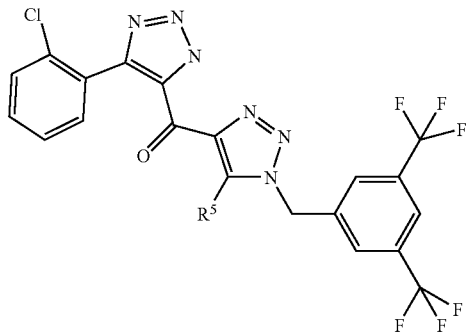

| Ex. # | R[5] | Physical Data |
|---|---|---|
| 149 | pyridin-3-yl | Exact Mass 577.09; MS (ESI) m/z 576.3 (M−1). $^1$H NMR (300 MHz, CDCl$_3$) δ 5.66 (s, 2H), 7.30–7.56 (m, 8H), 7.84 (s, 1H), 8.54 (d, 1H, J = 1.87 Hz), 8.76 (m, 1H) |
| 150 | pyridin-4-yl | Exact Mass 577.09, MS (ESI) m/z 576.3 (M−1); $^1$H NMR (300 MHz, CDCl$_3$) δ 5.61 (s, 2H), 7.16 (d, J = 5.85 Hz, 2H), 7.34 (m, 2H), 7.42 (m, 1H), 7.50 (m, 3H), 7.87 (s, 1H), 8.77 (d, 2H, J = 5.66 Hz). |
| 151 | methyl | MS [ES] 515.1 (M+H)$^+$, 513.1 (M−H)$^-$; $^1$H NMR (400 MHz, CHCl$_3$) δ 15.25 (br s, 1H), 7.90 (s, 1H), 7.71 (s, 2H), 7.48–7.57 (m, 2H), 7.35–7.44 (m, 2H), 5.74 (s, 2H), 2.61 (s, 3H). |

Example 152

[1-(3,5-bis-trifluoromethyl-benzyl)-5-phenyl-1H-[1,2,3]triazol-4-yl]-[5-(2-chloro-phenyl)-1-(2-hydroxy-ethyl)-1H-[1,2,3]thiazol-4-yl]-methanone

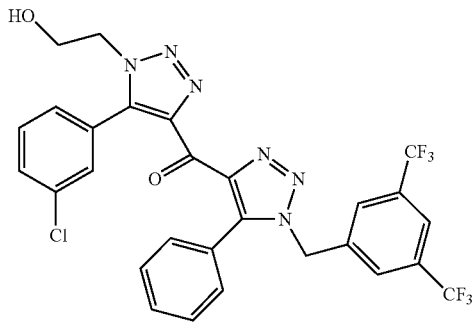

Dissolve [1-(3,5-Bis-trifluoromethyl-benzyl)-5-phenyl-1H-[1,2,3]triazol-4-yl]-[1-[2-(tert-butyl-dimethyl-silanyloxy)-ethyl]-5-(2-chloro-phenyl)-1H-[1,2,3]triazol-4-yl]-methanone (0.43 g, 0.58 mmol) in THF (5 mL, 0.2 M), add t-butyl ammonium flouride (0.88 mL of a 1M soln. in THF, 1.5 eq.), and stir at RT. When the reaction is complete, concentrate and purify by chromatography on silica gel. MS (ES) 621.0 (M+1); $^1$H NMR (300 MHz, CDCl$_3$): δ 7.82 (s, 1H), 7.53–7.19 (m, 11H), 5.59 (s, 2H), 4.40–3.98 (s, 4H), 2.06 (br s, 1H).

Example 153

[1-(3,5-bis-trifluoromethyl-benzyl)-5-phenyl-1H-[1,2,3]triazol-4-yl]-[5-(2-chloro-phenyl)-3-(2-hydroxy-ethyl)-3H-[1,2,3]triazol-4-yl]-methanone

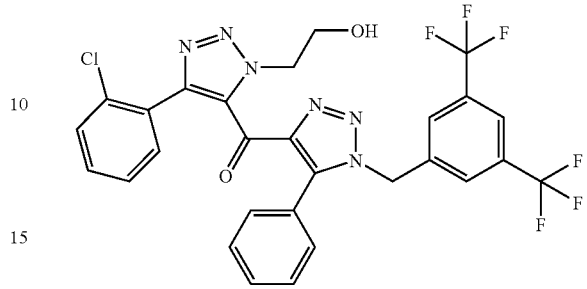

Using a method similar to Example 152, the title compound may be prepared and isolated. MS (ES) 621.0 (M+1); $^1$H NMR (300 MHz, CDCl$_3$): δ 7.86–7.09 (m, 12H), 5.44 (s, 2H), 4.80 (t, J=5.0 Hz, 2H), 4.16 (m, 2H), 2.56 (t, J=6.0 Hz, 1H).

General Example H

Add Dess-Martin periodinane (1.5 eq.) to a solution of the appropriate alcohol (1 eq.) in dichloromethane (0.05M–0.5M). Stir at 0° C. for 30 min., then at RT for 1–5 h. Dilute with ether and wash with cold 0.1N NaOH, water, and brine. Dry, filter, and concentrate the organic phase and purify the crude material by flash chromatography to give the title compound.

Alternatively, under N$_2$, charge an oven-dried flask with oxalyl chloride (2M in CH$_2$Cl$_2$, 1.2 eq.) and chill in a dry ice/acetone slush. Add DMSO (3 eq.) slowly by syringe and stir 15 min. Add the alcohol of interest (1 eq.) in anhydrous CH$_2$Cl$_2$ (0.4 M) slowly by syringe and stir 1 h. Add TEA (5 eq.) slowly by syringe and stir 2 h. while bath is allowed to expire. Quench with H$_2$O, extract with ether, dry over MgSO$_4$, filter and concentrate under vacuum to give the title compound.

Using one of the methods of General Example H, the following compounds are prepared and isolated.

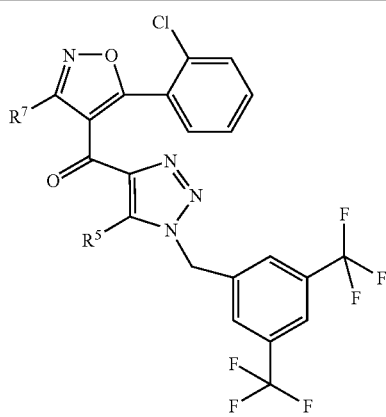

| Ex. # | R$^5$ | R$^7$ | Physical Data |
|---|---|---|---|
| 154 | morpholino | —CHO | MS (ES) 614.0 (M+1), MS (ES−) 612.0 (M−1); $^1$H NMR (400 MHz, CDCl$_3$) δ 10.15 (s, 1H), 7.87 (s, 1H), 7.69 (s, 2H), 7.67 (m, 1H), 7.41 (m, 3H), 5.54 (s, 2H), 3.72 (m, 4H), 3.01 (m,, 4H). |

-continued

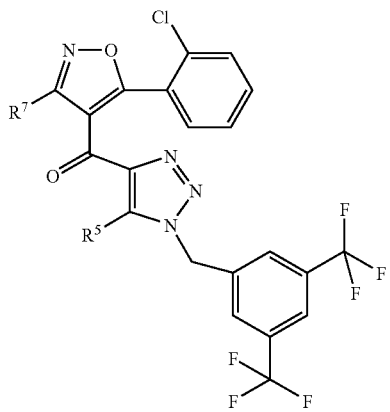

| Ex. # | R⁵ | R⁷ | Physical Data |
|---|---|---|---|
| 155 | morpholino | —CH₂—CHO | MS (ES) 628.1 (M+1), MS (ES−) 626.0 (M−1); ¹H NMR (400 MHz, CDCl₃) δ 9.82 (t, 1H, J = 1.0 Hz), 7.86 (s, 1H), 7.70 (dd, 1H, J = 1.9, 7.8 Hz), 7.63 (s, 2H), 7.38 (dt, 1H, J = 1.3, 7.8 Hz), 7.31 (dt, 1H, J = 1.9, 7.8 Hz), 7.16 (dd, 1H, J = 1.0, 7.8 Hz), 5.43 (s, 2H), 4.10 (d, 2H, J = 1.0 Hz), 3.72 (m, 4H), 2.97 (m, 4H). |
| 156 | dimethylamino | —CHO | MS (ES) 572.1 (M+H), 570.1 (M−H). ¹H NMR (400 MHz, CDCl₃) δ 10.21 (s, 1H), 7.89 (s, 1H), 7.68 (m, 1H), 7.60 (s, 2H), 7.38–7.46 (m, 3H), 5.52 (s, 2H), 3.44 (s, 6H). |
| 157 | thiomorpholine-1,1-dioxide | —CH₂—CHO | MS (ES) 572.1 (M+H), 570.1 (M—H). ¹H NMR (400 MHz, CDCl₃) δ 9.81 (s, 1H), 7.92 (s, 1H), 7.74 (dd, 1H, J = 7.8, 1.5 Hz), 7.60 (s, 2H), 7.45 (dt, 1H, J = 7.8, 1.5 Hz), 7.38 (dt, 1H, 7.8, 1.5 Hz), 7.21 (dd, 1H, J = 7.8, 1.5 Hz), 5.48 (s, 2H), 4.18 (s, 2H), 3.53 (m, 4H), 3.12 (m, 4H). |
| 158 | methyl | —CHO | MS (ES) 543.0 (M+H), 541.0 (M−H); ¹H NMR (400 MHz, CDCl₃) δ 10.21 (s, 1H), 7.89 (s, 1H), 7.68 (m, 1H), 7.60 (s, 2H), 7.38–7.46 (m, 3H), 5.60 (s, 2H), 2.58 (s, 3H). |
| 159 | methyl | —CH₂—CHO | MS (ES) 556.9 (M+1), MS (ES−) 554.9 (M−1); ¹H NMR (400 MHz, CDCl₃) δ 9.83 (s, 1H), 7.87 (s, 1H), 7.70 (dd, 1H, J = 2.0, 7.8), 7.52 (s, 2H), 7.36 (m, 2H), 7.22 (m, 1H), 5.50 (s, 2H), 4.08 (s, 2H), 2.49 (s, 3H). |
| 160 | pyridin-4-yl | —CHO | MS (ES) 606.0 (M+1); ¹H NMR (400 MHz, CDCl₃) δ 10.17 (s, 1H), 8.74 (m, 2H), 7.84 (s, 1H), 7.65 (m, 1H), 7.44 (s, 2H), 7.42 (m, 1H), 7.38 (m, 2H), 7.21 (m, 2H), 5.56 (s, 2H). |
| 161 | phenyl | —CHO | MS (ES) 605.0 (M+1); ¹H NMR (300 MHz, CDCl₃): δ 10.11 (s, 1H), 7.74 (s, 1H), 7.62–7.10 (m, 11H), 5.48 (s, 2H). |
| 162 | pyrazin-2-yl | —CHO | TLC R_f 0.54 (EtOAc); ¹H NMR (300 MHz, CDCl₃): δ 10.20 (s, 1H), 9.07 (s, 1H), 8.67 (m, 2H), 7.81 (s, 1H), 7.67 (m, 3H), 7.43 (m, 3H), 5.93 (s, 2H). |

General Example I

Dissolve the acetal of interest (1 eq.) in acetone/H₂O (4:1) and add p-toluenesulfonic acid (1 eq). Attach a reflux condenser and heat the mixture overnight at 60° C. Neutralize with saturated aqueous NaHCO₃, extract with EtOAc, dry over MgSO₄, filter, and concentrate under vacuum.

Alternatively, in a pressure vessel, dilute the acetal of interest (1 eq) with acetic acid/H₂O (2:1, 0.1 M) and heat at 125° C. for 48 h. Concentrate the mixture and dissolve the residue in EtOAc. Wash with saturated aqueous NaHCO₃ and brine, then dry the organic layer over MgSO₄, filter, and concentrate under vacuum.

Using one of the above methods and the appropriate starting materials, the following compounds may be prepared and isolated.

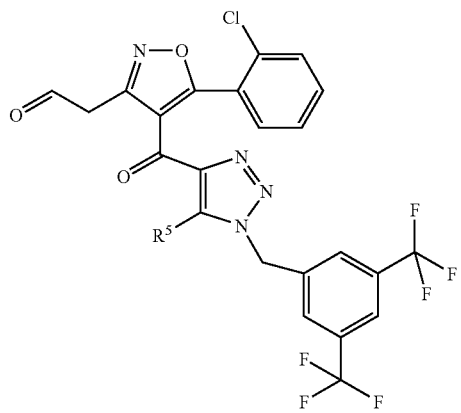

| Ex. # | R⁵ | Physical Data |
|---|---|---|
| 163 | phenyl | MS (ES) 619.0 (M+1), ¹H NMR (300 MHz, CDCl₃): δ 9.82 (s, 1H), 7.84 (s, 1H), 7.76 (m, 1H), 7.59–7.19 (m, 10H), 5.45 (s, 2H), 4.10 (d, J = 1.3 Hz, 2H). |
| 164 | pyrazin-2-yl | MS (ES) 621.1 (M+1), TLC (50% EtOAc/Hexane × 3), $R_f$ = 0.30. |

By the methods of General Example I, the following compounds may be prepared and isolated.

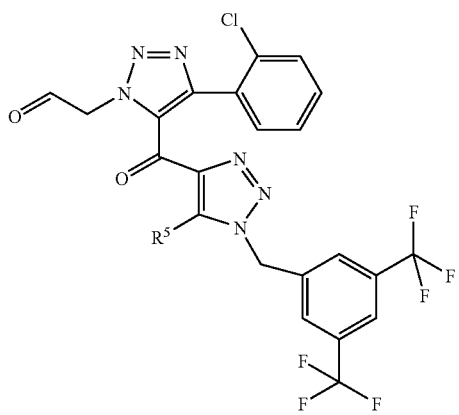

| Ex. # | R⁵ | Physical Data |
|---|---|---|
| 165 | phenyl | MS (ES) 619.0 (M+1), ¹H NMR (300 MHz, CDCl₃): δ 9.70 (s, 1H), 7.87–7.07 (m, 12H), 5.49(s, 2H), 5.43(s, 2H). |
| 166 | pyridin-3-yl | TLC $R_f$ 0.04 (75% EtOAc/Hexane), ¹H NMR (300 MHz, CDCl₃): δ 9.60 (s, 1H) indicates aldehyde |
| 167 | pyridin-4-yl | TLC $R_f$ 0.07 (75% EtOAc/Hexane), ¹H NMR (300 MHz, CDCl₃): δ 9.61 (s, 1H) indicates aldehyde |
| 168 | pyrazin-2-yl | TLC $R_f$ 0.07 (50% EtOAc/Hexane), ¹H NMR (300 MHz, CDCl₃): δ 9.75 (s, 1H) indicates aldehyde |

General Example J

Combine the appropriate alcohol (1.0 eq.) in dichloromethane, add Dess-Martin periodinane (2.0 eq.) and allow the mixture to stir at RT. After 1 h., concentrate in vacuo and dilute the residue with ether and wash with saturated aqueous sodium bicarbonate solution, dry the organic layer with anhydrous MgSO₄, filter and concentrate in vacuo. Purify by chromatography on silica gel to give the title compound.

By the method of General Example J, the following compounds may be prepared and isolated.

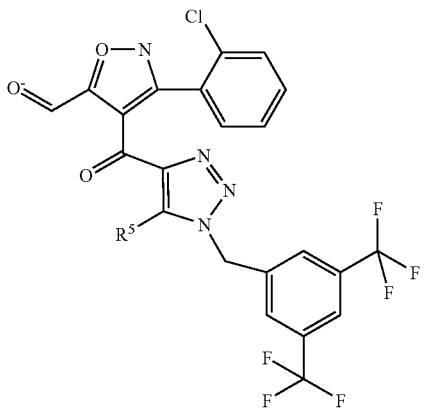

| Ex. # | R⁵ | Physical Data |
|---|---|---|
| 169 | morpholino | MS (ES) 614.1 (M+1); TLC (50% ether in hexanes): $R_f$ = 0.1. |
| 170 | phenyl | MS ES 605.0 (M+1); TLC (33% EtOAc in hexanes): $R_f$ = 0.1. |

Example 171

[1-(3,5-bis-trifluoromethyl-benzyl)-5-phenyl-1H-[1,2,3]triazol-4-yl]-[5-(2-chloro-phenyl)-3-(1-hydroxy-ethyl)-isoxazol-4-yl]-methanone Example 172

[1-(3,5-bis-trifluoromethyl-benzyl)-5-phenyl-1H-[1,2,3]triazol-4-yl]-[3-(2-chloro-6-fluorophenyl)-5-methyl-isoxazol-4-yl]-methanone

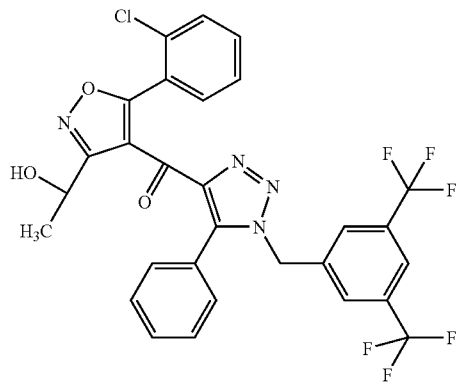

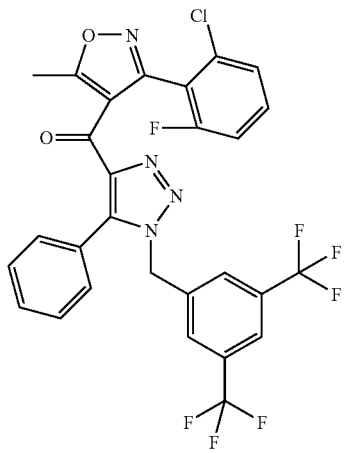

To a solution of 4-[1-(3,5-bis-trifluoromethyl-benzyl)-5-phenyl-1H-[1,2,3]triazole-4-carbonyl]-5-(2-chloro-phenyl)-isoxazole-3-carbaldehyde (75 mg, 0.12 mmol) in THF (0.6 mL) at −78° C. under $N_2$, add methylmagnesium bromide (120 μL, 3.0 M in $Et_2O$). Allow the reaction to warm to 0° C. and stir for two h., then quench the reaction with a saturated solution of $NH_4Cl$ (1 mL). Dilute the mixture with $CH_2Cl_2$ (1 mL), wash with $H_2O$ (1 mL) and brine (1 mL). Pass the organic layer through a Varian ChemElute® drying cartridge and concentrate. Purify the residue by chromatography on silica gel using a gradient of 10:1 Hex/EtOAc to 2:1 Hex/EtOAc to afford the title compound (4.3 mg, 6%). MS/ES (M+1)=620.9.

Heat a mixture of 3-(2-chloro-6-fluoro-phenyl)-5-methyl-isoxazole-4-carbonyl chloride (187 mg, 0.681 mmol) and 1-(3,5-bis-trifluoromethyl-benzyl)-4-(tri-n-butylstannanyl)-5-phenyl-1H-[1,2,3]triazole (300 mg, 0.454 mmol) in the presence of $PdCl_2(PPh_3)_2$ (32 mg) in degassed 1,4-dioxane (3.0 mL) at 80° C. After 18 h., concentrate in vacuo and purify the residue by chromatography on silica gel to provide the title compound (50% yield) as a light yellow foam. MS (ES) 609.0 (M⁺+1); TLC $R_f$=0.1 (6% acetone in hexanes).

By a method analogous to Example 172, the following compounds may be prepared and isolated.

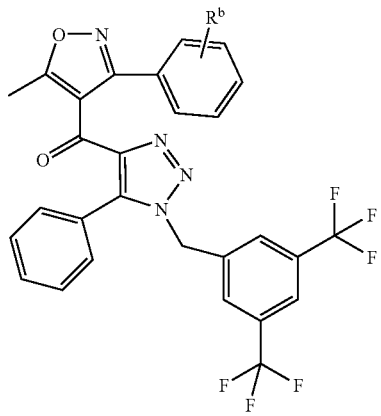

| Ex. # | R$^b$ | Physical Data |
|---|---|---|
| 173 | 2-chloro | MS (ES) 591.0 (M$^+$+1); TLC R$_f$ = 0.1 (10% acetone in hexanes). |
| 174 | 2,6-dichloro | MS ES 625.0 (M$^+$+1); TLC R$_f$ = 0.1 (6% acetone in hexanes). |

Example 175

[1-(3,5-bis-trifluoromethyl-benzyl)-5-morpholin-4-yl-1H-[1,2,3]triazol-4-yl]-[5-chloromethyl-3-(2-chloro-phenyl)-isoxazol-4-yl]-methanone

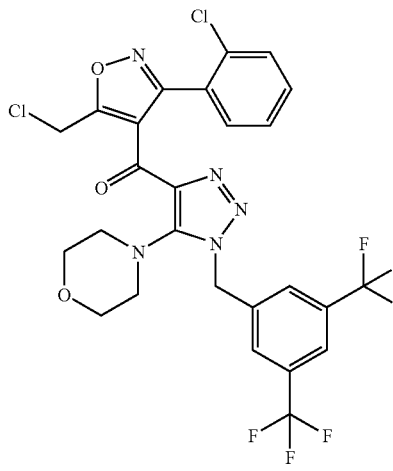

Add N,N-dimethylaminopyridine (119 mg, 0.974 mmol), p-toluenesulfonyl chloride (465 mg, 2.44 mmol) and triethylamine into an ice-cold solution of [1-(3,5-bis-trifluoromethyl-benzyl)-5-morpholin-4-yl-1H-[1,2,3]triazol-4-yl]-[3-(2-chlorophenyl)-5-hydroxymethyl-isoxazol-4-yl]-methanone (1.0 g, 1.62 mmol) in dichloromethane (5.0 mL) and THF (5.0 mL). Warm the mixture to RT. After 1 h., concentrate in vacuo. Dilute the mixture with dichloromethane (50 mL) and wash with water (3×40 mL). Dry (MgSO$_4$), filter, and concentrate in vacuo. Purify the residue by flash chromatography on silica gel to provide the title compound (59% yield) as a brown oil. MS (ES) 634.1 (M$^+$+1); TLC R$_f$=0.5 (50% EtOAc in hexanes).

Example 176

[1-(3,5-bis-trifluoromethyl-benzyl)-5-morpholin-4-yl-1H-[1,2,3]triazol-4-yl]-[3-(2-chloro-phenyl)-5-morpholin-4-ylmethyl-isoxazol-4-yl]-methanone

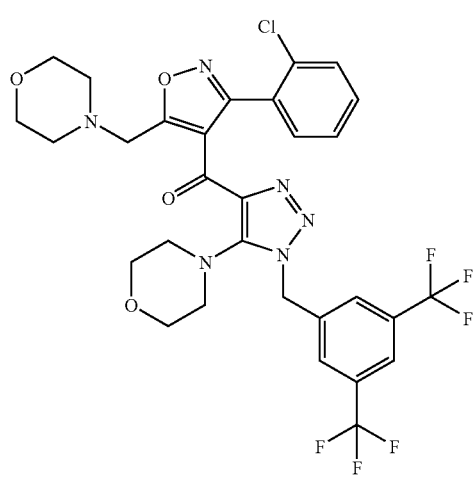

Heat a mixture of [1-(3,5-bis-trifluoromethyl-benzyl)-5-morpholin-4-yl-1H-[1,2,3]triazol-4-yl]-[5-chloromethyl-3-(2-chloro-phenyl)-isoxazol-4-yl]-methanone (100 mg, 0.158 mmol), triethylamine (80 mg, 0.790 mL) and morpholine (0.79 mL) at 50° C. for 18 h. Cool to RT, dilute the mixture with dichloromethane (50 mL) and wash with water (4×40 mL). Dry the organic layer with anhydrous MgSO$_4$, filter, and concentrate in vacuo. Purify the residue by flash chromatography on silica gel to give the title compound (93% yield) as a brown oil. MS (ES) 685.2 (M$^+$+1); TLC R$_f$=0.1 (75% EtOAc in hexanes).

Example 177

[1-(3,5-bis-trifluoromethyl-benzyl)-5-morpholin-4-yl-1H-[1,2,3]triazol-4-yl]-[3-(2-chloro-phenyl)-5-dimethylaminomethyl-isoxazol-4-yl]-methanone

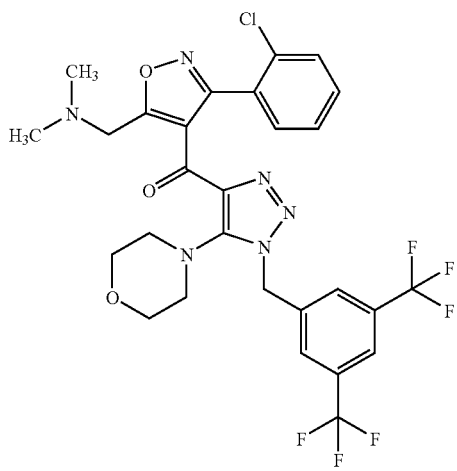

Using a method similar to Example 176, the title compound may be prepared and isolated. MS (ES) 643.2 (M$^+$+1); TLC R$_f$=0.1 (75% EtOAc in hexanes).

Example 178

1-[4-[1-(3,5-bis-trifluoromethyl-benzyl)-5-morpholin-4-yl-1H-[1,2,3]triazole-4-carbonyl]-3-(2-chloro-phenyl)-isoxazol-5-yl]-ethanone

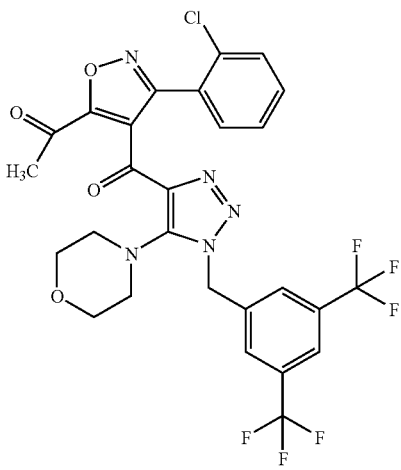

Add Dess-Martin periodinane (27.0 mg, 0.064 mmol) to a solution of [1-(3,5-bis-trifluoromethyl-benzyl)-5-morpholin-4-yl-1H-[1,2,3]triazol-4-yl]-[3-(2-chloro-phenyl)-5-(1-hydroxy-ethyl)-isoxazol-4-yl]-methanone (20.0 mg, 0.032 mmol). Stir at RT for 1 h., then concentrate in vacuo and dilute the residue with ether and wash with saturated aqueous sodium bicarbonate solution. Dry the organic layer with anhydrous MgSO$_4$, filter, and concentrate in vacuo. Purify the residue by flash chromatography on silica gel to provide the title compound (99% yield) as a brown oil. MS (ES) 628.1 (M$^+$+1); TLC R$_f$=0.1 (50% EtOAc in hexanes).

Example 179

[1-(3,5-bis-trifluoromethyl-benzyl)-5-phenyl-1H-[1,2,3]triazol-4-yl]-{3-(2-chloro-phenyl)-5-[(2-morpholin-4-yl-ethylamino)-methyl]-isoxazol-4-yl}-methanone

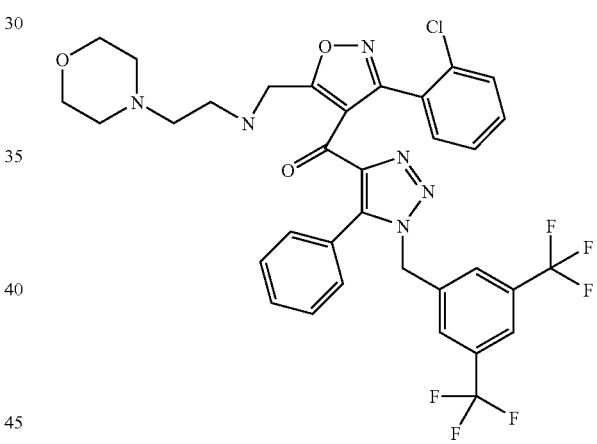

Add 4-(2-aminoethyl)-morpholine (129 mg, 0.992 mmol) to a solution of 4-[1-(3,5-bis-trifluoromethyl-benzyl)-5-phenyl-1H-[1,2,3]triazole-4-carbonyl]-3-(2-chloro-phenyl)-isoxazole-5-carbaldehyde (150 mg, 0.248 mmol) in 1,2-dichloroethane (2.5 mL). Then add NaBH(OAc)$_3$ (157 mg, 0.744 mmol) and allow the mixture to stir at RT. After 3 h., quench the reaction with water and extract with EtOAc (2×50 mL). Dry the organic layer over MgSO$_4$, filter, and concentrate in vacuo. Purify the residue by flash chromatography on silica gel to provide the title compound (61% yield) as a brown oil. MS (ES) 720.1 (M$^+$+1); TLC R$_f$=0.1 (EtOAc).

By a method analogous to Example 179, the following compounds may be prepared and isolated.

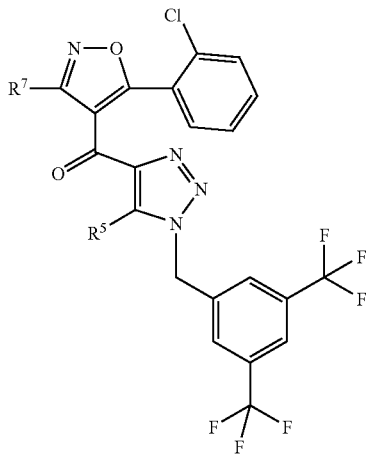

| Ex. # | R⁵ | R⁷ | Physical Data |
|---|---|---|---|
| 180 | phenyl | isopropyl-amino-methyl | MS (ES) 648.0 (M+1), ¹H NMR (300 MHz, CDCl₃): δ 7.74 (s, 1H), 7.63–7.10 (m, 11H), 5.36 (s, 2H), 3.98 (s, 2H), 2.73 (m, 1H), 0.93 (d, J = 6.3 Hz, 6H). |
| 181 | phenyl | morpholino-methyl | MS (ES) 676.0 (M+1), ¹H NMR(300 MHz, CDCl₃): δ 7.84 (s, 1H), 7.72–7.22 (m, 11H), 5.53 (s, 2H), 3.88 (s, 2H), 3.48 (m, 4H), 2.43 (m, 4H). |
| 182 | phenyl | dimethyl-amino-methyl | MS (ES) 634.1 (M+1), ¹H NMR (300 MHz, CDCl₃): δ 7.73 (s, 1H), 7.63–7.05 (m, 11H), 5.44 (s, 2H), 3.69 (s, 2H), 2.06 (s, 6H). |
| 183 | phenyl | diethyl-amino-methyl | MS (ES) 662.1 (M+1), ¹H NMR (300 MHz, CDCl₃): δ 7.84 (s, 1H), 7.72–7.22 (m, 11H), 5.54 (s, 2H), 3.88 (s, 2H), 2.40 (q, J = 7.2 Hz, 4H), 0.78 (t, J = 7.2 Hz, 6H). |
| 184 | phenyl | pyrrolidin-1-yl-methyl | MS (ES) 660.1 (M+1), ¹H NMR (300 MHz, CDCl₃): δ 7.73 (s, 1H), 7.62–7.11 (m, 11H), 5.45 (s, 2H), 3.88 (s, 2H), 2.36 (br s, 4H), 1.53 (br s, 4H). |
| 185 | phenyl | 2-(diethyl-amino)-ethyl | MS (ES) 676.2 (M+1), ¹H NMR (300 MHz, CDCl₃): δ 7.79 (s, 1H), 7.47 (s, 2H), 7.74–6.96 (m, 9H), 5.43 (s, 2H), 3.93 (t, J = 8.1 Hz, 2H), 3.47 (t, J = 7.1 Hz, 2H), 3.23 (qd, J = 7.2, 2.0 Hz, 4H), 1.19 (t, J = 7.2 Hz, 6H). |
| 186 | phenyl | 2-(isopropyl-amino)-ethyl | MS (ES) 662.2 (M+1), ¹H NMR (300 MHz, CDCl₃): δ 7.84 (s, 1H), 7.72 (dd, J = 7.5, 2.0 Hz, 1H), 7.60–7.14 (m, 10H), 5.45 (s, 2H), 3.17 (app t, 2H), 3.00 (m, 1H), 2.79 (m, 2H), 1.14 (d, J = 6.6 Hz, 6H). |
| 187 | phenyl | 2-(morpholino)-ethyl | MS (ES) 690.2 (M+1), ¹H NMR (300 MHz, CDCl₃): δ 7.84 (s, 1H), 7.73 (dd, J = 7.6, 1.7 Hz, 1H), 7.60–7.16 (m, 10H), 5.44 (s, 2H), 3.62 (t, J = 4.5 Hz, 4H), 3.13 (t, J = 7.6 Hz, 2H), 2.79 (t, J = 7.6 Hz, 2H), 2.50 (ap t, J = 4.5 Hz, 4H). |
| 188 | phenyl | 2-(dimethyl-amino)-ethyl | MS (ES) 648.1 (M+1), ¹H NMR (300 MHz, CDCl₃): δ 7.80 (s, 1H), 7.45–6.85 (m, 11H), 5.39 (s, 2H), 4.01 (t, J = 7.7 Hz, 2H), 3.62 (t, J = 7.7 Hz, 2H), 3.14 (s, 6H). |
| 189 | phenyl | 2-(pyrrolidin-1-yl)-ethyl | MS (ES) 674.1 (M+1), ¹H NMR (300 MHz, CDCl₃): δ 7.70 (s, 1H), 7.40–6.85 (m, 11H), 5.34 (s, 2H), 3.82 (t, J = 7.6 Hz, 2H), 3.55 (t, J = 7.6 Hz, 2H), 3.30 (m, 4H), 1.85 (m, 4H). |
| 190 | phenyl | methylamino-methyl | MS/ES(M+1): 620.0; R_f = 0.38 (10:1 CHCl₃/MeOH) |
| 191 | phenyl | ethylamino-methyl | MS/ES(M+1): 634.1; R_f = 0.39 (10:1 CHCl₃/MeOH) |
| 192 | methyl | pyrrolidin-1-yl-methyl | LC/MS (ES) 598.0 (M+H). ¹H NMR (400 MHz, CHCl₃) δ 7.89 (s, 1H), 7.68 (m, 1H), 7.61 (s, 2H), 7.35 (m, 2H), 7.28 (m, 1H), 5.57 (s, 2H), 3.96 (s, 2H), 2.51 (s, 3H), 2.43 (m, 4H), 1.58 (m, 4H). |
| 193 | methyl | morpholino-methyl | LC/MS (ES) 614.0 (M+H). ¹H NMR (400 MHz, CHCl₃) δ 7.89 (s, 1H), 7.68 (m, 1H), 7.61 (s, 2H), 7.35 (m, 2H), 7.28 (m, 1H), 5.57 (s, 2H), 3.84 (s, 2H), 3.38 (s, 3H), 2.55 (s, 3H), 2.36 (m, 4H). |
| 194 | morpholino | morpholino-methyl | MS (ES+) 685.1 (M+1), MS (ES−) 683.1 (M−1). ¹H NMR (400 MHz, CDCl₃) δ 7.87 (s, 1H), 7.69 (s, 2H), 7.68 (m, 1H), 7.34 (m, 2H), 7.24 (m, 1H), 5.50 (s, 2H), 3.85 (s, 2H), 3.74 (m, 4H), 3.39 (m, 4H), 3.00 (m, 4H), 2.38 (m, 4H). |

-continued

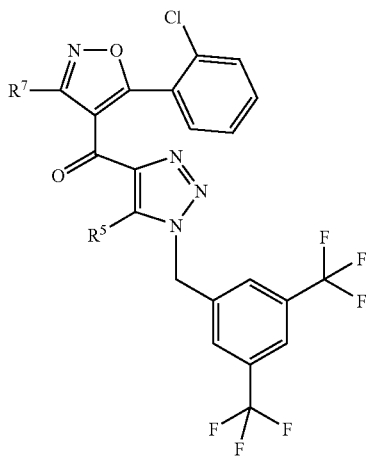

| Ex. # | R⁵ | R⁷ | Physical Data |
|---|---|---|---|
| 195 | morpholino | pyrrolidin-1-yl-methyl | MS (ES+) 669.1 (M+1), MS (ES−) 667.1 (M−1). ¹H NMR (400 MHz, CDCl₃) δ 7.86 (s, 1H), 7.72 (s, 2H), 7.65 (m, 1H), 7.33 (m, 2H), 7.27 (m, 1H), 5.49 (s, 2H), 3.96 (s, 2H), 3.72 (m, 4H), 2.98 (m, 4H), 2.44 (m, 4H), 1.65 (m, 4H). |
| 196 | morpholino | dimethyl-amino-methyl | MS (ES+) 643.0 (M+1), MS (ES−) 641.1 (M−1). ¹H NMR (400 MHz, CDCl₃) δ 7.86 (s, 1H), 7.72 (s, 2H), 7.67 (m, 1H), 7.34 (m, 2H), 7.27 (m, 1H), 5.49 (s, 2H), 3.72 (m, 6H), 2.98 (m, 4H), 2.06 (s, 6H). |
| 197 | pyridin-3-yl | morpholino-methyl | Exact Mass 676.5; MS (ESI) m/z 677.5 (M+1); ¹H NMR (300 MHz, CDCl₃) δ 2.41–2.43 (t, 4H, J = 4.62 Hz), 3.44–3.46 (t, 4H, J = 4.44 Hz), 3.86 (s, 2H), 5.54 (s, 2H), 7.26–7.44 (m, 6H), 7.58 (dt, 1H), 7.68–7.70 (m, 1H), 7.84 (s, 1H), 8.53 (d, 1H), 8.77–8.78 (dd, 1H). |
| 198 | pyridin-4-yl | morpholino-methyl | ¹H NMR (300 MHz, CDCl₃) δ 2.41 (br s, 4H), 3.49 (br s, 4H), 3.91 (br s, 2H), 5.48(s, 2H), 7.17 (d, J = 5.12 Hz, 2H), 7.27 (m, 1H), 7.34–7.41 (m, 4H), 7.69 (d, J = 7.78 Hz, 1H), 7.85 (s, 1H), 8.77 (m, 2H); MS (ESI) m/z 677.3(M+1). |

Example 199

[3-Aminomethyl-5-(2-chloro-phenyl)-isoxazol-4-yl]-[1-(3,5-bis-trifluoromethyl-benzyl)-5-pyridin-4-yl-1H[1,2,3]triazol-4-yl]-methanone

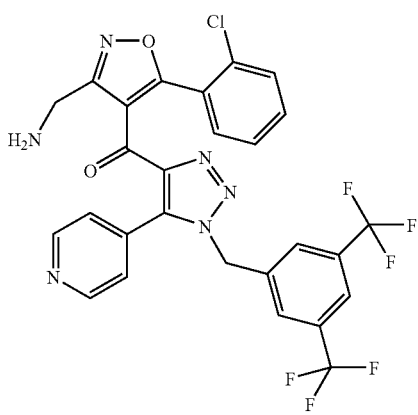

Combine [1-(3,5-bis-trifluoromethyl-benzyl)-5-pyridin-4-yl-1H-[1,2,3]triazol-4-yl]-[5-(2-chloro-phenyl)-3-hydroxymethyl-isoxazol-4-yl]-methanone (0.30 g, 0.49 mmol), diphenyl phosphoryl azide (0.13 mL, 0.59 mmol), 1,8-diazabicyclo[5.4.0]undec-7-ene (0.09 mL, 0.59 mmole) in THF (2 mL) and stir at RT overnight. Filter off the solid and concentrate the filtrate. Dissolve the crude product in THF (2 mL), add triphenylphosphine (0.16 g, 0.59 mmole), and a few drops of water. Stir the mixture overnight. Purify the resulting amine by sequentially passing through a short silica gel column (gradient elution with EtOAc, 2% MeOH in EtOAc, 5% MeOH/2% NH₄OH(aq) in EtOAc), a SCX column (elution with 1:1 MeOH/CH₂Cl₂ and then 3.5 M NH₃ in MeOH) and again a short silica gel column (gradient elution with EtOAc, 5% MeOH/2% NH₄OH (aq) in EtOAc) to provide a yellow oil (0.14 g, 47%). ¹H NMR (400 MHz, CDCl₃) δ 4.07 (s, 2H), 5.45 (s, 2H), 7.18–7.25 (m, 3H), 7.30–7.40 (m, 3H), 7.44 (t, J=7.42 Hz, 1H), 7.74 (d, J=7.62 Hz, 1H), 7.87 (s, 1H), 8.81 (m, 2H); MS (ESI) m/z 607.1 (M+1).

General Example K

To a solution of the appropriate alkyne (1 eq.) in toluene (0.25 M), add the azide of interest (2 eq.). Heat this reaction at 120° C. for 18 h. in a sealed tube. Concentrate the solution and purify the residue by chromatography on silica gel to yield title compound.

By the method of General Example K, the following compounds may be prepared and isolated.

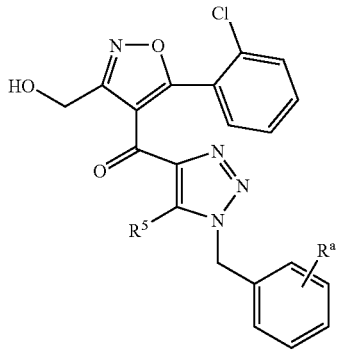

| Ex. # | R<sup>a</sup> | R<sup>5</sup> | Physical Data |
|---|---|---|---|
| 200 | 3,5-dichloro | isopropyl | $R_f$ = 0.12 (2:1 Hex/EtOAc). MS (ES) 505.0 (M+1) |
| 201 | 3,5-dimethyl | isopropyl | $R_f$=0.19 (2:1 Hex/EtOAc). MS (ES) 465.1 (M+1) |
| 202 | 3,5-dichloro | methyl | $R_f$ = 0.11 (2:1 Hex/EtOAc). MS (ES) 477.0 (M+1) |
| 203 | 3,5-dimethyl | methyl | $R_f$ = 0.14 (2:1 Hex/EtOAc). MS (ES) 437.1 (M+1) |
| 204 | 3-fluoro-5-trifluromethyl | methyl | $R_f$ = 0.11 (2:1 Hex/EtOAc). MS (ES) 495.0 (M+1) |
| 205 | 3,5-bis-trifluoromethyl | isopropyl | $R_f$ = 0.53 (2:1 Hex/EtOAc). MS (ES) 573.0 (M+1) |
| 206 | 3-fluoro-5-trifluoromethyl | isopropyl | $R_f$ = 0.11 2:1 Hex/EtOAc. MS (ES) 523.0 (M+1) |
| 207 | 2-fluoro-5-trifluoromethyl | isopropyl | $R_f$ = 0.18 2:1 Hex/EtOAc. MS (ES) 523.0 (M+1) |
| 208 | 4-fluoro-3-trifluoromethyl | isopropyl | $R_f$ = 0.08 2:1 Hex/EtOAc. MS (ES) 523.0 (M+1) |
| 209 | 3,5-dimethyl | methyl | $R_f$ = 0.14 2:1 Hex/EtOAc. MS (ES) 437.1 (M+1) |

Example 210

[1-(3,5-bis-trifluoromethyl-benzyl)-5-pyridin-2-yl-1H-[1,2,3]triazol-4-yl]-[5-(2-chloro-phenyl)-3-hydroxymethyl-isoxazol-4-yl]-methanone

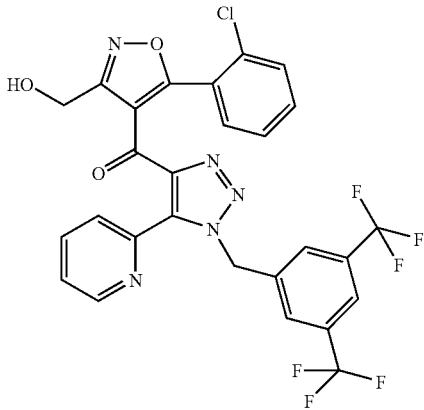

Dissolve 1-[5-(2-chloro-phenyl)-3-(tetrahydro-pyran-2-yloxymethyl)-isoxazol-4-yl]-3-pyridin-2-yl-propynone (0.27 g, 0.64 mmol) in toluene (10.0 mL), add 1-azidomethyl-3,5-bis-trifluoromethyl-benzene (0.26 g, 0.95 mmol) and heat to 100° C. After 18 h., concentrate the reaction mixture and purify crude material by flash chromatography using a linear gradient of 15% to 40% EtOAc in hexanes to give [1-(3,5-bis-trifluoromethyl-benzyl)-5-pyridin-2-yl-1H-[1,2,3]triazol-4-yl]-[5-(2-chloro-phenyl)-3-cyclohexyloxymethyl-isoxazol-4-yl]-methanone. Dissolve this material in methanol (15.0 mL), add p-toluenesulfonic acid monohydrate (0.09 g, 0.48 mmol) and stir at RT for 3 h.

Dilute reaction mixture with 1N NaOH and extract with EtOAc. Wash the organic layer with water and brine, then dry, filter, and concentrate. Purify the residue by flash chromatography using a linear gradient of 50% to 70% EtOAc in hexanes to give the title compound (0.11 g, 46%). MS [ES] 607.1 (M)<sup>+</sup>. <sup>1</sup>H NMR (400 MHz, CHCl<sub>3</sub>) δ 8.79 (d, 1H, J=4.1 Hz), 7.88 (m, 2H), 7.81 (s, 1H), 7.67 (dd, 1H, J=7.9, 1.6 Hz), 7.62 (s, 2H), 7.47 (m, 1H), 7.39 (t, 1H, J=7.4 Hz), 7.30 (dt, 1H, J=7.4, 1.8 Hz), 7.17 (d, 1H, J=7.9 Hz), 5.87 (s, 2H), 4.87 (s, 2H), 3.92 (br s, 1H).

Example 211

[3-(2-chloro-phenyl)-5-(1-hydroxy-1-methyl-ethyl)-isoxazol-4-yl]-[1-(3-fluoro-5-trifluoromethyl-benzyl)-5-pyridin-3-yl-1H-[1,2,3]triazol-4-yl]-methanone

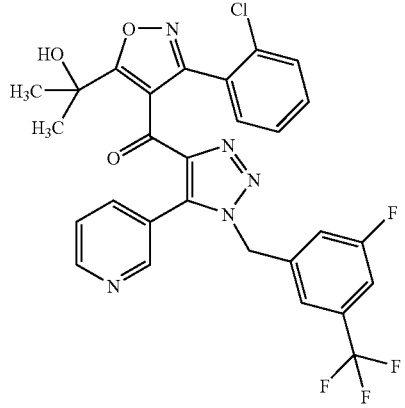

In a 10 mL screwcap test tube, dissolve 1-[3-(2-chloro-phenyl)-5-(1-methyl-1-trimethylsilanyloxy-ethyl)-isoxazol-4-yl]-3-pyridin-3-yl-propynone (60 mg, 0.137 mmol) in toluene (1 mL) and add 1-azidomethyl-3-fluoro-5-trifluoromethyl-benzene (60 mg, 0.273 mmol, 2 eq.). Seal the test tube and warm to 120° C. in block heater. After 24 h., cool to RT, and add TBAF (0.25 mL of a 1M soln. in THF, 0.25 mmol, 1.8 eq.). After 1 h., concentrate the mixture and purify the residue by chromatography (silica gel, hexanes/EtOAc 3:1 to 1:2 gradient) to provide 26 mg (33%) of the title compound as a solid. m.p. 180° C.; TLC: $R_f$=0.38 (1:2 hexanes/EtOAc); MS(ES) 586.1 (M+1), 568.1 [(M−OH)+].

Example 212

[3-(2-chloro-phenyl)-5-(1-hydroxy-1-methyl-ethyl)-isoxazol-4-yl]-{5-pyridin-3-yl-1-[1-(3-trifluoromethyl-phenyl)-ethyl]-1H-[1,2,3]triazol-4-yl}-methanone

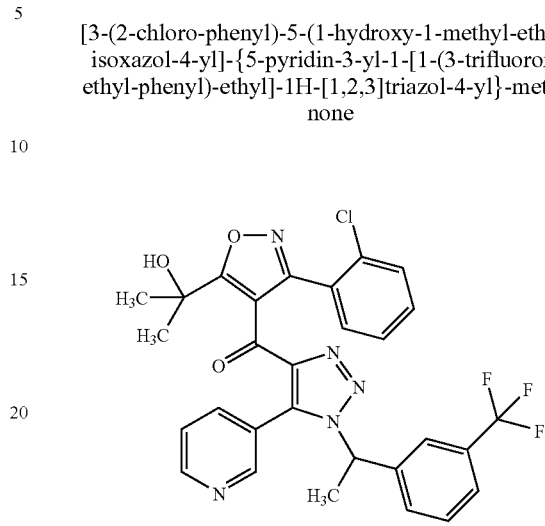

By a method similar to Example 211, using the appropriate starting materials, the title compound may be prepared and isolated. TLC: $R_f$=0.27 (1:2 hexanes/EtOAc); MS(ES) 582.1 (M+1), 564.1 [(M−OH)+].

The following compounds may be prepared and isolated using a method analogous to Example 211.

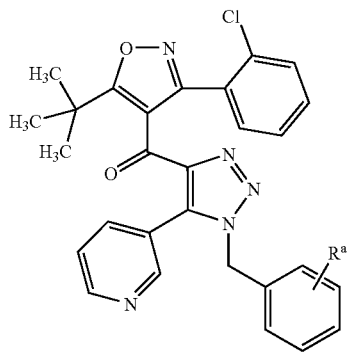

| Ex. # | $R^a$ | Physical Data |
|---|---|---|
| 213 | 3,5-dichloro | m.p. 187° C.; TLC: $R_f$ = 0.35 (1:2 hexanes/EtOAc); MS(ES) 568.1 (M+1), 550.0 [(M—OH)+] |
| 214 | 3,5-dimethyl | TLC: $R_f$ = 0.52 (1:2 hexanes/EtOAc); MS(ES) 528.2 (M+1), 510.2 [(M—OH)+] |
| 215 | 2-methoxy-5-trifluoromethoxy | TLC: $R_f$ = 0.23 (1:2 hexanes/EtOAc); MS(ES) 614.1 (M+1), 596.1 [(M—OH)+] |
| 216 | 3-trifluoromethyl | m.p. 161° C.; TLC: $R_f$ = 0.24 (1:2 hexanes/EtOAc); MS(ES) 568.1 (M+1), 550.1 [(M—OH)+] |
| 217 | 3,5-difluoro | m.p. 136° C.; TLC: $R_f$ = 0.40(1:2 hexanes/EtOAc); MS(ES) 536.1 (M+1), 518.1 [(M—OH)+] |
| 218 | 3-trifluoromethoxy | m.p. 133° C.; TLC: $R_f$ = 0.37 (1:2 hexanes/EtOAc); MS(ES) 584.1 (M+1), 566.1 [M—OH)+] |
| 219 | 2-fluoro-5-trifluoromethyl | TLC: $R_f$ = 0.44 (1:2 hexanes/EtOAc); MS(ES) 586.1 (M+1), 568.1 [(M—OH)+] |

By a method analogous to Example 211, the following compounds may be prepared and isolated.

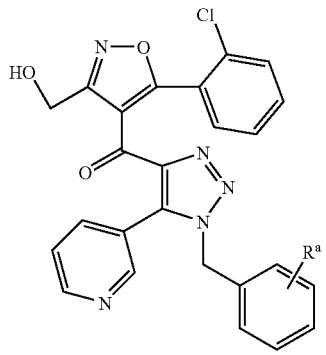

| Ex. # | $R^a$ | Physical Data |
|---|---|---|
| 220 | 3-fluoro-5-trifluoromethyl | MS (ES) 557.0 (M$^+$+1); TLC $R_f$ = 0.1 (50% EtOAc in hexanes). |
| 221 | 2-fluoro-5-trifluoromethyl | MS (ES) 557.0 (M$^+$+1); TLC $R_f$ = 0.1 (50% EtOAc in hexanes). |
| 222 | 4-fluoro-3-trifluoromethyl | MS (ES) 557.0 (M$^+$+1); TLC $R_f$ = 0.1 (50% EtOAc in hexanes). |
| 223 | 3-trifluoromethoxy | MS (ES) 555.8 (M$^+$+1); TLC $R_f$ = 0.1 (50% EtOAc in hexanes). |
| 224 | 3,4-difluoro | MS (ES) 508.1, 510.1 (M$^+$+1); TLC $R_f$ = 0.11 (50% EtOAc/CH$_2$Cl$_2$) |

General Example L

Add (diethylamino)sulfur trifluoride (1 eq.) to a solution of the alcohol of interest (1 eq.) in dichloromethane (0.05 M) at −78° C. Stir at −78° C. for 10 min., warm to RT for 30 min. to 3 h. Treat reaction mixture with water and extract with dichloromethane. Wash the organic phase with brine then dry over MgSO$_4$, filter, and concentrate. Purify the residue by flash chromatography using a linear gradient of 50% to 70% EtOAc in hexane to give the title compound.

By the method of General Example L, the following compounds may be prepared and isolated.

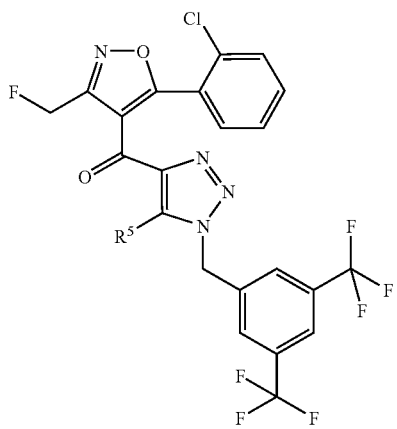

| Ex. # | $R^5$ | Physical Data |
|---|---|---|
| 225 | 4-isopropyl-piperazin-1-yl | MS (ES) 659.2 (M+H); $^1$H NMR (400 MHz, CHCl$_3$) δ 7.87 (s, 1H), 7.69 (dd, 1H, J = 7.8, 1.4 Hz), 7.65 (s, 2H), 7.30–7.40 (m, 2H), 7.21 (dd, 1H, J = 7.8, 1.0 Hz), 5.71 (d, 2H, J = 46.5 Hz), 5.45 (s, 2H), 3.04 (m, 4H), 2.73 (s, 1H, J = 6.5 Hz), 2.54 (m, 4H), 1.03 (d, 6H, J = 6.5 Hz). |

-continued

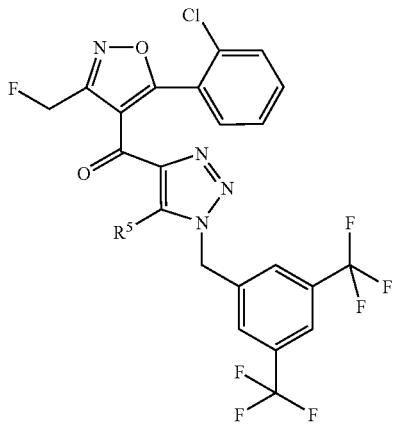

| Ex. # | R⁵ | Physical Data |
|---|---|---|
| 226 | pyridin-3-yl | MS (ES) 610.1 (M+H). |
| 227 | pyridin-4-yl | MS (ES) 610.1 (M+H). |

General Example M

Add [bis(2-methoxyethyl)amino]sulfur trifluoride (2.5 eq.) to a solution of the appropriate carbaldehyde (1 eq.) in dichloromethane (0.1 M) and stir at RT for 4 h. Dilute with water and extract with EtOAc (2×). Combine the EtOAc extracts and wash with brine, then dry over MgSO$_4$, filter, and concentrate. Purify the residue by flash chromatography using a linear gradient of 60% to 90% EtOAc in hexane to give the product.

By the method of General Example M, the following compounds may be prepared and isolated.

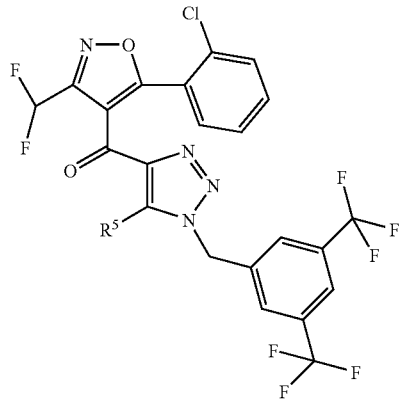

| Ex. # | R⁵ | Physical Data |
|---|---|---|
| 228 | pyridin-4-yl | MS (ES+) 628.1 (M+H); $^1$H NMR (400 MHz, CHCl$_3$) δ 8.80 (br s, 2H), 7.87 (s, 1H), 7.74 (dd, 1H, J = 7.5, 2.0 Hz), 7.44 (m, 2H), 7.39 (s, 2H), 7.27 (dd, 1H, J = 7.8, 1.5 Hz), 7.19 (m, 2H), 7.08 (t, 1H, J = 53.3 Hz) 5.49 (s, 2H). |
| 229 | pyridin-3-yl | MS [ES] 628.0 (M+H)⁺; $^1$H NMR (400 MHz, CHCl$_3$) δ 8.78 (d, 1H, J = 3.4 Hz), 8.50 (s, 1H), 7.84 (s, 1H), 7.73 (dd, 1H, J = 6.9, 2.4 Hz), 7.73 (dd, 1H, J = 6.9, 2.4 Hz), 7.60 (dt, 1H, J = 8.4, 2.4 Hz), 7.39–7.47 (m, 3H), 7.35 (s, 2H), 7.29 (dd, 1H, J = 7.5, 2.4Hz), 7.08 (t, 1H, J = 53.3 Hz), 5.51 (s, 2H). |

Example 230

[1-(3,5-bis-trifluoromethyl-benzyl)-5-phenyl-1H-[1,2,3]triazol-4-yl]-[4-(2-chloro-phenyl)-2H-pyrazol-3-yl]-methanone

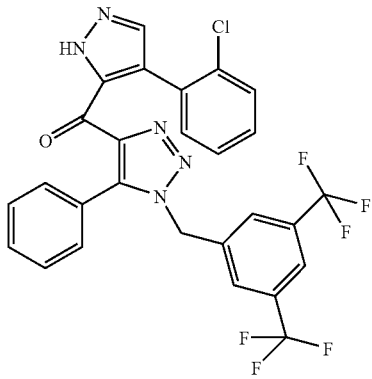

Dissolve 1-[1-(3,5-bis-trifluoromethyl-benzyl)-5-phenyl-1H-[1,2,3]triazol-4-yl]-3-(2-chloro-phenyl)-propynone (48 mg, 0.090 mmol) in THF/ether (1.0 mL of 50/50 mix) and add trimethylsilyl diazomethane (50.0 μL of a 2.0 molar solution in hexanes, 0.099 mmol). Stir the mixture at RT in a sealed tube. After 48 h., concentrate and purify by chromatography (silica gel, hexanes/EtOAc gradient) to provide 25.0 mg of a clear colorless liquid. Exact Mass 575.1: MS (aspci): m/z=576.0 (M+1), 574.0 (M−1); $^1$H NMR (250 MHz, Pyridine doped CDCl$_3$) δ 8.97 (s, 0.5H), 7.69 (s, 1H), 7.40–7.00 (m, 12.5H), 5.46 (s, 2H).

By a method similar to Example 230, the following compounds may be prepared and isolated.

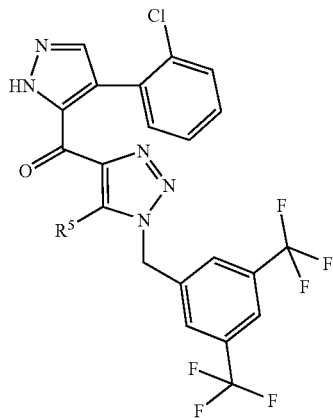

| Ex. # | R$^5$ | Physical Data |
|---|---|---|
| 231 | pyridin-3-yl | Exact Mass 576.09; MS (ESI) m/z 575.2 (M−1). $^1$H NMR (300 MHz, CDCl$_3$) δ 5.62 (s, 2H), 7.21–7.27 (m, 2H), 7.30–7.33 (m, 1H), 7.36–7.41 (m, 2H), 7.47 (s, 2H), 7.52–7.54 (m, 1H), 7.69 (s, 1H), 7.84 (s, 1H), 8.5 (d, 1H, J = 1.36 Hz), 8.72 (dd, 1H, J = 4.80, 1.67 Hz). |
| 232 | pyridin-4-yl | MS (ES) 577.1, 579.1 (M$^+$+1). R$_f$ = 0.13 (66.6% EtOAc/Hex) |
| 233 | methyl | MS [ES] 514.1 (M+H)$^+$, 512.1 (M−H)$^−$. $^1$H NMR (400 MHz, CHCl$_3$) δ 13.35 (br s, 1H), 7.90 (s, 1H), 7.70 (br s, 3H), 7.48 (m, 1H), 7.38 (m, 1H), 7.30–7.33 (m, 2H), 5.69 (s, 2H), 2.58 (s, 3H). |

By a method similar to Example 230, the following compounds may be prepared.

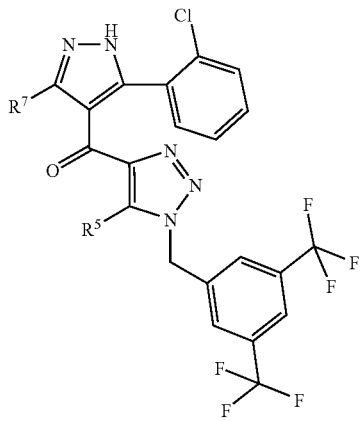

| Ex. # | R⁵ | R⁷ | Physical Data |
|---|---|---|---|
| 234 | pyridin-3-yl | hydrogen | Exact Mass 575.1; MS (aspci): m/z = 576.1 (M+1), 574.1 (M−1); ¹H NMR (500 MHz, CDCl₃) δ 9.54 (s, 1H), 8.89 (d, J = 1.7 Hz, 1H), 8.68 (dd, J = 4.8, 1.7 Hz, 1H), 8.05 (s, 1H), 7.91 (s, 2H), 7.84 (m, 1H), 7.70 (dd, J = 8.3, 3.0 Hz, 1H), 7.40 (d, J = 8.3 Hz, 1H), 7.27–7.20(m, 2H), 6.02 (s, 2H). |
| 235 | phenyl | ethoxy-carbonyl | Exact Mass 648.1: MS (aspci): m/z = 648.1 (M+1), 646.0 (M−1); ¹H NMR (250 MHz, CDCl₃) δ 7.82 (s, 1H), 7.55–7.38 (m, 5H), 7.35–7.15 (m, 6H), 5.58 (s, 2H), 4.25 (q, J = 6.2 Hz, 2H), 1.13 (t, J = 6.3 Hz, 3H). |
| 236 | pyridin-4-yl | hydrogen | MS (ES) 577.1, 579.1 (M⁺+1). $R_f$ = 0.23 (66.6% EtOAc/Hex) |
| 237 | methyl | hydrogen | MS [ES] 514.1 (M+H)⁺, 512.1 (M—H)⁻. ¹H NMR (400 MHz, CHCl₃) δ 11.86 (br s, 1H), 8.98 (s, 1H), 7.88 (s, 1H), 7.68 (s, 2H), 7.44–7.48 (m, 2H), 7.32–7.40 (m, 2H), 5.62 (s, 2H), 2.52 (s, 3H). |

General Example N

Dissolve the pyrazole of interest in THF (10 mL) and cool in an ice bath under N₂. Add BuLi (1.6 M in hexanes, 0.50 mL) and stir for 1 h., then add iodomethane and all the bined mixture to stir overnight while warming to RT. Quench the reaction with water and extract with EtOAc. Dry the comex tracts over Na₂SO₄, filter, and concentrate in vacuo. Purify the residue by chromatography over silica gel (Hex/EtOAc gradient).

By the method of General Example N, the following compounds may be prepared and isolated.

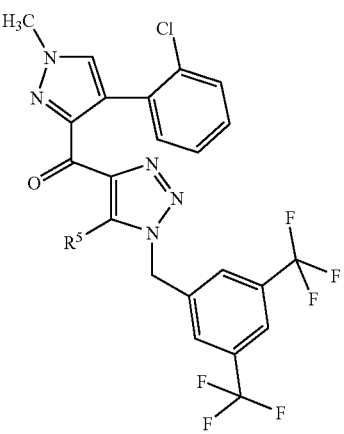

| Ex. # | R⁵ | Physical Data |
|---|---|---|
| 238 | pyridin-4-yl | MS (ES) 591.1, 593.1 (M⁺+1). $R_f$ = 0.06(66.6% EtOAc/Hex) |
| 239 | pyridin-3-yl | MS (ES) 591.1, 593.2 (M⁺+1). $R_f$ = 0.06(66.6% EtOAc/Hex) |

-continued

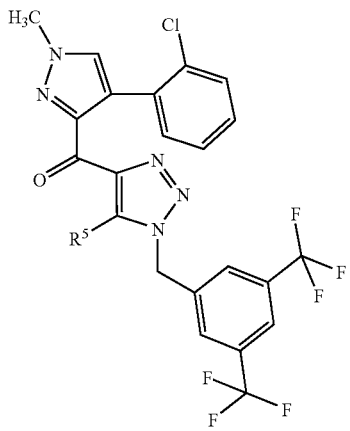

| Ex. # | R⁵ | Physical Data |
|---|---|---|
| 240 | methyl | LC/MS [ES] 528.0 (M+H)⁺; ¹H NMR (400 MHz, CHCl₃) δ 7.88 (s, 1H), 7.70 (s, 2H), 7.53 (s, 1H), 7.33–7.40 (m, 2H), 7.21–7.25 (m, 2H), 5.60 (s, 2H), 4.10 (s, 3H), 2.50 (s, 3H). |
| 241 | dimethyl-amino | MS [ES] 556.9 (M+1)⁺; ¹H NMR (400 MHz, CHCl₃) δ 7.86 (s, 1H), 7.81 (s, 2H), 7.52 (s, 1H), 7.33–7.36 (m, 2H), 7.16–7.24 (m, 2H), 5.50 (s, 2H), 4.01 (s, 3H), 2.71 (s, 6H). |
| 242 | morpholino | MS [ES] 599.1 (M+H)⁺; ¹H NMR (400 MHz, CHCl₃) δ 7.87 (s, 1H), 7.83 (s, 2H), 7.52 (s, 1H), 7.33–7.36 (m, 2H), 7.18–7.25 (m, 2H), 5.53 (s, 2H), 4.01 (s, 3H), 3.72 (m, 4H), 2.99 (m, 4H). |
| 243 | thio-morpholine-1,1-dioxide | MS [ES] 647.0 (M+H)⁺; ¹H NMR (400 MHz, CHCl₃) δ 7.91 (s, 1H), 7.63 (s, 2H), 7.55 (s, 1H), 7.40 (m, 1H), 7.20 (m, 1H), 7.04 (m, 2H), 5.42 (s, 2H), 4.16 (s, 3H), 3.57 (m, 4H), 3.17 (m, 4H). |

By the method of General Example N, the following compounds may be prepared.

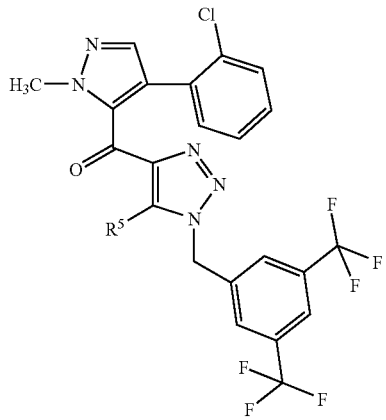

| Ex. # | R⁵ | Physical Data |
|---|---|---|
| 244 | methyl | MS-[ES] 528.0, (M+H)⁺. ¹H NMR (400 MHz, CHCl₃) δ 7.90 (s, 1H), 7.58 (s, 1H), 7.56 (s, 2H), 7.35 (dd, 1H, J = 7.6, 1.5 Hz), 7.15 (dt, 1H, J = 6.9, 2.0 Hz), 7.00–7.09 (m, 2H), 5.46 (s, 2H), 4.15 (s, 3H), 2.52 (s, 3H). |
| 245 | dimethyl-amino | MS [ES] 556.9 (M)⁺. ¹H NMR (400 MHz, CHCl₃) δ 7.87 (s, 1H), 7.63 (s, 2H), 7.55 (s, 1H), 7.29 (dd, 1H, J = 7.2, 1.5 Hz), 7.10 (dd, 1H, J = 7.2, 1.5 Hz), 7.05 (dd, 1H, J = 7.9, 1.5 Hz), 6.95 (dt, 1H, J = 7.9, 1.5 Hz), 5.37 (s, 2H), 4.15 (s, 3H), 2.78 (s, 6H). |

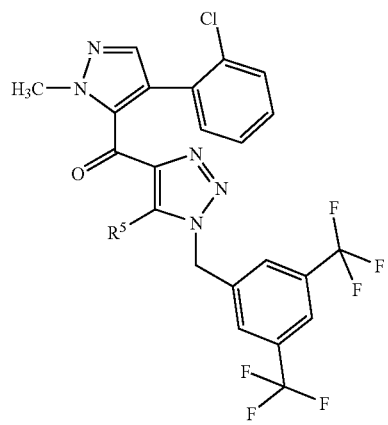

| Ex. # | R⁵ | Physical Data |
|---|---|---|
| 246 | morpholino | MS [ES] 599.1 (M+H). $^1$H NMR (400 MHz, CHCl$_3$) δ 7.89 (s, 1H), 7.60 (s, 2H), 7.55 (s, 1H), 7.30 (dd, 1H, J = 7.8, 1.8 Hz), 7.10 (dt, 1H, J = 7.4, 1.4 Hz), 7.02 (dd, 1H, J = 7.8, 1.4 Hz), 6.96 (dt, 1H, J = 7.4, 1.4 Hz), 5.39 (s, 2H), 4.16 (s, 3H), 3.76 (m, 4H), 3.04 (m, 4H). |
| 247 | thio-morpholine-1,1-dioxide | MS [ES] 647.0 (M+H)⁺. $^1$H NMR (400 MHz, CHCl$_3$) δ 7.91 (s, 1H), 7.63 (s, 2H), 7.55 (s, 1H), 7.40 (m, 1H), 7.20 (m, 1H), 7.04 (m, 2H), 5.42 (s, 2H), 4.16 (s, 3H), 3.57 (m, 4H), 3.17 (m, 4H). |

Example 248

[1-(3,5-bis-trifluoromethyl-benzyl)-5-pyridin-3-yl-1H-[1,2,3]triazol-4-yl]-[5-(2-chloro-phenyl)-1-methyl-1H-pyrazol-4-yl]-methanone

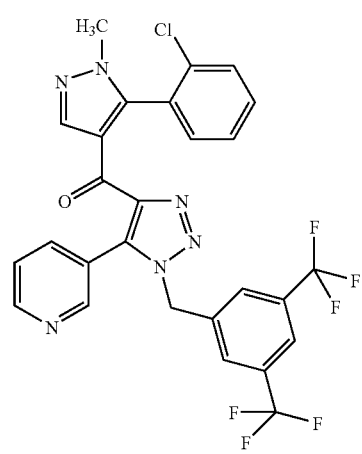

Using the method of General Example N, the title compound may be prepared and isolated. MS (ES)591.1, 593.1 (M⁺+1). R$_f$=0.30 (66.6% EtOAc/Hex).

Example 249

[1-(3,5-bis-trifluoromethyl-benzyl)-5-methyl-1H-[1,2,3]triazol-4-yl]-[3-(2-chloro-phenyl)-1-methyl-1H-pyrazol-4-yl]-methanone

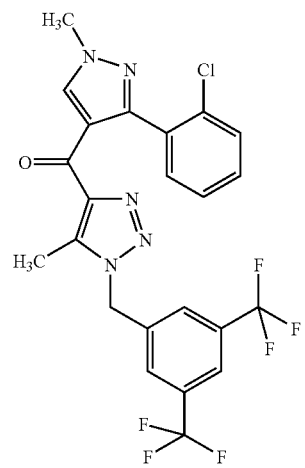

Using the method of General Example N, the title compound may be prepared and isolated. MS [ES] 528.1 (M+H)⁺, 526.1 (M−H)⁻. ¹H NMR (400 MHz, CHCl₃) δ 8.98 (s, 1H), 7.87 (s, 1H), 7.68 (s, 2H), 7.45 (m, 2H), 7.40 (m, 2H), 5.61 (s, 2H), 4.04 (s, 3H), 2.49 (s, 3H).

Example 250

[1-(3,5-Bis-trifluoromethyl-benzyl)-5-methyl-1H-[1,2,3]triazol-4-yl]-[5-(2-chloro-phenyl)-1-methyl-1H-pyrazol-4-yl]-methanone

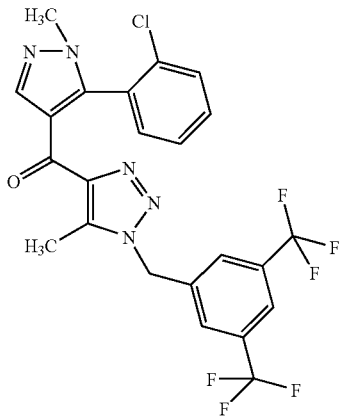

Using the method of General Example N, the title compound may be prepared and isolated. MS [ES] 528.1 (M+H)⁺, 526.1 (M−H)⁻; ¹H NMR (400 MHz, CHCl₃) δ 8.91 (s, 1H), 7.87 (s, 1H), 7.67 (s, 2H), 7.53 (dd, 1H, J=8.3, 1.5 Hz), 7.32–7.55 (m, 3H), 5.62 (s, 2H), 3.69 (s, 3H), 2.49 (s, 3H).

Example 251

[1-(3,5-bis-trifluoromethyl-benzyl)-5-pyridin-3-yl-1H-[1,2,3]triazol-4-yl]-[1-(2-chloro-phenyl)-1H-imidazol-2-yl]-methanone

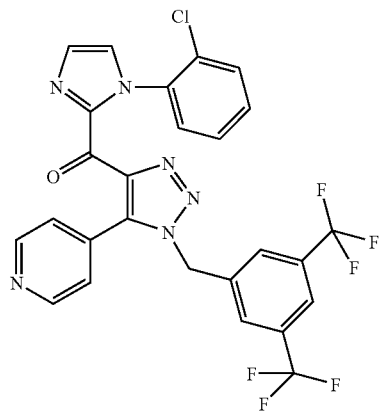

Add BuLi (0.80 mL, 1.28 mmol) to a −78° C. solution of 1-(2-chloro-phenyl)-1H-imidazole (200 mg, 1.12 mmol) in THF (3 mL). Stir at −78° C. for 20 min., then add a solution of 1-(3,5-bis-trifluoromethyl-benzyl)-5-pyridin-3-yl-1H-[1,2,3]triazole-4-carboxylic acid methoxy-methyl-amide (261 mg, 0.57 mmol) in THF (2 mL) via cannula. Stir the resulting solution at −78° C. for 10 min., then allow to warm to RT and stir for 2 h. Add 1N HCl (1.3 mL) and stir for 30 min. Dilute reaction with EtOAc (50 mL) and wash with water (20 mL), saturated NaHCO₃ (20 mL) and brine (20 mL). Dry, filter and concentrate the organic solution and purify the crude material by silica gel chromatography (20% to 80% EtOAc/hexanes) to give a brown solid. Trituration with cold ether gives the title compound as a fine white powder. MS [ES] 577.2 (M+H)+. ¹H NMR (400 MHz, CHCl₃) δ 8.68 (dd, 1H, J=1.4, 4.8 Hz), 8.48 (d, 1H, J=1.8 Hz), 7.81 (s, 1H), 7.48 (m, 3H), 7.46 (m, 1H), 7.44 (m, 1H), 7.34 (m, 4H), 7.17 (m, 1H), 5.60 (s, 2H).

General Example O

Add Mg turnings (1.2 eq.) and a small crystal of iodine to a solution of 5-bromo-oxazole (1 eq.) in freshly distilled THF (0.2 M). Stir the mixture at reflux for 1.5 h., then cool to RT. Add via cannula a solution of the appropriate methoxy-methyl-amide (0.8 eq.) in THF (0.2 M). Stir the solution at reflux for 30 min., then cool to RT and stir for 1 h. Dilute solution with water, neutralize with 1N HCl, and extract with EtOAc. Combine the organic layers and wash with saturated aqueous NaHCO₃ and brine, then dry, filter, and concentrate. Purify the crude material by flash chromatography.

By the method of General Example O, the following compounds may be prepared and isolated.

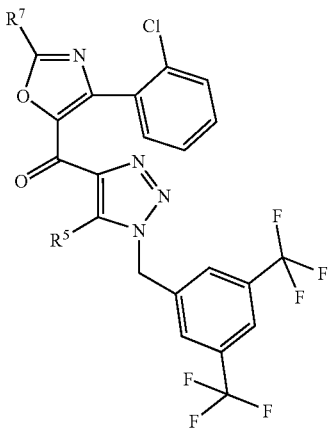

| Ex. # | R⁵ | R⁷ | Physical Data |
|---|---|---|---|
| 252 | pyridin-3-yl | methyl | MS (ES+) 592.0 (M+1), MS (ES−) 590.1 (M−1). ¹H NMR (400 MHz, CDCl₃) δ 8.73 (dd, 1H, J = 1.5, 4.9 Hz), 8.50 (d, 1H, J = 2.1 Hz), 7.82 (s, 1H), 7.58 (dt, 1H, J = 1.7, 7.8 Hz), 7.53 (dd, 1H, J = 2.0, 6.8 Hz), 7.41 (s, 2H), 7.37 (dd, 1H, J = 5.0, 7.9 Hz), 7.31 (dt, 1H, J = 2.4, 6.8 Hz), 7.26 (m, 2H), 5.52,(s, 2H), 2.63 (s, 3H). |
| 253 | pyridin-3-yl | isopropyl | MS (ES+) 620.1 (M+1), MS (ES−) 618.2 (M−1). ¹H NMR (400 MHz, CDCl₃) δ 8.73 (m, 1H), 8.51 (m, 1H), 7.82 (s, 1H), 7.60 (m, 1H), 7.57 (m, 1H), 7.40 (s, 2H), 7.37 (dd, 1H, J = 4.9, 7.8 Hz), 7.32 (dt, 1H, J = 2.0, 7.3 Hz), 7.24 (m, 2H), 3.23 (septet, 1H, J = 6.8 Hz), 1.44 (d, 6H, J = 6.8 Hz). |
| 254 | pyridin-3-yl | cyclo-propyl | MS (ES+) 618.1 (M+H)⁺; ¹H NMR (400 MHz, CDCl₃) δ 8.73 (dd, 1H, J = 4.9, 1.5 Hz), 8.50(d, 1H, J = 2.1 Hz), 7.82 (s, 1H), 7.60 (dt, 1H, J = 1.7, 7.8 Hz), 7.53 (dd, 1H, J = 7.8, 2.0Hz), 7.41 (s, 2H), 7.37 (dd, 1H, J = 7.9, 5.0 Hz), 7.22–7.33 (m, 3H), 5.52 (s, 2H), 2.22 (m, 1H), 1.18–1.32 (m, 4H). |
| 255 | pyridin-4-yl | cyclo-propyl | MS (ES+) 618.1 (M+H)⁺; ¹H NMR (400 MHz, CDCl₃) δ 8.71 (d, 2H, J = 6.0Hz), 7.83 (s, 1H), 7.50 (dd, 1H, J = 7.8, 1.9 Hz), 7.43 (s, 2H), 7.18–7.30 (m, 3H), 7.16 (m, 2H), 5.48 (s, 2H), 2.20 (m, 1H), 1.17–1.31 (m, 4H). |

General Example P

Add MnO₂ (5–10 eq.) to a solution of the appropriate alcohol (1 eq.) in CH₂Cl₂ or toluene (~0.1 M) and stir the mixture at RT. (The reaction may be heated if necessary.) When the reaction is complete, filter the mixture through Celite® and concentrate the filtrate. Purify the crude material by flash chromatography on silica gel.

Using the method of General Example P, the following compounds may be prepared and isolated.

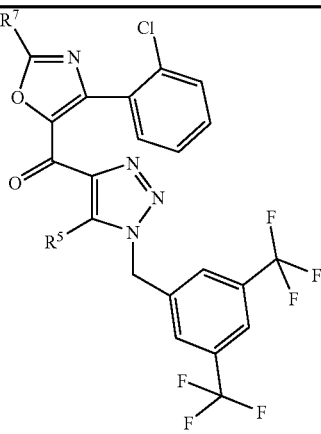

| Ex. # | R⁵ | R⁷ | Physical Data |
|---|---|---|---|
| 256 | pyridin-4-yl | methyl | ¹H NMR (400 MHz, CDCl₃) δ 8.73 (s, 2H), 7.84 (s, 1H), 7.52 (dd, 1H, J = 1.9, 7.8 Hz), 7.44 (s, 2H), 7.37 (dd, 1H, |

-continued

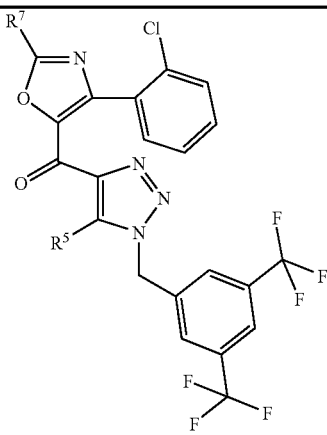

| Ex. # | R⁵ | R⁷ | Physical Data |
|---|---|---|---|
| | | | J = 5.0, 7.9 Hz), 7.30 (dt, 1H, J = 2.0, 6.9 Hz), 7.27 (dd, 1H, J = 1.5, 7.4 Hz), 7.23 (m, 2H), 5.49 (s, 2H), 2.62 (s, 3H). |
| 257 | chloro | iso-propyl | MS (ES+) 577.0 (M+1)⁺. ¹H NMR (400 MHz, CDCl₃) δ 7.90 (s, 1H), 7.76 (s, 2H), 7.54 (d, 1H, J = 7.3 Hz), 7.27 (m, 3H), 5.60 (s, 2H), 3.28 (septet, 1H, J = 6.8 Hz), 1.47 (d, 6H, J = 6.8 Hz). |
| 258 | chloro | cyclo-propyl | MS (ES+) 575.1 (M+H). ¹H NMR (400 MHz, CDCl₃) δ 7.91 (s, 1H), 7.76 (s, 2H), 7.50 (m, 1H), 7.24-7.31 (m, 3H), 5.61 (s, 2H), 2.60 (m, 1H), 1.33 (m, 2H), 1.23 (m, 2H). |
| 259 | chloro | methyl | MS (ES+) 549.0 (M+1)+. ¹H NMR (400 MHz, CDCl₃) δ 7.92 (s, 1H), 7.77 (s, 2H), 7.52 (dd, IH, J = 1.9, 5.8 Hz), 7.28 (m, 3H), 5.62 (s, 2H), 2.68 (s, 3H). |

Example 260

[5-Amino-3-(2-chloro-phenyl)-pyridazin-4-yl]-[1-(3,5-bis-trifluoromethyl-benzyl)-5-pyridin-4-yl-1H-[1,2,3]triazol-4-yl]-methanone

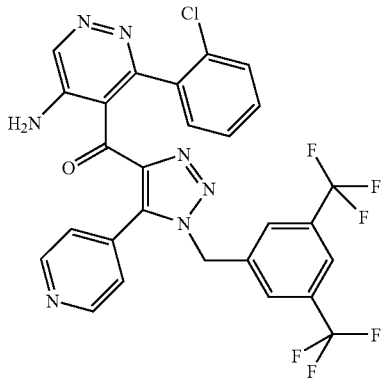

To 3-[1-(3,5-bis-trifluoromethyl-benzyl)-5-pyridin-4-yl-1H-[1,2,3]triazol-4-yl]-4-(2-chloro-phenyl)-isoxazolo[3,4-d]pyridazine (100 mg, 0.166 mmol), add 8.0 ml of acetonitrile, and 170 μL of water, followed by molybdenum hexacarbonyl (22 mg, 0.083 mmol). Heat the mixture to 80° C. for 4 h., then cool to RT. Pour the mixture through a plug of Celite® (1 cm) and silica gel (2 cm). Concentrate and purify the residue by chromatography (silica gel, hexanes/EtOAc gradient) to provide 42 mg of a yellow solid. Exact Mass 603.1: MS (aspci): m/z=603.9 (M+1), m/z=601.9 (M−1); ¹H NMR (300 MHz, CDCl₃) δ 8.65–8.80 (m, 3H), 7.79 (s, 1H), 7.65 (br d, J=7.4 Hz, 1H), 7.31 (s, 2H), 7.15–7.00 (m, 2H), 6.96 (d, J=7.4 Hz, 1H), 6.87 (br t, J=7.4 Hz, 1H), 6.12 (br s, 2H), 5.21 (ABq, J=22.5, 7.5 Hz, 2H).

Example 261

[5-amino-3-(2-chloro-phenyl)-pyridazin-4-yl]-[1-(3,5-bis-trifluoromethyl-benzyl)-5-phenyl-1H-[1,2,3]triazol-4-yl]-methanone

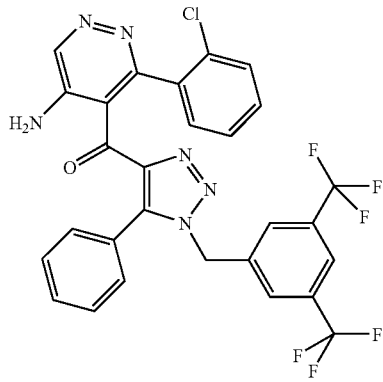

By the method of Example 260, using the appropriate starting materials, the title compound may be prepared and isolated. Exact Mass 602.9: MS (aspci): m/z=602.9 (M+1), m/z=601.0 (M−1); ¹H NMR (300 MHz, CDCl₃) δ 8.68 (s, 1H), 7.62 (s, 1H), 7.61 (m, 1H), 7.43 (d, J=7.8 Hz, 1H), 7.19–7.40 (m, 3H), 7.09 (s, 2H), 6.88–6.97 (m, 2H), 6.83 (m, 1H), 6.71 (m, 1H), 6.11 (br s, ~1H), 5.02–5.19 (m, 2H).

Using a method analogous to Example 260, the following compounds may be prepared and isolated.

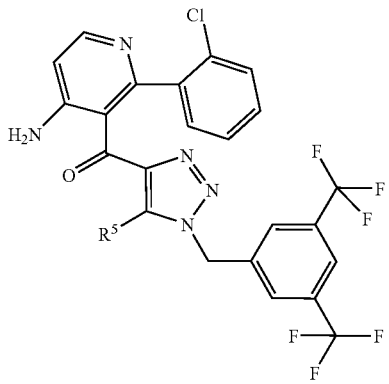

| Ex. # | R⁵ | Physical Data |
|---|---|---|
| 262 | pyridin-4-yl | Exact Mass 602.9; MS (aspci): m/z = 602.9 (M+1), m/z = 600.1 (M−1); $^1$H NMR (300 MHz, CDCl$_3$) δ 8.71 (br s, 2H), 8.22 (d, J = 7.1 Hz, 1H), 7.80 (s, 1H), 7.38 (dd, J = 7.2, 0.6 Hz, 1H), 7.32 (s, 2H), 7.04 (d, J = 6.0 Hz, 2H), 6.91–7.00 (m, 2H), 6.78 (m, 1H), 6.54 (d, J = 6.0, Hz, 2H), 5.67 (s, 2H), 5.24 (ABq, J = 21.6, 10.5 Hz, 2H). |
| 263 | phenyl | Exact Mass 601.1: MS (aspci): m/z = 601.9 (M+1); $^1$H NMR (300 MHz, CDCl$_3$) δ 8.22 (d, J = 3.2 Hz, 1H), 7.75 (s, 1H), 7.51–7.34 (m, 4H), 7.27 (s, 2H), 7.10–6.90 (m, 4H), 6.76 (dt, J = 0.5, 7.5 Hz, 1H), 6.55 d, J = 2.8 Hz, 1H, 5.61 s, 2H, 5.23 app d, J = 7.8 Hz, 2H). |

Example 264

[1-(3,5-bis-trifluoromethyl-benzyl)-5-phenyl-1H-[1,2,3]triazol-4-yl]-(2'-chloro-biphenyl-2-yl)-methanone

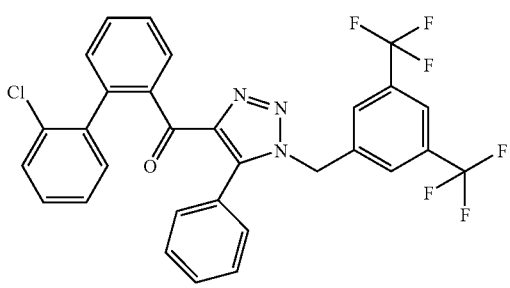

Dissolve 1-[1-(3,5-bis-trifluoromethyl-benzyl)-5-phenyl-1H-[1,2,3]triazol-4-yl]-3-(2-chloro-phenyl)-propynone (100 mg, 0.188 mmol) in chlorobenzene (1 mL), add pyrone (19.8 mg, 16.6 μL, 0.206 mmol) and heat the mixture at 130° C. After 24 h., add more pyrone (19.8 mg, 16.6 μL, 0.206 mmol). After another 24 h., cool to RT and concentrate. Purify by silica gel chromatography (hexanes/EtOAc gradient) to provide 88 mg of a clear colorless liquid. Exact Mass 585.9: MS (aspci): m/z=586.1 (M+1); $^1$H NMR (300 MHz, CDCl$_3$) δ 7.77–7.66 (m, 3H), 7.25–7.6 (m, 6H), 7.30 (s, 2H), 7.05–7.20 (m, 2H), 7.05–6.90 (m, 3H), 5.31 (s, 2H).

Example 265

1-[1-(3,5-bis-trifluoromethyl-benzyl)-5-phenyl-1H-[1,2,3]triazol-4-yl]-3-(2-chloro-phenyl)-propenone

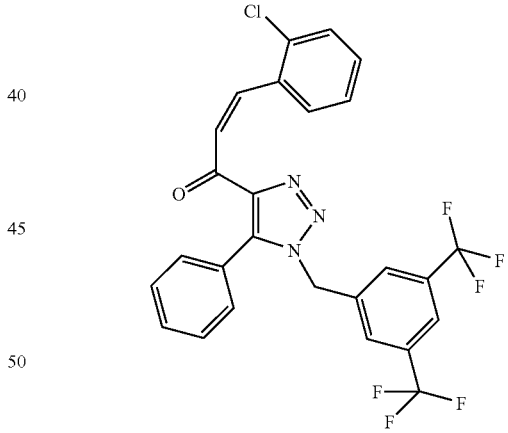

To 1-[1-(3,5-bis-trifluoromethyl-benzyl)-5-phenyl-1H-[1,2,3]triazol-4-yl]-3-(2-chloro-phenyl)-propynone (50 mg, 0.0094 mmol), add 15 ml of pyridine, followed by 5% palladium on barium sulfate (6.2 mg); stir at RT for 3 h. at 60 psi of hydrogen. Pour the mixture through a plug of Celite® (1 cm) and silica gel (2 cm). Concentrate the clear, colorless liquid to 1.0 mL with azeotropic removal of the pyridine with heptane. Purify by radial chromatography (hexanes/EtOAc gradient) to provide the desired product as a clear colorless liquid (25 mg). Exact Mass 535.9: MS (aspci): m/z=536.0 (M+1), 534.0 (M−1); $^1$H NMR (300 MHz, CDCl$_3$) δ 7.83(s, 1H), 7.64–7.40 (m, 2H), 7.51 (s, 2H), 7.38 (m, 1H), 7.28 (s, 3H), 7.24–7.10 (m, 2H), 5.62 s, 1H), 5.55 (d, J=3.0 Hz, 1H).

Example 266

1-[1-(3,5-bis-trifluoromethyl-benzyl)-5-phenyl-1H-[1,2,3]triazol-4-yl]-3-(2-fluoro-phenyl)-propenone

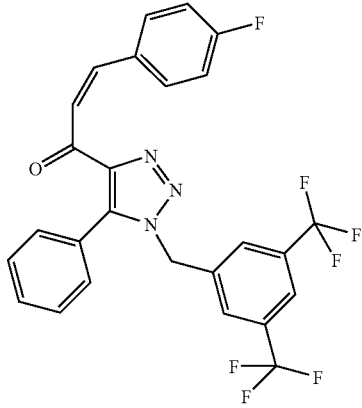

Using a similar procedure as Example 265, with the appropriate starting materials, the title compound may be prepared and isolated. Exact Mass 519.45: MS (aspci): m/z=520.1 (M+1), 518.1 (M+1); $^1$H NMR (300 MHz, CDCl$_3$) δ 7.74 (s, 1H), 7.58 (m, 1H), 7.55–7.35 (m, 2H), 7.40 (s, 2H), 7.19 (s, 2H), 7.15 (m, 1H), 7.03 (appt, J=12.0 Hz, 2H), 5.51 (s, 2H).

Example 267

1-[1-(3,5-bis-trifluoromethyl-benzyl)-5-phenyl-1H-[1,2,3]triazol-4-yl]-3-(2-chlorophenyl)-propan-1-one

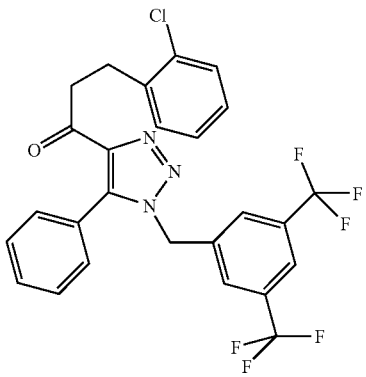

Dissolve 1-[1-(3,5-bis-trifluoromethyl-benzyl)-5-phenyl-1H-[1,2,3]triazol-4-yl]-3-(2-chloro-phenyl)-propynone (1.04 g, 1.949 mmol) in THF (36 mL), add Platinum (IV) oxide (260 mg, 1.15 mmol) and stir at RT for 48 h. under 60 psi of hydrogen. Filter through a plug of Celite® (1 cm) and silica gel (2 cm). Concentrate the filtrate and purify the residue by chromatography (silica gel, EtOAc/Hexanes gradient) to provide the desired product as a clear colorless liquid (550 mg). Exact Mass 537.10: MS (aspci): m/z=540.0 (M+1); $^1$H NMR (300 MHz, CDCl$_3$) δ 8.32 (s, 1H), 7.60–7.44 (m, 2H), 7.47 (s, 2H), 7.22–7.40 (m, 3H), 7.33–7.10 (m, 4H), 5.57 (s, 2H), 3.52 (t, J=8.1 Hz, 6H), 3.14 (t, J=8.1 Hz, 2H).

Example 268

3-[1-(3,5-Bis-trifluoromethyl-benzyl)-5-imidazol-1-yl-1H-[1,2,3]triazol-4-yl]-2-(2-chloro-benzoyl)-3-oxo-propionitrile

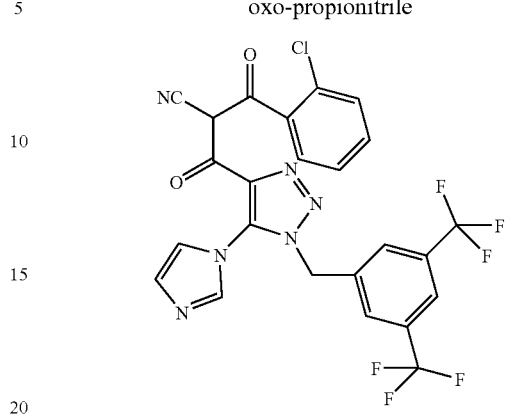

Add Dess-Martin periodinane (1.5 g, 3.54 mmol) to a solution of [1-(3,5-Bis-trifluoromethyl-benzyl)-5-imidazol-1-yl-1H-[1,2,3]triazol-4-yl]-[5-(2-chloro-phenyl)-3-hydroxymethyl-isoxazol-4-yl]-methanone (0.7 g, 1.17 mmol) in dichloromethane (10.0 mL). Stir at RT for 4 h, dilute with EtOAc and wash with 2N NaOH, water and brine, then dry, filter, and concentrate. Recyrstallize crude material from dichloromethane to give the title compound. (0.10 g, 15%). MS [ES] 567.0 (M+H)$^+$, 565.0 (M−H); $^1$H NMR (400 MHz, DMSO-d$_6$) δ 8.04 (s, 1H), 7.70 (s, 2H), 7.69 (s, 1H), 7.25 (br s, 2H), 7.19 (m, 2H), 7.03 (s, 1H), 6.98 (m, 1H), 5.68 (s, 2H).

Example 269

[1-(3,5-bistrifluoromethylbenzyl)-5-imidazol-1-yl-1H-[1,2,3]triazol-4-yl]-[5-(2-chlorophenyl)-3-hydroxymethyl-isoxazol-4-yl]-methanone

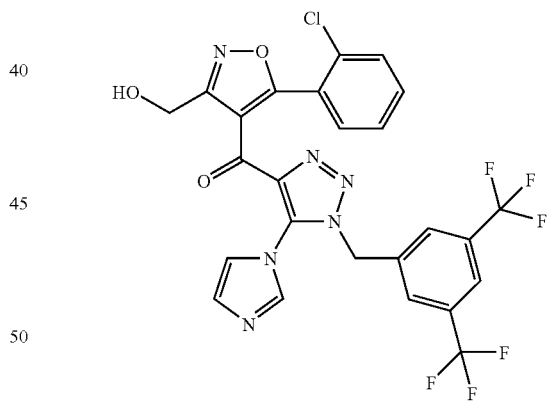

Heat a solution of [1-(3,5-bistriflurormethylbenzyl)-5-chloro-1H-[1,2,3]triazol-4-yl]-[5-(2-chlorophenyl)-3-(tetrahydropyran-2-yloxymethyl)-isoxazol-4-yl]-methanone (25.0 g, 0.039 mol) and imidazole (10.5 g, 0.154 mol) in DMSO (180 mL) at 90° C. for 24 h. Cool the solution to RT, add to ice water (700 mL), stir for 15 min. and filter. Add methylene chloride (400 mL) to the wet cake and place in a separatory funnel. Separate the layers and extract the aqueous with methylene chloride (200 mL). Back extract the combined organic layers with water (2×200 mL), dry (magnesium sulfate), filter, and concentrate to a foam. Add MeOH (250 mL) and p-toluenesulfonic acid monohydrate (7.3 g, 0.039 mol) and stir at RT for 2 h. Remove MeOH under vacuum and add methylene chloride (250 mL), water (200 mL), and saturated sodium bicarbonate (50 mL). Separate layers and extract the aqueous layer with methylene chloride (100 mL). Combine the organic layers, back extract with water (200 mL), dry (magnesium sulfate), treat with acid-washed carbon, filter through Celite®, and concentrate under vacuum to an oil. Add diethyl ether (100 mL), stir for 1 h., add heptane (100 mL) over 20 min., stir for 1 h., filter, and dry to give crude title compound. Recrystallize as follows: add diethyl ether (500 mL), methylene chloride (100 mL) and MeOH (100 mL), concentrate solution, add heptane (350 mL) over 30 min., stir for 2 h., filter, and dry to give the title compound. m.p. 148.8° C.; MS [ES] 597.1 (M+H)+, 595.1 (M–H)−. $^1$H NMR (400 MHz, CHCl$_3$) δ 7.91 (s, 1H), 7.74 (dd, 1H, J=7.6, 1.6 Hz) 7.70 (br s, 1H), 7.45–7.49 (m, 3H), 7.41 (dt, 1H, J=7.6, 2.0 Hz), 7.34 (br s, 1H), 7.21 (dd, 1H, J=8.0, 1.2 Hz), 6.92 (br s, 1H), 5.42 (s, 2H), 4.83 (m, 2H), 3.00 (br s, 1H).

Example 270

[1-(3,5-Bis-trifluoromethyl-benzyl)-5-phenyl-1H-[1,2,3]triazol-4-yl]-(3-phenyl-3H-[1,2,3]triazol-4-yl)-methanone

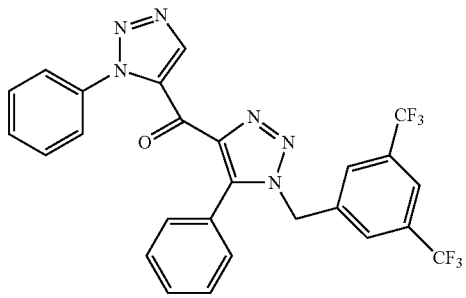

To a solution of [1-(3,5-Bis-trifluoromethyl-benzyl)-5-phenyl-1H-[1,2,3]triazol-4-yl]-(3-phenyl-5-trimethylsilanyl-3H-[1,2,3]triazol-4-yl)-methanone (0.050 g, 0.08 mmol) in THF (2 mL) add t-butyl ammonium fluoride (1 M soln. in THF, 1.2 mL, 1.2 mmol) and acetic acid (120 μL, 2.0 mmol) and heat at 65° C. After 72 h., remove from heat, and quench with sat. aq. NH$_4$C$_1$ and H$_2$O. Extract with EtOAc, dry over MgSO$_4$, filter, and purify by flash chromatography (EtOAc/Hexane 0%–50%) to give the title compound. $^1$H NMR (300 MHz, CDCl$_3$) δ 8.88 (s, 1H), 7.75 (s, 1H), 7.57–7.29 (m, 10H), 7.09 (m, 2H), 5.50 (s, 2H).

Example 271

4-[1-(3,5-Bis-trifluoromethyl-benzyl)-5-phenyl-1H-[1,2,3]triazole-4-carbonyl]-5-(2-chloro-phenyl)-isoxazole-3-carbaldehyde oxime

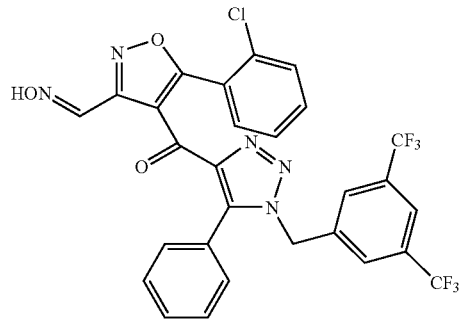

To a solution of 4-[1-(3,5-Bis-trifluoromethyl-benzyl)-5-phenyl-1H-[1,2,3]triazole-4-carbonyl]-5-(2-chloro-phenyl)-isoxazole-3-carbaldehyde (0.076 g, 0.13 mmol) in CH$_2$Cl$_2$ (2 mL) and MeOH (2 mL), add sodium acetate trihydrate (0.034 g, 0.25 mmol) and hydroxylamine.HCl (0.018 g, 0.25 mmol) and stir at RT. After 1 h., quench with 75% sat. aq. NH$_4$Cl (4 mL), extract with ethyl acetate, and wash with brine. Dry over MgSO$_4$, filter and concentrate under vacuum. Purify by flash chromatography, (EtOAc/Hexane 10%–50%) to give the title compound. MS(ES) 620.1 (M+1), $^1$H NMR (300 MHz, CDCl$_3$) δ 8.34 (s, 1H), 7.83 (br s, 2H), 7.74–7.16 (m, 9H), 5.50 (s, 2H).

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

Thus, the present invention provides pharmaceutical compositions comprising a compound of the Formula I and a pharmaceutically acceptable diluent.

The compounds of Formula I can be administered by a variety of routes. In effecting treatment of a patient afflicted with disorders described herein, a compound of Formula I can be administered in any form or mode that makes the compound bioavailable in an effective amount, including oral and parenteral routes. For example, compounds of Formula I can be administered orally, by inhalation, or by the subcutaneous, intramuscular, intravenous, transdermal, intranasal, rectal, occular, topical, sublingual, buccal, or other routes. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as povidone, hydroxypropyl cellulose, microcrystalline cellulose, gum tragacanth or gelatin; excipients such as dicalcium phosphate, starch, or lactose; disintegrating agents such as alginic acid, Primogel, corn starch and the like; lubricants such as talc, magnesium stearate or Sterotex; glidants such as colloidal silicon dioxide; and sweetening agents, such as sucrose, aspartame, or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and nontoxic in the amounts used.

For the purpose of parenteral therapeutic administration, the compounds of the present invention may be incorporated into a solution or suspension. These preparations typically contain at least 0.001% of a compound of the invention, but may be varied to be between 0.001 and about 90% of the weight thereof. The amount of the compound of Formula I present in such compositions is such that a suitable dosage will be obtained. The solutions or suspensions may also include one or more of the following adjuvants: sterile diluents, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so, the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of a compound of Formula I or its pharmaceutical salt from about 0.1 to about 10% w/v (weight per unit volume).

The compounds of Formula I are antagonists of NK-1 receptors. Furthermore, the compounds of Formula I selectively antagonize NK-1 receptors relative to other tachykinin receptors. The antagonist activity of NK-1 receptor antagonists may be determined by the methods below.

NK-1 Receptor Binding Assay

The IM-9 cell line is a well-characterized and readily available human cell line. See e.g., *Annals of the New York Academy of Science*, 190: 221–234 (1972); *Nature (London)*, 251:443–444 (1974); *Proceedings of the National Academy of Sciences (USA)*, 71:84–88 (1974). These cells are routinely cultured in RPMI 1640 supplemented with 50 µg/ml gentamicin sulfate and 10% fetal calf serum.

The IM-9 cells are homogenized from cell pellets for crude membranes. The membranes are isolated by homogenizing tissue samples in 30 ml w/v with 50 mM Tris buffer (pH 7.4). After an initial spin at 900×g, the supernatant is transferred to a clean centrifuge tube and the membranes isolated by centrifugation at 38,000×g.

Approximately 25 µg of membranes are incubated with 0.2 nM [$^{125}$I]-substance P (NEN, Boston, Mass.) in a receptor binding assay. The assay buffer contains 50 mM Tris, 3 mM $MnCl_2$, 0.02% bovine serum albumin, 40 µg/ml bacitracin, 2 µg/ml chymostatin, 4 µg/ml leupeptin and 40 µg/ml thiorphan (pH 7.4). Binding studies are conducted in a final volume of 200 µl containing various concentrations of test compounds. Non-specific binding is determined by incubating some tubes in the presence of 1 µM substance P (Peninsula, Belmont, Calif.).

Binding is terminated 1 hour later by rapid filtration using a TOMTEC 96-well cell harvester (TOMTEC, Orange, Conn.) through GF/A filters that have been presoaked with 0.3% polyethyleneimine (Sigma, St Louis) for 1 hour. The filters are washed with 5 ml of ice-cold 50 mM Tris buffer (pH 7.4) and placed in a drying oven at 60° C. The dried filters are treated with MeltiLex A melt-on scintillator sheets (Wallac, Gaithersburg, Md.), and the radioactivity retained on the filters counted using the Wallac 1205 Betaplate scintillation counter. The results are analyzed using a Log-Logit plot from a Microsoft Excel™ workbook and converted to Ki values with the Cheng-Prusoff equation. Protein concentrations are measured using Coomassie® protein assay reagent (Pierce, Rockford, Ill.), with BSA for standards (Bradford, 1976).

Binding studies are carried out to evaluate the ability of compounds of the present invention to inhibit NK-1 receptor activation. Such studies provide in vitro data regarding the efficacy of the compounds of the present invention. Representative Examples of the compounds of Formula (I) were tested in the receptor binding assay described herein and were demonstrated to have binding affinities ($K_i$ values) of $\leq 100$ nM.

Several preclinical laboratory animal models have been described for a number of the disorders associated with an excess of tachykinins. One such in vivo assay, described below, may be used to determine whether NK-1 receptor antagonists are CNS-penetrant.

Gerbil Foot-Tapping

The gerbil foot-tapping assay is well recognized in the art. For example, see Rupniak et al., *Eur. J. Pharmacol.* (1997) 326: 201–209.

Male Gerbils (Mongolian), weighing between 20–40 gm (Harlan Labs, Indianapolis, Ind.) are used for the experiments. Animals are allowed to acclimate prior to any testing.

An NK-1 receptor agonist, such as GR73632 (δ-Aminovaleryl [Pro$^9$, N-Me-Leu$^{10}$]-Substance P(7–11)) (Peninsula Labs), is dissolved in acidified saline (1 ml acetic acid in 1 liter of 0.09% saline) to make a 1 mg/ml solution (corrected for peptide content). The stock solution is further diluted to 10 µg/ml in saline (0.9% normal saline), aliquoted and kept frozen until use. The stock solution is further diluted to 3 pmol/5 µl in saline for i.c.v. injections.

Test compounds are formulated in appropriate vehicle to a concentration of 1 ml/100 gm body weight. Compounds are dosed by oral gavage (p.o.) or subcutaneously (s.c.) or intraperitoneally (i.p.) at pre-determined times prior to intracerebroventricular (i.c.v.) challenge of agonist. For i.c.v. administration, test compound is co-injected with agonist.

Free hand i.c.v. injection is performed by direct vertical insertion of a cuffed 27-gauge needle with a Hamilton 50 µl syringe, to a depth of 4.5 mm below bregma. Light anesthesia with isoflurane may be needed prior to the injection, but is not used routinely.

Following i.c.v. injection of agonist, animals are placed in a plexiglas observation box, and hind foot tapping events are counted for 5 minutes. Data collection is computerized.

Data are analyzed by ANOVA followed by Dunnett's test using JMP statistical program (IBM platform). Data are expressed as number of events/5 minutes.

The results of NK-1 receptor binding studies demonstrate the ability of compounds of the present invention to act as antagonists of NK-1 receptors. It is recognized that the compounds of the present invention would be expected to inhibit the effects of NK-1 receptor activation. Thus, the compounds of the present invention are expected to be useful in the treatment of various disorders associated with excess tachykinins, as described to be treated herein, and other disorders that can be treated by such antagonists, as are appreciated by those skilled in the art.

In one embodiment, the present invention provides methods of treating disorders selected from the group consisting of anxiety, depression, psychosis, schizophrenia and other psychotic disorders, neurodegenerative disorders (including senile dementia of the Alzheimer's type, Alzheimer's disease, AIDS-associated dementia, and Down's syndrome), seizure disorders (including generalized and partial seizures), demyelinating diseases (including multiple sclerosis and amyotrophic lateral sclerosis), neuropathological disorders (including peripheral neuropathy, diabetic and chemotherapy-induced neuropathy, and post-herpetic and other neuralgias), acute and chronic obstructive airway diseases (including adult respiratory distress syndrome, bronchopneumonia, bronchospasm, chronic bronchitis, drivercough, and asthma), inflammatory diseases (including inflammatory bowel disease, psoriasis, fibrositis, osteoarthritis, and rheumatoid arthritis), disorders of the musculo-skeletal system (such as osteoporosis), allergies (including eczema and rhinitis), hypersensitivity disorders (such as poison ivy), ophthalmic diseases (such as conjunctivitis, vernal conjunctivitis, and the like), cutaneous diseases (including contact dermatitis), atopic dermatitis, urticaria, other eczematoid dermatites, addiction disorders (including alcoholism), stress-related somatic disorders, reflex sympathetic dystrophy (such as shoulder/hand syndrome), dysthymic disorders, adverse immunological reactions (such as rejection of transplanted tissues), disorders related to immune enhancement or suppression (such as systemic lupus erythematosis), gastrointestinal disorders, diseases associated with the neuronal control of viscera (such as ulcerative colitis, Crohn's disease and irritable bowel syndrome); disorders of bladder function (such as bladder detrusor hyper-reflexia and incontinence), atherosclerosis, fibrosis and collagen diseases (such as scleroderma and eosinophilic fascioliasis), irritative symptoms of benign prostatic hypertrophy, disorders associated with blood pressure (such as hypertension), disorders of blood flow caused by vasodilation or vasospastic diseases (such as angina, migraine, and Reynaud's disease), emesis (including chemotherapy-induced nausea and acute or delayed emesis), and pain or nociception (including that attributable to or associated with any of the foregoing conditions), comprising: administering to a patient in need thereof an effective amount of a compound of Formula I or a pharmaceutical composition thereof. That is, the present invention provides methods of treating disorders associated with an excess of tachykinins, comprising: administering to a patient in need thereof an effective amount of a compound of Formula I or a pharmaceutical composition thereof.

The present invention contemplates the various disorders described to be treated herein and others that can be treated by such antagonists, as appreciated by those skilled in the art.

The disorders associated with an excess of tachykinins are treated by administering an effective amount of a compound or pharmaceutical composition of Formula I. An effective amount can be readily determined by the attending diagnostician; as one skilled in the art, by the use of conventional techniques and by observing results obtained under analogous circumstances. In determining an effective amount, the dose of a compound of Formula I, a number of factors are considered by the attending diagnostician, including, but not limited to: the compound of Formula I to be administered; the species of mammal—its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.001 milligram per kilogram of body weight per day (mg/kg/day) to about 100 mg/kg/day. Preferred amounts may be readily determined by one skilled in the art.

Of the disorders associated with an excess of tachykinins that are treated according to the present invention, the treatment of depression, anxiety, inflammatory bowel disease, irritable bowel syndrome, and emesis (chemotherapy-induced nausea and acute or delayed emesis) are particularly preferred.

Thus, in a preferred embodiment, the present invention provides a method for treating a depressive disorder, including major depressive disorder, comprising: administering to a patient in need thereof an effective amount of a compound of Formula I or a pharmaceutical composition thereof.

In another preferred embodiment, the present invention provides a method for treating anxiety, including generalized anxiety disorder, panic disorder, and obsessive-compulsive disorder, comprising: administering to a patient in need thereof an effective amount of a compound of Formula I or a pharmaceutical composition thereof.

Disorders of the central nervous system, including depressive and anxiety disorders, have been characterized in the Diagnostic and Statistical Manual of Mental Disorders (DSM-IV™) (1994, American Psychiatric Association, Washington, D.C.). The DSM-IV™ provides clear descriptions of diagnostic categories. The skilled artisan will recognize that there are alternative nomenclatures, nosologies, and classification systems for these disorders, and that these systems may evolve with medical scientific progress. For instance, the ICHPPC-2 (International Classification of Health Problems in Primary Care) ($3^{rd}$ edition, 1983, Oxford University Press, Oxford) provides an alternative classification system. Thus, the terms "depression," "depressive disorders," "anxiety," and "anxiety disorders" are intended to include like disorders that are described in other diagnostic sources.

According to the fourth edition of the DSM-IV™, major depressive disorders are characterized by one or more major depressive episodes, which consist of a period of at least two weeks of depressed mood or loss of pleasure, in addition to other symptoms. Thus, the skilled artisan will recognize that the present invention is useful for the treatment of either a single episode or recurrent episodes of major depressive disorder.

The skilled artisan will appreciate that other depressive disorders may also be treated by administering an effective amount of a compound of Formula (I). Such other depressive disorders include dysthymic disorder, and depressive disorders not otherwise specified (for example, premenstrual dysphoric disorder, minor depressive disorder, recurrent brief depressive disorder, or postpsychotic depressive disorder of schizophrenia). In addition, the treatment of depression by the compounds of Formula (I) may also include the treatment of mood disorders due to a general medical condition and substance-induced mood disorders.

The DSM-IV™ also provides a diagnostic tool for anxiety and related disorders. These disorders include: panic disorder with or without agoraphobia, agoraphobia without history of panic disorder, specific phobia, social phobia or social anxiety disorder, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein, the term "anxiety" includes treatment of those anxiety disorders and related disorders described in the DSM-IV.

What is claimed is:
1. A compound of Formula I:

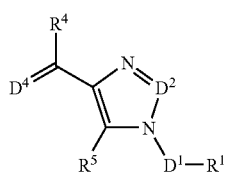

(I)

wherein:
$D^1$ is a $C_1$–$C_3$ alkane-diyl;
$D^2$ is CH or nitrogen;
$D^4$ is oxygen or sulfur;
$R^1$ is phenyl,
which is optionally substituted with one to three substitutents independently selected from the group consisting of halo, $C_1$–$C_4$ alkyl, $C_1$–$C_4$ alkoxy, cyano, difluoromethyl, trifluoromethyl, and trifluoromethoxy;
$R^4$ is a radical selected from the group consisting of:

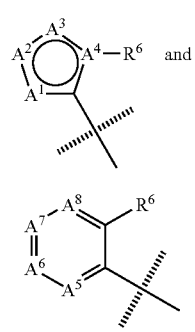

(IA)

and (IB)

wherein
$A^1$, $A^2$, $A^3$, and $A^4$, together with the atoms to which they are attached, form an unsaturated heterocyclic ring in which each of $A^1$, $A^2$, and $A^3$ is independently $CR^7$, nitrogen, which nitrogen is optionally substituted with $R^8$, oxygen, or sulfur, and $A^4$ is carbon or nitrogen, wherein only one of $A^1$, $A^2$, and $A^3$ can be oxygen or sulfur;
$A^5$, $A^6$, $A^7$, and $A^8$, together with the atoms to which they are attached, form an unsaturated carbocyclic or heterocyclic ring in which each of $A^5$, $A^6$, $A^7$, and $A^8$ is independently $CR^7$ or nitrogen, wherein at least one of $A^5$, $A^6$, $A^7$, and $A^8$ must be $CR^7$;
each $R^7$ is independently selected from the group consisting of hydrogen, halo, $C_1$–$C^4$ alkyl, substituted $C_1$–$C_4$ alkyl, $C_3$–$C_6$ cycloalkyl, $C_1$–$C_4$ alkoxycarbonyl, trifluoromethyl, trifluoromethoxy, and —$NR^9R^{10}$;
$R^9$ and $R^{10}$ are each independently hydrogen, $C_1$–$C_4$ alkyl, or —C(O)—$CH_3$, or $R^9$ and $R^{10}$, together with the nitrogen to which they are attached, form a 4–7 membered saturated heterocyclic ring;
each $R^8$ is independently selected from the group consisting of hydrogen, $C_1$–$C_4$ alkyl, substituted $C_1$–$C_4$ alkyl, and $C_1$–$C_3$ cycloalkyl;
$R^6$ is $C_1$–$C_4$ alkyl, $C_3$–$C_6$ cycloalkyl, phenyl, or pyridyl, which phenyl or pyridyl is optionally substituted with one to three substituents independently selected from the group consisting of halo, cyano, $C_1$–$C_4$ alkyl, $C_1$–$C_4$ alkoxy, trifluoromethyl, trifluoromethoxy, and —$NR^{11}R^{12}$;
$R^{11}$ and $R^{12}$ are each independently hydrogen or $C_1$–$C_4$ alkyl, or $R^{11}$ and $R^{12}$, together with the nitrogen to which they are attached, form a 4–7 membered saturated heterocyclic ring;
$R^5$ is hydrogen, halo, trifluoromethyl, $C_1$–$C_4$ alkyl, $C_3$–$C_6$ cycloalkyl, furyl, thienyl, pyrrolyl, imidazolyl, —$NR^{13}R^{14}$, pyridyloxy, phenyl, phenoxy, phenylthio, anilino,
which phenyl, phenoxy, phenylthio, or anilino group may be optionally substituted on the phenyl ring with one or two substituents independently selected from the group consisting of halo, $C_1$–$C_4$ alkyl, $C_1$–$C_4$ alkoxy, and —$S(O)_q(C_1$–$C_4$ alkyl),
or a radical selected from the group consisting of:

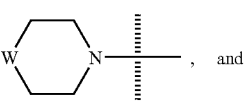

(IC)

and

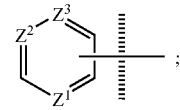

(ID)

wherein
W is a bond, $CHR^{15}$, O, $NR^{15}$, or $S(O)_q$;
q is 0, 1, or 2;
$R^{15}$ is selected from the group consisting of hydrogen, $C_1$–$C_4$ alkyl, acetyl, carbamoyl, phenyl, benzyl, and —$S(O)_2CH_3$;
$Z^1$, $Z^2$, and $Z^3$ are each independently CH or nitrogen;
$R^{13}$ and $R^{14}$ are each independently hydrogen or $C_1$–$C_4$ alkyl;
or a pharmaceutically acceptable salt thereof.

2. The compound of claim 1 wherein
$D^1$ is methylene or ethane-1,1-diyl;
$D^2$ is CH or nitrogen;
$D^4$ is oxygen;

$R^1$ is phenyl,
which is optionally substituted with one or two substituents independently selected from the group consisting of halo, $C_1$–$C_4$ alkyl, $C_1$–$C_4$ alkyoxy, trifluoromethyl, and trifluoromethoxy;

$R^4$ is a radical selected from the group consisting of:

(IA)

(IB)

wherein
$A^1$ is $CR^7$, $A^2$ is nitrogen, $A^3$ is oxygen, and $A^4$ is carbon;
$A^1$ is $CR^7$, $A^2$ is oxygen, $A^3$ is nitrogen, and $A^4$ is carbon;
$A^1$ is oxygen, $A^2$ is nitrogen, $A^3$ is $CR^7$, and $A^4$ is carbon;
$A^1$ is oxygen, $A^2$ is $CR^7$, $A^3$ is nitrogen, and $A^4$ is carbon;
$A^1$ is nitrogen, $A^2$ is nitrogen, $A^3$ is $NR^8$, and $A^4$ is carbon;
$A^1$ is $NR^8$, $A^2$ is nitrogen, $A^3$ is nitrogen, and $A^4$ is carbon;
$A^1$ is $CR^7$, $A^2$ is nitrogen, $A^3$ is nitrogen, and $A^4$ is nitrogen;
$A^1$ is nitrogen, $A^2$ is $CR^7$, $A^3$ is $CR^7$, and $A^4$ is nitrogen;
$A^1$ is $NR^8$, $A^2$ is nitrogen, $A^3$ is $CR^7$, and $A^4$ is carbon;
$A^1$ is nitrogen, $A^2$ is $NR^8$, $A^3$ is $CR^7$, and $A^4$ is carbon;
$A^1$ is $CR^7$, $A^2$ is $NR^8$, $A^3$ is nitrogen, and $A^4$ is carbon;
$A^1$ is $CR^7$, $A^2$ is nitrogen, $A^3$ is $NR^8$, and $A^4$ is carbon;
$A^5$ is $CR^7$, $A^6$ is $CR^7$, $A^7$ is nitrogen, and $A^8$ is nitrogen;
$A^5$ is $CR^7$, $A^6$ is $CR^7$, $A^7$ is $CR^7$, and $A^8$ is nitrogen; or
$A^5$ is $CR^7$, $A^6$ is $CR^7$, $A^7$ is $CR^7$, and $A^8$ is $CR^7$;

each $R^7$ is independently selected from the group consisting of hydrogen, $C_1$–$C_4$ alkyl, substituted $C_1$–$C_4$ alkyl, $C_3$–$C_6$ cycloalkyl, $C_1$–$C_4$ alkoxycarbonyl, and —$NR^9R^{10}$;

$R^9$ and $R^{10}$ are each independently hydrogen, or $C_1$–$C_4$ alkyl, or $R^9$ and $R^{10}$, together with the nitrogen to which they are attached, form a 4–7 membered saturated heterocyclic ring;

each $R^8$ is independently selected from the group consisting of hydrogen, $C_1$–$C_4$ alkyl, and substituted $C_1$–$C_4$ alkyl;

$R^6$ is phenyl or pyridyl,
which phenyl or pyridyl is optionally substituted with one to two substituents independently selected from the group consisting of halo, and trifluoromethyl;

$R^5$ is hydrogen, halo, $C_1$–$C_4$ alkyl, imidazolyl, —$NR^{13}R^{14}$, phenyl, or a radical selected from the group consisting of:

(IC)

-continued (ID)

wherein
W is —$CHR^{15}$—, —O—, —$NR^{15}$—, or $S(O)_q$—;
q is 0, 1, or 2;
$R^{15}$ is selected from the group consisting of $C_1$–$C_4$ alkyl, and carbamoyl;
$Z^1$, $Z^2$, and $Z^3$ are each independently CH or nitrogen;
$R^{13}$ and $R^{14}$ are each independently $C_1$–$C_4$ alkyl;
or a pharmaceutically acceptable salt thereof.

3. The compound of claim 1 wherein
$D^1$ is methylene or ethane-1,1-diyl;
$D^2$ is CH or nitrogen;
$D^4$ is oxygen;
$R^1$ is phenyl,
which is optionally substituted with one or two substituents independently selected from the group consisting of halo, $C_1$–$C_4$ alkyl, $C_1$–$C_4$ alkyoxy, trifluoromethyl, and trifluoromethoxy;

$R^4$ is a radical selected from the group consisting of:

(IA-1)

(IA-2)

(IA-3)

(IA-4)

(IA-5)

-continued (IA-6) 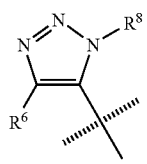

(IA-7) 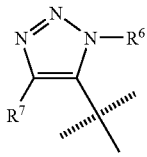

(IA-8) 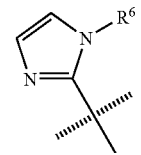

(IA-9) 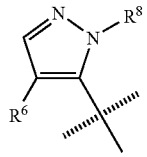

(IA-10) 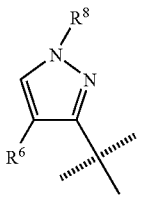

(IA-11) 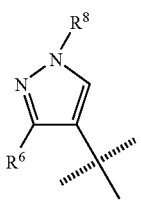

(IA-12) 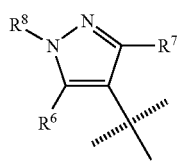

(IB-1) 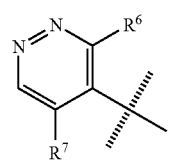

(IB-2) 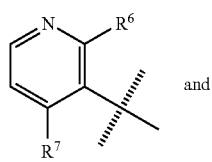

and

-continued (IB-3) 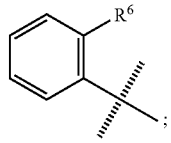

each $R^7$ is independently selected from the group consisting of hydrogen, $C_1-C_4$ alkyl, substituted $C_1-C_4$ alkyl, $C_3-C_6$ cycloalkyl, $C_1-C_4$ alkoxycarbonyl, and $-NR^9R^{10}$;

$R^9$ and $R^{10}$ are each independently hydrogen, or $C_1-C_4$ alkyl, or $R^9$ and $R^{10}$, together with the nitrogen to which they are attached, form a 4–7 membered saturated heterocyclic ring;

each $R^8$ is independently selected from the group consisting of hydrogen, $C_1-C_4$ alkyl, and substituted $C_1-C_4$ alkyl;

$R^6$ is phenyl or pyridyl, which phenyl or pyridyl is optionally substituted with one to two substituents independently selected from the group consisting of halo, and trifluoromethyl;

$R^5$ is hydrogen, halo, $C_1-C_4$ alkyl, imidazolyl, $-NR^{13}R^{14}$, phenyl, or a radical selected from the group consisting of:

(IC) 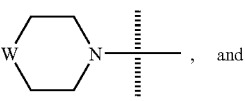, and (ID) 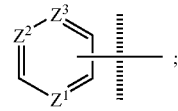;

wherein

W is $-CHR^{15}-$, $-O-$, $-NR^{15}-$, or $-S(O)_q-$;

q is 0, 1, or 2;

$R^{15}$ is selected from the group consisting of $C_1-C_4$ alkyl, and carbamoyl;

$Z^1$, $Z^2$, and $Z^3$ are each independently CH or nitrogen;

$R^{13}$ and $R^{14}$ are each independently $C_1-C_4$ alkyl;

or a pharmaceutically acceptable salt thereof.

4. The compound of claim 1 wherein $D^2$ is nitrogen.

5. The compound of claim 1 wherein $D^1$ is methylene.

6. The compound of claim 1 wherein $R^1$ is 3,5-bis-trifluoromethyl-phenyl.

7. The compound of claim 1 wherein $R^6$ is phenyl, which is substituted with one halo or trifluoromethyl.

8. The compound of claim 7 wherein $R^6$ is 2-chlorophenyl.

9. The compound of claim 1 wherein $R^5$ is imidazolyl or a radical of Formula (ID).

10. The compound of claim 9 wherein $R^5$ is imidazolyl.

11. The compound of claim 9 wherein $R^5$ is a radical of Formula (ID) in which $Z^2$ is nitrogen.

12. The compound of claim 1 wherein $R^4$ is a radical of Formula (IA).

13. The compound of claim 12 wherein R⁴ is a radical selected from the group consisting of:

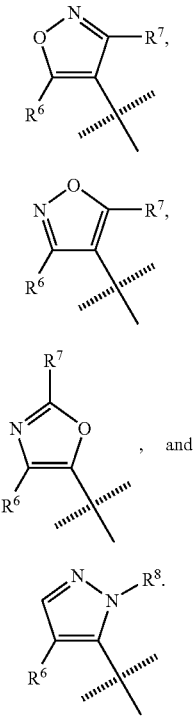

14. The compound of claim 1 wherein the compound is selected from the group consisting of:
- [1-(3,5-bis-trifluoromethylbenzyl)-5-imidazol-1-yl-1H-[1,2,3]triazol-4-yl]-[5-(2-chlorophenyl)-3-hydroxymethyl-isoxazol-4-yl]-methanone,
- [1-(3,5-bis-trifluoromethyl-benzyl)-5-imidazol-1-yl-1H-[1,2,3]triazol-4-yl]-[4-(2-chloro-phenyl)-2-cyclopropyl-oxazol-5-yl]-methanone,
- [1-(3,5-bis-trifluoromethyl-benzyl)-5-pyridin-3-yl-1H-[1,2,3]triazol-4-yl]-[5-(2-chloro-phenyl)-3-(1-hydroxy-1-methyl-ethyl)-isoxazol-4-yl]-methanone,
- [1-(3,5-bis-trifluoromethyl-benzyl)-5-pyrimidin-5-yl-1H-[1,2,3]triazol-4-yl]-[5-(2-chloro-phenyl)-3-(1-hydroxy-1-methyl-ethyl)-isoxazol-4-yl]-methanone,
- [1-(3,5-bis-trifluoromethyl-benzyl)-5-imidazol-1-yl-1H-[1,2,3]triazol-4-yl]-[5-(2-chloro-phenyl)-3-methyl-isoxazol-4-yl]-methanone,
- [1-(3,5-bis-trifluoromethyl-benzyl)-5-pyridin-4-yl-1H-[1,2,3]triazol-4-yl]-[4-(2-chloro-phenyl)-2-cyclopropyl-oxazol-5-yl]-methanone,
- [1-(3,5-bis-trifluoromethyl-benzyl)-5-pyridin-4-yl-1H-[1,2,3]triazol-4-yl]-[4-(2-chloro-phenyl)-2-cyclopropyl-oxazol-5-yl]-methanone,
- [1-(3,5-bis-trifluoromethyl-benzyl)-5-morpholin-4-yl-1H-[1,2,3]triazol-4-yl]-[4-(2-chloro-phenyl)-1-methyl-1H-pyrazol-5-yl]-methanone, and
- [1-(3,5-bis-trifluoromethyl-benzyl)-5-pyridin-3-yl-1H-[1,2,3]triazol-4-yl]-[3-(2-chloro-phenyl)-5-hydroxymethyl-isoxazol-4-yl]-methanone, or a pharmaceutically acceptable salt thereof.

15. A compound selected from the group consisting of:
- {1-(3,5-Bis-trifluoromethyl-benzyl)-5-[(2-dimethylamino-ethyl)-methyl-amino]-1H-[1,2,3]triazol-4-yl}-[3-(2-chloro-phenyl)-5-hydroxymethyl-isoxazol-4-yl]-methanone,
- [1-(3,5-Bis-trifluoromethyl-benzyl)-5-phenyl-1H-[1,2,3]triazol-4-yl]-{3-(2-chloro-phenyl)-5-[(2-morpholin-4-yl-ethylamino)-methyl]-isoxazol-4-yl}-methanone,
- 1-[1-(3,5-Bis-trifluoromethyl-benzyl)-5-phenyl-1H-[1,2,3]triazol-4-yl]-3-(2-chloro-phenyl)-propenone,
- 1-[1-(3,5-Bis-trifluoromethyl-benzyl)-5-phenyl-1H-[1,2,3]triazol-4-yl]-3-(2-fluoro-phenyl)-propenone,
- 1-[1-(3,5-Bis-trifluoromethyl-benzyl)-5-phenyl-1H-[1,2,3]triazol-4-yl]-3-(2-chlorophenyl)-propan-1-one, and
- 3-[1-(3,5-Bis-trifluoromethyl-benzyl)-5-imidazol-1-yl-1H-[1,2,3]triazol-4-yl]-2-(2-chloro-benzoyl)-3-oxo-propionitrile, or a pharmaceutically acceptable salt thereof.

16. A pharmaceutical composition comprising a compound of claim 1, or a pharmaceutically acceptable salt thereof, in combination with a pharmaceutically acceptable carrier, excipient, or diluent.

17. A method of treating a condition associated with an excess of tachykinins, wherein the condition associated with an excess of tachykinins is selected from the group consisting of depression, anxiety, irritable bowel syndrome, and emesis comprising administering to a patient in need thereof an effective amount of a compound of claim 1, or a pharmaceutically acceptable salt thereof.

18. The compound of claim 14 wherein the compound is [1-(3,5-bis-trifluoromethylbenzyl)-5-imidazol-1-yl-1H-[1,2,3]triazol-4-yl]-[5-(2-chlorophenyl)-3-hydroxymethyl-isoxazol-4-yl]-methanone, or a pharmaceutically acceptable salt thereof.

* * * * *